(12) United States Patent
Zheng et al.

(10) Patent No.: US 11,535,607 B2
(45) Date of Patent: Dec. 27, 2022

(54) ISOINDOLINES AS HDAC INHIBITORS

(71) Applicant: Valo Health, Inc., Boston, MA (US)

(72) Inventors: Xiaozhang Zheng, Lexington, MA (US); Matthew W. Martin, Arlington, MA (US); Pui Yee Ng, Lexington, MA (US); Jennifer R. Thomason, Clinton, MA (US); Bingsong Han, Westwood, MA (US); Aleksandra Rudnitskaya, Roslindale, MA (US); David R. Lancia, Jr., Boston, MA (US)

(73) Assignee: Valo Health, Inc., Boston, MA (US)

( * ) Notice: Subject to any disclaimer, the term of this patent is extended or adjusted under 35 U.S.C. 154(b) by 0 days.

(21) Appl. No.: 17/049,094

(22) PCT Filed: Apr. 18, 2019

(86) PCT No.: PCT/US2019/028026
§ 371 (c)(1),
(2) Date: Oct. 20, 2020

(87) PCT Pub. No.: WO2019/204550
PCT Pub. Date: Oct. 24, 2019

(65) Prior Publication Data
US 2021/0253555 A1 Aug. 19, 2021

Related U.S. Application Data

(60) Provisional application No. 62/669,285, filed on May 9, 2019, provisional application No. 62/669,286, filed on May 9, 2018, provisional application No. 62/660,581, filed on Apr. 20, 2018, provisional application No. 62/660,572, filed on Apr. 20, 2018.

(51) Int. Cl.
*C07D 403/04* (2006.01)
*C07D 209/10* (2006.01)
*C07D 209/44* (2006.01)
*C07D 401/04* (2006.01)
*C07D 401/12* (2006.01)
*C07D 413/04* (2006.01)
*C07D 413/12* (2006.01)
*C07D 417/04* (2006.01)
*C07D 471/04* (2006.01)
*C07D 498/04* (2006.01)
*C07D 513/04* (2006.01)

(52) U.S. Cl.
CPC ......... *C07D 403/04* (2013.01); *C07D 209/10* (2013.01); *C07D 209/44* (2013.01); *C07D 401/04* (2013.01); *C07D 401/12* (2013.01); *C07D 413/04* (2013.01); *C07D 413/12* (2013.01); *C07D 417/04* (2013.01); *C07D 471/04* (2013.01); *C07D 498/04* (2013.01); *C07D 513/04* (2013.01)

(58) Field of Classification Search
CPC .. C07D 403/04; C07D 471/04; C07D 498/04; C07D 401/04; C07D 401/12; C07D 417/04; C07D 513/04; C07D 209/10; C07D 209/44
USPC ...................................... 514/230.5
See application file for complete search history.

(56) References Cited

U.S. PATENT DOCUMENTS

| | | | |
|---|---|---|---|
| 9,186,318 B2 | 11/2015 | Yun et al. | |
| 9,637,453 B2 | 5/2017 | Ng et al. | |
| 10,011,611 B2 | 7/2018 | Ma et al. | |
| 10,508,088 B2 | 12/2019 | Lee et al. | |
| 10,538,496 B2 | 1/2020 | Lee et al. | |
| 11,345,672 B2 | 5/2022 | Lee et al. | |
| 2005/0159347 A1 | 7/2005 | DiMartino | |
| 2011/0160399 A1 | 6/2011 | Nagase et al. | |
| 2011/0237663 A1 | 9/2011 | Mascagni et al. | |
| 2014/0039059 A1 | 2/2014 | Oldoni et al. | |
| 2014/0045850 A1 | 2/2014 | Mallais et al. | |
| 2015/0359794 A1 | 12/2015 | Benz et al. | |
| 2016/0222026 A1 | 8/2016 | Deziel et al. | |
| 2016/0264518 A1 | 9/2016 | Bair et al. | |
| 2018/0127386 A1 | 5/2018 | Lee et al. | |

(Continued)

FOREIGN PATENT DOCUMENTS

| | | |
|---|---|---|
| CN | 103755595 A | 4/2014 |
| CN | 105131082 A | 12/2015 |

(Continued)

OTHER PUBLICATIONS

American Cancer Society, Cancer Facts & Figures, 7 pages 2016. URL: www.cancer.org/acs/groups/content/@research/documents/document/acspc-047079.pdf [Retrieved Aug. 2, 2018].

(Continued)

*Primary Examiner* — Kahsay Habte
(74) *Attorney, Agent, or Firm* — Choate, Hall & Stewart LLP; John P. Rearick

(57) ABSTRACT

The present disclosure relates to inhibitors of zinc-dependent histone deacetylases (HDACs), having the formula: (I) wherein Z, $X^1$, $X^2$, $Y^1$, $Y^2$, $Y^3$, L, Z, and R are described herein.

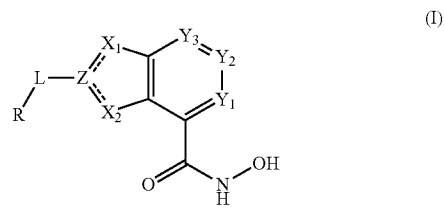

(I)

16 Claims, No Drawings

(56) References Cited

U.S. PATENT DOCUMENTS

| | | |
|---|---|---|
| 2019/0084945 A1 | 3/2019 | Lee et al. |
| 2019/0084946 A1 | 3/2019 | Lee et al. |
| 2019/0119364 A1 | 4/2019 | McKinsey et al. |
| 2019/0270733 A1 | 9/2019 | Ma et al. |
| 2020/0079744 A1 | 3/2020 | Lee et al. |
| 2022/0235018 A1 | 7/2022 | Lee et al. |

FOREIGN PATENT DOCUMENTS

| | | |
|---|---|---|
| EP | 3950677 A1 | 2/2022 |
| WO | WO-2005/066151 A2 | 7/2005 |
| WO | WO-2005/071079 A1 | 8/2005 |
| WO | WO-2007/038073 A2 | 4/2007 |
| WO | WO-2009/112550 A1 | 9/2009 |
| WO | WO-2010/034693 A1 | 4/2010 |
| WO | WO-2014/096386 A1 | 6/2014 |
| WO | WO-2015/106272 A1 | 7/2015 |
| WO | WO-2018/075959 A1 | 4/2018 |
| WO | WO-2018/177126 A1 | 10/2018 |
| WO | WO-2019/204550 A1 | 10/2019 |
| WO | WO-2020/232399 A1 | 11/2020 |
| WO | WO-2021/195598 A2 | 9/2021 |

OTHER PUBLICATIONS

Buglio, D. et al., HDAC11 plays an essential role in regulating OX40 ligand expression in Hodgkin lymphoma, Blood, 117(10): 2910-2917 (2011).
Cheng, F. et al., Divergent Roles of Histone Deacetylase 6 (HDAC6) and Histone Deacetylase 11 (HDAC11) on the Transcriptional Regulation of IL10 in Antigen Presenting Cells, Mol Immunol., 60(1):44-53 (2014).
Deubzer, H. et al., HDAC11 is a novel drug target in carcinomas, Int J Cancer, 132(9): 2200-2208 (2013).
Dokmanovic, M. et al., Histone Deacetylase Inhibitors: Overview and Perspectives, Mol Cancer Res., 981-989 (2007).
Ganai, S. et al., Histone deacetylase inhibitor pracinostat in doublet therapy: a unique strategy to improve therapeutic efficacy and to tackle herculean cancer chemoresistance, Pharmaceutical Biology, 54(9): 1926-1935 (2016).
Gao, L. et al., Cloning and Functional Characterization of HDAC11, A Novel Member of the Human Histone Deacetylase Family, J Biol Chem., 277(28): 25748-25755 (2002).
Gobert, M. et al., Regulatory T Cells Recruited through CCL22/CCR4 Are Selectively Activated in Lymphoid Infiltrates Surrounding Primary Breast Tumors and Lead to an Adverse Clinical Outcome, Cancer Res., 69: 2000-2009 (2009).
International Search Report for Ganai, S. et al., Histone deacetylase inhibitor pracinostat in doublet therapy: a unique strategy to improve therapeutic efficacy and to tackle herculean cancer chemoresistance, Pharmaceutical Biology, 54(9): 1926-1935 (2016)., 6 pages, ISA/US (dated Feb. 12, 2018).
International Search Report for PCT/US2019/028026, 4 pages (dated Aug. 8, 2019).
Joshi, P. et al., The functional interactome landscape of the human histone deacetylase family, Molecular Systems Biology, 9(672): 1-21 (2013).
Lozada, E.M. et al., Acetylation and deacetylation of Cdc25A constitutes a novel mechanism for modulating Cdc25A functions with implications for cancer, Oncotarget. 7(15): 20425-20439 (2016).
Martin, M.W et al., Discovery of novel N-hydroxy-2-arylisoindoline-4-carboxamides as potent and selective inhibitors of HDAC11, Bioorganic & Medicinal Chemistry Letters, 28(12): 2143-2147 (2018).
Sahakian, E. et al., Histone deacetylase 11: A novel epigenetic regulator of myeloid derived suppressor cell expansion and function, Mol Immunol., 63(2): 579-85 (2015).
Sonbol, M.B. et al., Comprehensive review of JAK inhibitors in myeloproliferative neoplasms, Ther Adv Hematol., 4(1): 15-35 (2013).
Villagra, A. et al., The histone deacetylase HDAC11 regulates the expression of interleukin 10 and immune tolerance, Nat Immunol., 10(1): 92-100 (2009).
Watanabe, Y. et al., Dendrite Development Regulated by the Schizophrenia-Associated Gene FEZ1 Involves the Ubiquitin Proteasome System, Cell Rep., 7(2): 552-564 (2014).
Weina, K. et al., SOX2 and cancer: current research and its implications in the clinic, Clin and Translational Med., 3(19): 1-10 (2014).
Wong, et al., Chromatin unfolding by Cdt1 regulates MCM loading via opposing functions of HBO1 and HDAC11-geminin, Cell Cycle., 9(21): 4351-63 (2010).
Written Opinion for PCT/US2017/057715, 9 pages, ISA/US (dated Feb. 12, 2018).
Written Opinion for PCT/US2019/028026, 7 pages (dated Aug. 8, 2019).
Zdanov, S. et al., Mutant KRAS conversion of conventional T cells into regulatory T cells, Cancer Immunol Res., 38 pages (Feb. 15, 2016), URL: http://cancerimmunolres.aacrjournals.org/content/early/2016/02/13/2326-6066.CIR-15-0241 [Retrieved Aug. 2, 2018].

ISOINDOLINES AS HDAC INHIBITORS

RELATED APPLICATIONS

The present application is a national phase entry of international application Ser. No. PCT/US2019/028026, filed Apr. 18, 2019 which claims the benefit of U.S. Provisional Patent Application Ser. No. 62/660,572, filed Apr. 20, 2018, U.S. Provisional Patent Application Ser. No. 62/660,581, filed Apr. 20, 2018, U.S. Provisional Patent Application Ser. No. 62/669,286, filed May 9, 2018, and U.S. Provisional Patent Application Ser. No. 62/669,285, filed May 9, 2018, each of which is incorporated herein by reference in its entirety.

TECHNICAL FIELD

The present invention relates to inhibitors of zinc-dependent histone deacetylases (HDACs).

BACKGROUND

Acetylation of lysine residues is an important post-translational modification that occurs on cellular proteins including, but not limited to, histones. Protein acetylation levels are controlled by histone deacetylases (HDACs) that catalyze the removal of acetyl groups and histone acetyltransferases (HATs) that are responsible for the addition of acetyl groups. HDACs regulate a range of cellular processes including gene expression, transcription factor activity, cell signaling pathways, and protein degradation.

Many members of the HDAC family require zinc (Zn) to function properly. For instance, the isozyme histone deacetylase 11 (HDAC11) is a zinc-dependent histone deacetylase. Other family members include HDACs 1-10 (De Ruijter et al., *Biochem. J.* 2003. 370; 737-749). HDAC11 is a class IV HDAC (Gao et al., *J. Biol Chem.* 2002, July 12; 277(28):25748-55) and is reported to deacetylate or associate with cell cycle-related proteins including Cdt1 (Glozak et al., *J. Biol Chem.* 2009, April 24; 284(17):11446-53), geminin (Wong et al., *Cell Cycle.* 2010, November 1; 9(21):4351-63), BubR1 (Watanabe et al., *Cell Rep.* 2014, April 24; 7(2):552-64), and Cdc25 (Lozada et al., *Oncotarget.* 2016, March 7). HDAC11 is also reported to function in RNA splicing as part of the survival of the motor neuron complex (Joshi et al., *Mol. Syst. Biol.* 2013, 9:672). Diseases in which HDAC11 inhibition could have potential benefit include cancer (Deubzer et al., *Int. J. Cancer.* 2013, May 1; 132(9):2200-8) and specifically, Hodgkin lymphoma (Buglio et al., *Blood.* 2011, March 10; 117(10):2910-7).

Inhibition of HDAC11 may also have a role in inflammatory or autoimmune diseases through effects on IL-10 on immune cells, including antigen presenting cells and myeloid-derived suppressor cells (Villagra et al., *Nat. Immunol.* 2009, January; 10(1):92-100; Cheng et al., *Mol. Immunol.* 2014, July; 60(1):44-53; Sahakian et al., *Mol. Immunol.* 2015, February; 63(2):579-85). In addition to deacetylase activity, HDAC11 has also been reported to have fatty acid deacylase activity (Kutil et al., *ACS Chem. Biol.* 2018, 13(3):685-693).

Four HDAC inhibitors are currently approved for the treatment of certain cancers. These are suberanilohydroxamic acid (Vorinostat; Zolinza®; SAHA) for the treatment of cutaneous T cell lymphoma and multiple myeloma; Romidepsin (FK228; FR901228; Istodax®) for the treatment of peripheral T cell lymphoma; Panobinostat (LBH-589; Farydak®) for the treatment of multiple myeloma; and belinostat (PXD101; Beleodaq®) for the treatment of peripheral T cell lymphoma. However, these drugs are of limited effectiveness and can give rise to unwanted side effects. Thus, there is a need for HDAC inhibitors with an improved safety-efficacy profile.

SUMMARY

One aspect of the invention relates to compounds of Formula I:

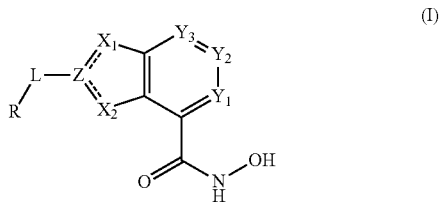

and pharmaceutically acceptable salts thereof, wherein:

$Z$ is N, C or CH;

$X_1$ and $X_2$ are each independently, at each occurrence, $-CR^1R^2-$, $=CR^1-$, $-NR^3-$, or $-C(O)-$, as valency permits, provided that only one of $X_1$ and $X_2$ is $-C(O)-$;

the dotted line between $Z\text{---}X_1$ and $Z\text{---}X_2$ is absent or represents a bond, provided that, at most, only one of the dotted lines represents a bond;

$Y_1$, $Y_2$, and $Y_3$ are each independently N or $CR^1$;

L is a bond, $-(CR^1R^2)_p-$, $-C(O)NR^3-$, $-NR^3C(O)-$, $-O(CR^1R^2)_pC(O)-$, $-C(O)(CR^1R^2)_pO-$, $-(CR^1R^2)_pC(O)-$, or $-C(O)(CR^1R^2)_p-$;

R is $-C_4\text{-}C_8$cycloalkenyl, $-C_3\text{-}C_8$cycloalkyl, heterocyclyl, aryl, or heteroaryl containing 1-5 heteroatoms selected from the group consisting of N, S, P, and O, wherein each cycloalkenyl, cycloalkyl, heterocyclyl, aryl, or heteroaryl is optionally substituted with one or more substituents selected from the group consisting of $-OH$, halogen, oxo, $-NO_2$, $-CN$, $-R^1$, $-R^2$, $-SR^3$, $-OR^3$, $-NHR^3$, $-NR^3R^4$, $-S(O)_2NR^3R^4$, $-S(O)_2R^1$, $-C(O)R^1$, $-C(O)OR^1$, $-NR^3S(O)_2R^1$, $-S(O)R^1$, $-S(O)NR^3R^4$, and $-NR^3S(O)R^1$;

$R^1$ and $R^2$ are independently, at each occurrence, $-H$, $-R^3$, $-R^4$, $-C_1\text{-}C_6$alkyl, $-C_2\text{-}C_6$alkenyl, $-C_4\text{-}C_8$cycloalkenyl, $-C_2\text{-}C_6$alkynyl, $-C_3\text{-}C_8$cycloalkyl, heterocyclyl, aryl, heteroaryl containing 1-5 heteroatoms selected from the group consisting of N, S, P and O, $-OH$, halogen, $-NO_2$, $-CN$, $-NHC_1\text{-}C_6$alkyl, $-N(C_1\text{-}C_6\text{alkyl})_2$, $-S(O)_2N(C_1\text{-}C_6\text{alkyl})_2$, $-N(C_1\text{-}C_6\text{alkyl})S(O)_2R^5$, $-S(O)_2(C_1\text{-}C_6\text{alkyl})$, $-(C_1\text{-}C_6\text{alkyl})S(O)_2R^5$, $-C(O)C_1\text{-}C_6\text{alkyl}$, $-C(O)OC_1\text{-}C_6\text{alkyl}$, $-N(C_1\text{-}C_6\text{alkyl})S(O)_2C_1\text{-}C_6\text{alkyl}$, or $-(CHR^5)_pNR^3R^4$, wherein each alkyl, alkenyl, cycloalkenyl, alkynyl, cycloalkyl, heterocyclyl, aryl, or heteroaryl is optionally substituted with one or more substituents selected from the group consisting of $-OH$, halogen, $-NO_2$, oxo, $-CN$, $-R^5$, $-OR^3$, $-NHR^3$, $-NR^3R^4$, $-S(O)_2N(R^3)_2-$, $-S(O)_2R^5$, $-C(O)R^5$, $-C(O)OR^5$, $-NR^3S(O)_2R^5$, $-S(O)R^5$, $-S(O)NR^3R^4$, $-NR^3S(O)R^5$, heterocyclyl, aryl, and heteroaryl;

or $R^1$ and $R^2$ can combine with the carbon atom to which they are both attached to form a spirocycle, spiroheterocycle, or spirocycloalkenyl, each optionally substituted with one or more independent occurrences of $R^3$ and $R^4$;

or $R^1$ and $R^2$, when on adjacent atoms, can combine to form a cycloalkyl, a heterocycle, heteroaryl containing 1-5 heteroatoms selected from the group consisting of N, S, P and O, or a cycloalkenyl, each optionally substituted with one or more independent occurrences of $R^3$ and $R^4$;

or $R^1$ and $R^2$, when on non-adjacent atoms, can combine to form an optionally bridging cycloalkyl, an optionally bridging heterocycle, or an optionally bridging cycloalkenyl, each optionally substituted with one or more independent occurrences of $R^3$ and $R^4$;

$R^3$ and $R^4$ are independently, at each occurrence, —H, —$C_1$-$C_6$alkyl, —$C_2$-$C_6$alkenyl, —$C_4$-$C_8$cycloalkenyl, —$C_2$-$C_6$alkynyl, —$C_3$-$C_8$cycloalkyl, heterocyclyl, aryl, heteroaryl containing 1-5 heteroatoms selected from N, S, P, and O, —$S(O)_2N(C_1$-$C_6$alkyl$)_2$, —$S(O)_2(C_1$-$C_6$alkyl), —$(C_1$-$C_6$alkyl)$S(O)_2R^5$, —$C(O)C_1$-$C_6$alkyl, —$C(O)OC_1$-$C_6$alkyl, or —$(CHR^5)_pN(C_1$-$C_6$alkyl$)_2$, wherein each alkyl, alkenyl, cycloalkenyl, alkynyl, cycloalkyl, heterocyclyl, aryl, or heteroaryl is optionally substituted with one or more substituents selected from the group consisting of —OH, halogen, —$NO_2$, oxo, —CN, —$R^5$, —$O(C_1$-$C_6)$alkyl, —NH$(C_1$-$C_6)$alkyl, —$N(C_1$-$C_6$alkyl$)_2$, —$S(O)_2N(C_1$-$C_6$alkyl$)_2$, —$S(O)_2NHC_1$-$C_6$alkyl, —$C(O)C_1$-$C_6$alkyl, —$C(O)OC_1$-$C_6$alkyl, —$N(C_1$-$C_6$alkyl)$S(O)_2C_1$-$C_6$alkyl, —$S(O)R^5$, —$S(O)N(C_1$-$C_6$alkyl$)_2$, —$N(C_1$-$C_6$alkyl)$S(O)R^5$, heterocyclyl, aryl, and heteroaryl;

$R^5$ is independently, at each occurrence, —H, —$C_1$-$C_6$alkyl, —$C_2$-$C_6$alkenyl, —$C_4$-$C_8$cycloalkenyl, —$C_2$-$C_6$alkynyl, —$C_3$-$C_8$cycloalkyl, heterocyclyl, aryl, heteroaryl containing 1-5 heteroatoms selected from N, S, P and O, —OH, halogen, —$NO_2$, —CN, —$NHC_1$-$C_6$alkyl, —$N(C_1$-$C_6$alkyl$)_2$, —$S(O)_2NH(C_1$-$C_6$alkyl), —$S(O)_2N(C_1$-$C_6$alkyl$)_2$, —$S(O)_2C_1$-$C_6$alkyl, —$C(O)C_1$-$C_6$alkyl, —$C(O)OC_1$-$C_6$alkyl, —$N(C_1$-$C_6$alkyl)$SO_2C_1$-$C_6$alkyl, —$S(O)(C_1$-$C_6$alkyl), —$S(O)N(C_1$-$C_6$alkyl$)_2$, —$N(C_1$-$C_6$alkyl)$S(O)(C_1$-$C_6$alkyl) or —$(CH_2)_pN(C_1$-$C_6$alkyl$)_2$; and p is 0, 1, 2, 3, 4, 5, or 6;

provided that when $X_2$ is —C(O)—, $X_1$ is $CH_2$, $Y_2$, and $Y_3$ are each CH, and L is a bond, then R is a group other than substituted or unsubstituted phenyl; and provided that $X^1$ and $X^2$ are not both nitrogen.

In certain embodiments, a compound of Formula I is other than:

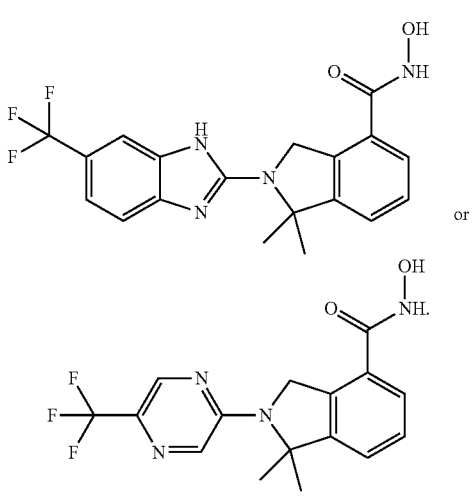

Another aspect of the invention relates to a method of treating a disease or disorder associated with HDAC11 modulation in a subject in need thereof, comprising administering to the subject an effective amount of a compound of Formula I.

Another aspect of the invention is directed to a method of inhibiting a histone deacetylase. The histone deacetylase can be a zinc-dependent histone deacetylase. The histone deacetylase can be HDAC11. The method involves administering to a subject in need thereof an effective amount of a compound of Formula I.

Another aspect of the invention is directed to pharmaceutical compositions comprising a compound of Formula I and a pharmaceutically acceptable carrier. The pharmaceutically acceptable carrier can further include an excipient, diluent, or surfactant. The pharmaceutical composition can be effective for treating a disease or disorder associated with HDAC11 modulation in a subject in need thereof. The pharmaceutical compositions can comprise the compounds of the present invention for use in treating diseases described herein. The compositions can contain at least one compound of the invention and a pharmaceutically acceptable carrier.

Another aspect of the invention is directed to the use of the compounds of Formula I in the manufacture of a medicament for the treatment of a disease associated with HDAC (e.g., HDAC11) modulation.

Another aspect of the present disclosure relates to a compound of Formula I, or a pharmaceutically acceptable salt thereof, for use in treating or preventing a disease associated with HDAC11 modulation.

The present invention further provides compounds that can inhibit HDAC11. In some embodiments, the efficacy-safety profile of the compounds of the current invention can be improved relative to other known pan-HDAC (e.g. SAHA) inhibitors. Additionally, the present disclosure also has the advantage of being able to be used for a number of different types of diseases, including cancer and non-cancer indications. Additional features and advantages of the present disclosure will be apparent to one of skill in the art upon reading the Detailed Description of the Invention below.

DETAILED DESCRIPTION

The details of the invention are set forth in the accompanying description below. Although methods and materials similar or equivalent to those described herein can be used in the practice or testing of the present invention, illustrative methods and materials are now described. Other features, objects, and advantages of the invention will be apparent from the description and from the claims. In the specification and the appended claims, the singular forms also include the plural unless the context clearly dictates otherwise. Unless defined otherwise, all technical and scientific terms used herein have the same meaning as commonly understood by one of ordinary skill in the art to which this invention belongs. All patents and publications cited in this specification are incorporated herein by reference in their entireties.

Compounds of the present disclosure include those described generally for Formula (I) above, and are further illustrated by the classes, subclasses, and species disclosed herein. It will be appreciated that some subsets described for each variable herein can be used for any of the structural subsets as well. As used herein, the following definitions shall apply unless otherwise indicated.

As described herein, compounds of the present disclosure may be optionally substituted with one or more substituents, such as are disclosed generally above, or as exemplified by particular classes, subclasses, and species disclosed herein.

The term "optionally substituted" is understood to mean that a given chemical moiety (e.g., an alkyl group) can (but is not required to) be bonded to other substituents (e.g., heteroatoms). For instance, an optionally substituted alkyl group can be a fully saturated alkyl chain (i.e., a pure hydrocarbon). Alternatively, the same optionally substituted alkyl group can have substituents in place of one or more hydrogen atoms. For instance, it can, at any point along the chain be bonded to a halogen atom, a hydroxyl group, or any other substituent described herein. Thus the term "optionally substituted" means that a given chemical moiety has the potential to contain other functional groups, but does not necessarily have any further functional groups. It will be appreciated that the phrase "optionally substituted" is used interchangeably with the phrase "substituted or unsubstituted". In general, the term "substituted" whether preceded by the term "optionally" or not, means that a hydrogen radical of the designated moiety is replaced with the radical of a specified substituent, provided that the substitution results in a stable or chemically feasible compound. The term "substitutable", when used in reference to a designated atom, means that attached to the atom is a hydrogen radical, which hydrogen radical can be replaced with a substituent. Unless otherwise indicated, an "optionally substituted" group may have a substituent at each substitutable position of the group, and when there is more than one substitutable position in any given structure, the substituents may be either the same or different at every position. Combinations of substituents envisioned by this disclosure are those that result in the formation of stable or chemically feasible compounds.

The phrase "one or more substituents", as used herein, refers to a number of substituents that equals from one to the maximum number of substituents possible based on the number of available bonding sites, provided that the above conditions of stability and chemical feasibility are met.

As used herein, the term "independently selected" means that the same or different values may be selected for multiple instances of a given variable in a single compound.

The articles "a" and "an" are used in this disclosure to refer to one or more than one (i.e., to at least one) of the grammatical object of the article. By way of example, "an element" means one element or more than one element.

The term "and/or" is used in this disclosure to mean either "and" or "or" unless indicated otherwise.

The term "aryl" refers to cyclic, aromatic hydrocarbon groups that have 1 to 2 aromatic rings, including monocyclic or bicyclic groups such as phenyl, biphenyl, or naphthyl. Where containing two aromatic rings (bicyclic, etc.), the aromatic rings of the aryl group may be joined at a single point (e.g., biphenyl), or fused (e.g., naphthyl). The aryl group may be optionally substituted by one or more substituents, e.g., 1 to 5 substituents, at any point of attachment. Exemplary substituents include, but are not limited to, —H, -halogen, —O—$C_1$-$C_6$alkyl, —$C_1$-$C_6$alkyl, —O$C_2$-$C_6$alkenyl, —O$C_2$-$C_6$alkynyl, —$C_2$-$C_6$alkenyl, —$C_2$-$C_6$alkynyl, —OH, —OP(O)(OH)$_2$, —OC(O)$C_1$-$C_6$alkyl, —C(O)$C_1$-$C_6$alkyl, —OC(O)O$C_1$-$C_6$alkyl, —NH$_2$, —NH($C_1$-$C_6$alkyl), —N($C_1$-$C_6$alkyl)$_2$, —S(O)$_2$—$C_1$-$C_6$alkyl, —S(O)NH$C_1$-$C_6$alkyl, and —S(O)N($C_1$-$C_6$alkyl)$_2$. The substituents can themselves be optionally substituted. Furthermore when containing two fused rings the aryl groups herein defined may have an unsaturated or partially saturated ring fused with the aromatic ring. Exemplary ring systems of these aryl groups include indanyl, indenyl, tetrahydronaphthalenyl, and tetrahydrobenzoannulenyl.

Unless otherwise specifically defined, "heteroaryl" means a monovalent monocyclic aromatic radical or a polycyclic aromatic radical of 5 to 24 ring atoms, containing one or more ring heteroatoms selected from N, S, P, and O, the remaining ring atoms being C. Heteroaryl as herein defined also means a bicyclic heteroaromatic group wherein the heteroatom is selected from N, S, P, and O. The aromatic radical is optionally substituted independently with one or more substituents described herein. Examples include, but are not limited to, furyl, thienyl, pyrrolyl, pyridyl, pyrazolyl, pyrimidinyl, imidazolyl, isoxazolyl, oxazolyl, oxadiazolyl, pyrazinyl, indolyl, thiophen-2-yl, quinolyl, benzopyranyl, isothiazolyl, thiazolyl, thiadiazole, indazole, benzimidazolyl, thieno[3,2-b]thiophene, triazolyl, triazinyl, imidazo[1,2-b]pyrazolyl, furo[2,3-c]pyridinyl, imidazo[1,2-a]pyridinyl, indazolyl, pyrrolo[2,3-c]pyridinyl, pyrrolo[3,2-c]pyridinyl, pyrazolo[3,4-c]pyridinyl, thieno[3,2-c]pyridinyl, thieno[2,3-c]pyridinyl, thieno[2,3-b]pyridinyl, benzothiazolyl, indolyl, indolinyl, indolinonyl, dihydrobenzothiophenyl, dihydrobenzofuranyl, benzofuran, chromanyl, thiochromanyl, tetrahydroquinolinyl, dihydrobenzothiazine, dihydrobenzoxanyl, quinolinyl, isoquinolinyl, 1,6-naphthyridinyl, benzo[de]isoquinolinyl, pyrido[4,3-b][1,6]naphthyridinyl, thieno[2,3-b]pyrazinyl, quinazolinyl, tetrazolo[1,5-a]pyridinyl, [1,2,4]triazolo[4,3-a]pyridinyl, isoindolyl, pyrrolo[2,3-b]pyridinyl, pyrrolo[3,4-b]pyridinyl, pyrrolo[3,2-b]pyridinyl, imidazo[5,4-b]pyridinyl, pyrrolo[1,2-a]pyrimidinyl, tetrahydropyrrolo[1,2-a]pyrimidinyl, 3,4-dihydro-2H-1$\lambda^2$-pyrrolo[2,1-b]pyrimidine, dibenzo[b,d]thiophene, pyridin-2-one, furo[3,2-c]pyridinyl, furo[2,3-c]pyridinyl, 1H-pyrido[3,4-b][1,4]thiazinyl, benzooxazolyl, benzoisoxazolyl, furo[2,3-b]pyridinyl, benzothiophenyl, 1,5-naphthyridinyl, furo[3,2-b]pyridine, [1,2,4]triazolo[1,5-a]pyridinyl, benzo [1,2,3]triazolyl, imidazo[1,2-a]pyrimidinyl, [1,2,4]triazolo[4,3-b]pyridazinyl, benzo[c][1,2,5]thiadiazolyl, benzo[c][1,2,5]oxadiazole, 1,3-dihydro-2H-benzo[d]imidazol-2-one, 3,4-dihydro-2H-pyrazolo[1,5-b][1,2]oxazinyl, 4,5,6,7-tetrahydropyrazolo[1,5-a]pyridinyl, thiazolo[5,4-d]thiazolyl, imidazo[2,1-b][1,3,4]thiadiazolyl, thieno[2,3-b]pyrrolyl, 3H-indolyl, and derivatives thereof. Furthermore when containing two fused rings the heteroaryl groups herein defined may have an unsaturated or partially saturated ring fused with the heteroaromatic ring. Exemplary ring systems of these heteroaryl groups include indolinyl, indolinonyl, dihydrobenzothiophenyl, dihydrobenzofuran, chromanyl, thiochromanyl, tetrahydroquinolinyl, dihydrobenzothiazine, 3,4-dihydro-1H-isoquinolinyl, 2,3-dihydrobenzofuran, indolinyl, indolyl, and dihydrobenzoxanyl.

"Alkyl" refers to a straight or branched chain saturated hydrocarbon containing 1-12 carbon atoms. $C_1$-$C_6$alkyl groups contain 1 to 6 carbon atoms. Examples of a $C_1$-$C_6$alkyl group include, but are not limited to, methyl, ethyl, propyl, butyl, pentyl, isopropyl, isobutyl, sec-butyl, tert-butyl, isopentyl, and neopentyl. An alkyl group may be substituted by one or more substituents.

"Alkenyl" refers to a straight or branched chain unsaturated hydrocarbon containing 2-12 carbon atoms. The "alkenyl" group contains at least one double bond in the chain. The double bond of an alkenyl group can be unconjugated or conjugated to another unsaturated group. Examples of alkenyl groups include ethenyl, propenyl, n-butenyl, iso-butenyl, pentenyl, or hexenyl. An alkenyl group can be unsubstituted or substituted.

"Alkynyl" refers to a straight or branched chain unsaturated hydrocarbon containing 2-12 carbon atoms. The "alkynyl" group contains at least one triple bond in the chain. Examples of alkynyl groups include ethynyl, propynyl, n-butynyl, iso-butynyl, pentynyl, or hexynyl. An alkynyl group can be unsubstituted or substituted.

The term "cycloalkyl" means monocyclic or polycyclic saturated carbon rings containing 3-18 carbon atoms. Examples of cycloalkyl groups include, without limitations, cyclopropyl, cyclobutyl, cyclopentyl, cyclohexyl, cycloheptanyl, cyclooctanyl, norboranyl, norborenyl, bicyclo[2.2.2]octanyl, or bicyclo[2.2.2]octenyl. A $C_3$-$C_8$cycloalkyl is a cycloalkyl group containing between 3 and 8 carbon atoms. A cycloalkyl group can be fused (e.g., decalin) or bridged (e.g., norbornane). A cycloalkyl group can be unsubstituted or substituted.

The term "cycloalkenyl" means monocyclic, non-aromatic unsaturated carbon rings containing 4-18 carbon atoms. Examples of cycloalkenyl groups include, without limitation, cyclopentenyl, cyclohexenyl, cycloheptenyl, cyclooctenyl, and norborenyl. A $C_4$-$C_8$cycloalkenyl is a cycloalkenyl group containing between 4 and 8 carbon atoms. Cycloalkenyl groups may be substituted or unsubstituted.

The terms "heterocyclyl" or "heterocycloalkyl" or "heterocycle" refer to monocyclic or polycyclic 3- to 24-membered non-aromatic rings containing carbon and heteroatoms selected from the group consisting of oxygen, phosphorous, nitrogen, and sulfur, and wherein there are not delocalized n electrons (aromaticity) shared among the ring carbon or heteroatoms. Heterocyclyl rings include, but are not limited to, oxetanyl, azetadinyl, tetrahydrofuranyl, pyrrolidinyl, oxazolinyl, oxazolidinyl, thiazolinyl, thiazolidinyl, pyranyl, thiopyranyl, tetrahydropyranyl, dioxalinyl, piperidinyl, morpholinyl, thiomorpholinyl, thiomorpholinyl S-oxide, thiomorpholinyl S-dioxide, piperazinyl, azepinyl, oxepinyl, diazepinyl, tropanyl, and homotropanyl. A heterocyclyl or heterocycloalkyl ring can also be fused or bridged, e.g., can be a bicyclic ring. Heterocyclyl groups may be substituted or unsubstituted.

As used herein, the term "halo" or "halogen" means a fluoro, chloro, bromo, or iodo group.

The term "carbonyl" refers to a functional group composing a carbon atom double-bonded to an oxygen atom. It can be abbreviated herein as "oxo", as C(O), or as C=O.

"Spirocycle" or "spirocyclic" means carbogenic bicyclic ring systems with both rings connected through a single atom. The rings can be different in size and nature, or identical in size and nature. Examples include spiropentane, spirohexane, spiroheptane, spirooctane, spirononane, or spirodecane. One or both of the rings in a spirocycle can be fused to another carbocyclic, heterocyclic, aromatic, or heteroaromatic ring. A $C_5$-$C_{12}$ spirocycle is a spirocycle containing between 5 and 12 carbon atoms. One or more of the carbon atoms can be substituted with a heteroatom.

The term "spirocycloalkenyl" means a carbogenic bicyclic ring system containing 5-12 atoms with both ring systems connected through a single atom and wherein at least one ring contains a carbon-carbon double bond. The rings can be different in size and nature, or identical in size and nature. One or both rings may contain a double-bond. One or both of the rings in a spirocycloalkenyl can further be fused to another carbocyclic, heterocyclic, aromatic, or heteroaromatic ring.

The term "spirocyclic heterocycle," "spiroheterocyclyl," or "spiroheterocycle" is understood to mean a spirocycle wherein at least one of the rings is a heterocycle (e.g., at least one of the rings is furanyl, morpholinyl, or piperadinyl). A spirocyclic heterocycle can contain between 5 and 12 atoms, at least one of which is a heteroatom selected from N, O, S and P.

The disclosure also includes pharmaceutical compositions comprising an effective amount of a disclosed compound and a pharmaceutically acceptable carrier.

"Pharmaceutically acceptable salts" are well known in the art. For example, S. M. Berge et al. describe pharmaceutically acceptable salts in detail in J. Pharmaceutical Sciences, 1977, 66, 1-19, incorporated herein by reference. Representative pharmaceutically acceptable salts include, e.g., water-soluble and water-insoluble salts, such as acetate, amsonate (4,4-diaminostilbene-2,2-disulfonate), benzenesulfonate, benzonate, bicarbonate, bisulfate, bitartrate, borate, bromide, butyrate, calcium, calcium edetate, camsylate, carbonate, chloride, citrate, clavulariate, dihydrochloride, edetate, edisylate, estolate, esylate, fiunarate, gluceptate, gluconate, glutamate, glycollylarsanilate, hexafluorophosphate, hexylresorcinate, hydrabamine, hydrobromide, hydrochloride, hydroxynaphthoate, iodide, sethionate, lactate, lactobionate, laurate, magnesium, malate, maleate, mandelate, mesylate, methylbromide, methylnitrate, methyl sulfate, mucate, napsylate, nitrate, N-methylglucamine ammonium salt, 3-hydroxy-2-naphthoate, oleate, oxalate, palmitate, pamoate (1,1-methene-bis-2-hydroxy-3-naphthoate, einbonate), pantothenate, phosphate/diphosphate, picrate, polygalacturonate, propionate, p-toluenesulfonate, salicylate, stearate, subacetate, succinate, sulfate, sulfosalicylate, suramate, tannate, tartrate, teoclate, tosylate, triethiodide, and valerate salts. The compounds of Formula I may form salts which are also within the scope of this disclosure. Reference to a compound of Formula I herein is understood to include reference to the salts thereof, unless otherwise indicated.

Unless otherwise stated, all tautomeric forms of compounds described herein are within the scope of the invention. The term "tautomers" refers to a set of compounds that have the same number and type of atoms, but differ in bond connectivity and are in equilibrium with one another. A "tautomer" is a single member of this set of compounds. Typically, a single tautomer is drawn, but it is understood that this single structure is meant to represent all possible tautomers that might exist. A non-limiting example includes enol-ketone tautomerism, where a depicted ketone is understood to mean that both the enol and ketone forms are part of the invention.

The term "isomer" refers to compounds that have the same composition and molecular weight but differ in physical and/or chemical properties. The structural difference may be in constitution (e.g., geometric isomers) or in the ability to rotate the plane of polarized light (stereoisomers). With regard to stereoisomers, the compounds of Formula I may have one or more asymmetric carbon atom and may occur as racemates, racemic mixtures and as individual enantiomers or diastereomers.

The term "stereoisomers" refers to the set of compounds which have the same number and type of atoms and share the same bond connectivity between those atoms, but differ in three dimensional structure. The term "stereoisomer" refers to any member of this set of compounds. For instance, a stereoisomer may be an enantiomer or a diastereomer.

The term "enantiomers" refers to a pair of stereoisomers which are non-superimposable mirror images of one another. The term "enantiomer" refers to a single member of this pair of stereoisomers. The term "racemic" refers to a 1:1 mixture of a pair of enantiomers.

The term "diastereomers" refers to the set of stereoisomers which cannot be made superimposable by rotation around single bonds. For example, cis- and trans-double bonds, endo- and exo-substitution on bicyclic ring systems, and compounds containing multiple stereogenic centers with different relative configurations are considered to be diastereomers. The term "diastereomer" refers to any member of this set of compounds. In some examples presented, the synthetic route may produce a single diastereomer or a mixture of diastereomers. In some cases these diastereomers were separated and in other cases a wavy bond is used to indicate the structural element where configuration is variable.

An "effective amount" when used in connection with a compound is an amount effective for treating or preventing a disease in a subject as described herein.

The term "carrier", as used in this disclosure, encompasses carriers, excipients, and diluents and means a material, composition or vehicle, such as a liquid or solid filler, diluent, excipient, solvent or encapsulating material, involved in carrying or transporting a pharmaceutical agent from one organ, or portion of the body, to another organ, or portion of the body of a subject.

The term "treating" with regard to a subject, refers to improving at least one symptom of the subject's disorder. Treating includes curing, improving, or at least partially ameliorating the disorder.

The term "disorder" is used in this disclosure to mean, and is used interchangeably with, the terms disease, condition, or illness, unless otherwise indicated.

The term "administer", "administering", or "administration" as used in this disclosure refers to either directly administering a disclosed compound, a pharmaceutically acceptable salt of a disclosed compound, or a composition to a subject.

A "patient" or "subject" is a mammal, e.g., a human, mouse, rat, guinea pig, dog, cat, horse, cow, pig, or non-human primate, such as a monkey, chimpanzee, baboon, or rhesus.

In a first aspect of the invention, compounds of Formula I are described:

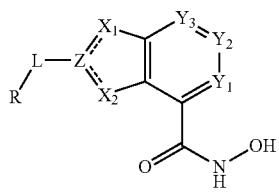

(I)

and pharmaceutically acceptable salts thereof wherein Z, $X_1$, $X_2$, $Y_1$, $Y_2$, $Y_3$, L, R, and $Z\text{---}X_1$ and $Z\text{---}X_2$ are as described above.

In one or more embodiments, compounds of Formula I-A are provided:

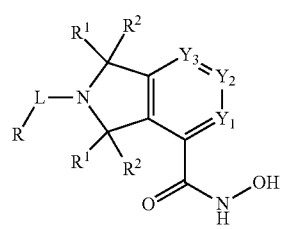

(I-A)

wherein $Y_1$, $Y_2$, $Y_3$, L, R, $R^1$, and $R^2$ are as described generally above and in classes, subclasses, and species herein.

In one or more embodiments, compounds of Formula I-B are provided:

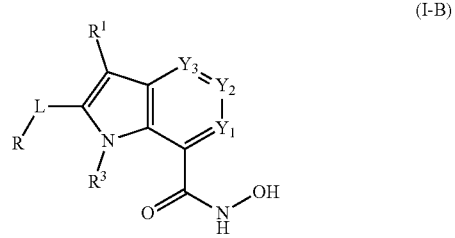

(I-B)

wherein $Y_1$, $Y_2$, $Y_3$, L, R, $R^1$, and $R^3$ are as described generally above and in classes, subclasses, and species herein.

In one or more embodiments, compounds of Formula I-C are provided:

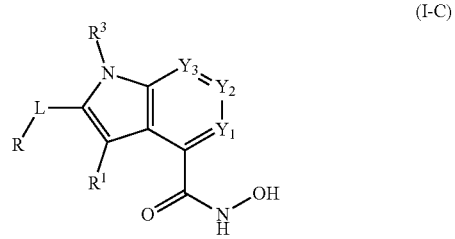

(I-C)

wherein $Y_1$, $Y_2$, $Y_3$, L, R, $R^1$, and $R^3$ are as described generally above and in classes, subclasses, and species herein.

In one or more embodiments, compounds of Formula I-D are provided:

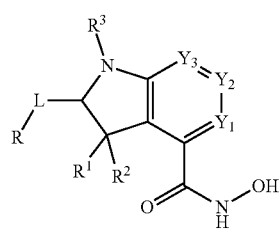

(I-D)

wherein $Y_1$, $Y_2$, $Y_3$, L, R, $R^1$, $R^2$, and $R^3$ are as described generally above and in classes, subclasses, and species herein.

In one or more embodiments, compounds of Formula I-E are provided:

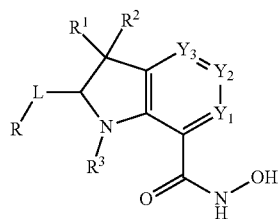

(I-E)

wherein $Y_1$, $Y_2$, $Y_3$, L, R, $R^1$, $R^2$, and $R^3$ are as described generally above and in classes, subclasses, and species herein.

In one or more embodiments, compounds of Formula I-F are provided:

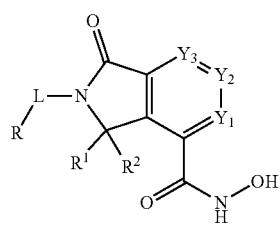

(I-F)

wherein $Y_1$, $Y_2$, $Y_3$, L, R, $R^1$, and $R^2$ are as described generally above and in classes, subclasses, and species herein.

In one or more embodiments, compounds of Formula I-G are provided:

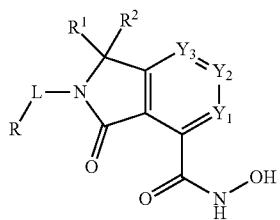

(I-G)

wherein $Y_1$, $Y_2$, $Y_3$, L, R, $R^1$, and $R^2$ are as described generally above and in classes, subclasses, and species herein.

In some embodiments for compounds of Formulae I, I-A, I-B, I-C, I-D, I-E, I-F, or I-G, one of $Y_1$, $Y_2$, or $Y_3$ is N and the other two of $Y_1$, $Y_2$, or $Y_3$ are $CR^1$. In some embodiments for compounds of Formulae I, I-A, I-B, I-C, I-D, I-E, I-F, or I-G, two of $Y_1$, $Y_2$, or $Y_3$ are N and the other one of $Y_1$, $Y_2$, or $Y_3$ is $CR^1$. In some embodiments for compounds of Formulae I, I-A, I-B, I-C, I-D, I-E, I-F, or I-G, $Y_1$, $Y_2$, and $Y_3$ are each $CR^1$. In some embodiments for compounds of Formulae I, I-A, I-B, I-C, I-D, I-E, I-F, or I-G, $Y_1$ is N and $Y_2$ and $Y_3$ are each $CR^1$. In some embodiments for compounds of Formulae I, I-A, I-B, I-C, I-D, I-E, I-F, or I-G, $Y_1$ and $Y_3$ are each $CR^1$ and $Y_2$ is N. In some embodiments for compounds of Formulae I, I-A, I-B, I-C, I-D, I-E, I-F, or I-G, $Y_x$ and $Y_2$ are each $CR^1$ and $Y_3$ is N.

In some embodiments for compounds of Formulae I, I-A, I-B, I-C, I-D, I-E, I-F, or I-G, L is a bond. In other embodiments for compounds of Formulae I, I-A, I-B, I-C, I-D, I-E, I-F, or I-G, L is —C(O)—. In other embodiments for compounds of Formulae I, I-A, I-B, I-C, I-D, I-E, I-F, or I-G, L is —$(CR^1R^2)_p$—, —C(O)$NR^3$—, —$NR^3$C(O)—, —C(O)$(CR^1R^2)_p$—, or —$(CR^1R^2)_p$C(O)—. In some embodiments, p is 1 or 2. In some embodiments, p is 1.

In one or more embodiments, compounds of Formula II-A-i are provided:

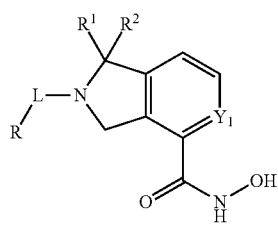

(II-A-i)

wherein $Y_1$, L, R, $R^1$, and $R^2$ are as described generally above and in classes, subclasses, and species herein.

In one or more embodiments, compounds of Formula II-A-ii are provided:

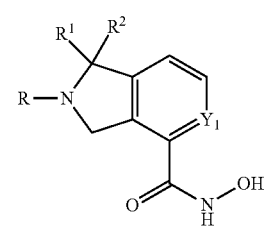

(II-A-ii)

wherein $Y_1$, R, $R^1$, and $R^2$ are as described generally above and in classes, subclasses, and species herein.

In one or more embodiments, compounds of Formula II-B-i are provided:

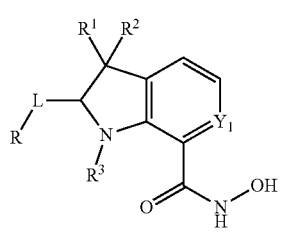

(II-B-i)

wherein $Y_1$, L, R, $R^1$, $R^2$, and $R^3$ are as described generally above and in classes, subclasses, and species herein.

In one or more embodiments, compounds of Formula II-B-ii are provided:

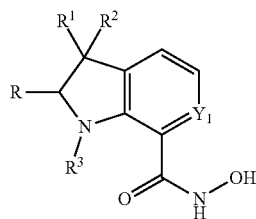
(II-B-ii)

wherein $Y_1$, R, $R^1$, $R^2$, and $R^3$ are as described generally above and in classes, subclasses, and species herein.

In one or more embodiments, compounds of Formula II-C-i are provided:

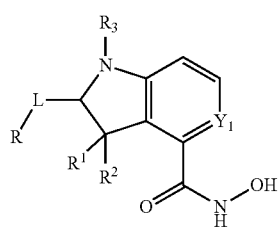
(II-C-i)

wherein $Y_1$, L, R, $R^1$, $R^2$, and $R^3$ are as described generally above and in classes, subclasses, and species herein.

In one or more embodiments, compounds of Formula II-C-ii are provided:

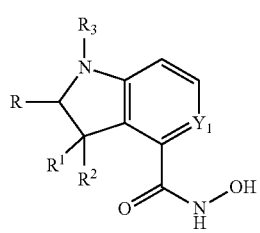
(II-C-ii)

wherein $Y_1$, R, $R^1$, $R^2$, and $R^3$ are as described generally above and in classes, subclasses, and species herein.

In one or more embodiments, compounds of Formula II-D-i are provided:

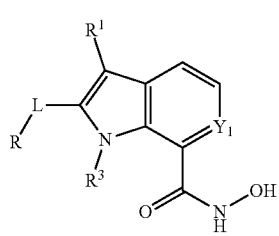
(II-D-i)

wherein $Y_1$, L, R, $R^1$, and $R^3$ are as described generally above and in classes, subclasses, and species herein.

In one or more embodiments, compounds of Formula II-D-ii are provided:

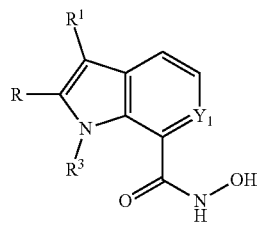
(II-D-ii)

wherein $Y_1$, R, $R^1$, and $R^3$ are as described generally above and in classes, subclasses, and species herein.

In one or more embodiments, compounds of Formula II-E-I are provided:

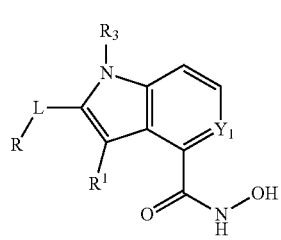
(II-E-i)

wherein $Y_1$, L, R, $R^1$, and $R^3$ are as described generally above and in classes, subclasses, and species herein.

In one or more embodiments, compounds of Formula II-E-ii are provided:

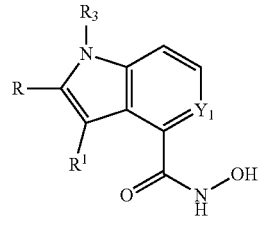
(II-E-ii)

wherein $Y_1$, R, $R^1$, and $R^3$ are as described generally above and in classes, subclasses, and species herein.

In one or more embodiments, compounds of Formula II-F-i are provided:

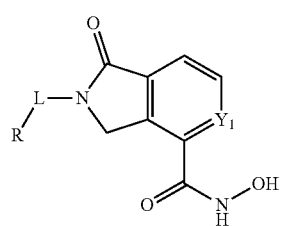
(II-F-i)

wherein $Y_1$, L, and R are as described generally above and in classes, subclasses, and species herein.

In one or more embodiments, compounds of Formula II-F-ii are provided:

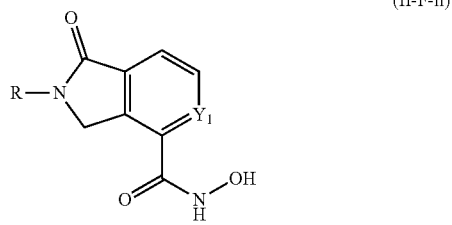

(II-F-ii)

wherein $Y_1$, and R are as described generally above and in classes, subclasses, and species herein.

In some embodiments compounds of Formulae I, I-A, I-B, I-C, I-D, I-E, I-F, I-G, II-A-i, II-A-ii, II-B-i, II-B-ii, II-C-i, II-C-ii, II-D-i, II-D-ii, II-E-i, II-E-ii, II-F-i, or II-F-ii are provided, wherein:

R is heterocyclyl, aryl, or heteroaryl containing 1-5 heteroatoms selected from the group consisting of N, S, P, or O, wherein each heterocyclyl, aryl, or heteroaryl is optionally substituted with one or more substituents selected from the group consisting of —OH, halogen, oxo, —NO$_2$, —CN, —R$^1$, —R$^2$, —SR$^3$, —OR$^3$, —NHR$^3$, —NR$^3$R$^4$, —S(O)$_2$NR$^3$R$^4$, —S(O)$_2$R$^1$, —C(O)R$^1$, —C(O)OR$^1$, —NR$^3$S(O)$_2$R$^1$, —S(O)R$^1$, —S(O)NR$^3$R$^4$, —NR$^3$S(O)R$^1$, heterocyclyl, aryl, or heteroaryl;

R$^1$ and R$^2$ are independently, at each occurrence, —H, —R$^3$, —R$^4$, —C$_1$-C$_6$alkyl, —C$_2$-C$_6$alkenyl, —C$_4$-C$_8$cycloalkenyl, —C$_2$-C$_6$alkynyl, —C$_3$-C$_8$cycloalkyl, heterocyclyl, aryl, heteroaryl containing 1-5 heteroatoms selected from the group consisting of N, S, P and O, —OH, halogen, —NO$_2$, —CN, —NHC$_1$-C$_6$alkyl, —N(C$_1$-C$_6$alkyl)$_2$, —S(O)$_2$N(C$_1$-C$_6$alkyl)$_2$, —N(C$_1$-C$_6$alkyl)S(O)$_2$R$^5$, —S(O)$_2$(C$_1$-C$_6$alkyl), —(C$_1$-C$_6$alkyl)S(O)$_2$R$^5$, —C(O)C$_1$-C$_6$alkyl, —C(O)OC$_1$-C$_6$alkyl, —N(C$_1$-C$_6$alkyl)S(O)$_2$C$_1$-C$_6$alkyl, or —(CHR$^5$)$_p$NR$^3$R$^4$, wherein each alkyl, alkenyl, cycloalkenyl, alkynyl, cycloalkyl, heterocyclyl, aryl, or heteroaryl is optionally substituted with one or more substituents selected from the group consisting of —OH, halogen, —NO$_2$, oxo, —CN, —R$^5$, —OR$^3$, —NHR$^3$, —NR$^3$R$^4$, —S(O)$_2$N(R$^3$)$_2$—, —S(O)$_2$R$^5$, —C(O)R$^5$, —C(O)OR$^5$, —NR$^3$S(O)$_2$R$^5$, —S(O)R$^5$, —S(O)NR$^3$R$^4$, —NR$^3$S(O)R$^5$, heteorcyclyl, aryl, or heteroaryl;

or R$^1$ and R$^2$ can combine with the carbon atom to which they are both attached to form a spirocycle, spiroheterocycle, or spirocycloalkenyl, each optionally substituted with one or more independent occurrences of R$^3$ and R$^4$;

or R$^1$ and R$^2$, when on adjacent atoms, can combine to form an optionally substituted group selected from cycloalkyl, cycloalkenyl, heterocycle, aryl, or heteroaryl containing 1-5 heteroatoms selected from the group consisting of N, S, P and O, each optionally substituted with one or more independent occurrences of R$^3$ and R$^4$;

or R$^1$ and R$^2$, when on non-adjacent atoms, can combine to form an optionally substituted optionally bridging cycloalkyl, an optionally bridging heterocycle, or an optionally bridging cycloalkenyl, each optionally substituted with one or more independent occurrences of R$^3$ and R$^4$;

R$^3$ and R$^4$ are independently, at each occurrence, —H, —C$_1$-C$_6$alkyl, —C$_2$-C$_6$alkenyl, —C$_4$-C$_8$cycloalkenyl, —C$_2$-C$_6$alkynyl, —C$_3$-C$_8$cycloalkyl, heterocyclyl, aryl, heteroaryl containing 1-5 heteroatoms selected from N, S, P, and O, —S(O)$_2$N(C$_1$-C$_6$alkyl)$_2$, —S(O)$_2$(C$_1$-C$_6$alkyl), —(C$_1$-C$_6$alkyl)S(O)$_2$R$^5$, —C(O)C$_1$-C$_6$alkyl, —C(O)OC$_1$-C$_6$alkyl, or —(CHR$^5$)$_p$N(C$_1$-C$_6$alkyl)$_2$, wherein each alkyl, alkenyl, cycloalkenyl, alkynyl, cycloalkyl, heterocyclyl, aryl, or heteroaryl is optionally substituted with one or more substituents selected from the group consisting of —OH, halogen, —NO$_2$, oxo, —CN, —R$^5$, —O(C$_1$-C$_6$)alkyl, —NH(C$_1$-C$_6$)alkyl, —N(C$_1$-C$_6$alkyl)$_2$, —S(O)$_2$N(C$_1$-C$_6$alkyl)$_2$, —S(O)$_2$NHC$_1$-C$_6$alkyl, —C(O)C$_1$-C$_6$alkyl, —C(O)OC$_1$-C$_6$alkyl, —N(C$_1$-C$_6$alkyl)S(O)$_2$C$_1$-C$_6$alkyl, —S(O)R$^5$, —S(O)N(C$_1$-C$_6$alkyl)$_2$, —N(C$_1$-C$_6$alkyl)S(O)R$^5$, heterocyclyl, aryl, and heteroaryl; and R$^5$ is independently, at each occurrence, —H, —C$_1$-C$_6$alkyl, —C$_2$-C$_6$alkenyl, —C$_4$-C$_8$cycloalkenyl, —C$_2$-C$_6$alkynyl, —C$_3$-C$_8$cycloalkyl, heterocyclyl, aryl, heteroaryl containing 1-5 heteroatoms selected from N, S, P and O, —OH, halogen, —NO$_2$, —CN, —NHC$_1$-C$_6$alkyl, —N(C$_1$-C$_6$alkyl)$_2$, —S(O)$_2$NH(C$_1$-C$_6$alkyl), —S(O)$_2$N(C$_1$-C$_6$alkyl)$_2$, —S(O)$_2$C$_1$-C$_6$alkyl, —C(O)C$_1$-C$_6$alkyl, —C(O)OC$_1$-C$_6$alkyl, —N(C$_1$-C$_6$alkyl)SO$_2$C$_1$-C$_6$alkyl, —S(O)(C$_1$-C$_6$alkyl), —S(O)N(C$_1$-C$_6$alkyl)$_2$, —N(C$_1$-C$_6$alkyl)S(O)(C$_1$-C$_6$alkyl) or —(CH$_2$)$_p$N(C$_1$-C$_6$alkyl)$_2$.

In some embodiments, compounds of Formulae I, I-A, I-B, I-C, I-D, I-E, I-F, I-G, II-A-i, II-A-ii, II-B-i, II-B-ii, II-C-i, II-C-ii, II-D-i, II-D-ii, II-E-i, II-E-ii, II-F-i, or II-F-ii are provided, wherein:

R is independently heteroaryl containing 1-5 heteroatoms selected from the group consisting of N, S, P, or O, wherein the heteroaryl is optionally substituted with one or more substituents selected from the group consisting of —OH, halogen, oxo, —NO$_2$, —CN, —R$^1$, —R$^2$, —SR$^3$, —OR$^3$, —NHR$^3$, —NR$^3$R$^4$, —S(O)$_2$NR$^3$R$^4$, —S(O)$_2$R$^1$, —C(O)R$^1$, —C(O)OR$^1$, —NR$^3$S(O)$_2$R$^1$, —S(O)R$^1$, —S(O)NR$^3$R$^4$, —NR$^3$S(O)R$^1$, heterocyclyl, aryl, and heteroaryl;

R$^1$ and R$^2$ are independently, at each occurrence, —H, —R$^3$, —R$^4$, —C$_1$-C$_6$alkyl, —C$_2$-C$_6$alkenyl, —C$_4$-C$_8$cycloalkenyl, —C$_2$-C$_6$alkynyl, —C$_3$-C$_8$cycloalkyl, heterocyclyl, aryl, heteroaryl containing 1-5 heteroatoms selected from the group consisting of N, S, P and O, —OH, halogen, —NO$_2$, —CN, —NHC$_1$-C$_6$alkyl, —N(C$_1$-C$_6$alkyl)$_2$, —S(O)$_2$N(C$_1$-C$_6$alkyl)$_2$, —N(C$_1$-C$_6$alkyl)S(O)$_2$R$^5$, —S(O)$_2$(C$_1$-C$_6$alkyl), —(C$_1$-C$_6$alkyl)S(O)$_2$R$^5$, —C(O)C$_1$-C$_6$alkyl, —C(O)OC$_1$-C$_6$alkyl, —N(C$_1$-C$_6$alkyl)S(O)$_2$C$_1$-C$_6$alkyl, or —(CHR$^5$)$_p$NR$^3$R$^4$, wherein each alkyl, alkenyl, cycloalkenyl, alkynyl, cycloalkyl, heterocyclyl, aryl, or heteroaryl is optionally substituted with one or more substituents selected from the group consisting of —OH, halogen, —NO$_2$, oxo, —CN, —R$^5$, —OR$^3$, —NHR$^3$, —NR$^3$R$^4$, —S(O)$_2$N(R$^3$)$_2$—, —S(O)$_2$R$^5$, —C(O)R$^5$, —C(O)OR$^5$, —NR$^3$S(O)$_2$R$^5$, —S(O)R$^5$, —S(O)NR$^3$R$^4$, —NR$^3$S(O)R$^5$, heterocyclyl, aryl, and heteroaryl;

or R$^1$ and R$^2$ can combine with the carbon atom to which they are both attached to form a spirocycle, spiroheterocycle, or spirocycloalkenyl, each optionally substituted with one or more independent occurrences of R$^3$ and R$^4$;

or R$^1$ and R$^2$, when on adjacent atoms, can combine to form an optionally substituted group selected from cycloalkyl, cycloalkenyl, heterocycle, aryl, or heteroaryl containing 1-5 heteroatoms selected from the group consisting of N, S, P and O, each optionally substituted with one or more independent occurrences of R$^3$ and R$^4$;

or R$^1$ and R$^2$, when on non-adjacent atoms, can combine to form an optionally substituted optionally bridging cycloalkyl, an optionally bridging heterocycle, or an optionally bridging cycloalkenyl, each optionally substituted with one or more independent occurrences of R$^3$ and R$^4$;

R$^3$ and R$^4$ are independently, at each occurrence, —H, —C$_1$-C$_6$alkyl, —C$_2$-C$_6$alkenyl, —C$_4$-C$_8$cycloalkenyl, —C$_2$-C$_6$alkynyl, —C$_3$-C$_8$cycloalkyl, heterocyclyl, aryl, heteroaryl containing 1-5 heteroatoms selected from N, S, P, and O, —S(O)$_2$N(C$_1$-C$_6$alkyl)$_2$, —S(O)$_2$(C$_1$-C$_6$alkyl), —($C_1$-$C_6$alkyl)S(O)$_2$R$^5$, —C(O)$C_1$-$C_6$alkyl, —C(O)O$C_1$-$C_6$alkyl, or —(CHR$^5$)$_p$N($C_1$-$C_6$alkyl)$_2$, wherein each alkyl, alkenyl, cycloalkenyl, alkynyl, cycloalkyl, heterocyclyl, aryl, or heteroaryl is optionally substituted with one or more substituents selected from the group consisting of —OH, halogen, —NO$_2$, oxo, —CN, —R$^5$, —O($C_1$-$C_6$)alkyl, —NH($C_1$-$C_6$)alkyl, —N($C_1$-$C_6$alkyl)$_2$, —S(O)$_2$N($C_1$-$C_6$alkyl)$_2$, —S(O)$_2$NH$C_1$-$C_6$alkyl, —C(O)$C_1$-$C_6$alkyl, —C(O)O$C_1$-$C_6$alkyl, —N($C_1$-$C_6$alkyl)S(O)$_2$$C_1$-$C_6$alkyl, —S(O)R$^5$, —S(O)N($C_1$-$C_6$alkyl)$_2$, —N($C_1$-$C_6$alkyl)S(O)R$^5$, heterocyclyl, aryl, and heteroaryl; and R$^5$ is independently, at each occurrence, —H, —$C_1$-$C_6$alkyl, —$C_2$-$C_6$alkenyl, —$C_4$-$C_8$cycloalkenyl, —$C_2$-$C_6$alkynyl, —$C_3$-$C_8$cycloalkyl, heterocyclyl, aryl, heteroaryl containing 1-5 heteroatoms selected from N, S, P and O, —OH, halogen, —NO$_2$, —CN, —NH$C_1$-$C_6$alkyl, —N($C_1$-$C_6$alkyl)$_2$, —S(O)$_2$NH($C_1$-$C_6$alkyl), —S(O)$_2$N($C_1$-$C_6$alkyl)$_2$, —S(O)$_2$$C_1$-$C_6$alkyl, —C(O)$C_1$-$C_6$alkyl, —C(O)O$C_1$-$C_6$alkyl, —N($C_1$-$C_6$alkyl)SO$_2$$C_1$-$C_6$alkyl, —S(O)($C_1$-$C_6$alkyl), —S(O)N($C_1$-$C_6$alkyl)$_2$, —N($C_1$-$C_6$alkyl)S(O)($C_1$-$C_6$alkyl) and —(CH$_2$)$_p$N($C_1$-$C_6$alkyl)$_2$.

In some embodiments, compounds of Formulae I, I-A, I-B, I-C, I-D, I-E, I-F, I-G, II-A-i, II-A-ii, II-B-i, II-B-ii, II-C-i, II-C-ii, II-D-i, II-D-ii, II-E-i, II-E-ii, II-F-i, or II-F-ii are provided, wherein: R is independently aryl, wherein the aryl is optionally substituted with one or more —OH, halogen, oxo, —NO$_2$, —CN, —R$^1$, —R$^2$, —SR$^3$, —OR$^3$, —NHR$^3$, —NR$^3$R$^4$, —S(O)$_2$NR$^3$R$^4$, —S(O)$_2$R$^1$, —C(O)R$^4$, —C(O)OR$^1$, —NR$^3$S(O)$_2$R$^1$, —S(O)R$^1$, —S(O)NR$^3$R$^4$, —NR$^3$S(O)R$^1$, heterocyclyl, aryl, and heteroaryl;

R$^1$ and R$^2$ are independently, at each occurrence, —H, —R$^3$, —R$^4$, —$C_1$-$C_6$alkyl, —$C_2$-$C_6$alkenyl, —$C_4$-$C_8$cycloalkenyl, —$C_2$-$C_6$alkynyl, —$C_3$-$C_8$cycloalkyl, heterocyclyl, aryl, heteroaryl containing 1-5 heteroatoms selected from the group consisting of N, S, P and O, —OH, halogen, —NO$_2$, —CN, —NH$C_1$-$C_6$alkyl, —N($C_1$-$C_6$alkyl)$_2$, —S(O)$_2$N($C_1$-$C_6$alkyl)$_2$, —N($C_1$-$C_6$alkyl)S(O)$_2$R$^5$, —S(O)$_2$($C_1$-$C_6$alkyl), —($C_1$-$C_6$alkyl)S(O)$_2$R$^5$, —C(O)$C_1$-$C_6$alkyl, —C(O)O$C_1$-$C_6$alkyl, —N($C_1$-$C_6$alkyl)S(O)$_2$$C_1$-$C_6$alkyl, or —(CHR$^5$)$_p$NR$^3$R$^4$, wherein each alkyl, alkenyl, cycloalkenyl, alkynyl, cycloalkyl, heterocyclyl, aryl, or heteroaryl is optionally substituted with one or more substituents selected from the group consisting of —OH, halogen, —NO$_2$, oxo, —CN, —R$^5$, —OR$^3$, —NHR$^3$, —NR$^3$R$^4$, —S(O)$_2$N(R$^3$)$_2$—, —S(O)$_2$R$^5$, —C(O)R$^5$, —C(O)OR$^5$, —NR$^3$S(O)$_2$R$^5$, —S(O)R$^5$, —S(O)NR$^3$R$^4$, —NR$^3$S(O)R$^5$, heterocyclyl, aryl, and heteroaryl;

or R$^1$ and R$^2$ can combine with the carbon atom to which they are both attached to form a spirocycle, spiroheterocycle, or spirocycloalkenyl, each optionally substituted with one or more independent occurrences of R$^3$ and R$^4$;

or R$^1$ and R$^2$, when on adjacent atoms, can combine to form an optionally substituted group selected from cycloalkyl, cycloalkenyl, heterocycle, aryl, or heteroaryl containing 1-5 heteroatoms selected from the group consisting of N, S, P and O, each optionally substituted with one or more independent occurrences of R$^3$ and R$^4$;

or R$^1$ and R$^2$, when on non-adjacent atoms, can combine to form an optionally substituted optionally bridging cycloalkyl, an optionally bridging heterocycle, or an optionally bridging cycloalkenyl, each optionally substituted with one or more independent occurrences of R$^3$ and R$^4$;

R$^3$ and R$^4$ are independently, at each occurrence, —H, —$C_1$-$C_6$alkyl, —$C_2$-$C_6$alkenyl, —$C_4$-$C_8$cycloalkenyl, —$C_2$-$C_6$alkynyl, —$C_3$-$C_8$cycloalkyl, heterocyclyl, aryl, heteroaryl containing 1-5 heteroatoms selected from N, S, P, and O, —S(O)$_2$N($C_1$-$C_6$alkyl)$_2$, —S(O)$_2$($C_1$-$C_6$alkyl), —($C_1$-$C_6$alkyl)S(O)$_2$R$^5$, —C(O)$C_1$-$C_6$alkyl, —C(O)O$C_1$-$C_6$alkyl, or —(CHR$^5$)$_p$N($C_1$-$C_6$alkyl)$_2$, wherein each alkyl, alkenyl, cycloalkenyl, alkynyl, cycloalkyl, heterocyclyl, aryl, or heteroaryl is optionally substituted with one or more substituents selected from the group consisting of —OH, halogen, —NO$_2$, oxo, —CN, —R$^5$, —O($C_1$-$C_6$)alkyl, —NH($C_1$-$C_6$)alkyl, —N($C_1$-$C_6$alkyl)$_2$, —S(O)$_2$N($C_1$-$C_6$alkyl)$_2$, —S(O)$_2$NH$C_1$-$C_6$alkyl, —C(O)$C_1$-$C_6$alkyl, —C(O)O$C_1$-$C_6$alkyl, —N($C_1$-$C_6$alkyl)S(O)$_2$$C_1$-$C_6$alkyl, —S(O)R$^5$, —S(O)N($C_1$-$C_6$alkyl)$_2$, —N($C_1$-$C_6$alkyl)S(O)R$^5$, heterocyclyl, aryl, and heteroaryl; and R$^5$ is independently, at each occurrence, —H, —$C_1$-$C_6$alkyl, —$C_2$-$C_6$alkenyl, —$C_4$-$C_8$cycloalkenyl, —$C_2$-$C_6$alkynyl, —$C_3$-$C_8$cycloalkyl, heterocyclyl, aryl, heteroaryl containing 1-5 heteroatoms selected from N, S, P and O, —OH, halogen, —NO$_2$, —CN, —NH$C_1$-$C_6$alkyl, —N($C_1$-$C_6$alkyl)$_2$, —S(O)$_2$NH($C_1$-$C_6$alkyl), —S(O)$_2$N($C_1$-$C_6$alkyl)$_2$, —S(O)$_2$$C_1$-$C_6$alkyl, —C(O)$C_1$-$C_6$alkyl, —C(O)O$C_1$-$C_6$alkyl, —N($C_1$-$C_6$alkyl)SO$_2$$C_1$-$C_6$alkyl, —S(O)($C_1$-$C_6$alkyl), —S(O)N($C_1$-$C_6$alkyl)$_2$, —N($C_1$-$C_6$alkyl)S(O)($C_1$-$C_6$alkyl) or —(CH$_2$)$_p$N($C_1$-$C_6$alkyl)$_2$.

In some embodiments, compounds of Formulae I, I-A, I-B, I-C, I-D, I-E, I-F, I-G, II-A-i, II-A-ii, II-B-i, II-B-ii, II-C-i, II-C-ii, II-D-i, II-D-ii, II-E-i, II-E-ii, II-F-i, or II-F-ii are provided, wherein:

R is independently phenyl, wherein the phenyl is optionally substituted with one or more substituents selected from the group consisting of —OH, halogen, oxo, —NO$_2$, —CN, —R$^1$, —R$^2$, —SR$^3$, —OR$^3$, —NHR$^3$, —NR$^3$R$^4$, —S(O)$_2$NR$^3$R$^4$, —S(O)$_2$R$^1$, —C(O)R$^1$, —C(O)OR$^1$, —NR$^3$S(O)$_2$R$^1$, —S(O)R$^1$, —S(O)NR$^3$R$^4$, —NR$^3$S(O)R$^1$, heterocyclyl, aryl, and heteroaryl;

R$^1$ and R$^2$ are independently, at each occurrence, —H, —R$^3$, —R$^4$, —$C_1$-$C_6$alkyl, —$C_2$-$C_6$alkenyl, —$C_4$-$C_8$cycloalkenyl, —$C_2$-$C_6$alkynyl, —$C_3$-$C_8$cycloalkyl, heterocyclyl, aryl, heteroaryl containing 1-5 heteroatoms selected from the group consisting of N, S, P and O, —OH, halogen, —NO$_2$, —CN, —NH$C_1$-$C_6$alkyl, —N($C_1$-$C_6$alkyl)$_2$, —S(O)$_2$N($C_1$-$C_6$alkyl)$_2$, —N($C_1$-$C_6$alkyl)S(O)$_2$R$^5$, —S(O)$_2$($C_1$-$C_6$alkyl), —($C_1$-$C_6$alkyl)S(O)$_2$R$^5$, —C(O)$C_1$-$C_6$alkyl, —C(O)O$C_1$-$C_6$alkyl, —N($C_1$-$C_6$alkyl)S(O)$_2$$C_1$-$C_6$alkyl, or —(CHR$^5$)$_p$NR$^3$R$^4$, wherein each alkyl, alkenyl, cycloalkenyl, alkynyl, cycloalkyl, heterocyclyl, aryl, or heteroaryl is optionally substituted with one or more substituents selected from the group consisting of —OH, halogen, —NO$_2$, oxo, —CN, —R$^5$, —OR$^3$, —NHR$^3$, —NR$^3$R$^4$, —S(O)$_2$N(R$^3$)$_2$—, —S(O)$_2$R$^5$, —C(O)R$^5$, —C(O)OR$^5$, —NR$^3$S(O)$_2$R$^5$, —S(O)R$^5$, —S(O)NR$^3$R$^4$, —NR$^3$S(O)R$^5$, heterocyclyl, aryl, and heteroaryl;

or R$^1$ and R$^2$ can combine with the carbon atom to which they are both attached to form a spirocycle, spiroheterocycle, or spirocycloalkenyl, each optionally substituted with one or more independent occurrences of R$^3$ and R$^4$;

or R$^1$ and R$^2$, when on adjacent atoms, can combine to form an optionally substituted group selected from cycloalkyl, cycloalkenyl, heterocycle, aryl, or heteroaryl containing 1-5 heteroatoms selected from the group consisting of N, S, P and O, each optionally substituted with one or more independent occurrences of R$^3$ and R$^4$;

or R$^1$ and R$^2$, when on non-adjacent atoms, can combine to form an optionally substituted optionally bridging cycloalkyl, an optionally bridging heterocycle, or an optionally bridging cycloalkenyl, each optionally substituted with one or more independent occurrences of R$^3$ and R$^4$;

R$^3$ and R$^4$ are independently, at each occurrence, —H, —$C_1$-$C_6$alkyl, —$C_2$-$C_6$alkenyl, —$C_4$-$C_8$cycloalkenyl, —$C_2$-$C_6$alkynyl, —$C_3$-$C_8$cycloalkyl, heterocyclyl, aryl, heteroaryl containing 1-5 heteroatoms selected from N, S, P, and O, —S(O)$_2$N(C$_1$-C$_6$alkyl)$_2$, —S(O)$_2$(C$_1$-C$_6$alkyl), —(C$_1$-C$_6$alkyl)S(O)$_2$R$^5$, —C(O)C$_1$-C$_6$alkyl, —C(O)OC$_1$-C$_6$alkyl, or —(CHR$^5$)$_p$N(C$_1$-C$_6$alkyl)$_2$, wherein each alkyl, alkenyl, cycloalkenyl, alkynyl, cycloalkyl, heterocyclyl, aryl, or heteroaryl is optionally substituted with one or more substituents selected from the group consisting of —OH, halogen, —NO$_2$, oxo, —CN, —R$^5$, —O(C$_1$-C$_6$)alkyl, —NH(C$_1$-C$_6$)alkyl, —N(C$_1$-C$_6$alkyl)$_2$, —S(O)$_2$N(C$_1$-C$_6$alkyl)$_2$, —S(O)$_2$NHC$_1$-C$_6$alkyl, —C(O)C$_1$-C$_6$alkyl, —C(O)OC$_1$-C$_6$alkyl, —N(C$_1$-C$_6$alkyl)S(O)$_2$C$_1$-C$_6$alkyl, —S(O)R$^5$, —S(O)N(C$_1$-C$_6$alkyl)$_2$, —N(C$_1$-C$_6$alkyl)S(O)R$^5$, heterocyclyl, aryl, and heteroaryl; and R$^5$ is independently, at each occurrence, —H, —C$_1$-C$_6$alkyl, —C$_2$-C$_6$alkenyl, —C$_4$-C$_8$cycloalkenyl, —C$_2$-C$_6$alkynyl, —C$_3$-C$_8$cycloalkyl, heterocyclyl, aryl, heteroaryl containing 1-5 heteroatoms selected from N, S, P and O, —OH, halogen, —NO$_2$, —CN, —NHC$_1$-C$_6$alkyl, —N(C$_1$-C$_6$alkyl)$_2$, —S(O)$_2$NH(C$_1$-C$_6$alkyl), —S(O)$_2$N(C$_1$-C$_6$alkyl)$_2$, —S(O)$_2$C$_1$-C$_6$alkyl, —C(O)C$_1$-C$_6$alkyl, —C(O)OC$_1$-C$_6$alkyl, —N(C$_1$-C$_6$alkyl)SO$_2$C$_1$-C$_6$alkyl, —S(O)(C$_1$-C$_6$alkyl), —S(O)N(C$_1$-C$_6$alkyl)$_2$, —N(C$_1$-C$_6$alkyl)S(O)(C$_1$-C$_6$alkyl) or —(CH$_2$)$_p$N(C$_1$-C$_6$alkyl)$_2$.

In some embodiments, compounds of Formulae I, I-A, I-B, I-C, I-D, I-E, I-F, I-G, II-A-i, II-A-ii, II-B-i, II-B-ii, II-C-i, II-C-ii, II-D-i, II-D-ii, II-E-i, II-E-ii, II-F-i, or II-F-ii are provided, wherein:

R is a group selected from:

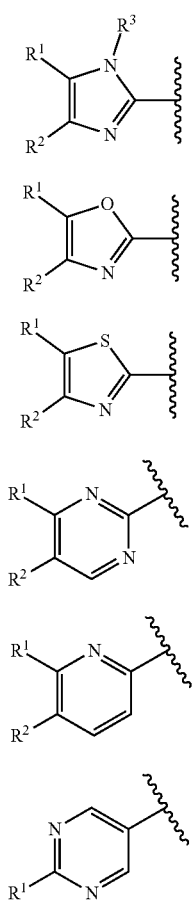

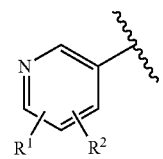

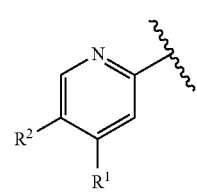

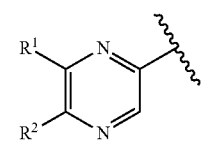

wherein R$^1$ and R$^2$ are independently, at each occurrence, —H, —R$^3$, —R$^4$, —C$_1$-C$_6$alkyl, —C$_2$-C$_6$alkenyl, —C$_4$-C$_8$cycloalkenyl, —C$_2$-C$_6$alkynyl, —C$_3$-C$_8$cycloalkyl, heterocyclyl, aryl, heteroaryl containing 1-5 heteroatoms selected from the group consisting of N, S, P and O, —OH, halogen, —NO$_2$, —CN, —NHC$_1$-C$_6$alkyl, —N(C$_1$-C$_6$alkyl)$_2$, —S(O)$_2$N(C$_1$-C$_6$alkyl)$_2$, —N(C$_1$-C$_6$alkyl)S(O)$_2$R$^5$, —S(O)$_2$(C$_1$-C$_6$alkyl), —(C$_1$-C$_6$alkyl)S(O)$_2$R$^5$, —C(O)C$_1$-C$_6$alkyl, —C(O)OC$_r$-C$_6$alkyl, —N(C$_1$-C$_6$alkyl)S(O)$_2$C$_1$-C$_6$alkyl, or —(CHR$^5$)$_p$NR$^3$R$^4$, wherein each alkyl, alkenyl, cycloalkenyl, alkynyl, cycloalkyl, heterocyclyl, aryl, or heteroaryl is optionally substituted with one or more substituents selected from the group consisting of —OH, halogen, —NO$_2$, oxo, —CN, —R$^5$, —OR$^3$, —NHR$^3$, —NR$^3$R$^4$, —S(O)$_2$N(R$^3$)$_2$—, —S(O)$_2$R$^5$, —C(O)R$^5$, —C(O)OR$^5$, —NR$^3$S(O)$_2$R$^5$, —S(O)R$^5$, —S(O)NR$^3$R$^4$, —NR$^3$S(O)R$^5$, heterocyclyl, aryl, and heteroaryl;

or R$^1$ and R$^2$ can combine with the carbon atom to which they are both attached to form a spirocycle, spiroheterocycle, or spirocycloalkenyl, each optionally substituted with one or more independent occurrences of R$^3$ and R$^4$;

or R$^1$ and R$^2$, when on adjacent atoms, can combine to form an optionally substituted group selected from cycloalkyl, cycloalkenyl, heterocycle, aryl, or heteroaryl containing 1-5 heteroatoms selected from the group consisting of N, S, P and O, each optionally substituted with one or more independent occurrences of R$^3$ and R$^4$;

or R$^1$ and R$^2$, when on non-adjacent atoms, can combine to form an optionally substituted optionally bridging cycloalkyl, an optionally bridging heterocycle, or an optionally bridging cycloalkenyl, each optionally substituted with one or more independent occurrences of R$^3$ and R$^4$;

R$^3$ and R$^4$ are independently, at each occurrence, —H, —C$_1$-C$_6$alkyl, —C$_2$-C$_6$alkenyl, —C$_4$-C$_8$cycloalkenyl, —C$_2$-C$_6$alkynyl, —C$_3$-C$_8$cycloalkyl, heterocyclyl, aryl, heteroaryl containing 1-5 heteroatoms selected from N, S, P, and O, —S(O)$_2$N(C$_1$-C$_6$alkyl)$_2$, —S(O)$_2$(C$_1$-C$_6$alkyl), —(C$_1$-C$_6$alkyl)S(O)$_2$R$^5$, —C(O)C$_1$-C$_6$alkyl, —C(O)OC$_1$-C$_6$alkyl, or —(CHR$^5$)$_p$N(C$_1$-C$_6$alkyl)$_2$, wherein each alkyl, alkenyl, cycloalkenyl, alkynyl, cycloalkyl, heterocyclyl, aryl, or heteroaryl is optionally substituted with one or more substituents selected from the group consisting of —OH, halogen, —NO$_2$, oxo, —CN, —R$^5$, —O(C$_1$-C$_6$)alkyl, —NH(C$_1$-C$_6$)alkyl, —N(C$_1$-C$_6$alkyl)$_2$, —S(O)$_2$N(C$_1$-C$_6$alkyl)$_2$, —S(O)₂NHC₁-C₆alkyl, —C(O)C₁-C₆alkyl, —C(O)OC₁-C₆alkyl, —N(C₁-C₆alkyl)S(O)₂C₁-C₆alkyl, —S(O)R⁵, —S(O)N(C₁-C₆alkyl)₂, —N(C₁-C₆alkyl)S(O)R⁵, heterocyclyl, aryl, and heteroaryl; and R⁵ is independently, at each occurrence, —H, —C₁-C₆alkyl, —C₂-C₆alkenyl, —C₄-C₈cycloalkenyl, —C₂-C₆alkynyl, —C₃-C₈cycloalkyl, heterocyclyl, aryl, heteroaryl containing 1-5 heteroatoms selected from N, S, P and O, —OH, halogen, —NO₂, —CN, —NHC₁-C₆alkyl, —N(C₁-C₆alkyl)₂, —S(O)₂NH(C₁-C₆alkyl), —S(O)₂N(C₁-C₆alkyl)₂, —S(O)₂C₁-C₆alkyl, —C(O)C₁-C₆alkyl, —C(O)OC₁-C₆alkyl, —N(C₁-C₆alkyl)SO₂C₁-C₆alkyl, —S(O)(C_rC₆alkyl), —S(O)N(C₁-C₆alkyl)₂, —N(C₁-C₆alkyl)S(O)(C₁-C₆alkyl) or —(CH₂)_pN(C₁-C₆alkyl)₂.

In some embodiments, compounds of Formulae I, I-A, I-B, I-C, I-D, I-E, I-F, I-G, II-A-i, II-A-ii, II-B-i, II-B-ii, II-C-i, II-C-ii, II-D-i, II-D-ii, II-E-i, II-E-ii, II-F-i, or II-F-ii are provided, wherein:

Z is N, C, or CH;

X₁ and X₂ are each independently, at each occurrence, —CR¹R²—, ═CR¹—, —NR³—, or —C(O)—, as valency permits, provided that only one of X₁ and X₂ is —C(O)—;

the dotted line between Z---X₁ and Z---X₂ is absent or represents a bond, provided that, at most, only one of the dotted lines represents a bond;

Y and Y₂ are each CR¹, and Y₃ is N or CR¹;

L is a bond, —(CR¹R²)_p—, —C(O)NR³—, —NR³C(O)—, —(CR¹R²)_pC(O)—, or —C(O)(CR¹R²)_p—;

R is independently —C₃-C₈cycloalkyl, heterocyclyl, aryl, or heteroaryl containing 1-5 heteroatoms selected from the group consisting of N, S, P, and O, wherein each cycloalkyl, heterocyclyl, aryl, or heteroaryl is optionally substituted with one or more substituents selected from the group consisting of —OH, —R¹, —R², and —OR³;

R¹ and R² are independently, at each occurrence, —H, —C₁-C₆alkyl, or aryl, wherein each alkyl or aryl is optionally substituted with one or more substituents selected from the group consisting of halogen and —OR³;

or R¹ and R², when on adjacent atoms, can combine to form a cycloalkyl or a heterocycle, each optionally substituted with one or more independent occurrences of R³ and R⁴;

R³ and R⁴ are independently, at each occurrence, —H, —C₁-C₆alkyl, or —C(O)C₁-C₆alkyl, wherein each alkyl is optionally substituted with one or more halogen; and p is 0 or 1;

provided that when X₂ is —C(O)—, X₁ is CH₂, Y₁, Y₂, and Y₃ are each CH, and L is a bond, then R is a group other than substituted or unsubstituted phenyl; and provided that X¹ and X² are not both nitrogen; and provided that the compound is not:

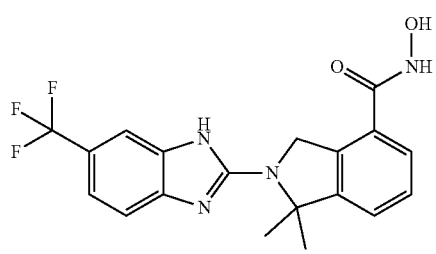

or

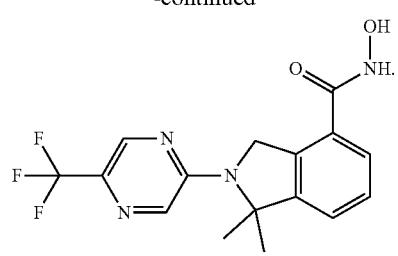

In some embodiments, compounds of Formulae I, I-A, II-A-i, or II-A-ii are provided, wherein:

Z is N;

X₁ and X₂ are each —CR¹R²—;

the dotted line between Z---X₁ and Z₂---X₂ absent;

Y₁, Y₂, and Y₃ are each CR¹;

L is a bond;

R is a 5- to 10-membered heteroaryl containing 1-5 heteroatoms selected from the group consisting of N, S, P, and O, wherein the heteroaryl is optionally substituted with one or more —R¹ and —R²;

R¹ and R² are independently, at each occurrence, —H or —C₁-C₆alkyl, wherein each alkyl is optionally substituted with one or more halogen;

or R¹ and R², when on adjacent atoms, can combine to form a cycloalkyl; and provided that the compound is not:

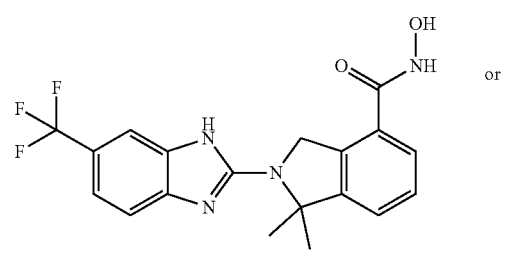

or

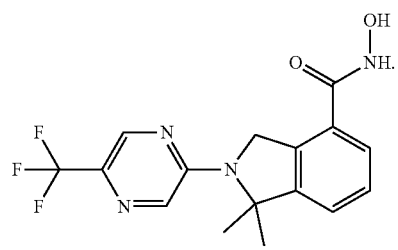

In one or more embodiments, a compound of Formula I can be selected from one of the compounds in Table 1:

TABLE 1

| Example | Structure | Name |
| --- | --- | --- |
| 1-1 | 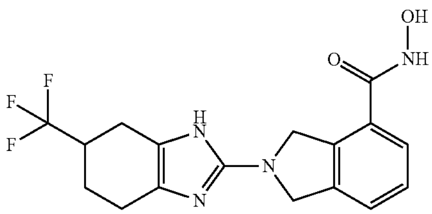 | N-hydroxy-2-(6-(trifluoromethyl)-4,5,6,7-tetrahydro-1H-benzo[d]imidazol-2-yl)isoindoline-4-carboxamide |
| 1-2 | 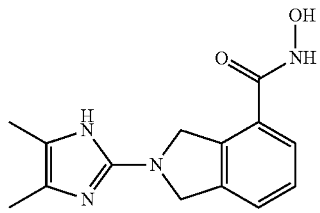 [SMILES: Cc1nc(N2Cc3cccc(C(=O)NO)c3C2)[nH]c1C] | 2-(4,5-dimethyl-1H-imidazol-2-yl)-N-hydroxyisoindoline-4-carboxamide |
| 1-3 | 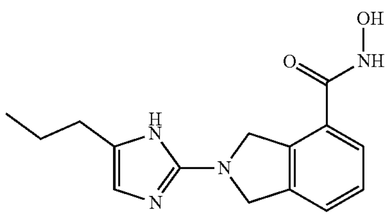 [SMILES: CCCc1cnc(N2Cc3cccc(C(=O)NO)c3C2)[nH]1] | N-hydroxy-2-(5-propyl-1H-imidazol-2-yl)isoindoline-4-carboxamide |
| 1-4 | 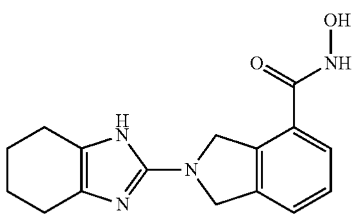 [SMILES: O=C(NO)c1cccc2c1CN(c1nc3c([nH]1)CCCC3)C2] | N-hydroxy-2-(4,5,6,7-tetrahydro-1H-benzo[d]imidazol-2-yl)isoindoline-4-carboxamide |
| 1-5 | 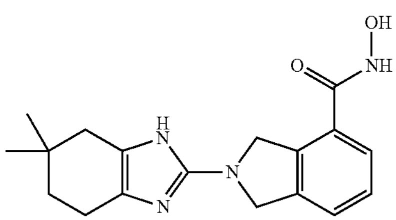 [SMILES: CC1(C)CCc2nc(N3Cc4cccc(C(=O)NO)c4C3)[nH]c2C1] | 2-(6,6-dimethyl-4,5,6,7-tetrahydro-1H-benzo[d]imidazol-2-yl)-N-hydroxyisoindoline-4-carboxamide |
| 1-6 | 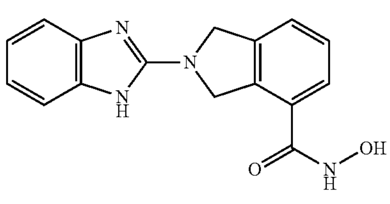 [SMILES: O=C(NO)c1cccc2c1CN(c1nc3ccccc3[nH]1)C2] | 2-(1H-benzo[d]imidazol-2-yl)-N-hydroxyisoindoline-4-carboxamide |
| 2-1 | 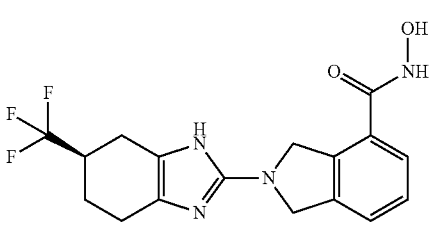 [SMILES: O=C(NO)c1cccc2c1CN(c1nc3c([nH]1)C[C@H](C(F)(F)F)CC3)C2] | (R)-N-hydroxy-2-(6-(trifluoromethyl)-4,5,6,7-tetrahydro-1H-benzo[d]imidazol-2-yl)isoindoline-4-carboxamide |

TABLE 1-continued

| Example | Structure | Name |
|---|---|---|
| 2-2 | 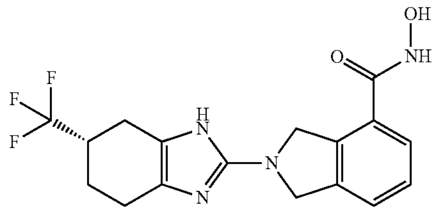 | (S)-N-hydroxy-2-(6-(trifluoromethyl)-4,5,6,7-tetrahydro-1H-benzo[d]imidazol-2-yl)isoindoline-4-carboxamide |
| 3-1 | 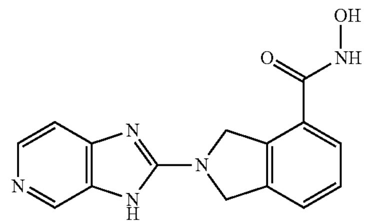 [SMILES: O=C(NO)c1cccc2c1CN(c1nc3ccncc3[nH]1)C2] | N-hydroxy-2-(3H-imidazo[4,5-c]pyridin-2-yl)isoindoline-4-carboxamide |
| 4-1 | 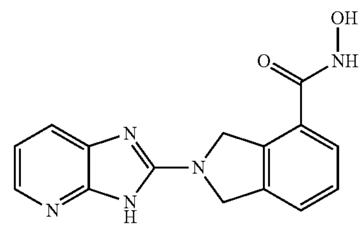 [SMILES: O=C(NO)c1cccc2c1CN(c1nc3cccnc3[nH]1)C2] | N-hydroxy-2-(3H-imidazo[4,5-b]pyridin-2-yl)isoindoline-4-carboxamide |
| 5-1 | 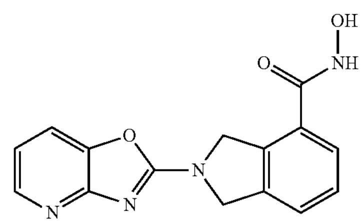 [SMILES: O=C(NO)c1cccc2c1CN(c1nc3ncccc3o1)C2] | N-hydroxy-2-(oxazolo[4,5-b]pyridin-2-yl)isoindoline-4-carboxamide |
| 5-2 | 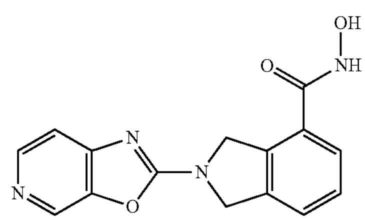 [SMILES: O=C(NO)c1cccc2c1CN(c1nc3ccncc3o1)C2] | N-hydroxy-2-(oxazolo[5,4-c]pyridin-2-yl)isoindoline-4-carboxamide |
| 6-1 | 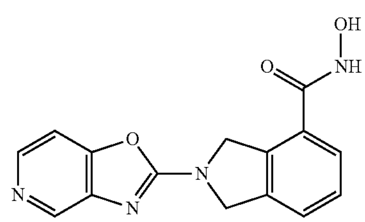 [SMILES: O=C(NO)c1cccc2c1CN(c1nc3cnccc3o1)C2] | N-hydroxy-2-(oxazolo[4,5-c]pyridin-2-yl)isoindoline-4-carboxamide |
| 6-2 | 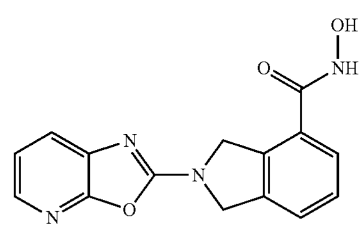 [SMILES: O=C(NO)c1cccc2c1CN(c1nc3cccnc3o1)C2] | N-hydroxy-2-(oxazolo[5,4-b]pyridin-2-yl)isoindoline-4-carboxamide |

TABLE 1-continued

| Example | Structure | Name |
|---|---|---|
| 7-1 | 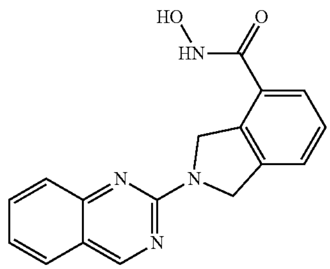 [SMILES: O=C(NO)c1cccc2c1CN(c1ncc3ccccc3n1)C2] | N-hydroxy-2-(quinazolin-2-yl)isoindoline-4-carboxamide |
| 7-2 | 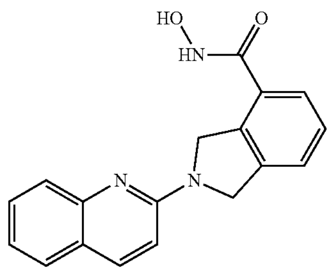 [SMILES: O=C(NO)c1cccc2c1CN(c1ccc3ccccc3n1)C2] | N-hydroxy-2-(quinolin-2-yl)isoindoline-4-carboxamide |
| 7-3 | 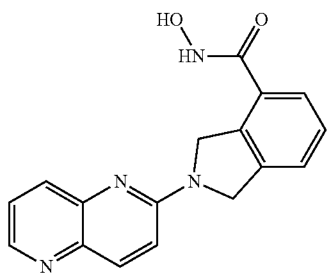 [SMILES: O=C(NO)c1cccc2c1CN(c1ccc3ncccc3n1)C2] | N-hydroxy-2-(1,5-naphthyridin-2-yl)isoindoline-4-carboxamide |
| 7-4 | 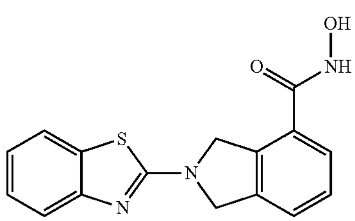 [SMILES: O=C(NO)c1cccc2c1CN(c1nc3ccccc3s1)C2] | 2-(benzo[d]thiazol-2-yl)-N-hydroxyisoindoline-4-carboxamide |
| 7-5 | 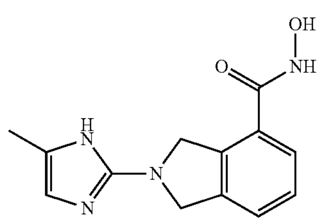 [SMILES: Cc1cnc(N2Cc3cccc(C(=O)NO)c3C2)[nH]1] | N-hydroxy-2-(5-methyl-1H-imidazol-2-yl)isoindoline-4-carboxamide |
| 8-1 | 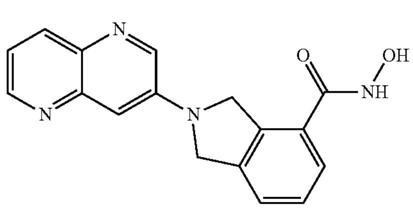 [SMILES: O=C(NO)c1cccc2c1CN(c1cnc3cccnc3c1)C2] | N-hydroxy-2-(1,5-naphthyridin-3-yl)isoindoline-4-carboxamide |

TABLE 1-continued

| Example | Structure | Name |
|---|---|---|
| 9-1 | 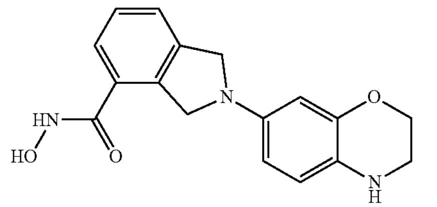 [SMILES: O=C(NO)c1cccc2c1CN(c1ccc3c(c1)OCCN3)C2] | 2-(3,4-dihydro-2H-benzo[b][1,4]oxazin-7-yl)-N-hydroxyisoindoline-4-carboxamide |
| 9-2 | 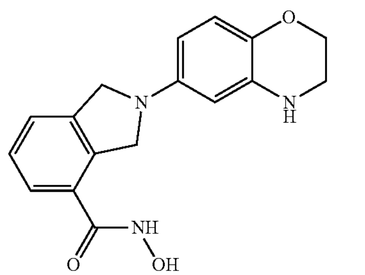 [SMILES: O=C(NO)c1cccc2c1CN(c1ccc3c(c1)NCCO3)C2] | 2-(3,4-dihydro-2H-benzo[b][1,4]oxazin-6-yl)-N-hydroxyisoindoline-4-carboxamide |
| 10-1 | 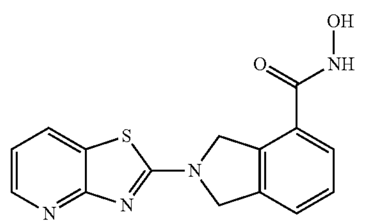 [SMILES: O=C(NO)c1cccc2c1CN(c1nc3ncccc3s1)C2] | N-hydroxy-2-(thiazolo[4,5-b]pyridin-2-yl)isoindoline-4-carboxamide |
| 11-1 | 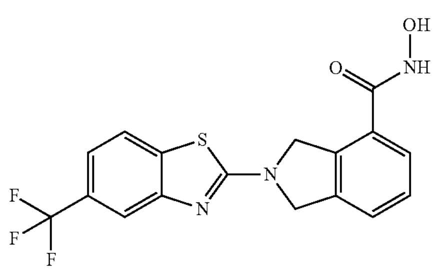 [SMILES: O=C(NO)c1cccc2c1CN(c1nc3cc(C(F)(F)F)ccc3s1)C2] | N-hydroxy-2-(5-(trifluoromethyl)benzo[d]thiazol-2-yl)isoindoline-4-carboxamide |
| 12-1 | 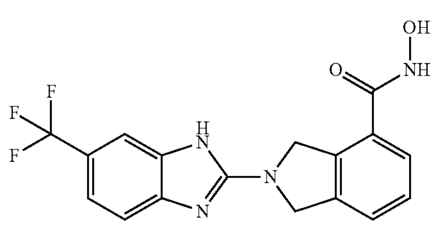 [SMILES: O=C(NO)c1cccc2c1CN(c1nc3ccc(C(F)(F)F)cc3[nH]1)C2] | N-hydroxy-2-(6-(trifluoromethyl)-1H-benzo[d]imidazol-2-yl)isoindoline-4-carboxamide |
| 13-1 | 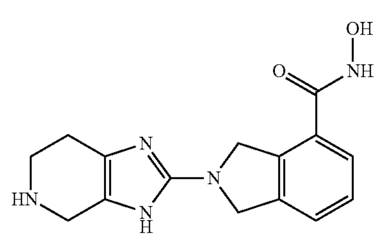 [SMILES: O=C(NO)c1cccc2c1CN(c1nc3c([nH]1)CNCC3)C2] | N-hydroxy-2-(4,5,6,7-tetrahydro-3H-imidazo[4,5-c]pyridin-2-yl)isoindoline-4-carboxamide |

TABLE 1-continued

| Example | Structure | Name |
|---|---|---|
| 14-1 | 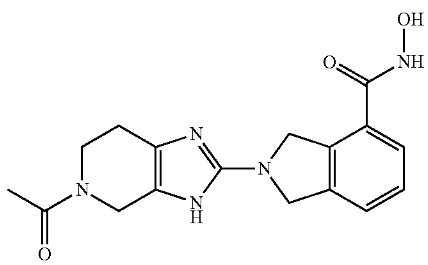 [SMILES: CC(=O)N1CCc2nc(N3Cc4cccc(C(=O)NO)c4C3)[nH]c2C1] | 2-(5-acetyl-4,5,6,7-tetrahydro-3H-imidazo[4,5-c]pyridin-2-yl)-N-hydroxyisoindoline-4-carboxamide |
| 15-1 | 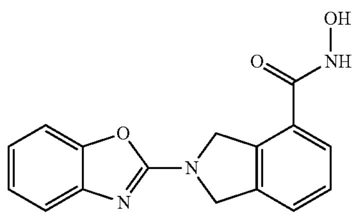 | 2-(benzo[d]oxazol-2-yl)-N-hydroxyisoindoline-4-carboxamide |
| 16-1 | 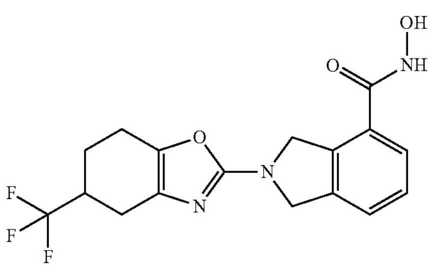 [SMILES: O=C(NO)c1cccc2c1CN(c1nc3c(o1)CCC(C(F)(F)F)C3)C2] | N-hydroxy-2-(5-(trifluoromethyl)-4,5,6,7-tetrahydrobenzo[d]oxazol-2-yl)isoindoline-4-carboxamide |
| 18-1 | 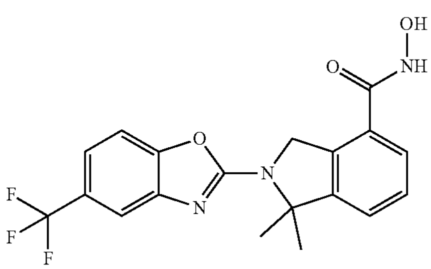 [SMILES: CC1(C)c2cccc(C(=O)NO)c2CN1c1nc2cc(C(F)(F)F)ccc2o1] | N-hydroxy-1,1-dimethyl-2-(5-(trifluoromethyl)benzo[d]oxazol-2-yl)isoindoline-4-carboxamide |
| 18-2 | 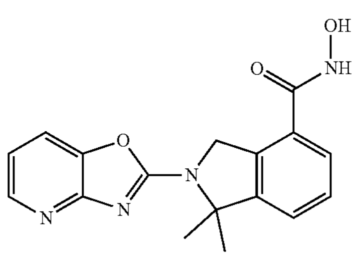 [SMILES: CC1(C)c2cccc(C(=O)NO)c2CN1c1nc2ncccc2o1] | N-hydroxy-1,1-dimethyl-2-(oxazolo[4,5-b]pyridin-2-yl)isoindoline-4-carboxamide |
| 18-3 | 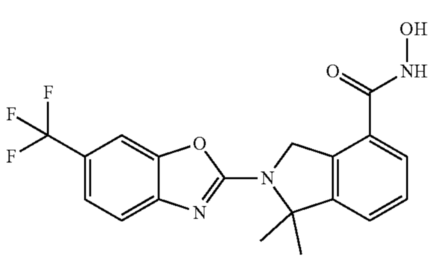 [SMILES: CC1(C)c2cccc(C(=O)NO)c2CN1c1nc2ccc(C(F)(F)F)cc2o1] | N-hydroxy-1,1-dimethyl-2-(6-(trifluoromethyl)benzo[d]oxazol-2-yl)isoindoline-4-carboxamide |

TABLE 1-continued

| Example | Structure | Name |
|---|---|---|
| 19-1 | 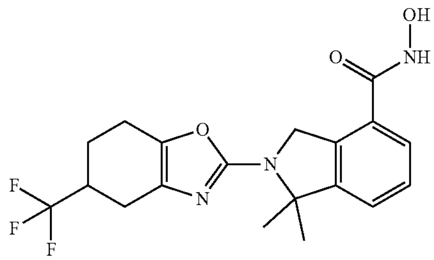 [SMILES: CC1(C)c2cccc(C(=O)NO)c2CN1c1nc2c(o1)CCC(C(F)(F)F)C2] | N-hydroxy-1,1-dimethyl-2-(5-(trifluoromethyl)-4,5,6,7-tetrahydrobenzo[d]oxazol-2-yl)isoindoline-4-carboxamide |
| 19-2 | 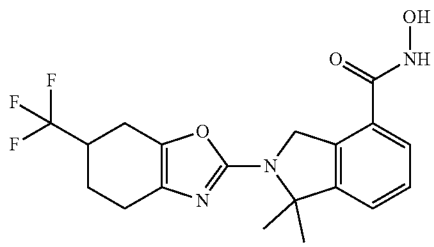 [SMILES: CC1(C)c2cccc(C(=O)NO)c2CN1c1nc2c(o1)CC(C(F)(F)F)CC2] | N-hydroxy-1,1-dimethyl-2-(6-(trifluoromethyl)-4,5,6,7-tetrahydrobenzo[d]oxazol-2-yl)isoindoline-4-carboxamide |
| 20-1 | 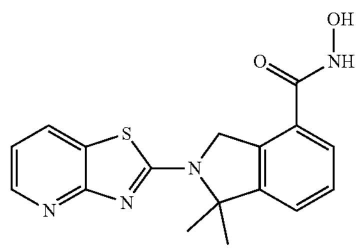 [SMILES: CC1(C)c2cccc(C(=O)NO)c2CN1c1nc2ncccc2s1] | N-hydroxy-1,1-dimethyl-2-(thiazolo[4,5-b]pyridin-2-yl)isoindoline-4-carboxamide |
| 20-2 | 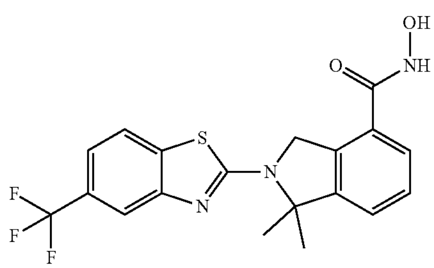 [SMILES: CC1(C)c2cccc(C(=O)NO)c2CN1c1nc2cc(C(F)(F)F)ccc2s1] | N-hydroxy-1,1-dimethyl-2-(5-(trifluoromethyl)benzo[d]thiazol-2-yl)isoindoline-4-carboxamide |
| 21-1 | 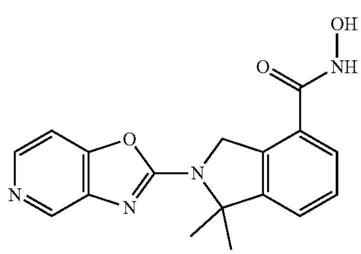 [SMILES: CC1(C)c2cccc(C(=O)NO)c2CN1c1nc2cnccc2o1] | N-hydroxy-1,1-dimethyl-2-(oxazolo[4,5-c]pyridin-2-yl)isoindoline-4-carboxamide |
| 22-1 | 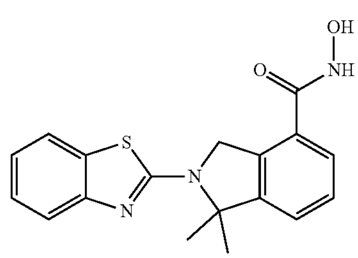 [SMILES: CC1(C)c2cccc(C(=O)NO)c2CN1c1nc2ccccc2s1] | 2-(benzo[d]thiazol-2-yl)-N-hydroxy-1,1-dimethylisoindoline-4-carboxamide |

TABLE 1-continued

| Example | Structure | Name |
|---|---|---|
| 22-2 | 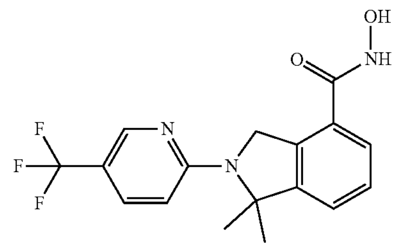 [SMILES: CC1(C)c2cccc(C(=O)NO)c2CN1c1ccc(C(F)(F)F)cn1] | N-hydroxy-1,1-dimethyl-2-(5-(trifluoromethyl)pyridin-2-yl)isoindoline-4-carboxamide |
| 22-3 | 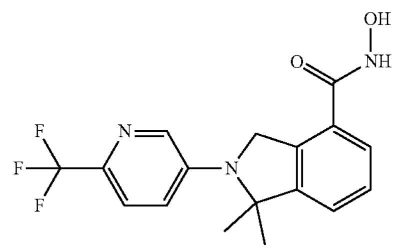 [SMILES: CC1(C)c2cccc(C(=O)NO)c2CN1c1ccc(C(F)(F)F)nc1] | N-hydroxy-1,1-dimethyl-2-(6-(trifluoromethyl)pyridin-3-yl)isoindoline-4-carboxamide |
| 22-4 | 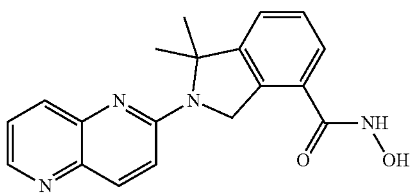 [SMILES: CC1(C)c2cccc(C(=O)NO)c2CN1c1ccc2ncccc2n1] | N-hydroxy-1,1-dimethyl-2-(1,5-naphthyridin-2-yl)isoindoline-4-carboxamide |
| 22-5 | 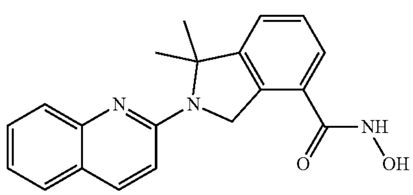 [SMILES: CC1(C)c2cccc(C(=O)NO)c2CN1c1ccc2ccccc2n1] | N-hydroxy-1,1-dimethyl-2-(quinolin-2-yl)isoindoline-4-carboxamide |
| 22-6 | 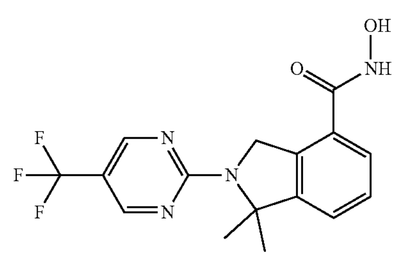 [SMILES: CC1(C)c2cccc(C(=O)NO)c2CN1c1ncc(C(F)(F)F)cn1] | N-hydroxy-1,1-dimethyl-2-(5-(trifluoromethyl)pyrimidin-2-yl)isoindoline-4-carboxamide |
| 22-7 | 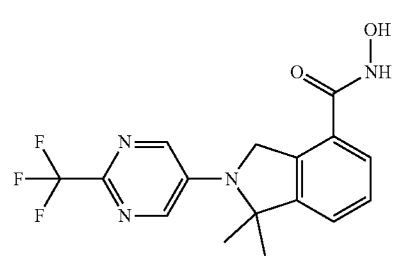 [SMILES: CC1(C)c2cccc(C(=O)NO)c2CN1c1cnc(C(F)(F)F)nc1] | N-hydroxy-1,1-dimethyl-2-(2-(trifluoromethyl)pyrimidin-5-yl)isoindoline-4-carboxamide |

TABLE 1-continued

| Example | Structure | Name |
|---|---|---|
| 22-9 | 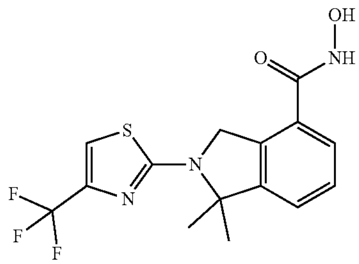 [SMILES: CC1(C)c2cccc(C(=O)NO)c2CN1c1nc(C(F)(F)F)cs1] | N-hydroxy-1,1-dimethyl-2-(4-(trifluoromethyl)thiazol-2-yl)isoindoline-4-carboxamide |
| 23-1 | 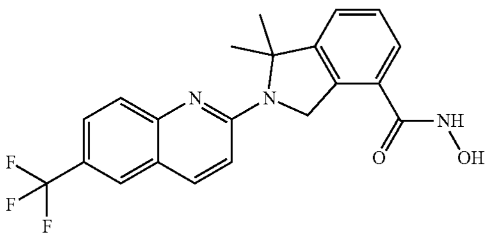 [SMILES: CC1(C)c2cccc(C(=O)NO)c2CN1c1ccc2cc(C(F)(F)F)ccc2n1] | N-hydroxy-1,1-dimethyl-2-(6-(trifluoromethyl)quinolin-2-yl)isoindoline-4-carboxamide |
| 23-2 | 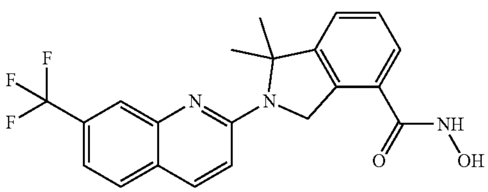 [SMILES: CC1(C)c2cccc(C(=O)NO)c2CN1c1ccc2ccc(C(F)(F)F)cc2n1] | N-hydroxy-1,1-dimethyl-2-(7-(trifluoromethyl)quinolin-2-yl)isoindoline-4-carboxamide |
| 24-1 | 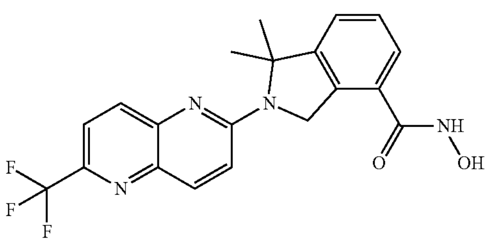 [SMILES: CC1(C)c2cccc(C(=O)NO)c2CN1c1ccc2nc(C(F)(F)F)ccc2n1] | N-hydroxy-1,1-dimethyl-2-(6-(trifluoromethyl)-1,5-naphthyridin-2-yl)isoindoline-4-carboxamide |
| 25-1 | 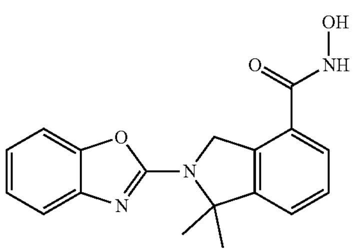 [SMILES: CC1(C)c2cccc(C(=O)NO)c2CN1c1nc2ccccc2o1] | 2-(benzo[d]oxazol-2-yl)-N-hydroxy-1,1-dimethylisoindoline-4-carboxamide |
| 26-1 | 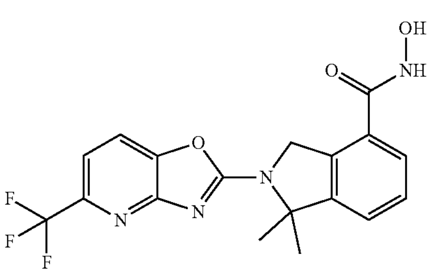 [SMILES: CC1(C)c2cccc(C(=O)NO)c2CN1c1nc2nc(C(F)(F)F)ccc2o1] | N-hydroxy-1,1-dimethyl-2-(5-(trifluoromethyl)oxazolo[4,5-b]pyridin-2-yl)isoindoline-4-carboxamide |

TABLE 1-continued

| Example | Structure | Name |
|---|---|---|
| 26-2 | 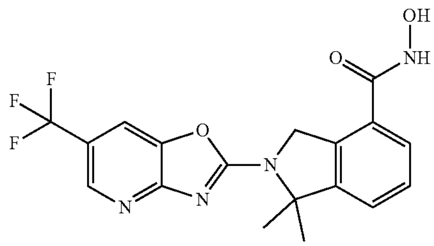 [SMILES: CC1(C)c2cccc(C(=O)NO)c2CN1c1nc2ncc(C(F)(F)F)cc2o1] | N-hydroxy-1,1-dimethyl-2-(6-(trifluoromethyl)oxazolo[4,5-b]pyridin-2-yl)isoindoline-4-carboxamide |
| 27-1 | 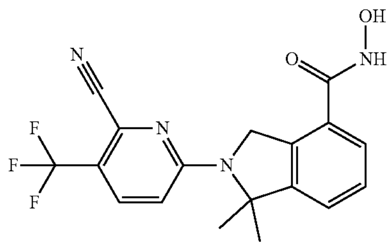 [SMILES: CC1(C)c2cccc(C(=O)NO)c2CN1c1ccc(C(F)(F)F)c(C#N)n1] | 2-(6-cyano-5-(trifluoromethyl)pyridin-2-yl)-N-hydroxy-1,1-dimethylisoindoline-4-carboxamide |
| 27-2 | 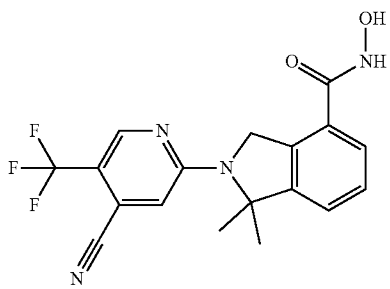 [SMILES: CC1(C)c2cccc(C(=O)NO)c2CN1c1cc(C#N)c(C(F)(F)F)cn1] | 2-(4-cyano-5-(trifluoromethyl)pyridin-2-yl)-N-hydroxy-1,1-dimethylisoindoline-4-carboxamide |
| 28-1 | 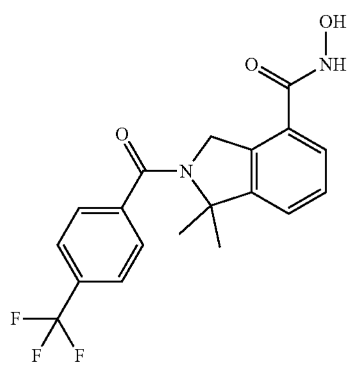 [SMILES: CC1(C)c2cccc(C(=O)NO)c2CN1C(=O)c1ccc(C(F)(F)F)cc1] | N-hydroxy-1,1-dimethyl-2-(4-(trifluoromethyl)benzoyl)isoindoline-4-carboxamide |
| 28-2 | 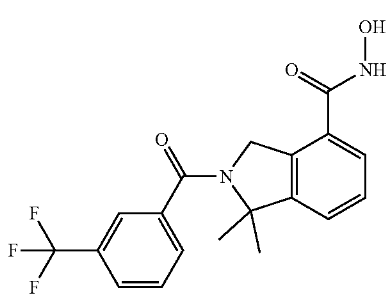 [SMILES: CC1(C)c2cccc(C(=O)NO)c2CN1C(=O)c1cccc(C(F)(F)F)c1] | N-hydroxy-1,1-dimethyl-2-(3-(trifluoromethyl)benzoyl)isoindoline-4-carboxamide |

TABLE 1-continued

| Example | Structure | Name |
|---|---|---|
| 29-1 | 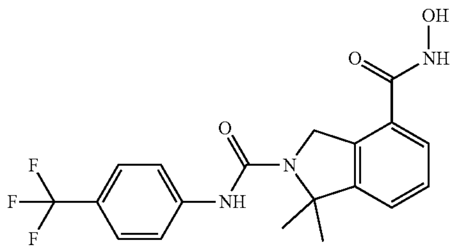 [SMILES: CC1(C)c2cccc(C(=O)NO)c2CN1C(=O)Nc1ccc(C(F)(F)F)cc1] | N4-hydroxy-1,1-dimethyl-N2-(4-(trifluoromethyl)phenyl)isoindoline-2,4-dicarboxamide |
| 30-1 | 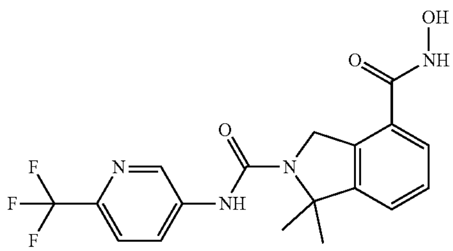 [SMILES: CC1(C)c2cccc(C(=O)NO)c2CN1C(=O)Nc1ccc(C(F)(F)F)nc1] | N4-hydroxy-1,1-dimethyl-N2-(6-(trifluoromethyl)pyridin-3-yl)isoindoline-2,4-dicarboxamide |
| 30-2 | 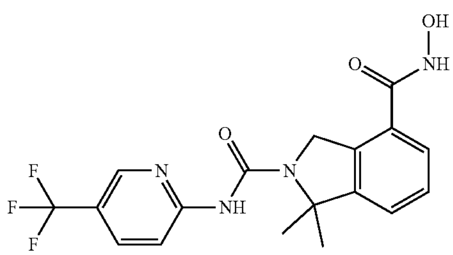 [SMILES: CC1(C)c2cccc(C(=O)NO)c2CN1C(=O)Nc1ccc(C(F)(F)F)cn1] | N4-hydroxy-1,1-dimethyl-N2-(5-(trifluoromethyl)pyridin-2-yl)isoindoline-2,4-dicarboxamide |
| 30-3 | 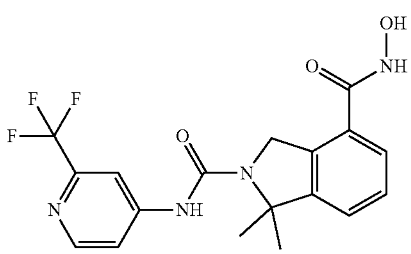 [SMILES: CC1(C)c2cccc(C(=O)NO)c2CN1C(=O)Nc1ccnc(C(F)(F)F)c1] | N4-hydroxy-1,1-dimethyl-N2-(2-(trifluoromethyl)pyridin-4-yl)isoindoline-2,4-dicarboxamide |
| 30-4 | 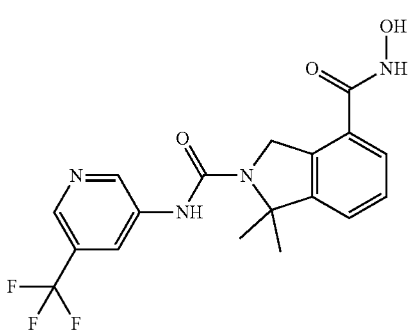 [SMILES: CC1(C)c2cccc(C(=O)NO)c2CN1C(=O)Nc1cncc(C(F)(F)F)c1] | N4-hydroxy-1,1-dimethyl-N2-(5-(trifluoromethyl)pyridin-3-yl)isoindoline-2,4-dicarboxamide |

TABLE 1-continued

| Example | Structure | Name |
|---|---|---|
| 30-5 | 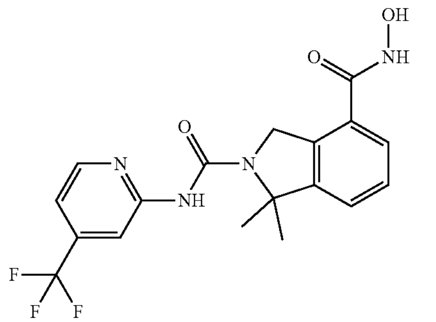 [SMILES: CC1(C)c2cccc(C(=O)NO)c2CN1C(=O)Nc1cc(C(F)(F)F)ccn1] | N4-hydroxy-1,1-dimethyl-N2-(4-(trifluoromethyl)pyridin-2-yl)isoindoline-2,4-dicarboxamide |
| 30-6 | 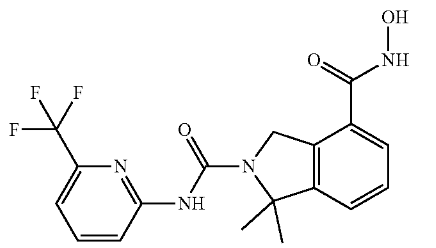 [SMILES: CC1(C)c2cccc(C(=O)NO)c2CN1C(=O)Nc1cccc(C(F)(F)F)n1] | N4-hydroxy-1,1-dimethyl-N2-(6-(trifluoromethyl)pyridin-2-yl)isoindoline-2,4-dicarboxamide |
| 30-7 | 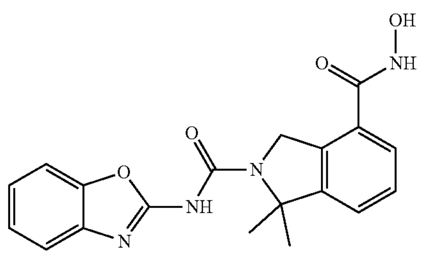 [SMILES: CC1(C)c2cccc(C(=O)NO)c2CN1C(=O)Nc1nc2ccccc2o1] | N2-(benzo[d]oxazol-2-yl)-N4-hydroxy-1,1-dimethylisoindoline-2,4-dicarboxamide |
| 31-1 | 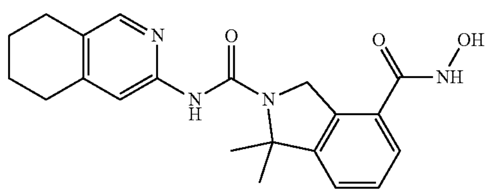 [SMILES: CC1(C)c2cccc(C(=O)NO)c2CN1C(=O)Nc1cc2c(cn1)CCCC2] | N4-hydroxy-1,1-dimethyl-N2-(5,6,7,8-tetrahydroisoquinolin-3-yl)isoindoline-2,4-dicarboxamide |
| 32-1 | 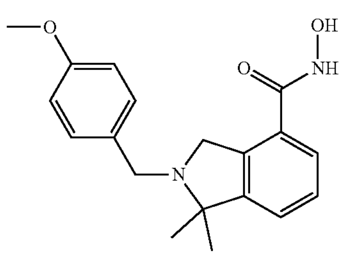 [SMILES: COc1ccc(CN2Cc3c(C(=O)NO)cccc3C2(C)C)cc1] | N-hydroxy-2-(4-methoxybenzyl)-1,1-dimethylisoindoline-4-carboxamide |
| 33-1 | 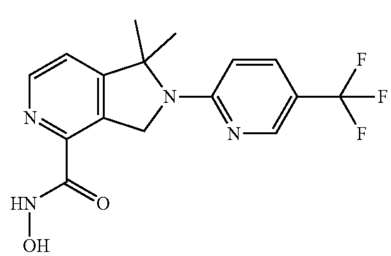 [SMILES: CC1(C)c2ccnc(C(=O)NO)c2CN1c1ccc(C(F)(F)F)cn1] | N-hydroxy-1,1-dimethyl-2-(5-(trifluoromethyl)pyridin-2-yl)-2,3-dihydro-1H-pyrrolo[3,4-c]pyridine-4-carboxamide |

TABLE 1-continued

| Example | Structure | Name |
|---|---|---|
| 34-1 | 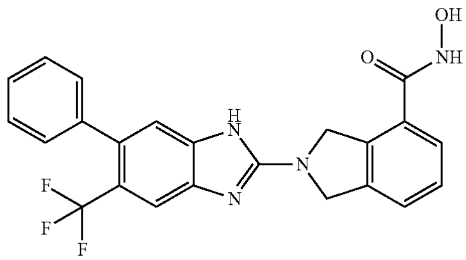 [SMILES: O=C(NO)c1cccc2c1CN(c1nc3cc(C(F)(F)F)c(-c4ccccc4)cc3[nH]1)C2] | N-hydroxy-2-(6-phenyl-5-(trifluoromethyl)-1H-benzo[d]imidazol-2-yl)isoindoline-4-carboxamide |
| 35-1 | 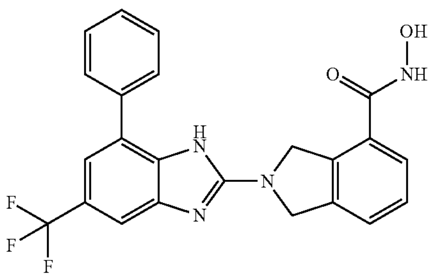 [SMILES: O=C(NO)c1cccc2c1CN(c1nc3cc(C(F)(F)F)cc(-c4ccccc4)c3[nH]1)C2] | N-hydroxy-2-(7-phenyl-5-(trifluoromethyl)-1H-benzo[d]imidazol-2-yl)isoindoline-4-carboxamide |
| 35-2 | 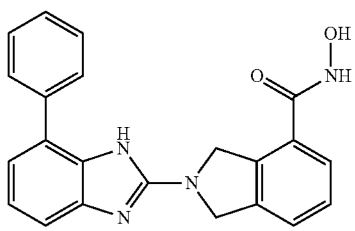 [SMILES: O=C(NO)c1cccc2c1CN(c1nc3cccc(-c4ccccc4)c3[nH]1)C2] | N-hydroxy-2-(7-phenyl-1H-benzo[d]imidazol-2-yl)isoindoline-4-carboxamide |
| 36-1 | 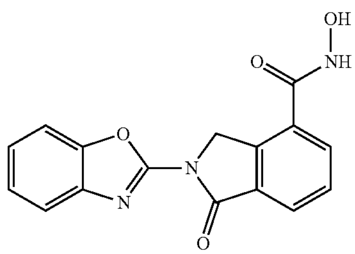 [SMILES: O=C(NO)c1cccc2c1CN(c1nc3ccccc3o1)C2=O] | 2-(benzo[d]oxazol-2-yl)-N-hydroxy-1-oxoisoindoline-4-carboxamide |
| 37-1 | 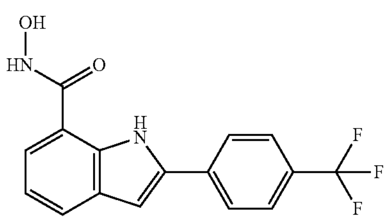 [SMILES: O=C(NO)c1cccc2cc(-c3ccc(C(F)(F)F)cc3)[nH]c12] | N-hydroxy-2-(4-(trifluoromethyl)phenyl)-1H-indole-7-carboxamide |
| 37-2 | 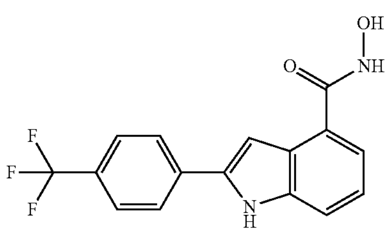 [SMILES: O=C(NO)c1cccc2[nH]c(-c3ccc(C(F)(F)F)cc3)cc12] | N-hydroxy-2-(4-(trifluoromethyl)phenyl)-1H-indole-4-carboxamide |

TABLE 1-continued

| Example | Structure | Name |
|---|---|---|
| 37-3 | 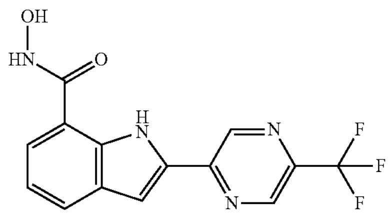 [SMILES: O=C(NO)c1cccc2cc(-c3cnc(C(F)(F)F)cn3)[nH]c12] | N-hydroxy-2-(5-(trifluoromethyl)pyrazin-2-yl)-1H-indole-7-carboxamide |
| 37-4 | 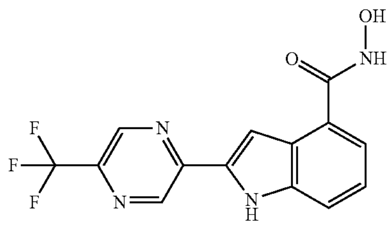 [SMILES: O=C(NO)c1cccc2[nH]c(-c3cnc(C(F)(F)F)cn3)cc12] | N-hydroxy-2-(5-(trifluoromethyl)pyrazin-2-yl)-1H-indole-4-carboxamide |
| 38-1 | 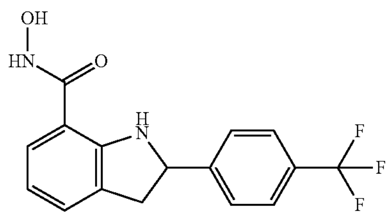 [SMILES: O=C(NO)c1cccc2c1NC(c1ccc(C(F)(F)F)cc1)C2] | N-hydroxy-2-(4-(trifluoromethyl)phenyl)indoline-7-carboxamide |
| 38-2 | 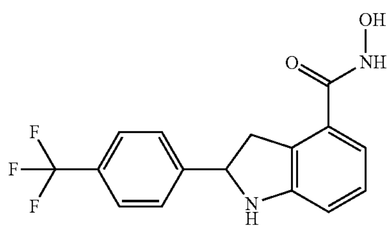 [SMILES: O=C(NO)c1cccc2c1CC(c1ccc(C(F)(F)F)cc1)N2] | N-hydroxy-2-(4-(trifluoromethyl)phenyl)indoline-4-carboxamide |
| 39-1 | 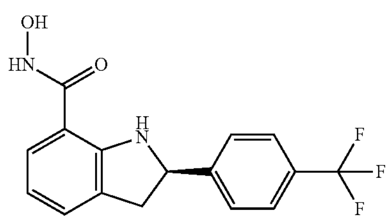 | (R)-N-hydroxy-2-(4-(trifluoromethyl)phenyl)indoline-7-carboxamide |
| 39-2 | 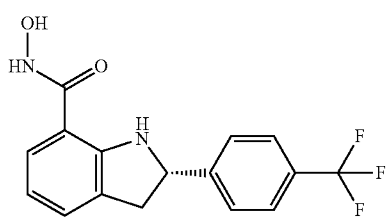 | (S)-N-hydroxy-2-(4-(trifluoromethyl)phenyl)indoline-7-carboxamide |
| 40-1 | 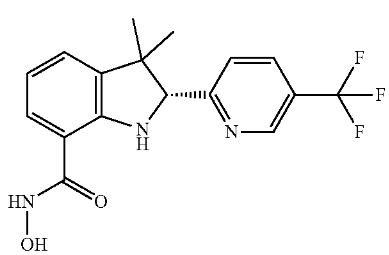 [SMILES: CC1(C)c2cccc(C(=O)NO)c2N[C@H]1c1ccc(C(F)(F)F)cn1] | (R)-N-hydroxy-3,3-dimethyl-2-(5-(trifluoromethyl)pyridin-2-yl)indoline-7-carboxamide |

TABLE 1-continued

| Example | Structure | Name |
|---|---|---|
| 40-2 | 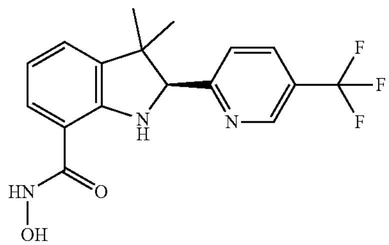 [SMILES: CC1(C)c2cccc(C(=O)NO)c2N[C@@H]1c1ccc(C(F)(F)F)cn1] | (S)-N-hydroxy-3,3-dimethyl-2-(5-(trifluoromethyl)pyridin-2-yl)indoline-7-carboxamide |
| 40-3 | 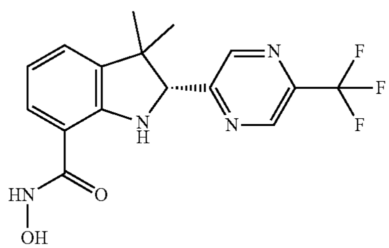 [SMILES: CC1(C)c2cccc(C(=O)NO)c2N[C@H]1c1cnc(C(F)(F)F)cn1] | (R)-N-hydroxy-3,3-dimethyl-2-(5-(trifluoromethyl)pyrazin-2-yl)indoline-7-carboxamide |
| 40-4 | 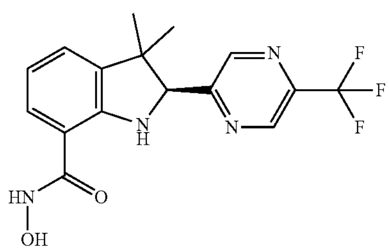 [SMILES: CC1(C)c2cccc(C(=O)NO)c2N[C@@H]1c1cnc(C(F)(F)F)cn1] | (S)-N-hydroxy-3,3-dimethyl-2-(5-(trifluoromethyl)pyrazin-2-yl)indoline-7-carboxamide |
| 40-5 | 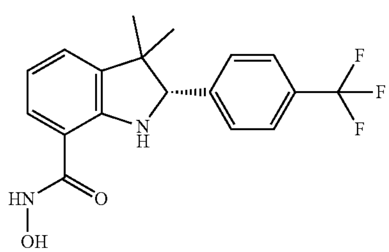 [SMILES: CC1(C)c2cccc(C(=O)NO)c2N[C@H]1c1ccc(C(F)(F)F)cc1] | (S)-N-hydroxy-3,3-dimethyl-2-(4-(trifluoromethyl)phenyl)indoline-7-carboxamide |
| 40-6 | 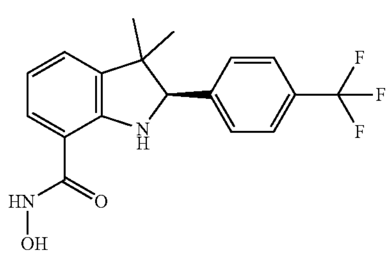 [SMILES: CC1(C)c2cccc(C(=O)NO)c2N[C@@H]1c1ccc(C(F)(F)F)cc1] | (R)-N-hydroxy-3,3-dimethyl-2-(4-(trifluoromethyl)phenyl)indoline-7-carboxamide |
| 1-6 | 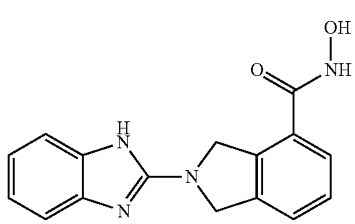 [SMILES: O=C(NO)c1cccc2c1CN(c1nc3ccccc3[nH]1)C2] | 2-(1H-benzo[d]imidazol-2-yl)-N-hydroxyisoindoline-4-carboxamide |

TABLE 1-continued

| Example | Structure | Name |
|---|---|---|
| 1-7 | 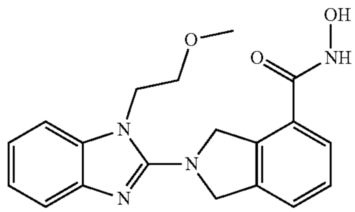 [SMILES: COCCn1c(N2Cc3cccc(C(=O)NO)c3C2)nc2ccccc21] | N-hydroxy-2-(1-(2-methoxyethyl)-1H-benzo[d]imidazol-2-yl)isoindoline-4-carboxamide |
| 28-3 | 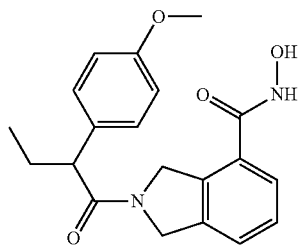 [SMILES: CCC(C(=O)N1Cc2cccc(C(=O)NO)c2C1)c1ccc(OC)cc1] | N-hydroxy-2-(2-(4-methoxyphenyl)butanoyl)isoindoline-4-carboxamide |
| 41-1 | 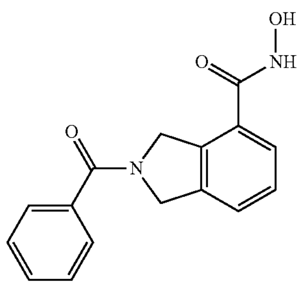 [SMILES: O=C(NO)c1cccc2c1CN(C(=O)c1ccccc1)C2] | 2-benzoyl-N-hydroxyisoindoline-4-carboxamide |
| 41-2 | 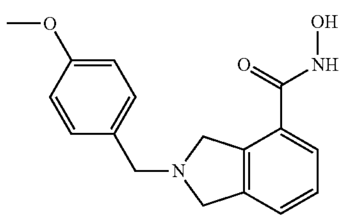 [SMILES: COc1ccc(CN2Cc3cccc(C(=O)NO)c3C2)cc1] | N-hydroxy-2-(4-methoxybenzyl)isoindoline-4-carboxamide |
| 42-1 | 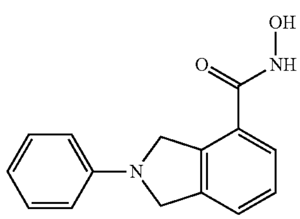 [SMILES: O=C(NO)c1cccc2c1CN(c1ccccc1)C2] | N-hydroxy-2-phenylisoindoline-4-carboxamide |
| 44-1 | 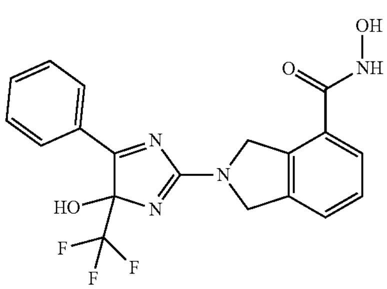 [SMILES: O=C(NO)c1cccc2c1CN(C1=NC(O)(C(F)(F)F)C(c3ccccc3)=N1)C2] | N-hydroxy-2-(4-hydroxy-5-phenyl-4-(trifluoromethyl)-4H-imidazol-2-yl)isoindoline-4-carboxamide |

TABLE 1-continued

| Example | Structure | Name |
|---|---|---|
| 45-1 | 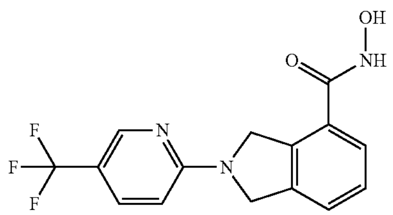 [SMILES: O=C(NO)c1cccc2c1CN(c1ccc(C(F)(F)F)cn1)C2] | N-hydroxy-2-(5-(trifluoromethyl)pyridin-2-yl)isoindoline-4-carboxamide |
| 45-2 | 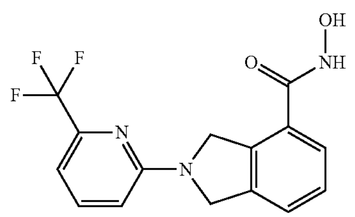 [SMILES: O=C(NO)c1cccc2c1CN(c1cccc(C(F)(F)F)n1)C2] | N-hydroxy-2-(6-(trifluoromethyl)pyridin-2-yl)isoindoline-4-carboxamide |
| 36-2 | 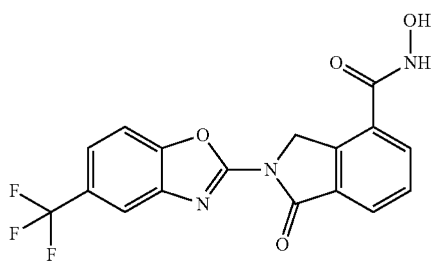 [SMILES: O=C(NO)c1cccc2c1CN(c1nc3cc(C(F)(F)F)ccc3o1)C2=O] | N-hydroxy-1-oxo-2-(5-(trifluoromethyl)benzo[d]oxazol-2-yl)isoindoline-4-carboxamide; and |
| 43-1 | 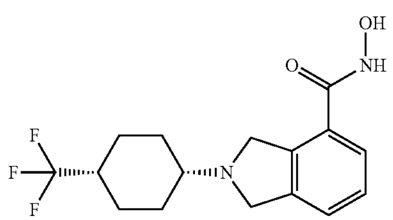 [SMILES: O=C(NO)c1cccc2c1CN([C@H]1CC[C@@H](C(F)(F)F)CC1)C2] | N-hydroxy-2-((1s,4s)-4-(trifluoromethyl)cyclohexyl)isoindoline-4-carboxamide |

In some embodiments, a compound of Formula I is selected from the group consisting of:

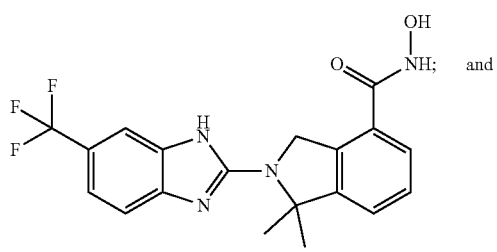

N-hydroxy-1,1-dimethyl-2-(6-(trifluoromethyl)-1H-benzo[d]imidazol-2-yl)isoindoline-4-carboxamide 17-1

-continued

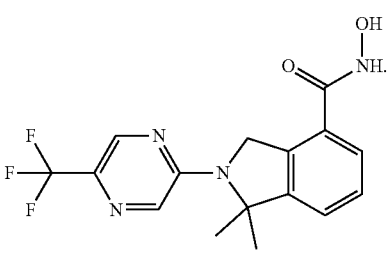

N-hydroxy-1,1-dimethyl-2-(5-(trifluoromethyl)pyrazin-2-yl)isoindoline-4-carboxamide 22-8

In some embodiments of the invention, the compounds of Formula I are enantiomers. In some embodiments, the compounds are the (S)-enantiomer. In other embodiments the compounds are the (R)-enantiomer. In other embodiments, the compounds of Formula I may be (+) or (−) enantiomers.

It should be understood that all isomeric forms are included within the present invention, including mixtures thereof. If the compound contains a double bond, the substituent may be in the E or Z configuration. If the compound contains a disubstituted cycloalkyl, the cycloalkyl substituent may have a cis- or trans-configuration. All tautomeric forms are also intended to be included.

Methods of Using the Disclosed Compounds

Another aspect of the invention relates to a method of treating a disease associated with HDAC11 modulation in a subject in need thereof. The method involves administering to a patient in need of treatment for diseases or disorders associated with HDAC11 modulation an effective amount of a compound of Formula I. In an embodiment, the disease can be, but is not limited to, cancer, a neurodegenerative disease, a neurodevelopmental disorder, an inflammatory disease, an autoimmune disease, infection, a metabolic disease, a hematologic disease, or a cardiovascular disease.

Another aspect of the present disclosure relates to a compound of Formula I, or a pharmaceutically acceptable salt thereof, for use in treating or preventing a disease associated with HDAC11 modulation. In some embodiments, the disease is cancer, neurodegenerative disease, neurodevelopmental disorder, inflammatory or autoimmune disease, infection, metabolic disease, hematologic disease, or cardiovascular disease. In some embodiments, the compound inhibits a histone deacetylase. In another embodiment, the compound inhibits a zinc-dependent histone deacetylase. In another embodiment, the compound inhibits the HDAC11 isozyme zinc-dependent histone deacetylase.

In another aspect, the present disclosure relates to the use of a compound of Formula I, or a pharmaceutically acceptable salt, thereof, in the manufacture of a medicament for treating or preventing a disease associated with HDAC11 modulation. In some embodiments, the disease is cancer, neurodegenerative disease, neurodevelopmental disorder, inflammatory or autoimmune disease, infection, metabolic disease, hematologic disease, or cardiovascular disease. In some embodiments, the compound inhibits a histone deacetylase. In another embodiment, the compound inhibits a zinc-dependent histone deacetylase. In another embodiment, the compound inhibits the HDAC11 isozyme zinc-dependent histone deacetylase.

The present invention relates to compositions capable of modulating the activity of (e.g., inhibiting) HDACs, and in particular HDAC11. The present invention also relates to the therapeutic use of such compounds.

One therapeutic use of the compounds of the present invention is to treat proliferative diseases or disorders such as cancer. Cancer can be understood as abnormal or unregulated cell growth within a patient and can include but is not limited to lung cancer, ovarian cancer, breast cancer, prostate cancer, pancreatic cancer, hepatocellular cancer, renal cancer and leukemias such as acute myeloid leukemia and acute lymphoblastic leukemia. Additional cancer types include T-cell lymphoma (e.g., cutaneous T-cell lymphoma, peripheral T-cell lymphoma), Hodgkin lymphoma, melanoma, and multiple myeloma. In other embodiments, treating proliferative diseases or disorders can include any cancer where there is evidence of an increase in Treg/effector T cell ratio or in an absolute Treg number, either in the periphery or in the tumor microenvironment or tertiary lymphoid structures, or increased expression of T cell tolerance-related genes. Such proliferative diseases or disorders can include but are not limited to: any Kras mutant carrying tumor (as set forth, for instance, by Zdanov et al., Cancer Immunol Res. 2016 April; 4(4):354-65, the contents of which are hereby incorporated by reference in their entirety); renal cancer (e.g., renal cell carcinoma); lung carcinoma; cervical cancer; prostate cancer; ovarian cancer; head and neck cancer; lymphoma; colorectal cancer, non-small cell lung carcinoma; breast cancers (Gobert, M. et al. (2009) Cancer Res. 69, 2000-2009); and bladder cancer. In one or more embodiments, the cancer is colon cancer, lung cancer, neuroblastoma, hepatocellular carcinoma, or gastric cancer.

One therapeutic use of the compounds of the present disclosure is to treat neurological diseases or disorders or neurodegeneration. Neurological disorders are understood as disorders of the nervous system (e.g., the brain and spinal cord). Neurological disorders or neurodegenerative diseases can include but are not limited to epilepsy, attention deficit disorder (ADD), Alzheimer's disease, Parkinson's Disease, Huntington's Disease, Muscular dystrophy, amyotrophic lateral sclerosis, spinal muscular atrophy, essential tremor, central nervous system trauma caused by tissue injury, oxidative stress-induced neuronal or axonal degeneration, ALS, and multiple sclerosis.

Another therapeutic use of the compounds of the present disclosure is to treat neurodevelopmental disorders. Neurodevelopmental disorders can include, but are not limited to, Rett syndrome, intellectual disability, intellectual and developmental disability, autism spectrum disorder, fetal alcohol syndrome, developmental coordination disorder, stereotypic movement disorder, Tourette syndrome, cerebral palsy, fragile X syndrome, attention deficit hyperactivity disorder, and Mendelsohnn's syndrome.

Another therapeutic use of the compounds of the present invention is also to treat inflammatory diseases or disorders. Inflammation can be understood as a host's response to an initial injury or infection. Symptoms of inflammation can include but are not limited to redness, swelling, pain, heat and loss of function. Inflammation may be caused by the upregulation of pro-inflammatory cytokines such as IL-1β, and increased expression of the FOXP3 transcription factor. In some embodiments, the inflammatory diseases include fibrosis or fibrotic diseases. Types of fibrotic diseases include but are not limited to lung fibrosis or pulmonary fibrosis, Liver fibrosis; Heart fibrosis; Mediastinal fibrosis; Retroperitoneal cavity fibrosis; Bone marrow fibrosis; Skin fibrosis; and Scleroderma or systemic sclerosis.

Another therapeutic use of the compounds of the present invention is also to treat autoimmune diseases or disorders. Autoimmune disorders are understood as disorders wherein a host's own immune system responds to tissues and substances occurring naturally in the host's body. Autoimmune diseases can include but are not limited to rheumatoid arthritis, Crohn's disease, type-1 diabetes, systemic juvenile idiopathic arthritis, inflammatory bowel disease, allograft transplantation, eczema, psoriasis, idiopathic thrombocytopenic purpra, autoimmune thrombocytopenia, acquired immune thrombocytopenia, autoimmune neutropenia, autoimmune hemolyitic anemia, parvovirus B19-associated red cell aplasia, acquired antifactor VIII autoimmunity, acquired von Willebrand disease, monoclonal gammopathy, aplastic anemia, pure red cell aplasia, Diamond-Blackfan anemia, hemolytic disease of the newborn, immune mediated-refractoriness to platelet transfusion, hemolytic uremic syndrome, Evan's syndrome, Guillain-Barre syndrome, chronic demyelinating polyradiculoneuropathy, paraproteinemic IgM demyelinating polyneuropathy, Lambert-Eaton myasthenic syndrome, myasthenia gravis, multifocal motor neuropathy, stiff man syndrome, paraneoplastic encephalomyelitis, sensory neuropathy with anti-Hu antibodies, myelitis, autoimmune diabetic neuropathy, acute idiopathic neuropathy, toxic epidermal necrolysis, gangrene, granuloma, pemphigus vulgaris, bullous pemphigoid, vitiligo, scleroderma, atomic dermatitis, systemic and diffuse sclerosis, primary biliary cirrhosis, Celiac disease, dermatitis herpetiformis, cryptogenic cirrhosis, reactive arthritis, Hashimoto's thryroditis, Wegner's granulomoatosis, micropolyarterits, Churg-Strauss syndrome Type I and Type II autoimmune polyglandular syndromes, linear IgA disease, epidermolysis bullosa acquisita, erythema *nodosa*, pemphigoid gestationis, cicatricial pemphigoid, mixed essential cryoglobulinemia, chronic bullous disease of childhood, Goodpasture's syndrome, sclerosis cholangitis, ankylosing spondylitis, Bechet's syndrome temporal arteritis, Takayasu's arteritis, autoimmune urticaria, and Kawasaki's disease.

Another therapeutic use of the compounds of the present invention is also to treat infectious diseases or disorders. Infections or infectious diseases are caused by the invasion of a foreign pathogen. The infection may be caused by, for instance, a bacteria, a fungus, a parasite, or virus. Bacterial infections include, but are not limited to *Streptococcus* infections, mycobacterial infections, *Bacillus* infections, *Salmonella* infections, *Vibrio* infections, spirochete infections, and *Neisseria* infections. Viral infections include, but are not limited to herpes virus infections, hepatitis virus infections, west Nile virus infections, flavivrus infections, influenza virus infections, rhinovirus infections, papillomavirus infections, paramyxovirus infections, parainfluenza virus infections, and retrovirus infections. In particular embodiments, the compounds of the present invention are useful for treating infections which result in an inflammatory cytokine burst. Non-limiting examples of such infections include Ebola and other viral hemorrhagic fever-causing viruses, and Malaria. In some embodiments, the parasitic infection is a malarial infection.

Yet another therapeutic use of the compounds of the present invention is also to prevent and/or treat transplant rejection. Tissues that are transplanted include (but are not limited to) whole organs such as kidney, liver, heart, lung; organ components such as skin grafts and the cornea of the eye; and cell suspensions such as bone marrow cells and cultures of cells selected and expanded from bone marrow or circulating blood, and whole blood transfusions.

Another therapeutic use of the compounds of the present invention is also to treat and/or prevent allergy and unwanted immune responses associated with allergy. A non-limiting list of allergies and related conditions includes, pollen allergy (e.g. Japanese Cedar Pollen), mold allergy, food allergies (including, but not limited to peanut, tree nut, milk, soy, gluten, and egg allergies), animal allergies (e.g. allergies to dogs, cats, rabbits), dust mite allergy, atopic dermatitis, allergic rhinitis, allergic otitis, allergic asthma, dry eye, ocular allergy, allergic urticaria, contact dermatitis, anaphylaxis, eosinophilic esophagitis.

Yet another therapeutic use of the compounds of the present invention is also to treat metabolic diseases or disorders. Metabolic diseases can be characterized as abnormalities in the way that a subject stores energy. Metabolic disorders can include but are not limited to metabolic syndrome, diabetes, obesity, high blood pressure, non-alcoholic fatty liver disease and heart failure.

Yet another therapeutic use of the compounds of the present invention is also to treat hematologic disorders. Hematologic diseases primarily affect the blood. Hematologic disorders can include but are not limited to anemia, multiple myeloma, lymphoma, and leukemia.

Yet another therapeutic use of the compounds of the present invention is also to treat cardiovascular diseases or disorders. Cardiovascular diseases affect the heart and blood vessels of a patient. Exemplary conditions include but are not limited to cardiovascular stress, pressure overload, chronic ischemia, infarction-reperfusion injury, hypertension, Brain infarct after cerebral artery occlusion, atherosclerosis, peripheral artery disease, cardiac hypertrophy, cardiac arrhythmias, stroke, and heart failure.

Administration of the disclosed compounds can be accomplished via any mode of administration for therapeutic agents. These modes include systemic or local administration such as oral, nasal, parenteral, transdermal, subcutaneous, vaginal, buccal, rectal or topical administration modes.

Depending on the intended mode of administration, the disclosed compositions can be in solid, semi-solid or liquid dosage form, such as, for example, injectables, tablets, suppositories, pills, time-release capsules, elixirs, tinctures, emulsions, syrups, powders, liquids, suspensions, or the like, sometimes in unit dosages and consistent with conventional pharmaceutical practices. Likewise, they can also be administered in intravenous (both bolus and infusion), intraperitoneal, subcutaneous or intramuscular form, all using forms well known to those skilled in the pharmaceutical arts.

Illustrative pharmaceutical compositions are tablets and gelatin capsules comprising a compound of the invention and a pharmaceutically acceptable carrier, such as a) a diluent, e.g., purified water, triglyceride oils, such as hydrogenated or partially hydrogenated vegetable oil, or mixtures thereof, corn oil, olive oil, sunflower oil, safflower oil, fish oils, such as EPA or DHA, or their esters or triglycerides or mixtures thereof, omega-3 fatty acids or derivatives thereof, lactose, dextrose, sucrose, mannitol, sorbitol, cellulose, sodium, saccharin, glucose and/or glycine; b) a lubricant, e.g., silica, talcum, stearic acid, its magnesium or calcium salt, sodium oleate, sodium stearate, magnesium stearate, sodium benzoate, sodium acetate, sodium chloride and/or polyethylene glycol; for tablets also; c) a binder, e.g., magnesium aluminum silicate, starch paste, gelatin, tragacanth, methylcellulose, sodium carboxymethylcellulose, magnesium carbonate, natural sugars such as glucose or beta-lactose, corn sweeteners, natural and synthetic gums such as acacia, tragacanth or sodium alginate, waxes and/or polyvinylpyrrolidone, if desired; d) a disintegrant, e.g., starches, agar, methyl cellulose, bentonite, xanthan gum, algiic acid or its sodium salt, or effervescent mixtures; e) absorbent, colorant, flavorant and sweetener; f) an emulsifier or dispersing agent, such as Tween 80, Labrasol, HPMC, DOSS, caproyl 909, labrafac, labrafil, peceol, transcutol, capmul MCM, capmul PG-12, captex 355, gelucire, vitamin E TGPS or other acceptable emulsifier; and/or g) an agent that enhances absorption of the compound such as cyclodextrin, hydroxypropyl-cyclodextrin, PEG400, PEG200.

Liquid, particularly injectable, compositions can, for example, be prepared by dissolution, dispersion, etc. For example, the disclosed compound is dissolved in or mixed with a pharmaceutically acceptable solvent such as, for example, water, saline, aqueous dextrose, glycerol, ethanol, and the like, to thereby form an injectable isotonic solution or suspension. Proteins such as albumin, chylomicron particles, or serum proteins can be used to solubilize the disclosed compounds.

The disclosed compounds can be also formulated as a suppository that can be prepared from fatty emulsions or suspensions; using polyalkylene glycols such as propylene glycol, as the carrier.

The disclosed compounds can also be administered in the form of liposome delivery systems, such as small unilamellar vesicles, large unilamellar vesicles and multilamellar vesicles. Liposomes can be formed from a variety of phospholipids, containing cholesterol, stearylamine or phosphatidylcholines. In some embodiments, a film of lipid components is hydrated with an aqueous solution of drug to a form lipid layer encapsulating the drug, as described in U.S. Pat. No. 5,262,564.

Disclosed compounds can also be delivered by the use of monoclonal antibodies as individual carriers to which the disclosed compounds are coupled. The disclosed compounds can also be coupled with soluble polymers as targetable drug carriers. Such polymers can include polyvinylpyrrolidone, pyran copolymer, polyhydroxypropylmethacrylamide-phenol, polyhydroxyethylaspanamidephenol, or polyethyleneoxidepolylysine substituted with palmitoyl residues. Furthermore, the disclosed compounds can be coupled to a class of biodegradable polymers useful in achieving controlled release of a drug, for example, polylactic acid, polyepsilon caprolactone, polyhydroxy butyric acid, polyorthoesters, polyacetals, polydihydropyrans, polycyanoacrylates and cross-linked or amphipathic block copolymers of hydrogels. In one embodiment, disclosed compounds are not covalently bound to a polymer, e.g., a polycarboxylic acid polymer, or a polyacrylate.

Parental injectable administration is generally used for subcutaneous, intramuscular or intravenous injections and infusions. Injectables can be prepared in conventional forms, either as liquid solutions or suspensions or solid forms suitable for dissolving in liquid prior to injection.

Another aspect of the invention relates to a pharmaceutical composition comprising a compound of Formula I and a pharmaceutically acceptable carrier. The pharmaceutically acceptable carrier can further include an excipient, diluent, or surfactant.

Compositions can be prepared according to conventional mixing, granulating or coating methods, respectively, and the present pharmaceutical compositions can contain from about 0.1% to about 99%, from about 5% to about 90%, or from about 1% to about 20% of the disclosed compound by weight or volume.

The dosage regimen utilizing the disclosed compound is selected in accordance with a variety of factors including type, species, age, weight, sex and medical condition of the patient; the severity of the condition to be treated; the route of administration; the renal or hepatic function of the patient; and the particular disclosed compound employed. A physician or veterinarian of ordinary skill in the art can readily determine and prescribe the effective amount of the drug required to prevent, counter or arrest the progress of the condition.

Effective dosage amounts of the disclosed compounds, when used for the indicated effects, range from about 0.5 mg to about 5000 mg of the disclosed compound as needed to treat the condition. Compositions for in vivo or in vitro use can contain about 0.5, 5, 20, 50, 75, 100, 150, 250, 500, 750, 1000, 1250, 2500, 3500, or 5000 mg of the disclosed compound, or, in a range of from one amount to another amount in the list of doses. In one embodiment, the compositions are in the form of a tablet that can be scored.

Without wishing to be bound by any particular theory, the compounds of the present invention can inhibit HDACs, such as HDAC11, by interacting with the zinc ($Zn^{2+}$) ion in the protein's active site via the hydroxamic acid group bound to the aromatic ring of the compound. The binding can prevent the zinc ion from interacting with its natural substrates, thus inhibiting the enzyme.

Methods of Synthesizing the Disclosed Compounds

The compounds of the present invention may be made by a variety of methods, including standard chemistry. Suitable synthetic routes are depicted in the schemes given below.

The compounds of Formula I may be prepared by methods known in the art of organic synthesis as set forth in part by the following synthetic schemes and examples. In the schemes described below, it is well understood that protecting groups for sensitive or reactive groups are employed where necessary in accordance with general principles or chemistry. Protecting groups are manipulated according to standard methods of organic synthesis (T. W. Greene and P. G. M. Wuts, "Protective Groups in Organic Synthesis", Third edition, Wiley, New York 1999). These groups are removed at a convenient stage of the compound synthesis using methods that are readily apparent to those skilled in the art. The selection processes, as well as the reaction conditions and order of their execution, shall be consistent with the preparation of compounds of Formula I.

Those skilled in the art will recognize if a stereocenter exists in the compounds of Formula I. Accordingly, the present invention includes both possible stereoisomers (unless specified in the synthesis) and includes not only racemic compounds but the individual enantiomers and/or diastereomers as well. When a compound is desired as a single enantiomer or diastereomer, it may be obtained by stereospecific synthesis or by resolution of the final product or any convenient intermediate. Resolution of the final product, an intermediate, or a starting material may be affected by any suitable method known in the art. See, for example, "Stereochemistry of Organic Compounds" by E. L. Eliel, S. H. Wilen, and L. N. Mander (Wiley-Interscience, 1994).

Preparation of Compounds

The compounds described herein may be made from commercially available starting materials or synthesized using known organic, inorganic, and/or enzymatic processes.

The compounds of the present invention can be prepared in a number of ways well known to those skilled in the art of organic synthesis. By way of example, compounds of the Formula I can be synthesized using the methods described below, together with synthetic methods known in the art of synthetic organic chemistry, or variations thereon as appreciated by those skilled in the art. These methods include but are not limited to those methods described below.

General Schemes

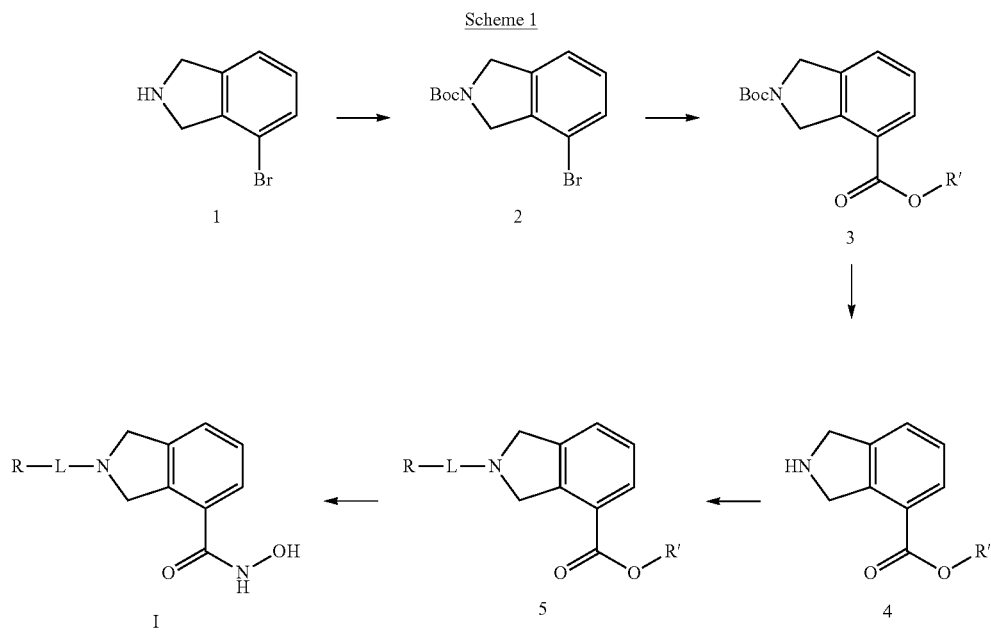

wherein L and R are defined as in Formula (I).

A general way of preparing the compounds of the present invention using a commercially available starting material such as indoline 1 is outlined in Scheme 1. Amine protection of the isoindoline 1 can be achieved using standard conditions and protective groups such as t-butoxycarbonyl (t-BOC), carbozylozy (Cbz), Benzyl (Bn), or Benzoyl (Bz) groups. The protected isoindoline 2 is then carboxylated via a metal-catalyzed carboxylation using metals such as palladium or copper to yield compound 3. An ensuing amine deprotection of compound 3 will yield a free isoindoline carboxylate 4. The resulting free isoindoline carboxylate 4 can further be alkylated, arylated, acylated, or sulfonated under standard conditions to provide the intermediate 5. A final condensation of intermediate 5 with a hydroxyamine will generally provide the compounds of formula I.

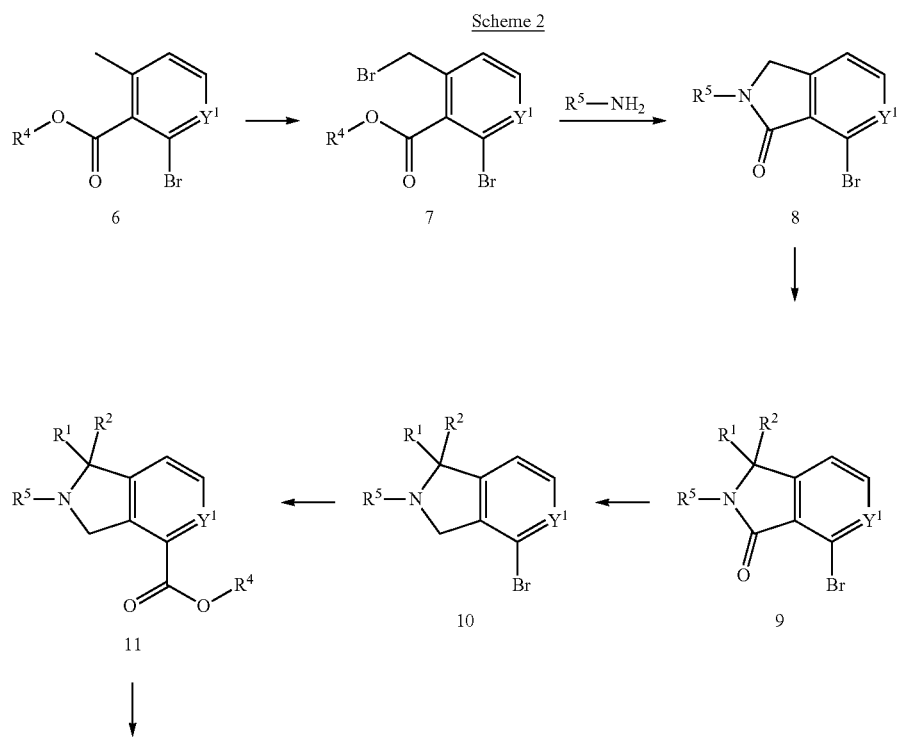

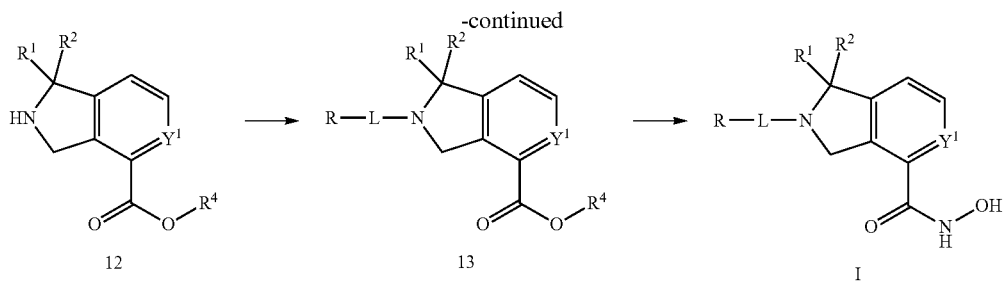

wherein $R^1$, $R^2$, L, $Y^1$ and R are defined as in Formula (I).

Another general way to prepare the compounds of Formula I is outlined in Scheme 2. Generally precursor 6 is halogenated to form the compound 7. Subsequent amination and cyclization of compound 7 will yield isoindolinone 8. Further optional alkylation, arylation, acylation, amination, or sulfonation of isoindolinone 8 to yield intermediate 9 are followed by a chemoselective reduction of the carbonyl group to provide the isoindoline 10. The isoindoline 10 is then carboxylated via a metal-catalyzed carboxylation using metal such as palladium or copper. An ensuing deprotection of the protected isoindoline carboxylate 11 will yield a free isoindoline carboxylate 12. The resulting free isoindoline carboxylate 12 can further be alkylated, arylated, acylated, or sulfonated under the standard conditions to provide the intermediate 13. A final condensation of intermediate 13 with a hydroxyamine will generally provide the compounds of formula I.

EXAMPLES

The disclosure is further illustrated by the following examples, which are not to be construed as limiting this disclosure in scope or spirit to the specific procedures herein described. It is to be understood that the examples are provided to illustrate certain embodiments and that no limitation to the scope of the disclosure is intended thereby. It is to be further understood that one may resort to various other embodiments, modifications, and equivalents thereof which may suggest themselves to those skilled in the art without departing from the spirit of the present disclosure and/or scope of the appended claims.

The present invention includes a number of unique features and advantages compared with other inhibitors of HDAC enzymes, e.g., HDAC11. For instance, the present invention features a unique class of small molecule therapeutic agents of Formula I. The compounds were designed by using crystal structure information of HDAC ligand-protein complexes as well as advanced computational chemistry tools. These techniques led to the development of new chemical scaffolds that were iteratively refined to optimize key recognition features between the ligand and receptor known to be necessary for potency.

List of Abbreviations

ACN acetonitrile
AcOH acetic acid
AIBN 2,2'-Azobis(2-methylpropionitrile)
$CH_3CN$ acetonitrile
DCE 1,2-dichloroethane
DCM dichloromethane or methylene chloride
DEA N,N-diethylamine
DIEA N,N-diisopropylethylamine
DMA N,N-Dimethylacetamide
DMF N,N-dimethylformamide
DMSO dimethyl sulfoxide
DMTMM 4-(4,6-dimethoxy-1,3,5-triazin-2-yl)-4-methyl-morpholinium chloride
dppf bis(diphenylphosphino)ferrocene
EtOAc ethyl acetate
EtOH ethanol
FA formic acid
h hours
HATU 2-(3H-[1,2,3]triazolo[4,5-b]pyridin-3-yl)-1,1,3,3-tetramethyl-isouronium hexafluorophosphate
HBr hydrogen bromide
HCl hydrogen chloride
HPLC high performance liquid chromatography
LC/MS liquid chromatography/mass spectrometry
LiOH lithium hydroxide
$K_2CO_3$ potassium carbonate
MeOH methanol
MS mass spectrometry
NaOH sodium hydroxide
$Na_2SO_4$ sodium sulfate
$NH_4HCO_3$ ammonium bicarbonate
NMM 4-methylmorpholine
NMP N-Methyl-2-pyrrolidone
$Pd_2(dba)_3$ tris(dibenzylideneacetone)dipalladium
$Pd(dppf)Cl_2$ [1,1'-Bis(diphenylphosphino)ferrocene]dichloropalladium (II)
PMB para-methoxybenzyl
$PPh_3$ triphenylphosphine
rt room temperature
RuPhos 2-Dicyclohexylphosphino-2',6'-diisopropoxybiphenyl
RuPhos 2G Chloro(2-dicyclohexylphosphino-2',6'-diisopropoxy-1,1'-biphenyl)[2-(2'-amino-1,1'-biphenyl)]palladium(II),
TEA triethylamine
TFA trifluoroacetic acid
THF tetrahydrofuran
XantPhos 4,5-Bis(diphenylphosphino)-9,9-dimethylxanthene
XPhos 2-Dicyclohexylphosphino-2',4',6'-triisopropylbiphenyl
XPhos 2G Chloro(2-dicyclohexylphosphino-2',4',6'-triisopropyl-1,1'-biphenyl)[2-(2'-amino-1,1'-biphenyl)]palladium(II)
XPhos 3G Methanesulfonato(2-dicyclohexylphosphino-2',4',6'-tri-i-propyl-1,1'-biphenyl)(2'-amino-1,1'-biphenyl-2-yl)palladium(II) dichloromethane adduct Unless otherwise noted, all materials were obtained from commercial suppliers and were used without further purification. Anhydrous solvents were obtained from Sigma- Aldrich (Milwaukee, Wis.) and used directly. All reactions involving air- or moisture-sensitive reagents were performed under a nitrogen atmosphere.

Unless otherwise noted, mass-triggered HPLC purification and/or purity and low resolution mass spectral data were measured using either: (1) Waters Acquity ultra performance liquid chromatography (UPLC) system (Waters Acquity UPLC with Sample Organizer and Waters Micromass ZQ Mass Spectrometer) with UV detection at 220 nm and a low resonance electrospray positive ion mode (ESI) (Column: Acquity UPLC BEH $C_{18}$ 1.7 μm 2.1×50 mm; gradient: 5-100% Solvent B (95/5/0.09%: Acetonitrile/Water/Formic Acid) in Solvent A (95/5/0.1%: 10 mM Ammonium Formate/Acetonitrile/Formic Acid) for 2.2 min then 100-5% Solvent B in Solvent A for 0.01 min then hold at 5% Solvent B in Solvent A for 0.29 min) or (2) Waters HT2790 Alliance high performance liquid chromatography (HPLC) system (Waters 996 PDA and Waters ZQ Single Quad Mass Spectrometer) with UV detection at 220 nm and 254 nm and a low resonance electrospray ionization (positive/negative) mode (ESI) (Column: XBridge Phenyl or C18, 5 μm 4.6×50 mm; gradient: 5-95% Solvent B (95% methanol/5% water with 0.1% Formic Acid) in Solvent A (95% water/5% methanol with 0.1% Formic Acid) for 2.5 min then hold at 95% Solvent B in Solvent A for 1 min (purity and low resolution MS only).

Unless otherwise noted, proton nuclear magnetic resonance (NMR) spectra were obtained on either: (1) Bruker BBFO ASCEND™400 AVANCE III spectrometer at 400 MHz or (2) Bruker BBFO ULTRASHIELD™300 AVANCE III spectrometer at 300 MHz. Spectra are given in ppm (δ) and coupling constants, J, are reported in Hertz (Hz). Tetramethylsilane (TMS) was used as an internal standard. Mass spectra were collected using a Waters ZQ Single Quad Mass Spectrometer (ion trap electrospray ionization (ESI)).

Intermediate 1. Methyl 1,1-dimethylisoindoline-4-carboxylate ing with ethyl acetate/petroleum ether (1:10)) to afford methyl 2-bromo-6-methylbenzoate (15 g, 66%) as a colorless oil. MS: (EI, m/z): 228.

Step 2: Methyl 2-bromo-6-(bromomethyl)benzoate

N-Bromosuccinimide (10.42 g, 58.55 mmol) and benzoyl peroxide (1.4 g, 5.46 mmol, 0.10 equiv) were added to a solution of methyl 2-bromo-6-methylbenzoate (13.4 g, 58.5 mmol) in carbon tetrachloride (350 mL). The resulting solution was stirred overnight at 80° C., and the reaction mixture was cooled to room temperature with a water bath. The mixture was filtered, and the filtrate was washed with 500 mL of brine, dried over anhydrous sodium sulfate, filtered, and concentrated under vacuum to afford methyl 2-bromo-6-(bromomethyl)benzoate (18 g, 100%) as yellow oil.

Step 3: 7-bromo-2-(4-methoxybenzyl)isoindolin-1-one

A solution of methyl 2-bromo-6-(bromomethyl)benzoate (18.0 g, 58.5 mmol), p-methoxybenzylamine (8.1 g, 59.05 mmol), and triethylamine (12.25 mL, 87.95 mmol) in methanol (700 mL) was stirred for 4 h at 80° C. The resulting mixture was cooled to room temperature with a water bath and concentrated under vacuum. The mixture was then quenched by the addition of 500 mL of water. The resulting solution was extracted with 2×500 mL of dichloromethane, washed with 1000 mL of brine, dried over anhydrous sodium sulfate, filtered, and concentrated under vacuum. The residue was purified via column chromatography on silica gel (eluting with ethyl acetate/petroleum ether (1:1)) to afford 7-bromo-2-(4-methoxybenzyl)isoindolin-1-one (7.1 g, 37%) as a yellow solid. MS: (ES, m/z): 332[M+H]$^+$ Step 4: 7-bromo-2-(4-methoxybenzyl)-3,3-dimethylisoindolin-1-one A solution of sodium hydride (60% dispersion in mineral oil, 7.44 g, 310.00 mmol) in tetrahydrofuran (150 mL) was

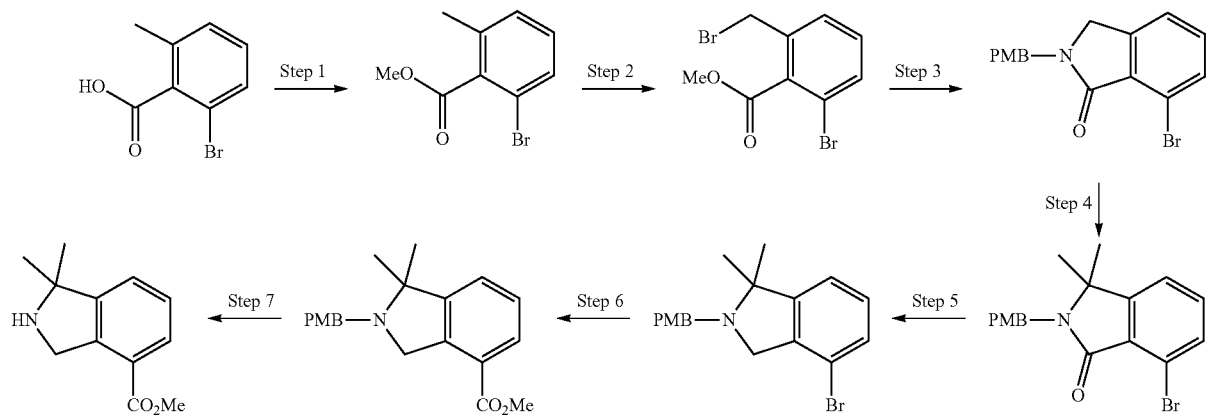

Step 1: Methyl 2-bromo-6-methylbenzoate (Trimethylsilyl)diazomethane (2 M in diethyl ether, 200 mL, 400 mmol) was added to a 10° C. solution of 2-bromo-6-methylbenzoic acid (21.4 g, 99.51 mmol) in methanol (100 mL) and toluene (300 mL), and the resulting solution was stirred overnight at room temperature. The reaction mixture was concentrated under vacuum, and the residue was purified via column chromatography on silica gel (elutplaced into a 500-mL, 3-necked round-bottom flask and purged and maintained with an inert atmosphere of nitrogen. This was followed by the dropwise addition of a solution of 7-bromo-2-(4-methoxybenzyl)isoindolin-1-one (8.82 g, 26.55 mmol) in tetrahydrofuran (20 mL). The resulting solution was stirred for 3 h at room temperature. Methyl iodide (15.1 g, 106.34 mmol) was added dropwise with stirring, and the resulting solution stirred overnight at room temperature. The reaction was then slowly poured into 1000 mL of water/ice. The resulting solution was extracted with 2×300 mL of ethyl acetate and the organic layers combined. The resulting mixture was washed with 1×500 mL of brine, dried over anhydrous sodium sulfate, filtered, and concentrated under vacuum. The residue was purified via column chromatography on silica gel (eluting with ethyl acetate/petroleum ether (1:2)) to afford 7-bromo-2-(4-methoxybenzyl)-3,3-dimethylisoindolin-1-one (5.8 g, 61%) as colorless oil. MS: (ES, m/z): 360[M+H]$^+$

Step 5: 4-bromo-2-(4-meihoxybenzyl)-1,1-dimethylisoindoline

A 500-mL sealed tube was charged with 7-bromo-2-(4-methoxybenzyl)-3,3-dimethylisoindolin-1-one (5.8 g, 16.10 mmol) and borane-THF complex (1.0 M, 200 mL, 200 mmol), and the resulting solution was stirred overnight at 80° C. The reaction mixture was cooled to room temperature with a water bath and transferred to a 1000-mL, 3-necked round-bottom flask. The reaction mixture was quenched by the addition of 300 mL of methanol and stirred for 3 h at 80° C. The resulting mixture was cooled to room temperature with a water bath and concentrated under vacuum. The residue was purified via column chromatography on silica gel (eluting with ethyl acetate/petroleum ether (1:10)) to afford 4-bromo-2-(4-methoxybenzyl)-1,1-dimethylisoindoline (4.6 g, 83%) as a yellow liquid. MS: (ES, m/z): 346[M+H]$^+$

Step 6: methyl 2-(4-meihoxybenzyl)-1,1-dimethylisoindoline-4-carboxylate

A 250-mL pressure tank reactor was charged with a solution of 4-bromo-2-(4-methoxybenzyl)-1,1-dimethylisoindoline (4.5 g, 13.00 mmol), [1,1'-bis(diphenylphosphino)ferrocene]-dichloropalladium (II), complex with dichloromethane (2.13 g, 2.6 mmol), triethyl amine (5.42 mL, 38.94 mmol) in methanol (60 mL). Carbon dioxide gas (60 atm) was introduced, and the resulting solution was stirred for 24 h at 130° C. The resulting mixture was concentrated under vacuum. The residue was purified via column chromatography on silica gel (eluting with ethyl acetate/petroleum ether (1:10)) to afford methyl 2-(4-methoxybenzyl)-1,1-dimethylisoindoline-4-carboxylate (2 g, 47%) as an off-white solid. MS: (ES, m/z): 326[M+H]$^+$

Step 7: methyl 1,1-dimethylisoindoline-4-carboxylate

Hydrogen gas was introduced into a solution of methyl 2-(4-methoxybenzyl)-1,1-dimethylisoindoline-4-carboxylate (4 g, 12.29 mmol), palladium hydroxide on carbon (1.2 g), and concentrated HCl (4 mL) in methanol (500 mL). The resulting mixture stirred overnight at room temperature. The mixture was filtered, and the filtrate was concentrated under vacuum. Potassium carbonate solution (10% aqueous, 50 mL) was added, and the resulting solution was extracted with 2×50 mL of dichloromethane, washed with 50 mL of brine, dried over anhydrous sodium sulfate, filtered, and concentrated under vacuum to give methyl 1,1-dimethylisoindoline-4-carboxylate (2 g) as a light yellow solid which was used without purification. MS: (ES, m/z): 206[M+H]$^+$

Intermediate 2. Ethyl isoindoline-4-carboxylate

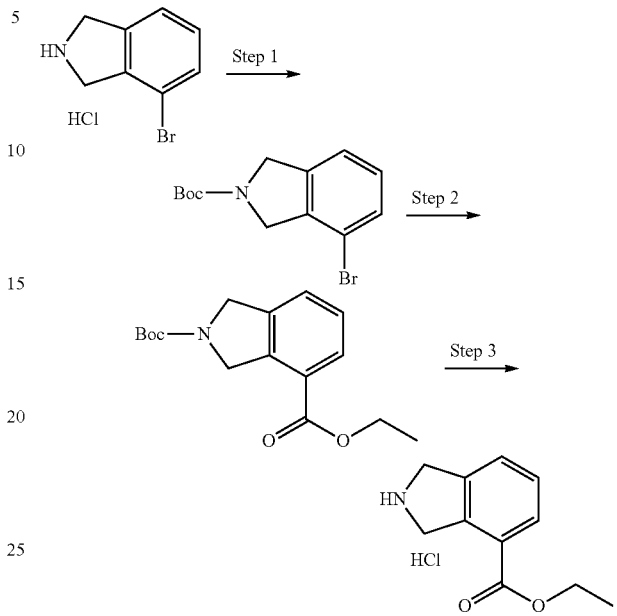

Step 1: tert-butyl 4-bromoisoindoline-2-carboxylate

A solution of 4-bromoisoindoline hydrochloride (8.00 g, 34.33 mmol) in dichloromethane (20 mL) and triethylamine (14.3 mL, 103.0 mmol) was cooled to 0° C., and then di-tert-butyl dicarbonate (15.0 g, 68.73 mmol) was added. The mixture stirred overnight at room temperature and was then quenched by the addition of 50 mL of water. The resulting solution was extracted with 3×50 mL of dichloromethane, washed with 1×50 mL of brine, dried over anhydrous sodium sulfate, filtered, and concentrated under vacuum. The residue was purified via column chromatography on silica gel (eluting with ethyl acetate/petroleum ether (1:5)) to afford tert-butyl 4-bromoisoindoline-2-carboxylate (9 g, 75%) as a white solid. MS: (ESI, m/z): 242 [M-t-Bu+H]+

Step 2: 2-(tert-butyl) 4-ethyl isoindoline-2,4-dicarboxylate

Carbon dioxide (g, 60 atm) was introduced into a 100-mL pressure tank reactor containing a solution of tert-butyl 4-bromo-2,3-dihydro-1H-isoindole-2-carboxylate (2.00 g, 6.71 mmol), triethylamine (2.80 mL, 20.1 mmol), and [1,1'-bis(diphenylphosphino)ferrocene]-dichloropalladium (II), complex with dichloromethane (820 mg, 1.12 mmol) in ethanol (50 mL). The resulting mixture stirred overnight at 120° C. The reaction was concentrated under vacuum and then quenched by the addition of 50 mL of water. The resulting solution was extracted with 3×50 mL of ethyl acetate, washed with 100 mL of brine, dried over anhydrous sodium sulfate, filtered, and concentrated under vacuum. The residue was purified via column chromatography on silica gel (eluting with ethyl acetate/petroleum ether (1:10)) to afford 2-(tert-butyl) 4-ethyl isoindoline-2,4-dicarboxylate (1.67 g, 85%) as an off-white solid. MS: (ESI, m/z): 292 [M+H]+

Step 3: ethyl isoindoline-4-carboxylate hydrochloride

A solution of 2-(tert-butyl) 4-ethyl 2,3-dihydro-1H-isoindole-2,4-dicarboxylate (1.67 g, 5.73 mmol) in HCl (2 M in 1,4-dioxane, 10 mL) stirred overnight at room temperature. The resulting mixture was concentrated under vacuum to give ethyl isoindoline-4-carboxylate hydrochloride (1.42 g) as a gray solid which was used without purification. MS: (ESI, m/z): 192[M−HCl+H]+

Intermediate 3. 2-chloro-5-(trifluoromethyl)-4,5,6,7-tetrahydro-1H-benzo[d]imidazole

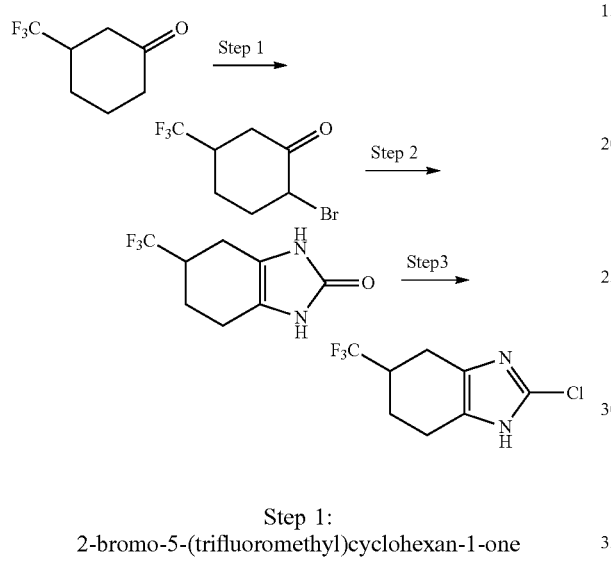

Step 1: 2-bromo-5-(trifluoromethyl)cyclohexan-1-one

Bromine (3.2 g, 20.02 mmol) was added dropwise to a solution of 3-(trifluoromethyl)cyclohexan-1-one (3 g, 18.06 mmol) in acetic acid (50 mL), and the resulting solution stirred for 3 h at room temperature. The reaction was then quenched by the addition of 200 mL of water. The resulting solution was extracted with 2×200 mL of ethyl acetate and the organic layers were combined. The resulting mixture was washed with 200 mL of 1 M aqueous sodium bicarbonate solution and then washed with 200 mL of brine. The mixture was dried over anhydrous sodium sulfate, filtered, and concentrated under vacuum to give 2-bromo-5-(trifluoromethyl)cyclohexan-1-one (4.7 g) as colorless oil that was used without purification. MS: (ESI, m/z): 245[M+H]+

Step 2. 5-(trifluoromethyl)-4,5,6,7-tetrahydro-1H-benzo[d]imidazol-2(3H)-one A solution of 2-bromo-5-(trifluoromethyl)cyclohexan-1-one (4.70 g, 19.18 mmol), urea (3.47 g, 57.8 mmol), ammonium acetate (4.60 g, 59.7 mmol), and acetic acid (3.4 mL, 60 mmol) in water (100 mL) stirred overnight at 100° C. The reaction mixture was cooled to room temperature with a water/ice bath. The solids were collected by filtration and dried to give 5-(trifluoromethyl)-4,5,6,7-tetrahydro-1H-benzo[d]imidazol-2(3H)-one (1.4 g) as a yellow solid that was used without purification. MS: (ESI, m/z): 207[M+H]+

Step 3. 2-chloro-5-(trifluoromethyl)-4,5,6,7-tetrahydro-1H-benzo[d]imidazole A mixture of 5-(trifluoromethyl)-4,5,6,7-tetrahydro-1H-benzo[d]imidazol-2(3H)-one (500 mg, 2.43 mmol) in phosphorous oxychloride (5 mL) stirred overnight at 90° C. The reaction was then poured into 20 mL of water. The pH value of the solution was adjusted to 8 with 2 M aqueous sodium carbonate solution. The resulting mixture was extracted with 3×20 mL of ethyl acetate and the organic layers were combined. The resulting mixture was washed with 20 mL of brine. The mixture was dried over anhydrous sodium sulfate, filtered, and concentrated under vacuum. The residue was purified via column chromatography on silica gel (eluting with ethyl acetate/petroleum ether (1:5)) to give 2-chloro-5-(trifluoromethyl)-4,5,6,7-tetrahydro-1H-benzo[d]imidazole (300 mg, 55%) as brown oil. MS: (ESI, m/z): 225[M+H]+

Example 1-1. N-hydroxy-2-(5-(trifluoromethyl)-4,5,6,7-tetrahydro-1H-benzo[d]imidazol-2-yl)isoindoline-4-carboxamide

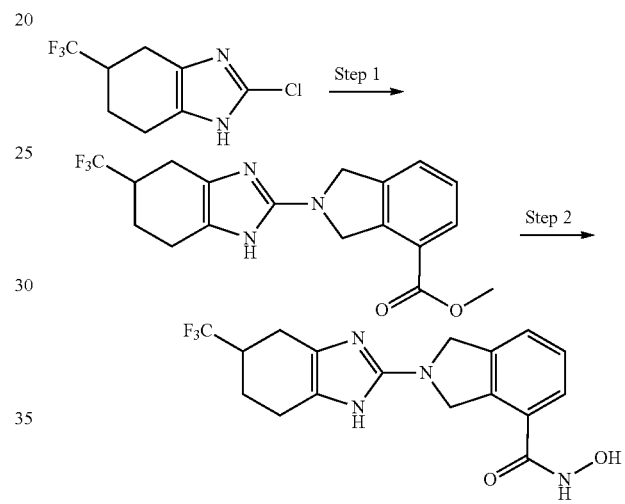

Step 1. methyl 2-(5-(trifluoromethyl)-4,5,6,7-tetrahydro-1H-benzo[d]imidazol-2-yl)isoindoline-4-carboxylate A solution of 2-chloro-5-(trifluoromethyl)-4,5,6,7-tetrahydro-1H-benzo[d]imidazole (200 mg, 0.89 mmol), methyl 2,3-dihydro-1H-isoindole-4-carboxylate hydrochloride (95 mg, 0.446 mmol) aqueous hydrogen chloride solution (6 M, 0.05 mL) in in butan-1-ol (3 mL) was irradiated with microwave radiation for 1 h at 170° C. The reaction was then quenched by the addition of 20 mL of water. The resulting solution was extracted with 3×20 mL of dichloromethane, washed with 20 mL of brine, dried over anhydrous sodium sulfate, filtered, and concentrated under vacuum. The residue was purified via column chromatography on silica gel (eluting with ethyl acetate/petroleum ether (1:5)) to give methyl 2-(5-(trifluoromethyl)-4,5,6,7-tetrahydro-1H-benzo[d]imidazol-2-yl)isoindoline-4-carboxylate (107 mg, 66%) as a gray solid MS: (ESI, m/z): 366[M+H]+.

Step 2. N-hydroxy-2-(5-(trifluoromethyl)-4,5,6,7-tetrahydro-1H-benzo[d]imidazol-2-yl)isoindoline-4-carboxamide A 10-mL sealed tube was charged with 2-(5-(trifluoromethyl)-4,5,6,7-tetrahydro-1H-benzo[d]imidazol-2-yl)isoindoline-4-carboxylate (100 mg, 0.27 mmol), hydroxyl amine solution (50% in water, 1.0 mL, 16.2 mmol), aqueous sodium hydroxide solution (1.0 M, 0.55 mL, 0.55 mmol), tetrahydrofuran (4.0 mL), and methanol (1.0 mL). The resulting solution stirred for 2 h at room temperature and was concentrated. The crude product was purified by Prep-HPLC with the following conditions: Column: X Bridge C18, 19×150 mm, 5 um; Mobile Phase A: Water/0.05% TFA, Mobile Phase B: ACN; Flow rate: 20 mL/min; Gradient: 30% B to 70% B in 10 min; 254 nm. The collected fractions were concentrated to afford N-hydroxy-2-(5-(trifluoromethyl)-4,5,6,7-tetrahydro-1H-benzo[d]imidazol-2-yl)isoindoline-4-carboxamide (32 mg, 32%) as an off-white solid. $^1$H-NMR (DMSO-$d_6$+$D_2O$, 400 MHz), δ (ppm): 6.85-6.68 (m, 3H), 4.32 (s, 2H), 4.07 (s, 2H), 2.05-1.87 (m, 5H), 1.46 (br, 1H), 1.03 (br, 1H), MS: (ESI, m/z): 367[M+H]$^+$ The following compounds were prepared according to the procedures described above for N-hydroxy-2-(5-(trifluoromethyl)-4,5,6,7-tetrahydro-1H-benzo[d]imidazol-2-yl)isoindoline-4-carboxamide.

| Ex. | Structure | Name | $^1$H NMR | (ESI, m/z) [M + H]+ |
|---|---|---|---|---|
| 1-2 | 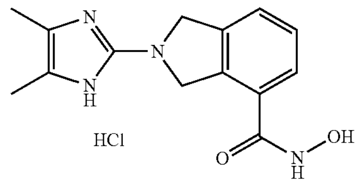 [SMILES: Cc1nc(N2Cc3cccc(C(=O)NO)c3C2)[nH]c1C ; Cl] | 2-(4,5-dimethyl-1H-imidazol-2-yl)-N-hydroxyisoindoline-4-carboxamide hydrochloride | (DMSO-$d_6$, 400 MHz, ppm): 12.29 (s, 2H), 11.33 (s, 1H), 9.12 (s, 1H), 7.65-7.57 (m, 2H), 7.48-7.44 (m, 1H), 5.00 (s, 2H), 4.80 (s, 2H), 2.08 (s, 6H) | 273[M − HCl + H]$^+$ |
| 1-3 | 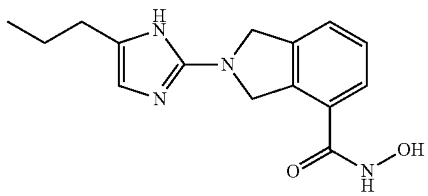 [SMILES: CCCc1cnc(N2Cc3cccc(C(=O)NO)c3C2)[nH]1] | N-hydroxy-2-(5-propyl-1H-imidazol-2-yl)isoindoline-4-carboxamide | (DMSO-$d_6$ + $D_2O$, 400 MHz, ppm): 6.84-6.68 (m, 3H), 5.91 (s, 1H), 4.33 (s, 2H), 4.08 (s, 2H), 1.77-1.75 (m, 2H), 0.92-0.83 (m, 2H), 0.25-0.13 (m, 3H). | 287 |
| 1-4 | 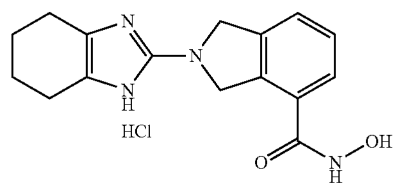 [SMILES: O=C(NO)c1cccc2c1CN(c1nc3c([nH]1)CCCC3)C2 ; Cl] | N-hydroxy-2-(4,5,6,7-tetrahydro-1H-benzo[d]imidazol-2-yl)isoindoline-4-carboxamide hydrochloride | (DMSO-$d_6$, 400 MHz, ppm): 12.43 (s, 2H), 11.33 (s, 1H), 9.12 (s, 1H), 7.79-7.57 (m, 2H), 7.48-7.43 (m, 1H), 4.94 (s, 2H), 4.81 (s, 2H), 2.45 (br, 4H), 1.75 (br, 4H). | 299[M − HCl + H]$^+$ |
| 1-5 | 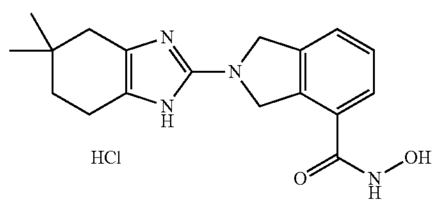 [SMILES: CC1(C)CCc2[nH]c(N3Cc4cccc(C(=O)NO)c4C3)nc2C1 ; Cl] | 2-(5,5-dimethyl-4,5,6,7-tetrahydro-1H-benzo[d]imidazol-2-yl)-N-hydroxyisoindoline-4-carboxamide hydrochloride | (DMSO-$d_6$, 400 MHz, ppm): 12.38 (br, 2H), 11.33 (s, 1H), 9.11 (s, 1H), 7.65-7.57 (m, 2H), 7.54-7.43 (m, 1H), 5.02 (s, 2H), 4.81 (s, 2H), 2.45-2.31 (m, 2H), 2.26 (s, 1H), 1.77-1.70 (m, 1H), 1.61-1.54 (m, 2H), 1.26 (s, 2H), 1.08-1.00 (m, 4H) | 327[M − HCl + H]$^+$ |
| 1-6 | 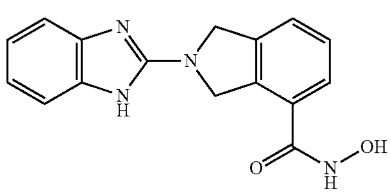 [SMILES: O=C(NO)c1cccc2c1CN(c1nc3ccccc3[nH]1)C2] | 2-(1H-benzo[d]imidazol-2-yl)-N-hydroxyisoindoline-4-carboxamide | $^1$H NMR (300 MHz, DMSO-$d_6$) δ ppm 10.37-11.85 (m, 2 H) 8.16 (s, 1 H) 7.52-7.66 (m, 2 H) 7.37-7.48 (m, 1 H) 7.24 (dd, J = 5.72, 3.08 Hz, 2 H) 6.96 (dd, J = 5.86, 3.22 Hz, 2 H) 5.06 (br s, 2 H) 4.85 (s, 2H) | 287 [M + H]+ |
| 1-7 | 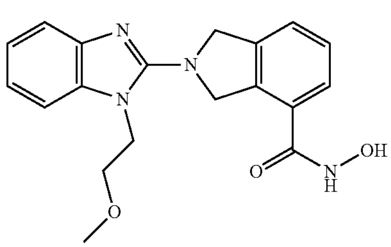 [SMILES: COCCn1c(N2Cc3cccc(C(=O)NO)c3C2)nc2ccccc21] | N-hydroxy-2-(1-(2-methoxyethyl)-1H-benzo[d]imidazol-2-yl)isoindoline-4-carboxamide | $^1$H NMR (300 MHz, DMSO-$d_6$) δ ppm 11.15 (br s, 1 H) 9.07 (br dd, J = 5.86, 2.64 Hz, 1 H) 7.47-7.52 (m, 1 H) 7.36 (d, J = 7.33 Hz, 1 H) 7.21-7.30 (m, 2 H) 6.95 (td, J = 7.11, 1.61 Hz, 3H) 5.13 (s, 2 H) 4.95 (s, 2 H) 4.36 (br t, J = 5.57 Hz, 2 H) 3.67 (t, J = 5.42 Hz, 2 H) 3.18 (s, 3 H) | 353 [M + H]+ |

Example 2-1. (R)—N-hydroxy-2-(5-(trifluoromethyl)-4,5,6,7-tetrahydro-1H-benzo[d]imidazol-2-yl)isoindoline-4-carboxamide hydrochloride

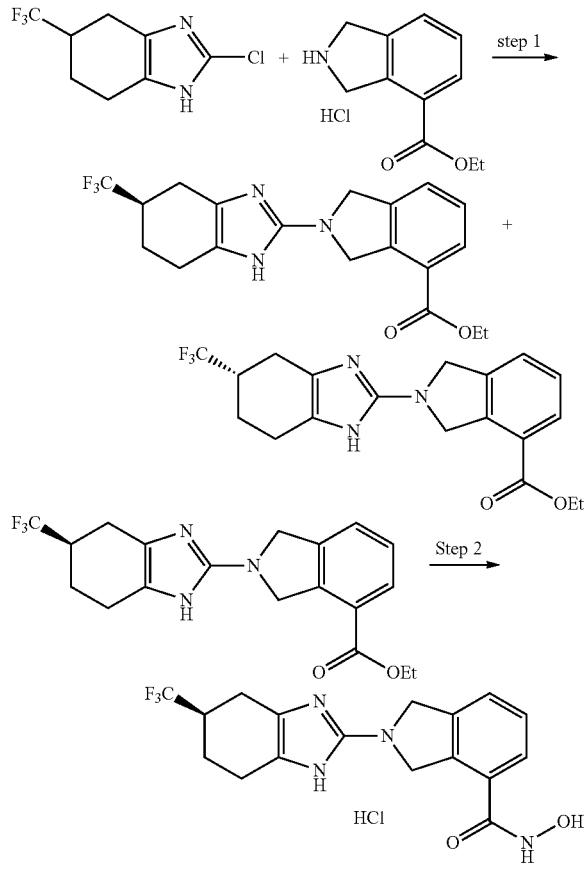

Step 1. (R)- and (S)-ethyl 2-(5-(trifluoromethyl)-4,5,6,7-tetrahydro-1H-benzo[d]imidazol-2-yl)isoindoline-4-carboxylate A 30-mL sealed tube was charged with 2-chloro-5-(trifluoromethyl)-4,5,6,7-tetrahydro-1H-1,3-benzodiazole (453 mg, 2.02 mmol), butan-1-ol (10 mL), ethyl 2,3-dihydro-1H-isoindole-4-carboxylate hydrochloride (680 mg, 2.99 mmol), and aqueous hydrogen chloride solution (6 M, 0.05 mL). The reaction mixture was irradiated with microwave radiation for 1.5 h at 170° C. The reaction was then quenched by the addition of 30 mL of water. The resulting solution was extracted with 3×50 mL of ethyl acetate and the organic layers combined. The resulting mixture was washed with 1×50 mL of brine. The mixture was dried over anhydrous sodium sulfate, filtered, and concentrated under vacuum. The residue was purified via column chromatography on silica gel (eluting with chloroform/methanol (1:10)) to afford 304 mg of racemic compound. This material was further purified by Chiral-Prep-HPLC with the following conditions: Column, ChiralPak IB 4.6×250 mm, 5μmHPLC chiral-A(IB)001 IB00CE-LA026; mobile phase, hexane (0.1% DEA):EtOH=90:10; Flow rate: 1 mL/min, RT1: 1.94,RT2:2.67, Detector, 254 nm. The first eluting isomer (Rt=1.94 min.) was collected and concentrated under vacuum to give (R)-ethyl 2-(5-(trifluoromethyl)-4,5,6,7-tetrahydro-1H-benzo[d]imidazol-2-yl)isoindoline-4-carboxylate (101 mg, 13%) as a yellow solid. MS: (ESI, m/z): 366[M+H]+. Absolute stereochemistry tentatively assigned.

The second eluting isomer (Rt=2.67 min.) was collected and concentrated to give (S)-ethyl 2-(5-(trifluoromethyl)-4,5,6,7-tetrahydro-1H-benzo[d]imidazol-2-yl)isoindoline-4-carboxylate (96 mg, 13%) as a light yellow solid. MS: (ESI, m/z): 366[M+H]+. Absolute stereochemistry tentatively assigned.

Step 2. (R)—N-hydroxy-2-(5-(trifluoromethyl)-4,5,6,7-tetrahydro-1H-benzo[d]imidazol-2-yl)isoindoline-4-carboxamide hydrochloride A solution of (R)-ethyl 2-(5-(trifluoromethyl)-4,5,6,7-tetrahydro-1H-benzo[d]imidazol-2-yl)isoindoline-4-carboxylate (100 mg, 0.26 mmol), hydroxyl amine (50 wt % in water, 2.8 mL, 42.2 mmol), 1 M aqueous sodium hydroxide solution (1.05 mL, 1.05 mmol), THF (4.0 mL) and methanol (1.0 mL) stirred for 2 h at room temperature. The mixture was cooled to 0° C., and the pH of the solution was adjusted to 6 with aqueous HCl solution (6.0 M). The resulting mixture was concentrated under vacuum. The crude product was purified by Prep-HPLC with the following conditions (Column: SunFire Prep C18 OBD Column, 5 um, 19×150 mm; mobile phase: water with 0.1% FA and ACN (5.0% ACN up to 30.0% in 9 min); Detector: UV 254 220 nm. The collected fraction was concentrated and then lyophilized with 1 mL of 2 M HCl solution to give (R)—N-hydroxy-2-(5-(trifluoromethyl)-4,5,6,7-tetrahydro-1H-benzo[d]imidazol-2-yl)isoindoline-4-carboxamide hydrochloride (14.4 mg, 14%) as an off-white solid. 1H-NMR (DMSO, 400 MHz), δ (ppm): 12.54 (s, 2H), 11.31 (s, 1H), 9.10 (s, 1H), 7.65-7.58 (m, 2H), 7.48-7.43 (t, J=7.5 Hz, 1H), 5.02 (s, 2H), 4.80 (s, 2H), 2.86-2.71 (m, 2H), 2.60-2.59 (d, J=3 Hz, 3H), 2.15-2.07 (t, J=13.2 Hz, 1H), 1.77-1.63 (m, 1H). MS: (ESI, m/z): 367[M−HCl+H]+. Absolute stereochemistry tentatively assigned.

Example 2-2. (S)—N-hydroxy-2-(5-(trifluoromethyl)-4,5,6,7-tetrahydro-1H-benzo[d]imidazol-2-yl)isoindoline-4-carboxamide hydrochloride (S)—N-hydroxy-2-(5-(trifluoromethyl)-4,5,6,7-tetrahydro-1H-benzo[d]imidazol-2-yl)isoindoline-4-carboxamide hydrochloride was prepared from (S)-ethyl 2-(5-(trifluoromethyl)-4,5,6,7-tetrahydro-1H-benzo[d]imidazol-2-yl)isoindoline-4-carboxylate (100 mg, 0.25 mmol) according to the procedure outlined above for give (R)—N-hydroxy-2-(5-(trifluoromethyl)-4,5,6,7-tetrahydro-1H-benzo[d]imidazol-2-yl)isoindoline-4-carboxamide hydrochloride to afford 3.3 mg (3%) of an off-white solid. 1H-NMR (DMSO, 400 MHz), δ (ppm): 12.05 (s, 2H), 11.33 (s, 1H), 9.12 (s, 1H), 7.66-7.59 (m, 2H), 7.50-7.45 (t, J=7.5 Hz, 1H), 5.03 (s, 2H), 4.81 (s, 2H), 2.87-2.84 (d, J=9.6 Hz, 1H), 2.79-2.72 (t, J=15.3 Hz, 1H), 2.60-2.58 (d, J=6.3 Hz, 3H), 2.16-2.13 (d, J=10.8 Hz, 1H), 1.75-1.66 (m, 1H). MS: (ESI, m/z): 367 [M+H-HCl]+. Absolute stereochemistry tentatively assigned.

Example 3-1. N-hydroxy-2-(3H-imidazo[4,5-c]pyridin-2-yl)isoindoline-4-carboxamide

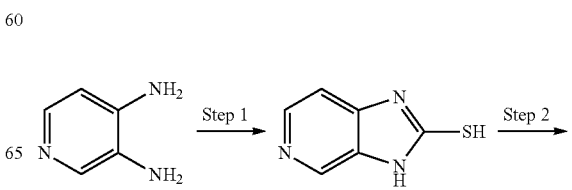

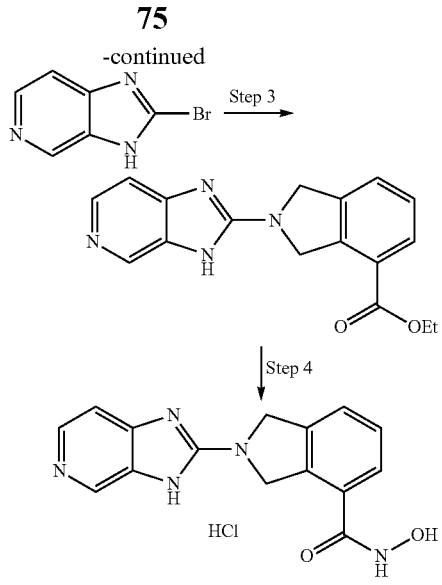

Step 1. 3H-imidazo[4,5-c]pyridine-2-thiol

A solution of pyridine-3,4-diamine (1.00 g, 9.16 mmol), carbon disulfide (14.00 g, 183.9 mmol), and potassium hydroxide (1.56 g, 27.8 mmol) in ethanol (25 mL) stirred overnight at 90° C. The resulting solution was diluted with 50 mL of water, and the pH value of the solution was adjusted to 6 with 6 M aqueous HCl solution. The solids were collected by filtration and dried to give 3H-imidazo[4,5-c]pyridine-2-thiol (500 mg) as an off-white solid which was used without purification. MS: (ESI, m/z): 152 [M+H]+.

Step 2. 2-bromo-3H-imidazo[4,5-c]pyridine

Bromine (837 mg, 5.24 mmol) was added to a solution of 3H-imidazo[4,5-c]pyridine-2-thiol (400 mg, 2.65 mmol) in HBr/AcOH (30 mL). The resulting mixture stirred for 2 h at room temperature and was then diluted with 100 mL of water. The pH value of the solution was adjusted to 5 with 2 M aqueous sodium hydroxide solution. The resulting solution was extracted with 100 mL of ethyl acetate and the combined organic layers were dried over anhydrous sodium sulfate, filtered, and concentrated. The residue was purified via column chromatography on silica gel (eluting with dichloromethane/methanol (10:1)) to afford 2-bromo-3H-imidazo[4,5-c]pyridine (250 mg, 48%) as a yellow solid. MS: (ESI, m/z): 198 [M+H]+.

Step 3. Ethyl 2-(3H-imidazo[4,5-c]pyridin-2-yl)isoindoline-4-carboxylate

A 10-mL microwave tube was charged with a solution of 2-bromo-3H-imidazo[4,5-c]pyridine (130 mg, 0.66 mmol), ethyl 2,3-dihydro-1H-isoindole-4-carboxylate hydrochloride (150 mg, 0.66 mmol), and HCl (6 M, 1 drop) in butan-1-ol (4 mL). The reaction mixture was irradiated with microwave radiation for 30 min at 160° C. The resulting solution was diluted with 15 mL of water and extracted with 3×15 mL of dichloromethane. The combined organic layers were dried over anhydrous sodium sulfate, filtered, and concentrated to afford ethyl 2-(3H-imidazo[4,5-c]pyridin-2-yl)isoindoline-4-carboxylate (90 mg, 44%) as a yellow oil. MS: (ESI, m/z): 309 [M+H]+.

Step 4. N-hydroxy-2-(3H-imidazo[4,5-c]pyridin-2-yl)isoindoline-4-carboxamide

A solution of ethyl 2-(3H-imidazo[4,5-c]pyridin-2-yl) isoindoline-4-carboxylate (90 mg, 0.29 mmol), hydroxyl amine (50 wt % in water, 0.6 mL, 17.4 mmol), 1 M aqueous sodium hydroxide solution (0.58 mL, 0.58 mmol), THF (4.0 mL) and methanol (1.0 mL) stirred for 2 h at room temperature. The crude product was purified by Prep-HPLC with the following conditions (Waters I): Column: SunFire Prep C18, 5 um, 19×100 mm; mobile phase: Water (0.05% NH4HCO3) and CH3CN (5% CH3CN up to 12% in 11 min); Detector, UV 220&254 nm. The collected fraction was lyophilized to give N-hydroxy-2-(3H-imidazo[4,5-c]pyridin-2-yl)isoindoline-4-carboxamide (2.2 mg, 3%) as a white solid. 1H-NMR (DMSO 400 MHz, ppm): δ 8.42 (s, 1H), 8.06 (s, 1H), 7.63-7.61 (d, J=7.6 Hz, 1H), 7.56-7.55 (d, J=7.2 Hz, 1H), 7.44-7.40 (m, 1H), 7.22-7.21 (d, J=5.2 Hz, 1H), 5.08 (s, 2H), 4.88 (s, 2H). MS: (ESI, m/z): 296 [M+H]+.

Example 4-1. N-hydroxy-2-(3H-imidazo[4,5-b]pyridin-2-yl)isoindoline-4-carboxamide

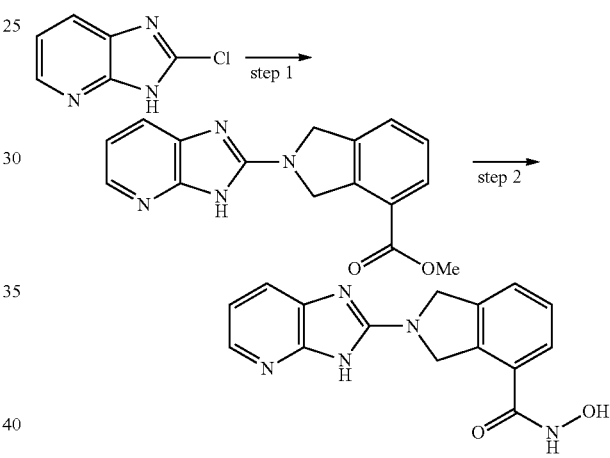

Step 1. methyl 2-(3H-imidazo[4,5-b]pyridin-2-yl)isoindoline-4-carboxylate

A 10-mL sealed tube was charged with 2-chloro-3H-imidazo[4,5-b]pyridine (72 mg, 0.47 mmol), n-butanol (3 mL), methyl 2,3-dihydro-1H-isoindole-4-carboxylate hydrochloride (100 mg, 0.47 mmol), and 6 M aqueous HCl solution (1 drop). The reaction mixture was irradiated with microwave radiation for 90 min at 180° C. The reaction was then quenched by the addition of 30 mL of water. The resulting solution was extracted with 3×50 mL of ethyl acetate, washed with 2×50 mL of brine, dried over anhydrous sodium sulfate, filtered, and concentrated under vacuum. The residue was purified via column chromatography on silica gel (eluting with dichloromethane/methanol (L10)) to afford methyl 2-(3H-imidazo[4,5-b]pyridin-2-yl)isoindoline-4-carboxylate (50 mg, 36%) of the title compound as a yellow solid. MS: (ESI, m/z): 295 [M+H]+.

Step 2. N-hydroxy-2-(3H-imidazo[4,5-b]pyridin-2-yl)isoindoline-4-carboxamide

Hydroxyl amine (50% in water, 674 mg, 10.2 mmol) and 1 M aqueous sodium hydroxide solution (0.34 mL, 0.34 mmol) were added to a solution of methyl 2-[3H-imidazo[4,5-b]pyridin-2-yl]-2,3-dihydro-1H-isoindole-4-carboxylate (50 mg, 0.17 mmol) in methanol:THF (1:4, 2 mL). The resulting solution was stirred for 4 h at room temperature, and the solids were filtered out. The crude product was purified by Prep-HPLC with the following conditions (Waters III: Column: X Bridge RP18, 19×150 mm, 5 μm; Mobile Phase A: Water/0.05% $NH_4HCO_3$, Mobile Phase B: ACN; Flow rate: 20 mL/min; Gradient: 30% B to 70% B in 10 min; 254 nm. The collected fraction was lyophilized to give N-hydroxy-2-(3H-imidazo[4,5-b]pyridin-2-yl)isoindoline-4-carboxamide (8 mg, 26%) as a white solid. $^1$H-NMR (DMSO 400 MHz, ppm): δ 7.86 (s, 1H), 7.65-7.39 (m, 4H), 6.96 (s, 1H), 5.08 (s, 2H), 4.86 (s, 2H). MS: (ESI, m/z): 296 [M+H]$^+$.

Example 5-1. N-hydroxy-2-(oxazolo[4,5-b]pyridin-2-yl)isoindoline-4-carboxamide hydrochloride

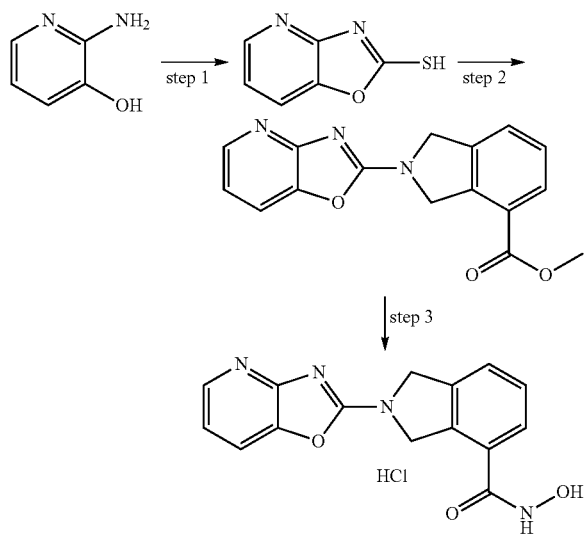

Step 1. oxazolo[4,5-b]pyridine-2-thiol

A solution of 2-aminopyridin-3-ol (3.00 g, 27.24 mmol), carbon disulfide (41.45 g, 544.8 mmol), and potassium hydroxide (5.40 g, 96.24 mmol) in ethanol (50 mL) was stirred for 2 h at 90° C. The reaction was then quenched by the addition of 150 mL of water. The resulting solution was extracted with 3×150 mL of ethyl acetate. The pH value of the combined aqueous layers was adjusted to 6 with 6 M aqueous HCl solution and then extracted with 3×150 mL of ethyl acetate. The organic layers were combined and dried over anhydrous sodium sulfate, filtered, and concentrated to give oxazolo[4,5-b]pyridine-2-thiol (3.0 g, 71%) as a red solid. MS: (ESI, m/z): 153[M+H]$^+$.

Step 2. 2-[[1,3]oxazolo[4,5-b]pyridin-2-yl]-2,3-dihydro-1H-isoindole-4-carboxylate A 10-mL microwave tube purged and maintained with an inert atmosphere of nitrogen, was charged with a solution of oxazolo[4,5-b]pyridine-2-thiol (142 mg, 0.93 mmol) and methyl 2,3-dihydro-1H-isoindole-4-carboxylate hydrochloride (100 mg, 0.47 mmol) in NMP (5 mL). The reaction mixture was irradiated with microwave radiation for 30 min at 160° C., and then diluted with 15 mL of water. The resulting solution was extracted with 3×15 mL of ethyl acetate, dried over anhydrous sodium sulfate, filtered, and concentrated under vacuum. The residue was purified via column chromatography on silica gel (eluting with 50% ethyl acetate-petroleum ether) to afford 2-[[1,3]oxazolo[4,5-b]pyridin-2-yl]-2,3-dihydro-1H-isoindole-4-carboxylate (60 mg, 43%) as a gray solid. MS: (ESI, m/z): 296[M+H]$^+$.

Step 3. N-hydroxy-2-(oxazolo[4f-b]pyridin-2-yl)isoindoline-4-carboxamide hydrochloride Hydroxyl amine (50% in water, 0.40 mL, 6.0 mmol) and 1 M aqueous sodium hydroxide solution (0.40 mL, 0.40 mmol) were added to a solution of methyl 2-[[1,3]oxazolo[4,5-b]pyridin-2-yl]-2,3-dihydro-1H-isoindole-4-carboxylate (60 mg, 0.20 mmol,) in THF:MeOH (4:1, 3 mL). The resulting solution was stirred for 2 h at room temperature. The crude product was purified by Prep-HPLC with the following conditions: Column: Xbridge RP18 5 μm, 19×150 mm; mobile phase, water (0.05% FA) and MeCN (5% $CH_3CN$ up to 23% in 7 min); Detector, UV 220/254 nm. The collected fraction was lyophilized with 1 mL of 2 M aqueous HCl solution to afford N-hydroxy-2-(oxazolo[4,5-b]pyridin-2-yl)isoindoline-4-carboxamide hydrochloride (11.7 mg, 17%) as an off-white solid. $^1$H-NMR (DMSO+$D_2O$ 300 MHz, ppm): δ 8.25-8.16 (m, 2H), 7.68-7.62 (m, 2H), 7.52-7.47 (t, J=7.8 Hz, 1H), 7.29-7.24 (m, 1H), 5.26 (s, 2H), 5.06 (s, 2H). MS: (ESI, m/z): 297[M+H]$^+$.

The following compound was prepared according to the procedures described above for N-hydroxy-2-(oxazolo[4,5-b]pyridin-2-yl)isoindoline-4-carboxamide hydrochloride.

| Ex. | Structure | Name | $^1$HNMR | (ESI, m/z) [M + H]$^+$ |
|---|---|---|---|---|
| 5-2 | 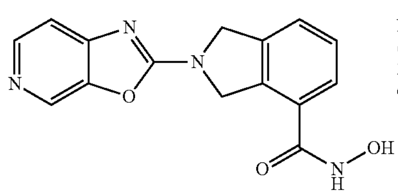 | N-hydroxy-2-(oxazolo[5,4-c]pyridin-2-yl)isoindoline-4-carboxamide | (DMSO, 300 MHz, ppm): 11.16 (s, 1H), 9.16 (s, 1H), 8.68 (s, 1H), 8.31-8.30 (d, J = 5.1 Hz, 1H), 7.66-7.58 (m, 2H), 7.48-7.43 (m, 1H), 7.37-7.35 (d, J = 5.1 Hz, 1H), 5.20 (s, 2H), 4.99 (s, 2H) | 297 |

Example 6-1. N-hydroxy-2-(oxazolo[4,5-c]pyridin-2-yl)isoindoline-4-carboxamide hydrochloride

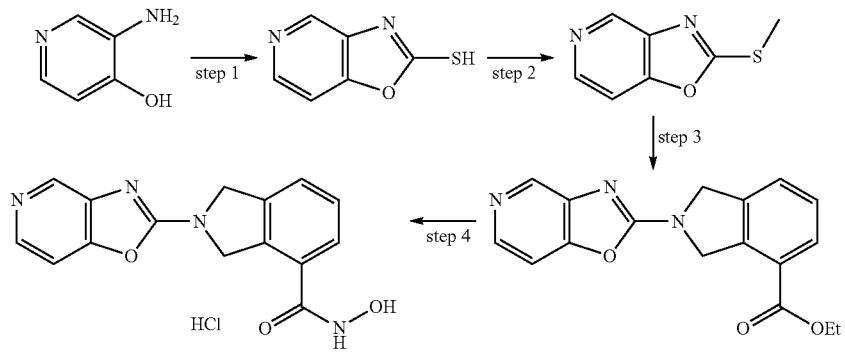

Step 1. oxazolo[4,5-c]pyridine-2-thiol

A solution of 3-aminopyridin-4-ol (2 g, 18.16 mmol), potassium hydroxide (3.6 g, 64.16 mmol), and carbon disulfide (27.4 g, 360 mmol) in ethanol (20 mL) was stirred overnight at 90° C. in an oil bath. The reaction was then quenched by the addition of 50 mL of water. The pH value of the solution was adjusted to 7 with 6M aqueous HCl solution. The resulting solution was extracted with 3×100 mL of ethyl acetate, dried over anhydrous sodium sulfate, filtered, and concentrated under vacuum. The residue was purified via column chromatography on silica gel (eluting with 10:1 dichloromethane/methanol) to afford oxazolo[4,5-c]pyridine-2-thiol (1 g, 36%) as a brown solid. MS: (ESI, m/z): 153[M+H]$^+$.

Step 2. 2-(methylthio)oxazolo[4,5-c]pyridine

A solution of oxazolo[4,5-c]pyridine-2-thiol (300 mg, 1.97 mmol), potassium carbonate (276 mg, 2.00 mmol), and methyl iodide (273 mg, 1.20 equiv) in N,N-dimethylformamide (3 mL) stirred for 2 h at room temperature. The reaction was then quenched by the addition of 10 mL of water. The resulting solution was extracted with 3×20 mL of ethyl acetate and the combined organic layers were washed with 30 mL of brine, dried over anhydrous sodium sulfate, filtered, and concentrated under vacuum to afford 2-(methylthio)oxazolo[4,5-c]pyridine (250 mg, 76%) of the as a yellow solid. MS: (ESI, m/z): 167[M+H]$^+$.

Step 3. ethyl 2-(oxazolo[4,5-c]pyridin-2-yl)isoindoline-4-carboxylate

A solution of 2-(methylthio)oxazolo[4,5-c]pyridine (60 mg, 0.36 mmol) and ethyl 2,3-dihydro-1H-isoindole-4-carboxylate hydrochloride (40 mg, 0.18 mmol) in NMP (2 mL) was irradiated with microwave radiation for 2 h at 160° C. The reaction was then quenched by the addition of 10 mL of water. The resulting solution was extracted with 3×10 mL of ethyl acetate, and the combined organic phases were washed with 20 mL of brine, dried over anhydrous sodium sulfate, filtered, and concentrated under vacuum. The residue was purified via preparative TLC (eluting with 10:1 dichloromethane/methanol) to afford ethyl 2-(oxazolo[4,5-c]pyridin-2-yl)isoindoline-4-carboxylate (30 mg, 27%) as a brown solid. MS: (ESI, m/z): 310[M+H]$^+$.

Step 4. N-hydroxy-2-(oxazolo[4,5-c]pyridin-2-yl)isoindoline-4-carboxamide hydrochloride Hydroxyl amine (50% in water, 0.37 mL, 6.0 mmol) and 1 M aqueous sodium hydroxide solution (0.10 mL, 0.10 mmol) were added to a solution of ethyl 2-[[1,3]oxazolo[4,5-c]pyridin-2-yl]-2,3-dihydro-1H-isoindole-4-carboxylate (30 mg, 0.10 mmol) in THF:MeOH (4:1, 3 mL). The resulting solution was stirred for 3 h at room temperature. The crude product was purified by Prep-HPLC with the following conditions (X-Bridge): Column: RP18 19×150; mobile phase, A: 0.05% FA, B:ACN 8-30/8 min; Detector, 254 nm. The collected fraction was lyophilized with 1 mL of 2M aqueous HCl solution to give N-hydroxy-2-(oxazolo[4,5-c]pyridin-2-yl)isoindoline-4-carboxamide hydrochloride (7.7 mg, 24%) as an off-white solid. $^1$H-NMR (DMSO, 300 MHz) δ (ppm): 1.36 (s, 1H), 10.28-10.08 (br, 1H), 9.01 (s, 1H), 8.64-8.62 (d, J=6.3 Hz, 1H), 8.21-8.19 (d, J=6.3 Hz, 1H), 7.70-7.61 (m, 2H), 7.51-7.46 (t, J=7.8 Hz, 1H), 5.26 (s, 2H), 5.17 (s, 2H). MS: (ESI, m/z): 297[M−HCl+H]$^+$ The following compound was prepared according to the procedures described above for N-hydroxy-2-(oxazolo[4,5-c]pyridin-2-yl)isoindoline-4-carboxamide hydrochloride.

| Ex. | Structure | Name | $^1$HNMR | (ESI, m/z) [M + H]$^+$ |
|---|---|---|---|---|
| 6-2 | 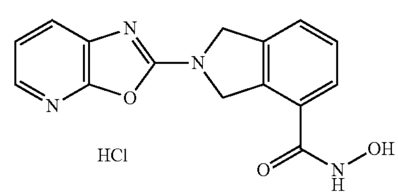 [SMILES: O=C(NO)c1cccc2c1CN(c1nc3cccnc3o1)C2 ; Cl] | N-hydroxy-2-(oxazolo[5,4-b]pyridin-2-yl)isoindoline-4-carboxamide hydrochloride | (DMSO, 300 MHz, ppm): 11.28 (s, 1H), 7.93-7.90 (m, 1H), 7.91-7.59 (m, 3H), 7.48-7.43 (t, J = 7.8 Hz, 1H), 7.29-7.22 (m, 1H), 5.17 (s, 2H), 4.98 (s, 2H). | 297 |

Example 7-1. N-hydroxy-2-(quinazolin-2-yl)isoindoline-4-carboxamide

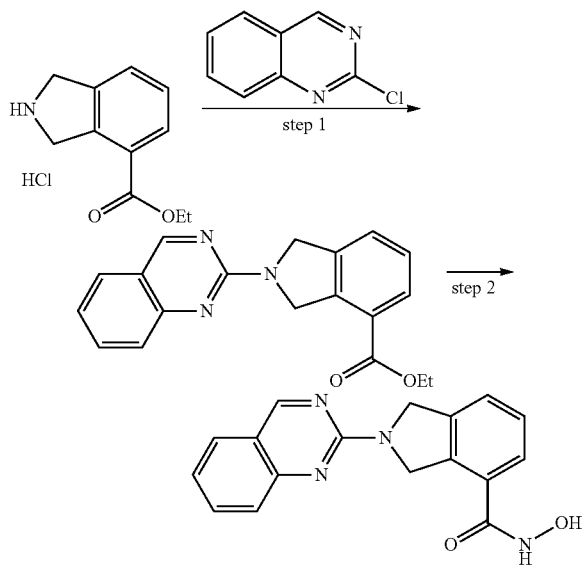

Step 1: ethyl 2-(quinazolin-2-yl)-2,3-dihydro-1H-isoindole-4-carboxylate

A solution of ethyl 2,3-dihydro-1H-isoindole-4-carboxylate hydrochloride (91.7 mg, 0.40 mmol), 2-chloroquinazoline (60 mg, 0.36 mmol) and 6 M aqueous HCl solution (1 drop) in n-butanol (3 mL) was irradiated with microwave radiation for 1 h at 170° C. The reaction was then quenched by the addition of 10 mL of water. The resulting solution was extracted with 2×20 mL of dichloromethane, and the combined organic layers were washed with 1×10 mL of brine, dried over anhydrous sodium sulfate, filtered, and concentrated under vacuum. The residue was purified via column chromatography on silica gel (eluting with 10:1 dichloromethane/methanol) to afford ethyl 2-(quinazolin-2-yl)-2,3-dihydro-1H-isoindole-4-carboxylate (92 mg, 79%) as yellow oil. MS: (ESI, m/z): 320[M+H]$^+$.

Step 2: N-hydroxy-2-(quinazolin-2-yl)-2,3-dihydro-1H-isoindole-4-carboxamide Hydroxyl amine (50% in water, 1.1 mL, 17.3 mmol) and 1 M aqueous sodium hydroxide solution (0.58 mL, 0.58 mmol) were added to a solution of ethyl 2-(quinazolin-2-yl)-2,3-dihydro-1H-isoindole-4-carboxylate (92 mg, 0.29 mmol,) in THF:MeOH (4:1, 5 mL). The resulting solution was stirred for 2 h at room temperature. The crude product was purified by Prep-HPLC with the following conditions: Column: SunFire Prep C18, 5 μm, 19×100 mm; mobile phase, Water (0.1% FA) and CH$_3$CN (3% CH$_3$CN up to 18% in 9 min); Detector, UV 220&254 nm. The collected fraction was lyophilized to give N-hydroxy-2-(quinazolin-2-yl)-2,3-dihydro-1H-isoindole-4-carboxamide (2.0 mg, 2%) as a yellow solid. $^1$H-NMR (DMSO, 400 Hz, ppm): δ 11.29 (s, 1H), 8.75 (s, 1H), 8.35-8.33 (d, J=7.6 Hz, 2H), 7.78-7.76 (m, 1H), 7.64-7.62 (d, J=7.6 Hz, 2H), 7.50-7.46 (t, J=7.6 Hz, 2H), 5.24 (s, 2H), 5.06 (s, 2H). MS: (ESI, m/z): 307[M+H]$^+$.

The following compounds were prepared according to the procedures described above for N-hydroxy-2-(quinazolin-2-yl)-2,3-dihydro-1H-isoindole-4-carboxamide:

| Ex. | Structure | Name | $^1$HNMR | (ESI, m/z) [M + H]$^+$ |
|---|---|---|---|---|
| 7-2 | 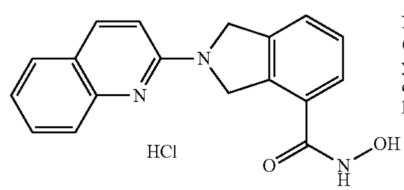 [SMILES: O=C(NO)c1cccc2c1CN(c1ccc3ccccc3n1)C2 ; Cl] | N-hydroxy-2-(quinolin-2-yl)isoindoline-4-carboxamide hydrochloride | (DMSO, 400 MHz, ppm): 11.44 (s, 1H), 9.21 (s, 1H), 8.53 (s, 1H), 8.25-7.84 (m, 3H), 7.75-7.39 (m, 5H), 5.47 (s, 2H), 5.17 (s, 2H) | 306 |
| 7-3 | 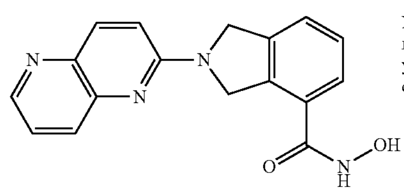 [SMILES: O=C(NO)c1cccc2c1CN(c1ccc3ncccc3n1)C2] | N-hydroxy-2-(1,5-naphthyridin-2-yl)isoindoline-4-carboxamide | (DMSO, 300 MHz, ppm): 11.32-11.16 (br, 1H), 9.16 (br, 1H), 8.58-8.56 (m, 1H), 8.16-8.13 (d, J = 9.3 Hz, 1H), 8.08-8.00 (m, 1H), 7.59-7.52 (m, 3H), 7.49-7.40 (t, J = 7.5 Hz, 1H), 7.25-7.22 (d, J = 9.3 Hz, 1H), 5.13 (s, 2H), 4.95 (s, 2H) | 307 |
| 7-4 | 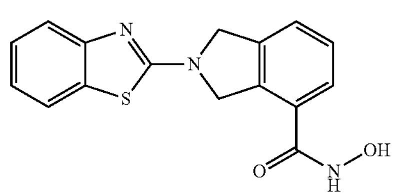 [SMILES: O=C(NO)c1cccc2c1CN(c1nc3ccccc3s1)C2] | 2-(benzo[d]thiazol-2-yl)-N-hydroxyisoindoline-4-carboxamide | (DMSO, 400 MHz, ppm): 9.18 (br, 1H), 7.83 (d, 8.0 Hz, 1H), 7.64-7.54 (m, 3H), 7.47-7.43 (m, 1H), 7.34-7.30 (t, J = 7.6 Hz, 1H), 7.11-7.07 (t, J = 7.6 Hz, 1H), 5.07 (s, 2H), 4.90 (s, 2H) | 312 |

| Ex. | Structure | Name | ¹HNMR | (ESI, m/z) [M + H]⁺ |
|---|---|---|---|---|
| 7-5 | 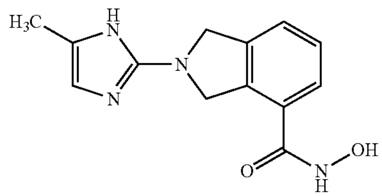 [SMILES: Cc1cnc(N2Cc3cccc(C(=O)NO)c3C2)[nH]1] | N-hydroxy-2-(5-methyl-1H-imidazol-2-yl)isoindoline-4-carboxamide | (DMSO, 400 MHz, ppm): 8.20 (s, 1H), 7.54-7.50 (m, 2H), 7.40-7.36 (m, 1H), 6.37 (s, 1H), 4.82 (s, 2H), 4.62 (s, 2H). 2.05 (s, 3H). | 259 |

Example 8-1. N-hydroxy-2-(1,5-naphthyridin-3-yl)isoindoline-4-carboxamide

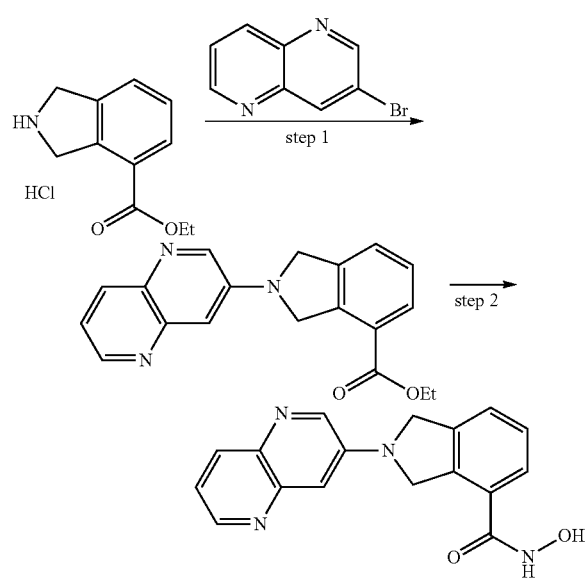

Step 1. ethyl 2-(1,5-naphthyridin-3-yl)-2,3-dihydro-1H-isoindole-4-carboxylate

A solution of ethyl 2,3-dihydro-1H-isoindole-4-carboxylate hydrochloride (80 mg, 0.35 mmol), 3-bromo-1,5-naphthyridine (144 mg, 0.69 mmol), Pd₂(dba)₃-chloroform adduct (18.2 mg, 0.018 mmol), XantPhos (20.3 mg, 0.04 mmol), and cesium carbonate (344 mg, 1.06 mmol) in toluene (5 mL) stirred for 16 h at 100° C. The reaction was then quenched by the addition of 10 mL of water. The resulting solution was extracted with 2×20 mL of dichloromethane, and the combined organic phases were washed with 1×10 mL of brine, dried over anhydrous sodium sulfate, filtered, and concentrated under vacuum. The residue was purified via column chromatography on silica gel (eluting with 20:1 dichloromethane/methanol) to afford ethyl 2-(1,5-naphthyridin-3-yl)-2,3-dihydro-1H-isoindole-4-carboxylate (110 mg, 98%) as a red solid. MS: (ESI, m/z): 320[M+H]⁺.

Step 2. N-hydroxy-2-(1,5-naphthyridin-3-yl)isoindoline-4-carboxamide

Hydroxyl amine (50% in water, 1.3 mL, 20.7 mmol) and 1 M aqueous sodium hydroxide solution (0.69 mL, 0.69 mmol) were added to a solution of ethyl 2-(1,5-naphthyridin-3-yl)-2,3-dihydro-1H-isoindole-4-carboxylate (110 mg, 0.34 mmol) in THF:MeOH (4:1, 5 mL). The resulting solution was stirred for 2 h at room temperature. The crude product was purified by Prep-HPLC with the following conditions: Column: SunFire Prep C18, 5 μm, 19×150 mm; mobile phase, Water (0.1% FA) and CH₃CN (5% CH₃CN up to 20% in 8 min). The collected fraction was lyophilized to give N-hydroxy-2-(1,5-naphthyridin-3-yl)isoindoline-4-carboxamide (17.4 mg, 16%) as a yellow solid. ¹H-NMR: (DMSO, 300 MHZ, ppm): δ 11.23 (br, 1H), 9.13 (br, 1H), 8.82-8.75 (m, 2H), 8.25-8.23 (d, J=7.5 Hz, 1H), 7.61-7.59 (d, J=7.5 Hz, 2H), 7.47-7.39 (m, 2H), 7.23-7.22 (d, J=2.4 Hz, 1H), 5.04 (s, 2H), 4.89 (s, 2H). MS: (ESI, m/z): 307[M+H]⁺

Example 9-1. 2-(3,4-dihydro-2H-benzo[b][1,4]oxazin-7-yl)-N-hydroxyisoindoline-4-carboxamide hydrochloride

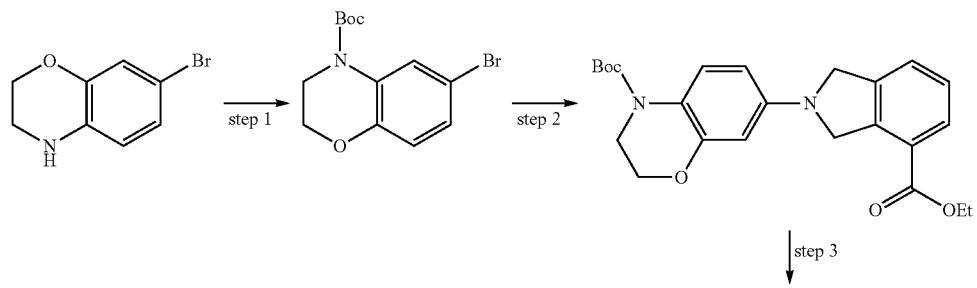

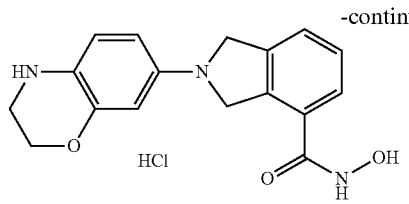 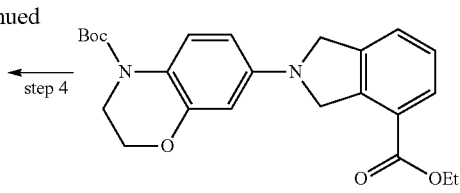

-continued step 4

Step 1. tert-butyl 7-bromo-3,4-dihydro-2H-1,4-benzoxazine-4-carboxylate

A solution of 7-bromo-3,4-dihydro-2H-1,4-benzoxazine (600 mg, 2.80 mmol), di-tert-butyl dicarbonate (1.82 g, 8.33 mmol), and 4-dimethylaminopyridine (203 mg, 1.66 mmol) in pyridine (5 mL) was stirred for 16 h at 90° C. The resulting mixture was concentrated under vacuum. The residue was purified via column chromatography on silica gel (eluting with 1:10 ethyl acetate/petroleum ether) to afford tert-butyl 7-bromo-3,4-dihydro-2H-1,4-benzoxazine-4-carboxylate (440 mg, 50%) as a yellow solid.

Step 2. tert-butyl 7-[4-(ethoxycarbonyl)-2,3-dihydro-1H-isoindol-2-yl]-3,4-dihydro-2H-1,4-benzoxazine-4-carboxylate A solution of tert-butyl 7-bromo-3,4-dihydro-2H-1,4-benzoxazine-4-carboxylate (440 mg, 1.40 mmol), ethyl 2,3-dihydro-1H-isoindole-4-carboxylate hydrochloride (159.7 mg, 0.70 mmol), $Pd_2(dba)_3$-chloroform adduct (36.2 mg, 0.035 mmol), RuPhos (32.6 mg, 0.07 mmol), cesium carbonate (685 mg, 2.10 mmol) in toluene (5 mL). The resulting solution was stirred for 16 h at 100° C. The reaction was then quenched by the addition of 10 mL of water. The resulting solution was extracted with 2×10 mL of dichloromethane, and the combined organic phases were washed with 10 mL of brine, dried over anhydrous sodium sulfate, filtered, and concentrated under vacuum. The residue was purified via column chromatography on silica gel (eluting with ethyl acetate/petroleum ether (1:10)) to afford tert-butyl 7-[4-(ethoxycarbonyl)-2,3-dihydro-1H-isoindol-2-yl]-3,4-dihydro-2H-1,4-benzoxazine-4-carboxylate (220 mg, 74%) as a red solid. MS: (ESI, m/z): 425[M+H]$^+$.

Step 3. ethyl 2-(3,4-dihydro-2H-1,4-benzoxazin-7-yl)-2,3-dihydro-1H-isoindole-4-carboxylate A solution of tert-butyl 7-[4-(ethoxycarbonyl)-2,3-dihydro-1H-isoindol-2-yl]-3,4-dihydro-2H-1,4-benzoxazine-4-carboxylate (210 mg, 0.49 mmol) and trifluoroacetic acid (0.5 mL) in dichloromethane (2 mL) was stirred for 1 h at room temperature and then concentrated under vacuum. Water (20 mL) was added, and the pH value of the solution was adjusted to 8 with 2 M potassium carbonate solution. The resulting solution was extracted with 2×20 mL of dichloromethane, and the combined organic layers were washed with 20 mL of brine, dried over anhydrous sodium sulfate, filtered, and concentrated under vacuum. The residue was purified via column chromatography on silica gel (eluting with ethyl acetate/petroleum ether (2:1)) to afford ethyl 2-(3,4-dihydro-2H-1,4-benzoxazin-7-yl)-2,3-dihydro-1H-isoindole-4-carboxylate (80 mg, 50%) as a green solid. MS: (ESI, m/z): 325[M+H]$^+$.

Step 4. 2-(3,4-dihydro-2H-1,4-benzoxazin-7-yl)-N-hydroxy-2,3-dihydro-1H-isoindole-4-carboxamide Hydroxyl amine (50% in water, 0.90 mL, 14.7 mmol) and 1 M aqueous sodium hydroxide solution (0.25 mL, 0.25 mmol) were added to a solution of ethyl 2-(3,4-dihydro-2H-1,4-benzoxazin-7-yl)-2,3-dihydro-1H-isoindole-4-carboxylate (40 mg, 0.12 mmol) in THF:MeOH (4:1, 5 mL). The resulting solution was stirred for 2 h at room temperature. The pH value of the solution was adjusted to 3 with 6 M aqueous HCl solution. The resulting mixture was concentrated under vacuum and diluted with 10 mL of tetrahydrofuran, and the solids were removed by filtration. The crude product was purified by Prep-HPLC with the following conditions: Column: XBridge BEH C18 OBD Prep Column, 5 µm, 19 mm×250 mm; mobile phase, water with 0.05% TFA and ACN (10.0% ACN up to 25.0% in 10 min); Detector, uv 254&220 nm. The collected fraction was lyophilized to give 2-(3,4-dihydro-2H-1,4-benzoxazin-7-yl)-N-hydroxy-2,3-dihydro-1H-isoindole-4-carboxamide (2.9 mg, 7%) as a brown solid. $^1$H-NMR: (DMSO, 300 MHZ, ppm): δ 11.19 (br, 1H), 10.93 (br, 1H), 9.07 (br, 1H), 7.57-7.52 (t, J=7.95 Hz, 2H), 7.72-7.37 (t, J=7.65 Hz, 1H), 7.20-7.03 (m, 1H), 6.35-6.33 (d, J=7.8 Hz, 1H), 6.15 (s, 1H), 4.75 (s, 2H), 4.58 (s, 2H), 4.37 (s, 2H), 3.48 (s, 2H). MS: (ESI, m/z): 312[M−HCl+H]$^+$.

The following compound was prepared according to the procedures described above for 2-(3,4-dihydro-2H-1,4-benzoxazin-7-yl)-N-hydroxy-2,3-dihydro-1H-isoindole-4-carboxamide.

| Ex. | Structure | Name | $^1$HNMR | (ESI, m/z) [M + H]$^+$ |
|---|---|---|---|---|
| 9-2 | 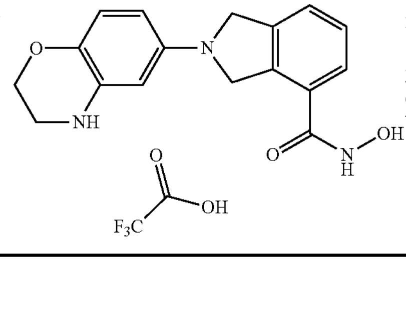 | 2-(3,4-dihydro-2H-benzo[b][1,4]oxazin-6-yl)-N-hydroxyisoindoline-4-carboxamide 2,2,2-trifluoroacetate | (DMSO, 300 MHz, ppm): 11.13 (br, 1H), 7.52-7.50 (d, J = 7.8 Hz, 2H), 7.37-7.31 (m, 1H), 6.59-6.56 (d, J = 8.7 Hz, 1H), 5.96-5.85 (m, 2H), 4.64 (s, 2H), 4.47 (s, 2H), 4.04 (s, 2H), 3.28 (s, 2H) | 312 |

Example 10-1. N-hydroxy-2-(thiazolo[4,5-b]pyridin-2-yl)isoindoline-4-carboxamide

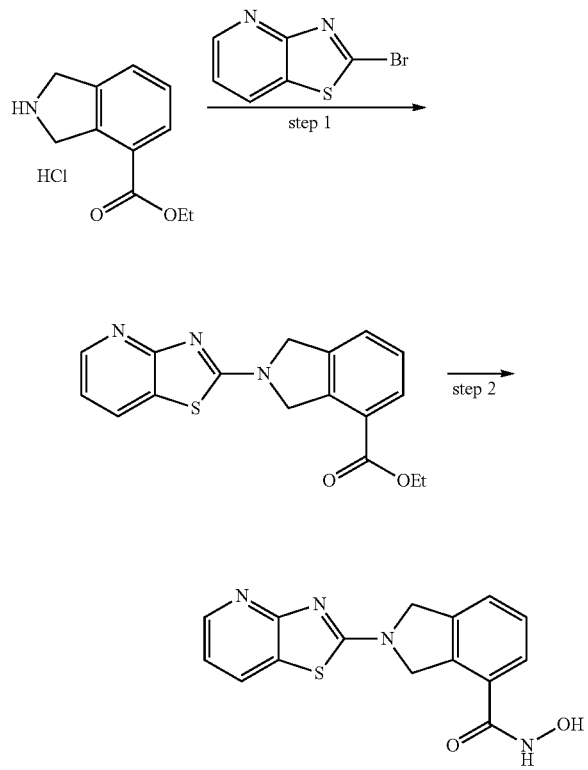

Step 1. ethyl 2-(thiazolo[4,5-b]pyridin-2-yl)isoindoline-4-carboxylate

A solution of 2-bromo-[1,3]thiazolo[4,5-b]pyridine (285 mg, 1.33 mmol), ethyl 2,3-dihydro-1H-isoindole-4-carboxylate hydrochloride (100 mg, 0.44 mmol), RuPhos 2G (51 mg, 0.044 mmol), RuPhos (32 mg, 0.044 mmol), cesium carbonate (645 mg, 1.98 mmol) in toluene (5 mL) stirred overnight at 100° C. in an oil bath. The residue was dissolved in 20 mL of dichloromethane-methanol (10:1), the solids were filtered off, and the resulting mixture was concentrated under vacuum. The residue was purified via column chromatography on silica gel (eluting with ethyl acetate/petroleum ether (99:1)) to give ethyl 2-(thiazolo[4,5-b]pyridin-2-yl)isoindoline-4-carboxylate (150 mg) as an orange solid. MS: (ESI, m/z): 326[M+H]$^+$

Step 2. N-hydroxy-2-(thiazolo[4,5-b]pyridin-2-yl)isoindoline-4-carboxamide

Hydroxyl amine (50% in water, 2.2 mL, 36.3 mmol) and 1 M aqueous sodium hydroxide solution (0.62 mL, 0.62 mmol) were added to a solution of ethyl 2-(thiazolo[4,5-b]pyridin-2-yl)isoindoline-4-carboxylate (100 mg, 0.31 mmol), in THF:MeOH (4:1, 3 mL). The resulting solution was stirred for 3 h at 25° C. in an oil bath. The crude product was purified by Prep-HPLC with the following conditions: Column: XBridge Prep C18 OBD Column, 5 um, 19×150 mm; mobile phase, water with 10 mmol NH$_4$HCO$_3$ and ACN (5.0% ACN up to 40.0% in 8 min); Detector: UV 254/220 nm. The collected fraction was lyophilized to give N-hydroxy-2-(thiazolo[4,5-b]pyridin-2-yl)isoindoline-4-carboxamide (31.7 mg, 33%) as a white solid. $^1$H-NMR: (DMSO, 400 MHz, ppm): 59.44 (s, 1H), 8.35-8.33 (m, 2H), 7.65-7.60 (m, 2H), 7.48-7.44 (m, 1H), 7.08-7.05 (m, 1H), 5.10-4.93 (br, 4H). MS: (ESI, m/z): 313[M+H]$^+$

Example 11-1. N-hydroxy-2-(5-(trifluoromethyl)benzo[d]thiazol-2-yl)isoindoline-4-carboxamide

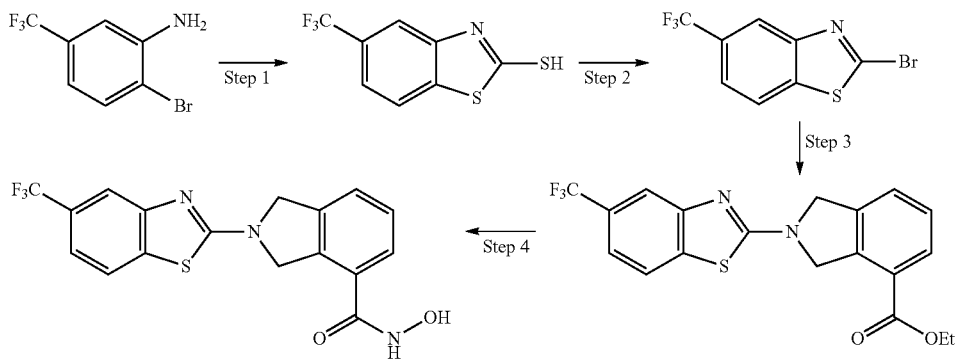

Step 1: 5-(trifluoromethyl)-1,3-benzothiazole-2-thiol

A solution of 2-bromo-5-(trifluoromethyl)aniline (5.0 g, 20.8 mmol) and potassium O-ethyl carbonodithioate (4.69 g, 29.26 mmol) in N,N-dimethylformamide (25 mL) stirred overnight at 130° C. in an oil bath. The reaction was then quenched by the addition of 100 mL of water. The pH value of the solution was adjusted to 6 with 2M aqueous HCl solution. The solids were collected by filtration and dried by air to give 5-(trifluoromethyl)-1,3-benzothiazole-2-thiol (3.0 g, 61%) as a brown solid. MS: (ESI, m/z): 234[M−H]$^-$.

Step 2: 2-bromo-5-(trifluoromethyl)benzo[d]thiazole

Bromine (3.4 g, 21.3 mmol) was added to a 5-10° C. solution of 5-(trifluoromethyl)-1,3-benzothiazole-2-thiol (5 g, 21.25 mmol) in hydrogen bromide (40% in acetic acid, 30 mL). The resulting solution was stirred for 1.5 h at 10° C. and then quenched by the addition of 15 mL of ice water. The pH value of the solution was adjusted to 5 with 2 M aqueous NaOH solution. The resulting solution was extracted with 3×100 mL of dichloromethane, and the combined organic phases were dried over anhydrous sodium sulfate, filtered, and concentrated under vacuum to give 2-bromo-5-(trifluoromethyl)benzo[d]thiazole (2.1 g, 35%) as a red solid. MS: (ESI, m/z): 282[M+H]+.

Step 3: ethyl 2-(5-(trifluoromethyl)benzo[d]thiazol-2-yl)isoindoline-4-carboxylate A solution of 22-bromo-5-(trifluoromethyl)benzo[d]thiazole (350 mg, 1.24 mmol), ethyl 2,3-dihydro-1H-isoindole-4-carboxylate hydrochloride (189 mg, 0.83 mmol), and 6 M aqueous HCl solution (1 drop) in n-BuOH (3 mL) was irradiated with microwave radiation for 1 h at 170° C. The reaction was then quenched by the addition of 15 mL of water. The resulting solution was extracted with 3×30 mL of ethyl acetate, and the combined organic layers were washed with 100 mL of brine, dried over anhydrous sodium sulfate, filtered, and concentrated under vacuum. The residue was purified via column chromatography on silica gel (eluting with ethyl acetate/petroleum ether (1:10)) to afford ethyl 2-(5-(trifluoromethyl)benzo[d]thiazol-2-yl)isoindoline-4- (80 mg, 25%) as a gray solid. MS: (ESI, m/z): 393[M+H]+.

Step 4: N-hydroxy-2-(5-(trifluoromethyl)benzo[d]thiazol-2-yl)isoindoline-4-carboxamide Hydroxyl amine (50% in water, 1.30 mL, 21.2 mmol) and 1 M aqueous sodium hydroxide solution (0.36 mL, 0.36 mmol) were added to a solution of ethyl 2-[5-(trifluoromethyl)-1,3-benzothiazol-2-yl]-2,3-dihydro-1H-isoindole-4-carboxylate (70 mg, 0.18 mmol) in THF:MeOH (4:1, 4 mL). The resulting solution was stirred for 2 h at room temperature. The pH value of the solution was adjusted to 6 with 6 M aqueous HCl solution. The crude product was purified by Prep-HPLC with the following conditions: Column: XBridge Prep C18 OBD Column, 5 um, 19×150 mm; Mobile Phase A:water with 0.1% FA, Mobile Phase B: ACN; Flow rate: 20 mL/min; Gradient: 30% B to 41% B in 10 min; 254&220 nm. This afforded N-hydroxy-2-(5-(trifluoromethyl)benzo[d]thiazol-2-yl)isoindoline-4-carboxamide (13 mg, 19%) as a white solid. 1H-NMR: (DMSO, 300 MHz, ppm): δ 8.09-8.06 (d, J=8.1 Hz, 1H), 7.82 (s, 1H), 7.65-7.57 (m, 2H), 7.48-7.38 (m, 2H), 5.10 (s, 2H), 4.92 (s, 2H). MS: (ESI, m/z): 380[M+H]+

Example 12-1. N-hydroxy-2-(6-(trifluoromethyl)-1H-benzo[d]imidazol-2-yl)isoindoline-4-carboxamide

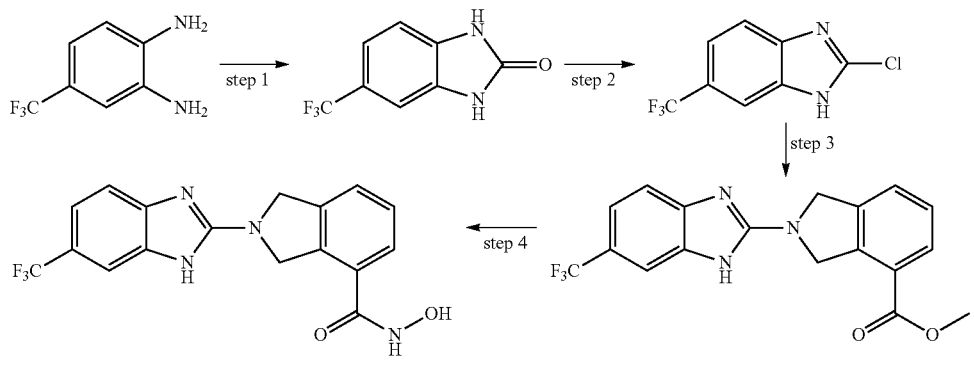

Step 1: 5-(trifluoromethyl)-1H-benzo[d]imidazol-2(3H)-one 1,1'-Carbonyldiimidazole (2.39 g, 14.7 mmol) was added to a solution of 4-(trifluoromethyl) benzene-1,2-diamine (2.0 g, 11.35 mmol) in tetrahydrofuran (20 mL), and the resulting solution stirred for 16 h at room temperature. The resulting mixture was concentrated under vacuum and then diluted with 50 mL of ethyl acetate. The resulting solution was washed with 2×50 mL of water, and the organic phase was separated and dried over anhydrous sodium sulfate, filtered, and concentrated to give 5-(trifluoromethyl)-1H-benzo[d]imidazol-2(3H)-one (2.867 g) as a light brown solid. MS: (ESI, m/z): 203 [M+H]+.

Step 2: 2-chloro-6-(trifluoromethyl)-1H-1,3-benzodiazole

A solution of 5-(trifluoromethyl)-2,3-dihydro-1H-1,3-benzodiazol-2-one (500 mg, 2.47 mmol) and phosphoryl trichloride (5 mL) stirred for 1 h at 105° C. in an oil bath. The resulting mixture was concentrated under vacuum and then dissolved in 20 mL of water. The pH value of the solution was adjusted to 8 with 2 M aqueous sodium bicarbonate solution. The resulting solution was extracted with 3×30 mL of ethyl acetate, and the combined organic phases were washed with 2×30 mL of water, dried over anhydrous sodium sulfate, filtered, and concentrated under vacuum to give 2-chloro-6-(trifluoromethyl)-1H-1,3-benzodiazole (429 mg, 79%) as a yellow solid. MS: (ESI, m/z): 221 [M+H]+.

Step 3. methyl 2-(6-(trifluoromethyl)-1H-benzo[d]imidazol-2-yl)isoindoline-4-carboxylate A solution of 2-chloro-6-(trifluoromethyl)-1H-1,3-benzodiazole (200 mg, 0.91 mmol), methyl 2,3-dihydro-1H-isoindole-4-carboxylate hydrochloride (387 mg, 1.81 mmol), potassium carbonate (624 mg, 4.51 mmol,), and copper (I) bromide (130 mg, 0.91 mmol,) in propan-2-ol (10 mL) stirred for 17 h at 110° C. The resulting mixture was concentrated under vacuum. The residue purified via column chromatography on silica gel (eluting with ethyl acetate/petroleum ether (1:1)) to afford methyl 2-(6-(trifluoromethyl)-1H-benzo[d]imidazol-2-yl)isoindoline-4-carboxylate (37 mg, 11%) as an orange solid. MS: (ESI, m/z): 362 [M+H]+.

Step 4. N-hydroxy-2-(6-(trifluoromethyl)-1H-benzo[d]imidazol-2-yl)isoindoline-4-carboxamide Hydroxyl amine (50% in water, 0.20 mL, 3.0 mmol) and 1 M aqueous sodium hydroxide solution (0.20 mL, 0.20 mmol) were added to a solution of methyl 2-[6-(trifluoromethyl)-1H-1,3-benzodiazol-2-yl]-2,3-dihydro-1H-isoindole-4-carboxylate (37 mg, 0.10 mmol) in THF:MeOH (4:1, 1.5 mL). The resulting solution was stirred for 3 h at room temperature. The crude product was purified by Prep-HPLC with the following conditions: Column: Sunfire C18, 5 um, 19×150 mm; Mobile Mobile phase: water with 0.05% TFA and ACN (5% ACN up to 42% in 6 min); Flow rate: 25 ml/min; Detector: 254, 220 nm. The collected fraction was lyophilized to give N-hydroxy-2-(6-(trifluoromethyl)-1H-benzo[d]imidazol-2-yl)isoindoline-4-carboxamide (17.7 mg, 48%) as an off-white solid. $^1$H-NMR (DMSO, 400 MHZ) δ (ppm): 11.35 (br, 1H), 9.14-9.10 (br, 1H), 7.75-7.67 (m, 3H), 7.64-7.55 (m, 2H), 7.52-7.48 (m, 1H), 5.22 (s, 2H), 5.04-4.99 (d, J=10.4 Hz, 2H). MS: (ESI, m/z): 363 [M+H]+.

Example 13-1. N-hydroxy-2-(4,5,6,7-tetrahydro-3H-imidazo[4,5-c]pyridin-2-yl)isoindoline-4-carboxamide Step 1. benzyl 6,7-dihydro-1H-imidazo[4,5-c]pyridine-5(4H)-carboxylate N-(Benzyloxycarbonyloxy)succinimide was added portion wise to a 0° C. solution of 4,5,6,7-tetrahydro-1H-imidazo[4,5-c]pyridine dihydrochloride (530 mg, 2.70 mmol) and sodium bicarbonate (625.4 mg, 7.44 mmol) in 1,4-dioxane/water (1:1, 20 mL). The resulting solution stirred overnight at room temperature. The reaction mixture was then poured into 50 mL of water, and extracted with 2×50 mL of ethyl acetate. The combined organic phases were washed with 100 mL of brine, dried over anhydrous sodium sulfate, filtered, and concentrated under vacuum. The residue was purified via column chromatography on silica gel (eluting with 10:1 dichloromethane/methanol) to afford benzyl 6,7-dihydro-1H-imidazo[4,5-c]pyridine-5(4H)-carboxylate (440 mg, 63%) as colorless oil. MS: (ESI, m/z): 258[M+H]+.

Step 2. benzyl 2-bromo-6,7-dihydro-1H-imidazo[4,5-c]pyridine-5(4H)-carboxylate

N-Bromosuccinimide (305 mg, 1.71 mmol) was added portionwise to a 0° C. solution of benzyl 6,7-dihydro-1H-imidazo[4,5-c]pyridine-5(4H)-carboxylate (440 mg, 1.71 mmol) in tetrahydrofuran (20 mL). The resulting solution stirred for 4 h at room temperature, and the reaction mixture was poured into 50 mL of water. The mixture was extracted with 2×50 mL of ethyl acetate, and the combined organic phases were washed with 50 mL of brine, dried over anhydrous sodium sulfate, filtered, and concentrated under vacuum. The residue was purified via column chromatography on silica gel (eluting with 10:1 dichloromethane/methanol) to afford benzyl 2-bromo-6,7-dihydro-1H-imidazo[4,5-c]pyridine-5(4H)-carboxylate (160 mg, 28%) as a colorless oil. MS: (ESI, m/z): 336[M+H]+.

Step 3. benzyl 2-(4-(ethoxycarbonyl)isoindolin-2-yl)-6,7-dihydro-3H-imidazo[4,5-c]pyridine-5(4H)-carboxylate A solution of benzyl 2-bromo-6,7-dihydro-1H-imidazo[4,5-c]pyridine-5(4H)-carboxylate (200 mg, 0.59 mmol), ethyl

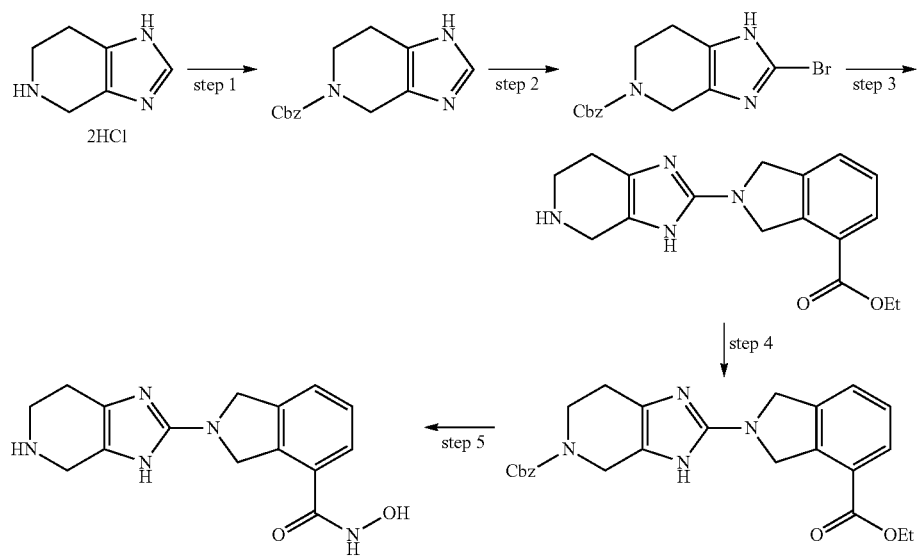

2,3-dihydro-1H-isoindole-4-carboxylate hydrochloride (135.7 mg, 0.60 mmol), and 6 M aqueous HCl (1 drop) in n-butanol (4 mL) was irradiated with microwave radiation for 1 h at 170° C. The reaction mixture was cooled to room temperature and then added dropwised into 20 mL of 1 M aqueous sodium bicarbonate solution. The resulting solution was extracted with 2×20 mL of dichloromethane, and the combined organic phases were washed with 50 mL of brine, dried over anhydrous sodium sulfate, filtered, and concentrated under vacuum. The residue was purified via column chromatography on silica gel (eluting with 10:1 dichloromethane/methanol) to afford benzyl 2-(4-(ethoxycarbonyl)isoindolin-2-yl)-6,7-dihydro-3H-imidazo[4,5-c]pyridine-5(4H)-carboxylate (120 mg, 45%) as a brown solid. MS: (ESI, m/z): 433[M+H]⁺.

Step 4. ethyl 2-(4,5,6,7-tetrahydro-3H-imidazo[4,5-c]pyridin-2-yl)isoindoline-4-carboxylate Hydrogen gas was introduced to a solution of benzyl 2-(4-(ethoxycarbonyl)isoindolin-2-yl)-6,7-dihydro-3H-imidazo[4,5-c]pyridine-5(4H)-carboxylate (120 mg, 0.27 mmol) and 10% palladium on carbon (20 mg) in ethanol (10 mL). The resulting solution was stirred overnight at room temperature and then filtered. The filtrate was concentrated under vacuum to give ethyl 2-(4,5,6,7-tetrahydro-3H-imidazo[4,5-c]pyridin-2-yl)isoindoline-4-carboxylate (29 mg, 36%) as yellow oil. MS: (ESI, m/z): 299[M+H]⁺.

Step 5. N-hydroxy-2-(4,5,6,7-tetrahydro-3H-imidazo[4,5-c]pyridin-2-yl)isoindoline-4-carboxamide Hydroxyl amine (50% in water, 0.34 mL, 5.57 mmol) and 1 M aqueous sodium hydroxide solution (0.19 mL, 0.19 mmol) were added to a solution of ethyl 2-(4,5,6,7-tetrahydro-3H-imidazo[4,5-c]pyridin-2-yl)isoindoline-4-carboxylate (29 mg, 0.09 mmol) in THF:MeOH (4:1, 2.0 mL). The resulting solution was stirred for 2 h at room temperature. The crude product was purified by Prep-HPLC with the following conditions: Column: T3 C18, 19×150 mm, 5 um; mobile phase, water with 0.05% NH₄HCO₃ and CH₃CN (1% up 7% in 6 min); Detector, 254 & 220 nm. The collected fraction was lyophilized to give N-hydroxy-2-(4,5,6,7-tetrahydro-3H-imidazo[4,5-c]pyridin-2-yl)isoindoline-4-carboxamide (2.4 mg, 9%) as an orange solid. 1H-NMR (DMSO, 400 MHz) δ (ppm): 8.29 (s, 2H), 7.61-7.51 (m, 2H), 7.37 (d, J=7.6 Hz, 1H), 4.81 (s, 2H), 4.61 (s, 2H), 3.77 (s, 2H), 3.13 (s, 2H), 2.57 (s, 2H). MS: (ESI, m/z): 300[M+H]⁺.

Example 14-1. 2-(5-acetyl-4,5,6,7-tetrahydro-3H-imidazo[4,5-c]pyridin-2-yl)-N-hydroxyisoindoline-4-carboxamide hydrochloride Step 1. ethyl 2-(5-acetyl-4,5,6,7-tetrahydro-3H-imidazo[4,5-c]pyridin-2-yl)isoindoline-4-carboxylate Acetyl chloride (22.5 mg, 0.29 mmol) was added to a 0° C. solution of ethyl 2-(4,5,6,7-tetrahydro-3H-imidazo[4,5-c]pyridin-2-yl)isoindoline-4-carboxylate (60 mg, 0.19 mmol) in dichloromethane (10 mL), and the resulting solution stirred for 1 h at room temperature. The resulting mixture was diluted with 20 mL of water and extracted with 2×15 mL of dichloromethane. The combined organic phases were washed with 20 mL of brine, dried over anhydrous sodium sulfate, filtered, and concentrated under vacuum to give ethyl 2-(5-acetyl-4,5,6,7-tetrahydro-3H-imidazo[4,5-c]pyridin-2-yl)isoindoline-4-carboxylate (56 mg, 82%) as a yellow oil. MS: (ESI, m/z): 355[M+H]⁺.

Step 2. tert-butyl 5-acetyl-2-(4-(ethoxycarbonyl)isoindolin-2-yl)-4,5,6,7-tetrahydroimidazo[4,5-c]pyridine-3-carboxylate A solution of ethyl 2-(5-acetyl-4,5,6,7-tetrahydro-3H-imidazo[4,5-c]pyridin-2-yl)isoindoline-4-carboxylate (100 mg, 0.28 mmol), di-tert-butyl dicarbonate (123 mg, 0.56 mmol, 2.00 equiv), 4-dimethylaminopyridine (6.8 mg, 0.06 mmol), and triethylamine (0.12 mL, 0.84 mmol) in tetrahydrofuran (15 mL) stirred overnight at 50° C. The resulting mixture was cooled to room temperature and then concentrated under vacuum. The residue was purified via column chromatography on silica gel (eluting with 10:1 dichloromethane/methanol) to afford tert-butyl 5-acetyl-2-(4-(ethoxycarbonyl)isoindolin-2-yl)-4,5,6,7-tetrahydroimidazo[4,5-c]pyridine-3-carboxylate (55 mg, 43%) as a yellow oil. MS: (ESI, m/z): 455[M+H]⁺.

Step 3. 2-(5-acetyl-4,5,6,7-tetrahydro-3H-imidazo[4f-c]pyridin-2-yl)-N-hydroxyisoindoline-4-carboxamide hydrochloride Hydroxyl amine (50% in water, 0.44 mL, 7.25 mmol) and 1 M aqueous sodium hydroxide solution (0.24 mL, 0.24 mmol) were added to a solution of tert-butyl 5-acetyl-2-(4-(ethoxycarbonyl)isoindolin-2-yl)-4,5,6,7-tetrahydroimidazo[4,5-c]pyridine-3-carboxylate (55 mg, 0.12 mmol) in THF:MeOH (4:1, 4.0 mL). The resulting solution was stirred for 1 h at room temperature. The pH value of the solution was adjusted to 6 with 6 M aqueous HCl solution, and the resulting mixture was concentrated under vacuum. The crude product was purified by Prep-HPLC with the following conditions: Column: Xbridge RPC18, 19×150 mm, 5 um; mobile phase, water (0.05% FA) and CH₃CN (5% CH₃CN up to 10% in 8 min); Detector: 220/254 nm. The collected fraction was lyophilized with 1 mL of 1 M aqueous

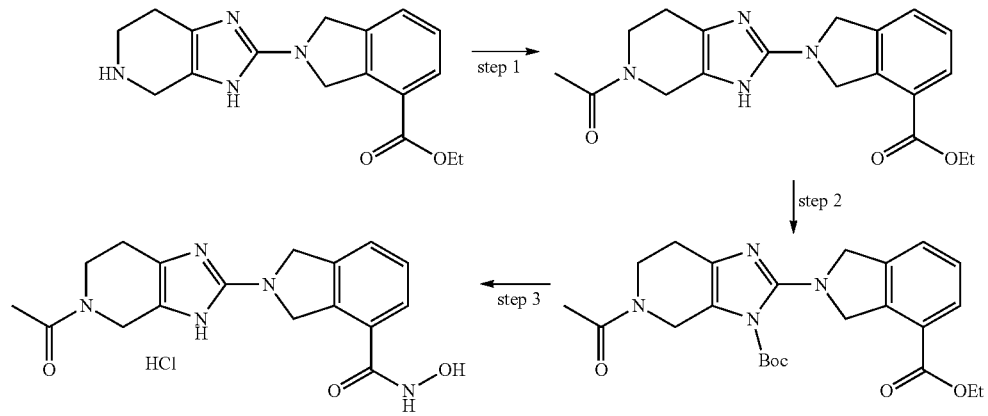

HCl solution to give 2-(5-acetyl-4,5,6,7-tetrahydro-3H-imidazo[4,5-c]pyridin-2-yl)-N-hydroxyisoindoline-4-carboxamide hydrochloride (2.5 mg, 5%) as a purple solid. $^1$H-NMR (DMSO, 300 MHz) δ (ppm): 12.86 (s, 2H), 11.30 (s, 1H), 9.08 (s, 1H), 7.76-7.54 (m, 2H), 7.49-7.42 (m, 1H), 4.99 (s, 2H), 4.79 (s, 2H), 4.39 (s, 2H), 3.72-3.67 (m, 2H), 2.68-2.61 (m, 2H), 2.08 (s, 3H). MS: (ESI, m/z): 342[M−HCl+H]$^+$.

Example 15-1. 2-(benzo[d]oxazol-2-yl)-N-hydroxyisoindoline-4-carboxamide

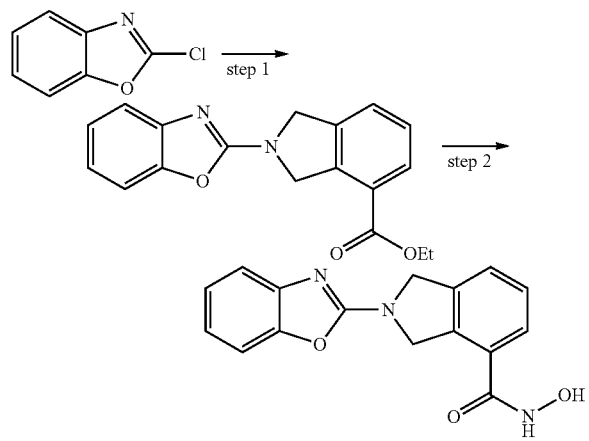

Step 1. ethyl 2-(benzo[d]oxazol-2-yl)isoindoline-4-carboxylate

A solution of 2-chloro-1,3-benzoxazole (202 mg, 1.32 mmol,), ethyl 2,3-dihydro-1H-isoindole-4-carboxylate hydrochloride (200 mg, 0.88 mmol), and triethylamine (0.37 mL, 2.64 mmol) in acetonitrile (8 mL) stirred for 2 h at 85° C. The reaction mixture was cooled to room temperature and concentrated under vacuum. The residue was purified via column chromatography on silica gel (eluting with 5:1 hexane/ethyl acetate) to give ethyl 2-(benzo[d]oxazol-2-yl)isoindoline-4-carboxylate (242 mg, 89%) as a gray solid. MS: (ESI, m/z): 309[M+H]$^+$.

Step 2. 2-(benzo[d]oxazol-2-yl)-N-hydroxyisoindoline-4-carboxamide

Hydroxyl amine (50% in water, 2.86 mL, 46.6 mmol) and 1 M aqueous sodium hydroxide solution (0.78 mL, 0.78 mmol) were added to a solution of ethyl 2-(benzo[d]oxazol-2-yl)isoindoline-4-carboxylate (120 mg, 0.39 mmol) in THF:MeOH (4:1, 10.0 mL). The resulting solution was stirred for 3 h at 30° C. The resulting mixture was partially concentrated under vacuum. The crude product was purified by Prep-HPLC with the following conditions: Column: SunFire Prep C18 OBD Column, 5 um, 19×150 mm; mobile phase: water with 0.1% FA and ACN (5.0% ACN up to 75.0% in 8 min); Detector, UV 254 & 220 nm. The collected fraction was lyophilized to give 2-(benzo[d]oxazol-2-yl)-N-hydroxyisoindoline-4-carboxamide (33 mg, 29%) as an off-white solid. $^1$H-NMR (DMSO, 300 MHz) δ (ppm): 11.24 (br, 1H), 9.14 (br, 1H), 7.64-7.58 (m, 2H), 7.49-7.43 (m, 2H), 7.34 (d, J=7.2 Hz, 1H), 7.20-7.16 (m, 1H), 7.06-7.02 (m, 1H), 5.14 (s, 2H), 4.95 (s, 2H). MS: (ESI, m/z): 296[M+H]$^+$.

Example 16-1. N-hydroxy-2-(5-(trifluoromethyl)-4,5,6,7-tetrahydrobenzo[d]oxazol-2-yl)isoindoline-4-carboxamide

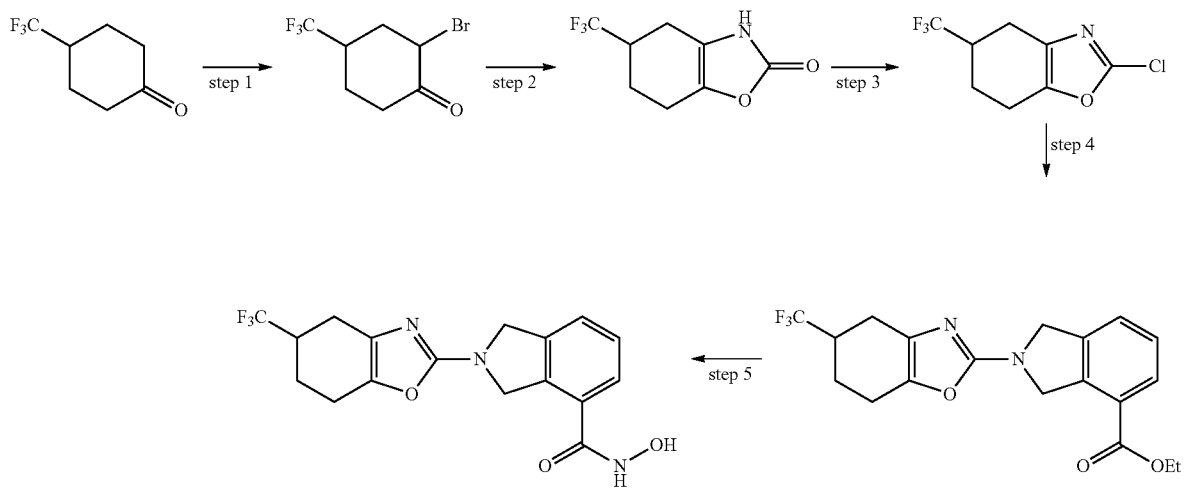

Step 1. 2-bromo-4-(trifluoromethyl)cyclohexanone

Bromine (4.99 g, 31.2 mmol) was added portion-wise to a 0° C. solution of 4-(trifluoromethyl)cyclohexanone (5.18 g, 31.18 mmol) in diethylether (80 mL). The resulting solution was stirred at 0° C. until the mixture turned colorless. The resulting solution was diluted with 80 mL of ice water and extracted with 3×80 mL of ethyl acetate. The combined organic phases were washed with 3×80 mL of brine, dried over anhydrous sodium sulfate, filtered, and concentrated under vacuum to give 2-bromo-4-(trifluoromethyl)cyclohexanone (9.1 g, 83%) as a yellow oil.

Step 2. 5-(trifluoromethyl)-4,5,6,7-tetrahydrobenzo[d]oxazol-2(3H)-one

A solution of 2-bromo-4-(trifluoromethyl)cyclohexanone (9.1 g, 37.14 mmol) and potassium cyanate (9.0 g, 111 mmol) in ethanol (90 mL) and water (10 mL) was heated to reflux for 3 h. The reaction mixture was cooled to room temperature and then concentrated under vacuum. The residue was dissolved in dichloromethane (100 mL) and filtered. The filtrate was concentrated under vacuum. The residue was purified via column chromatography on silica gel (eluting with 100:1 dichloromethane/methanol) to afford 5-(trifluoromethyl)-4,5,6,7-tetrahydrobenzo[d]oxazol-2(3H)-one (3.1 g, 40%) as a yellow syrup. MS: (ESI, m/z): 208[M+H]$^+$.

Step 3. 2-chloro-5-(trifluoromethyl)-4,5,6,7-tetrahydrobenzo[d]oxazole

Pyridine (1.18 g, 14.9 mmol) was added dropwise to a 0° C. solution of 5-(trifluoromethyl)-4,5,6,7-tetrahydrobenzo[d]oxazol-2(3H)-one (3.1 g, 14.97 mmol) in phosphorus oxychloride (60 mL). The resulting solution was heated to reflux for 2 h, and then cooled to room temperature. The resulting mixture was concentrated under vacuum, and the residue was diluted with 60 mL of ice water. The resulting solution was extracted with 3×60 mL of ethyl acetate, and the combined organic phases were washed with 3×60 mL of brine, dried over anhydrous sodium sulfate, filtered, and concentrated under vacuum. The residue purified via column chromatography on silica gel (eluting with 500:1 dichloromethane/methanol) to afford 2-chloro-5-(trifluoromethyl)-4,5,6,7-tetrahydrobenzo[d]oxazole (550 mg, 16%) as a yellow oil. MS: (ESI, m/z): 226[M+H]$^+$.

Step 4. ethyl 2-(5-(trifluoromethyl)-4,5,6,7-tetrahydrobenzo[d]oxazol-2-yl)isoindoline-4-carboxylate A solution of 2-chloro-5-(trifluoromethyl)-4,5,6,7-tetrahydrobenzo[d]oxazole (200 mg, 0.89 mmol), ethyl 2,3-dihydro-1H-isoindole-4-carboxylate hydrochloride (202 mg, 0.89 mmol), and potassium carbonate (367 mg, 2.66 mmol) in N,N-dimethylformamide (5 mL) stirred for 3 h at 100° C. The reaction mixture was cooled to room temperature and then diluted with 50 mL of water. The resulting solution was extracted with 3×50 mL of ethyl acetate, and the combined organic phases were washed with 3×100 mL of brine, dried over anhydrous sodium sulfate, filtered, and concentrated under vacuum. The residue was purified via column chromatography on silica gel (eluting with 100:1 dichloromethane/methanol) to afford ethyl 2-(5-(trifluoromethyl)-4,5,6,7-tetrahydrobenzo[d]oxazol-2-yl)isoindoline-4-carboxylate (140 mg, 42%) as a dark red solid. MS: (ESI, m/z): 381[M+H]$^+$.

Step 5. N-hydroxy-2-(5-(trifluoromethyl)-4,5,6,7-tetrahydrobenzo[d]oxazol-2-yl)isoindoline-4-carboxamide Hydroxyl amine (50% in water, 2.71 mL, 44.2 mmol) and 1 M aqueous sodium hydroxide solution (0.74 mL, 0.74 mmol) were added to a solution of ethyl 2-(5-(trifluoromethyl)-4,5,6,7-tetrahydrobenzo[d]oxazol-2-yl)isoindoline-4-carboxylate (140 mg, 0.37 mmol) in THF:MeOH (4:1, 4.0 mL). The resulting solution was stirred for 4 h at room temperature and then concentrated under vacuum. The crude product was purified by Prep-HPLC with the following conditions: Column: SunFire Prep C18 OBD Column, 5 um, 19×150 mm; mobile phase A: water with 10 mmol NH$_4$HCO$_3$, Mobile Phase B: ACN; Flow rate: 20 mL/min; Gradient: 10% B to 80% B in 9 min; Detector: 254 220 nm. The collected fraction was lyophilized to give N-hydroxy-2-(5-(trifluoromethyl)-4,5,6,7-tetrahydrobenzo[d]oxazol-2-yl)isoindoline-4-carboxamide (5 mg, 4%) as an off-white solid. $^1$H-NMR (DMSO, 300 MHZ) δ (ppm): 9.96 (br, 2H), 7.60-7.41 (m, 3H), 4.94 (s, 2H), 4.75 (s, 2H), 2.99-2.83 (m, 4H), 2.51 (br, 1H), 2.15-2.06 (m, 1H), 1.73-1.67 (m, 1H). MS: (ESI, m/z): 368[M+H]$^+$.

Example 17-1. N-hydroxy-1,1-dimethyl-2-(6-(trifluoromethyl)-1H-benzo[d]imidazol-2-yl)isoindoline-4-carboxamide

Step 1. methyl 1,1-dimethyl-2-(6-(trifluoromethyl)-1H-benzo[d]imidazol-2-yl)isoindoline-4-carboxylate A solution of methyl 1,1-dimethyl-2,3-dihydro-1H-isoindole-4-carboxylate (60 mg, 0.29 mmol,), 2-bromo-5-(trifluoromethyl)-1H-1,3-benzodiazole (155 mg, 0.58 mmol), 6 M aqueous HCl solution (0.05 mL) in n-butanol (2 mL) was irradiated with microwave radiation for 40 min at 170° C. The resulting mixture was concentrated under vacuum. The residue was purified via column chromatography on silica gel (eluting with 2:1 hexanes/ethyl acetate) to give methyl 1,1-dimethyl-2-(6-(trifluoromethyl)-1H-benzo[d]imidazol-2-yl)isoindoline-4-carboxylate (100 mg, 88%) as a yellow solid. MS: (ESI, m/z): 390 [M+H]$^+$

Step 2. N-hydroxy-1,1-dimethyl-2-(6-(trifluoromethyl)-1H-benzo[d]imidazol-2-yl)isoindoline-4-carboxamide Hydroxyl amine (50% in water, 0.57 mL, 9.24 mmol) and 1 M aqueous sodium hydroxide solution (0.31 mL, 0.31 mmol) were added to a solution of methyl 1,1-dimethyl-2-[6-(trifluoromethyl)-1H-1,3-benzodiazol-2-yl]-2,3-dihydro-1H-isoindole-4-carboxylate (60 mg, 0.15 mmol) in THF:MeOH (4:1, 1.0 mL). The resulting solution was stirred for 1 h at room temperature. The pH value of the solution was adjusted to 6 with 1 M aqueous HCl solution. The crude product was purified by Prep-HPLC with the following conditions: Column: X Bridge C18, 19×150 mm, 5 um; Mobile Phase A: Water/0.05% FA, Mobile Phase B: ACN; Flow rate: 20 mL/min; Gradient: 30% B to 70% B in 10 min; 254 nm. The collected fraction was lyophilized to give N-hydroxy-1,1-dimethyl-2-(6-(trifluoromethyl)-1H-benzo[d]imidazol-2-yl)isoindoline-4-carboxamide (7.1 mg, 12%) as yellow oil. H-NMR-PH-FMA-PJ94-1093-0: (400 MHz, DMSO-de, ppm): S 11.34 (s, 1H), 9.16 (br, 1H), 7.71-7.51 (m, 6H), 5.24-5.19 (m, 2H), 1.87 (s, 6H). MS: (ESI, m/z): 391[M+H]+.

Example 18-1. N-hydroxy-1,1-dimethyl-2-[5-(trifluoromethyl)-1,3-benzoxazol-2-yl]-2,3-dihydro-1H-isoindole-4-carboxamide

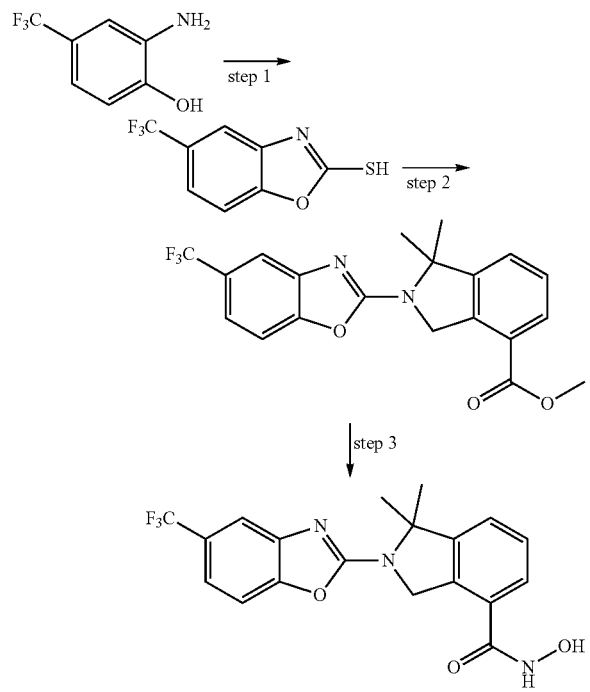

Step 1. 5-(trifluoromethyl)-1,3-benzoxazole-2-thiol

A solution of 2-amino-4-(trifluoromethyl)phenol (5 g, 28.23 mmol), potassium hydroxide (4.75 g, 84.7 mmol) and carbon disulfide (50 mL) in ethanol (100 mL) stirred for 1 h at 90° C. in an oil bath. The resulting mixture was concentrated under vacuum. The residue was dissolved in water (100 mL), and the pH value of the solution was adjusted to 4 with 3 M aqueous HCl solution. The crude product was purified by column chromatography on silica gel (eluting with 1:1 ethyl acetate/petroleum ether) to give 5-(trifluoromethyl)-1,3-benzoxazole-2-thiol (2.6 g, 42%) as a yellow solid. MS: (ESI, m/z): 220 [M+H]+.

Step 2. methyl 1,1-dimethyl-2-[5-(trifluoromethyl)-1,3-benzoxazol-2-yl]-2,3-dihydro-1H-isoindole-4-carboxylate A solution of 5-(trifluoromethyl)-1,3-benzoxazole-2-thiol (129 mg, 0.588 mmol), methyl 1,1-dimethylisoindoline-4-carboxylate (60 mg, 0.294 mmol), and 6 M aqueous HCl solution (1 drop) in n-butanol (10 mL) was irradiated with microwave radiation for 1.5 h at 180° C. The resulting mixture was combined and concentrated under vacuum. The residue was purified via column chromatography on silica gel (eluting with 1:20 ethyl acetate/petroleum ether (1:20) to give methyl 1,1-dimethyl-2-[5-(trifluoromethyl)-1,3-benzoxazol-2-yl]-2,3-dihydro-1H-isoindole-4-carboxylate (500 mg, 87%) as a white solid. MS: (ESI, m/z) 391 [M+H]+.

Step 3. N-hydroxy-1,1-dimethyl-2-[5-(trifluoromethyl)-1,3-benzoxazol-2-yl]-2,3-dihydro-1H-isoindole-4-carboxamide Hydroxyl amine (50% in water, 3.75 mL, 61.2 mmol) was added to a solution of methyl 1,1-dimethyl-2-[5-(trifluoromethyl)-1,3-benzoxazol-2-yl]-2,3-dihydro-1H-isoindole-4-carboxylate (400 mg, 1.03 mmol) in THF:MeOH (4:1, 8.0 mL) and the pH value of the solution was adjusted to 13 with 1M aqueous NaOH solution. The reaction mixture stirred for 3 h at room temperature. The mixture was purified directly by Prep-HPLC with the following conditions: Column: SunFire Prep C18 OBD Column, 5 um, 19×150 mm; mobile phase, water with 0.1% FA and ACN Flow rate: 20 mL/min; Gradient: 35% B to 62% B in 10 min; 254 &220 nm. The collected fraction was lyophilized to give N-hydroxy-1,1-dimethyl-2-[5-(trifluoromethyl)-1,3-benzoxazol-2-yl]-2,3-dihydro-1H-isoindole-4-carboxamide (109 mg, 27%) as an off-white solid. $^1$H-NMR (DMSO, 400 MHz) δ(ppm): δ 11.50-10.60 (br, 1H), 9.70-8.70 (br, 1H), 7.72-7.47 (m, 5H), 7.42-7.40 (d, 1H), 5.20 (s, 2H), 1.81 (s, 6H). MS: (ESI, m/z): 392 [M+H]+.

The following compounds were prepared according to the procedures described above for N-hydroxy-1,1-dimethyl-2-[5-(trifluoromethyl)-1,3-benzoxazol-2-yl]-2,3-dihydro-1H-isoindole-4-carboxamide.

| Ex. | Structure | Name | $^1$HNMR | (ESI, m/z) [M + H]+ |
|---|---|---|---|---|
| 18-2 | 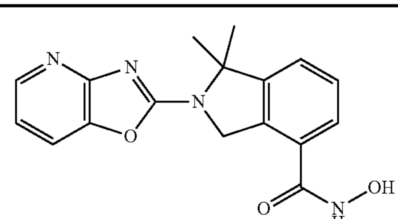 | N-hydroxy-1,1-dimethyl-2-(oxazolo[4,5-b]pyridin-2-yl)isoindoline-4-carboxamide | (DMSO, 400 MHz, ppm): δ 11.32 (s, 1H), 8.24-8.23 (d, 1H), 8.10-8.08 (m, 1H), 7.68-7.64 (m, 2H), 7.54-7.50 (m, 1H), 7.28-7.18 (m, 1H), 5.28 (s, 2H), 1.84 (s, 6H). | 325 |

| Ex. | Structure | Name | ¹HNMR | (ESI, m/z) [M + H]⁺ |
|---|---|---|---|---|
| 18-3 | 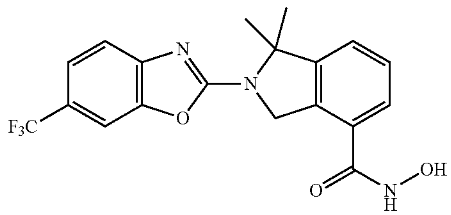 [SMILES: CC1(C)c2cccc(C(=O)NO)c2CN1c1nc2ccc(C(F)(F)F)cc2o1] | N-hydroxy-1,1-dimethyl-2-(6-(trifluoromethyl)benzo[d]oxazol-2-yl)isoindoline-4-carboxamide | (DMSO, 400 MHz, ppm): 11.16 (br, 1H), 9.15 (br, 1H), 7.94 (s, 1H), 7.64-7.60 (m, 2H), 7.56-7.47 (m, 3H), 5.21 (s, 2H), 1.81 (s, 6H) | 392 |

Example 19-1. Preparation of N-hydroxy-1,1-dimethyl-2-[5-(trifluoromethyl)-4,5,6,7-tetrahydro-1,3-benzoxazol-2-yl]-2,3-dihydro-1H-isoindole-4-carboxamide

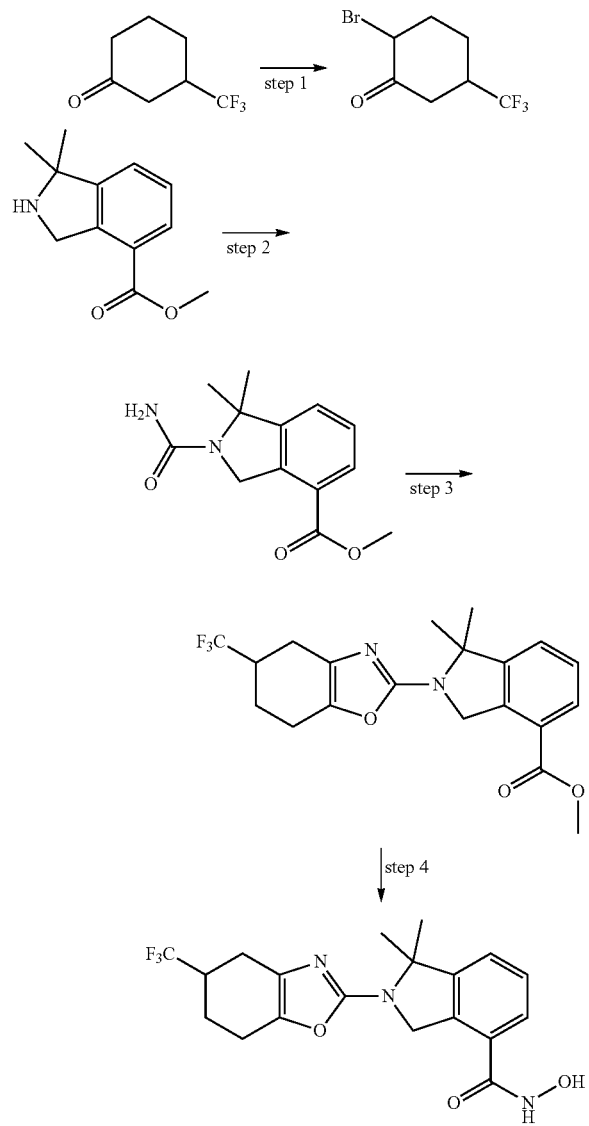

Step 1.
2-bromo-5-(trifluoromethyl)cyclohexan-1-one

Bromine (0.3 mL, 6.02 mmol) was added dropwise to a 0° C. solution of 3-(trifluoromethyl)cyclohexan-1-one (1 g, 6.02 mmol) in acetic acid (15 mL), and the resulting solution stirred for 4 h at room temperature. The reaction mixture was concentrated under vacuum to give 2-bromo-5-(trifluoromethyl)cyclohexan-1-one (1 g, 68%) as red oil. GCMS: 244 [M].

Step 2. methyl 2-carbamoyl-1,1-dimethyl-2,3-dihydro-1H-isoindole-4-carboxylate

A solution of methyl 1,1-dimethylisoindoline-4-carboxylate (500 mg, 2.44 mmol), triethylamine (1.02 mL, 7.30 mmol), 4-dimethylaminopyridine (298 mg, 2.44 mmol) and (trimethylsilyl)isocyanate (5 mL, 36.9 mmol) in dichloromethane (20 mL) stirred at 40° C. for 3.5 days. The resulting mixture was concentrated under vacuum. The residue was purified via column chromatography on silica gel (eluting with 1:1 ethyl acetate/petroleum ether) to afford methyl 2-carbamoyl-1,1-dimethyl-2,3-dihydro-1H-isoindole-4-carboxylate (300 mg, 50%) as yellow oil. MS: (ESI, m/z): 249 [M+H]⁺.

Step 3. methyl 1,1-dimethyl-2-[5-(trifluoromethyl)-4,5,6,7-tetrahydro-1,3-benzoxazol-2-yl]-2,3-dihydro-1H-isoindole-4-carboxylate A solution of methyl 2-carbamoyl-1,1-dimethyl-2,3-dihydro-1H-isoindole-4-carboxylate (90 mg, 0.36 mmol) and 2-bromo-5-(trifluoromethyl)cyclohexan-1-one (180 mg, 0.73 mmol) in DMF (1.2 mL) stirred for 3 h at 80° C. in an oil bath. The crude product was purified by Prep-HPLC with the following conditions (CombiFlash-1): Column: C18 silica gel; mobile phase A: water with 0.05% TFA; mobile phase B: CH₃CN; Gradient: 10%-70% B within 30 min; Detector, UV 254 nm. The collected fractions were combined and concentrated under vacuum to give methyl 1,1-dimethyl-2-[5-(trifluoromethyl)-4,5,6,7-tetrahydro-1,3-benzoxazol-2-yl]-2,3-dihydro-1H-isoindole-4-carboxylate (49 mg, 34%) as yellow oil. MS: (ESI, m/z): 395 [M+H]⁺.

Step 4. N-hydroxy-1,1-dimethyl-2-[5-(trifluoromethyl)-4,5,6,7-tetrahydro-1,3-benzoxazol-2-yl]-2,3-dihydro-1H-isoindole-4-carboxamide Hydroxyl amine (50% in water, 0.91 mL, 14.4 mmol) and 1 M aqueous sodium hydroxide solution (0.24 mL, 0.24 mmol) were added to a solution of methyl 1,1-dimethyl-2-

[5-(trifluoromethyl)-4,5,6,7-tetrahydro-1,3-benzoxazol-2-yl]-2,3-dihydro-1H-isoindole-4-carboxylate (49 mg, 0.12 mmol) in THF:MeOH (4:1, 1.0 mL). The resulting solution was stirred for 3 h at room temperature. The solids were filtered out. The crude product was purified by Flash-Prep-HPLC with the following conditions: Column: XBridge Prep C18 OBD Column, 5 um, 19×150 mm; Mobile Phase A: Water with 10 mmol NH$_4$HCO$_3$, Mobile Phase B: ACN; Flow rate: 20 mL/min; Gradient: 20% B to 45% B in 10 min; 254&220 nm. The collected fractions were combined and lyophilized to give N-hydroxy-1, 1-dimethyl-2-[5-(trifluoromethyl)-4,5,6,7-tetrahydro-1,3-benzoxazol-2-yl]-2,3-dihydro-1H-isoindole-4-carboxamide (5.3 mg, 11%) as an off-white solid. $^1$H-NMR (DMSO, 400 MHz) δ(ppm): δ$^1$H-NMR (DMSO, 400 MHz) δ(ppm): 511.05 (br, 1H), 9.09 (br, 1H), 7.59-7.41 (m, 3H), 4.91 (s, 2H), 2.68-2.48 (m, 5H), 2.20-2.10 (m, 1H), 1.76-1.74 (m, 1H), 1.66 (s, 6H). MS: (ESI, m/z): 396 [M+H]$^+$.

The following compound was prepared according to the procedures described above for N-hydroxy-1,1-dimethyl-2-[5-(trifluoromethyl)-4,5,6,7-tetrahydro-1,3-benzoxazol-2-yl]-2,3-dihydro-1H-isoindole-4-carboxamide.

to give thiazolo[4,5-b]pyridine-2-thiol 3 g (62%) as a yellow solid. MS: (ESI, m/z): 169 [M+H]$^+$.

Step 2. 2-bromothiazolo[4,5-b]pyridine

Bromine (2.82 g, 17.6 mmol) was added dropwise to a 0° C. solution of thiazolo[4,5-b]pyridine-2-thiol (1.00 g, 5.94 mmol) in HBr/AcOH (10 mL), and the resulting solution was stirred for 2 h at 0-10° C. in a water/ice bath. The reaction was then quenched by the addition of ice. The pH value of the solution was adjusted to 4-5 with 2 M aqueous NaOH solution at 0-10° C. The resulting solution was extracted with 5×100 mL of dichloromethane/MeOH (10:1), and the combined organic layers were dried over anhydrous sodium sulfate, filtered and concentrated under vacuum to give 2-bromothiazolo[4,5-b]pyridine (1.1 g, 86%) as a brown solid. MS: (ESI, m/z): 215 [M+H]$^+$.

Step 3. methyl 1,1-dimethyl-2-(thiazolo[4,5-b]pyridin-2-yl)isoindoline-4-carboxylate A solution of 2-bromothiazolo[4,5-b]pyridine (188 mg, 0.87 mmol), methyl 1,1-dimethylisoindoline-4-carboxylate

| Ex. | Structure | Name | $^1$HNMR | (ESI, m/z) [M + H]$^+$ |
|---|---|---|---|---|
| 19-2 | 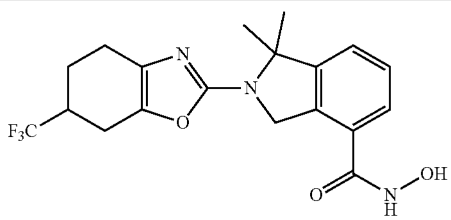 [SMILES: CC1(C)c2cccc(C(=O)NO)c2CN1c1nc2c(o1)CC(C(F)(F)F)CC2] | N-hydroxy-1,1-dimethyl-2-(6-(trifluoromethyl)-4,5,6,7-tetrahydrobenzo[d]oxazol-2-yl)isoindoline-4-carboxamide | (DMSO, 300 MHz, ppm): δ 9.12-9.07 (m, 1H), 7.67-7.40 (m, 3H), 4.91 (m, 2H), 2.87-2.49 (m, 5H), 2.08-2.05 (m, 1H), 1.67-1.65 (m, 7H). | 396 |

Example 20-1. N-hydroxy-1,1-dimethyl-2-(thiazolo[4,5-b]pyridin-2-yl)isoindoline-4-carboxamide

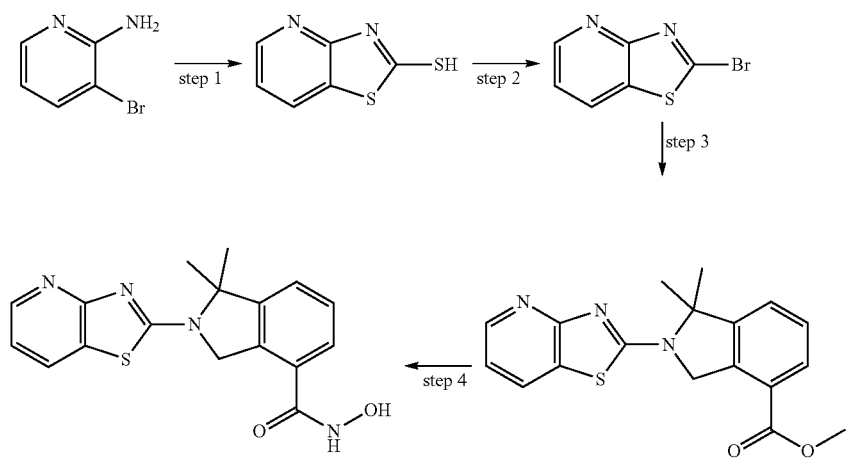 [SMILES: Nc1ncccc1Br ; Sc1nc2ncccc2s1 ; Brc1nc2ncccc2s1 ; CC1(C)c2cccc(C(=O)NO)c2CN1c1nc2ncccc2s1 ; COC(=O)c1cccc2c1CN(c1nc3ncccc3s1)C2(C)C]

Step 1. thiazolo[4,5-b]pyridine-2-thiol

A solution of 3-bromopyridin-2-amine (5.0 g, 28.9 mmol) and potassium O-ethyl carbonodithioate (6.51 g, 40.6 mmol) in DMF (25 mL) stirred overnight at 130° C. in an oil bath. The pH value of the solution was adjusted to 4 with 3 M aqueous HCl solution. The solids were collected by filtration (60 mg, 0.29 mmol), RuPhos 2G precatalyst (24 mg, 0.029 mmoL), RuPhos (24 mg, 0.058 mmoL) and cesium carbonate (0.284 g, 0.87 mmol) in toluene (3 mL) stirred overnight at 100° C. in an oil bath. The reaction mixture was filtered, and the filtrate was concentrated. The residue was purified via column chromatography on silica gel (eluting with 3:1 petroleum ether/ethyl acetate) to afford methyl 1,1-dimethyl-2-(thiazolo[4,5-b]pyridin-2-yl)isoindoline-4-carboxylate (70 mg, 7%) as an off-white solid. MS: (ESI, m/z): 340 [M+H]$^+$.

Step 4. N-hydroxy-1,1-dimethyl-2-(thiazolo[4,5-b]pyridin-2-yl)isoindoline-4-carboxamide Hydroxyl amine (50% in water, 0.86 mL, 14.1 mmol) and 1 M aqueous sodium hydroxide solution (0.24 mL, 0.24 mmol) were added to a solution of methyl 1,1-dimethyl-2-(thiazolo[4,5-b]pyridin-2-yl)isoindoline-4-carboxylate (70 mg, 0.10 mmol) in THF:MeOH (4:1, 1.0 mL). The resulting solution was stirred for 3 h at room temperature. The crude product was purified by Flash-Prep-HPLC with the following conditions: Column: XBridge Prep C18 OBD Column, 5 um, 19×150 mm; Mobile Phase A: Water with 10 mmol $NH_4HCO_3$, Mobile Phase B: ACN; Flow rate: 20 mL/min; Gradient: 20% B to 35% B in 10 min; 254 220 nm. The collected fraction was combined and lyophilized to give N-hydroxy-1,1-dimethyl-2-(thiazolo[4,5-b]pyridin-2-yl)isoindoline-4-carboxamide (6.2 mg, 18%) as an off-white solid. $^1$H-NMR (DMSO, 300 MHz) δ(ppm): 58.33-8.22 (m, 2H), 7.72-7.67 (m, 1H), 7.54-7.42 (m, 2H), 7.07-7.03 (m, 1H), 5.07 (s, 2H), 1.85 (s, 6H). MS: (ESI, m/z): 341 [M+H]$^+$.

The following compound was prepared according to the procedures described above for N-hydroxy-1,1-dimethyl-2-(thiazolo[4,5-b]pyri din-2-yl)isoindoline-4-carboxamide.

Step 1. oxazolo[4,5-c]pyridine

A mixture of 3-aminopyridin-4-ol (500 mg, 4.54 mmol), trimethoxymethane (5 mL), and acetic acid (0.4 mL) was irradiated with microwave radiation for 0.5 h at 160° C. The resulting mixture was concentrated under vacuum. The residue was purified via column chromatography on silica gel (eluting with 1:10 ethyl acetate/petroleum ether) to afford oxazolo[4,5-c]pyridine (0.23 g, 42%) as a yellow solid. MS: (ESI, m/z): 121 [M+H]$^+$.

Step 2. methyl (E)-2-(6(4-hydroxypyridin-3-yl)imino)methyl)-1,1-dimethylisoindoline-4-carboxylate A solution of oxazolo[4,5-c]pyridine (100 mg, 0.83 mmol), methyl 1,1-dimethyl-2,3-dihydro-1H-isoindole-4-carboxylate (340 mg, 1.66 mmol), and trifluoromethanesulfonic acid (12.5 mg, 0.083 mmol) in $CH_3CN$ (8 mL) was stirred overnight at 60° C. in an oil bath. The resulting mixture was concentrated under vacuum. The residue was purified via column chromatography on silica gel (eluting with 10-20% methanol-dichloromethane) to afford methyl (E)-2-(((4-hydroxypyridin-3-yl)imino)methyl)-1,1-dimethylisoindoline-4-carboxylate (100 mg, 37%) as a white solid. MS: (ESI, m/z): 326 [M+H]$^+$.

| Ex. | Structure | Name | $^1$HNMR | (ESI, m/z) [M + H]$^+$ |
|---|---|---|---|---|
| 20-2 | $F_3C$-[benzothiazole]-N-[dimethylisoindoline]-C(O)NHOH | N-hydroxy-1,1-dimethyl-2-(5-(trifluoromethyl)benzo[d]thiazol-2-yl)isoindoline-4-carboxamide | (DMSO, 400 MHz, ppm): δ 11.29 (s, 1H), 8.09 (d, J = 8 Hz, 1H), 7.83 (s, 1H), 7.64-7.60 (m, 2H), 7.51-7.48 (m, 1H), 7.41 (d, J = 7.2 Hz, 1H), 5.04 (s, 2H), 1.86 (s, 6H). | 408 |

Example 21-1. N-hydroxy-1,1-dimethyl-2-(oxazolo[4,5-c]pyridin-2-yl)isoindoline-4-carboxamide

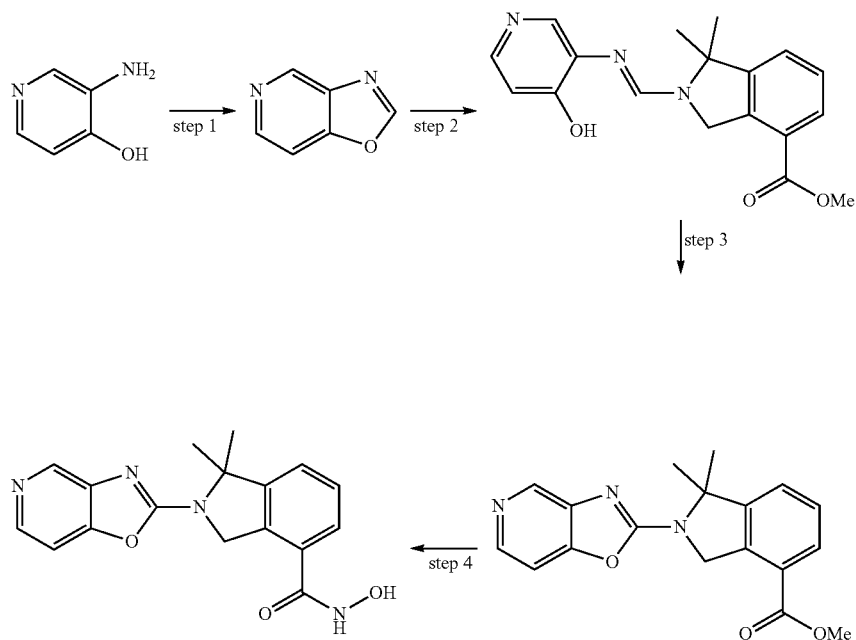

Step 3. methyl 1,1-dimethyl-2-(oxazolo[4,5-c]pyridin-2-yl)isoindoline-4-carboxylate A solution of methyl (E)-2-(((4-hydroxypyridin-3-yl)imino)methyl)-1,1-dimethylisoindoline-4-carboxylate (100 mg, 0.31 mmol) and (diacetoxyiodo)benzene (100 mg, 0.31 mmol) in dichloromethane (5 mL) stirred overnight at room temperature. The resulting mixture was concentrated under vacuum. The residue was purified via column chromatography on silica gel (eluting with 1:1 ethyl acetate/petroleum ether) to afford methyl 1,1-dimethyl-2-(oxazolo[4,5-c]pyridin-2-yl)isoindoline-4-carboxylate (79 mg, 79%) as a brown solid. MS: (ESI, m/z): 324 [M+H]$^+$.

Step 4. N-hydroxy-1,1-dimethyl-2-(oxazolo[4,5-c]pyridin-2-yl)isoindoline-4-carboxamide Hydroxyl amine (50% in water, 1.80 mL, 28.8 mmol) and 1 M aqueous sodium hydroxide solution (0.48 mL, 0.48 mmol) were added to a solution of methyl 1,1-dimethyl-2-(oxazolo[4,5-c]pyridin-2-yl)isoindoline-4-carboxylate (79 mg, 0.24 mmol) in THF:MeOH (4:1, 1.5 mL). The resulting solution was stirred for 30 min at room temperature. The solids were filtered out. The crude product was purified by Flash-Prep-HPLC with the following conditions: Column: Waters HSS C18, 19×150 mm; Mobile Phase A: Water/0.05% FA, Mobile Phase B: ACN; Flow rate: 0.7 mL/min; Gradient: 5% B to 30% B in 7.0 min; 254 nm. The collected fraction was lyophilized to give N-hydroxy-1,1-dimethyl-2-(oxazolo[4,5-c]pyridin-2-yl)isoindoline-4-carboxamide (33.3 mg, 38%) as an off-white solid. $^1$H-NMR (DMSO, 400 MHz) δ(ppm): 811.32 (s, 1H), 9.30-9.10 (m, 1H), 9.03 (s, 1H), 8.62 (d, J=6 Hz, 1H), 8.19 (d, J=6 Hz, 1H), 7.68-7.64 (m, 2H), 7.54-7.50 (m, 1H), 5.30 (s, 2H), 1.84 (s, 6H). MS: (ESI, m/z): 325 [M+H]$^+$.

Example 22-1. 2-(benzo[d]thiazol-2-yl)-N-hydroxy-1,1-dimethylisoindoline-4-carboxamide

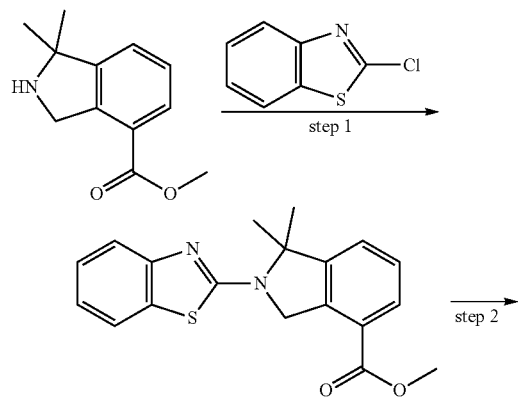

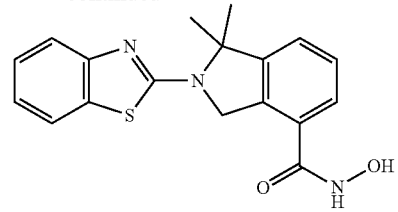

Step 1. methyl 2-(benzo[d]thiazol-2-yl)-1,1-dimethylisoindoline-4-carboxylate A solution of 2-chloro-1,3-benzothiazole (397 mg, 2.34 mmol), methyl 1,1-dimethyl-2,3-dihydro-1H-isoindole-4-carboxylate (240 mg, 1.17 mmol), RuPhos (109 mg, 0.23 mmol), RuPhos 2G (91 mg, 0.12 mmol), and cesium carbonate (1.143 g, 3.51 mmol) in toluene (10 mL) stirred overnight at 100° C. The reaction mixture was cooled to room temperature and filtered. The filtrate was concentrated under vacuum, and the residue was purified by preparative thin layer chromatography on silica gel plates (eluting with 1:5 ethyl acetate/petroleum ether) to afford methyl 2-(benzo[d]thiazol-2-yl)-1,1-dimethylisoindoline-4-carboxylate (90 mg, 23%) as a light yellow solid. MS: (ESI, m/z): 339[M+H]$^+$

Step 2. 2-(benzo[d]thiazol-2-yl)-N-hydroxy-1,1-dimethylisoindoline-4-carboxamide Hydroxyl amine (50% in water, 2.17 mL, 34.5 mmol) and 1 M aqueous sodium hydroxide solution (1.2 mL, 1.2 mmol) were added to a solution of methyl 2-(1,3-benzothiazol-2-yl)-1,1-dimethyl-2,3-dihydro-1H-isoindole-4-carboxylate (100 mg, 0.30 mmol) in THF:MeOH (4:1, 5.0 mL). The resulting solution stirred for 4 h at room temperature. The resulting mixture was partially concentrated under vacuum. The crude product was purified by Prep-HPLC with the following conditions: Column: XBridge Prep C18 OBD Column, 5 um, 19×150 mm; mobile phase, A: water with 0.1% FA, B: ACN; Flow rate, 20 mL/min; Gradient, 5% B to 80% B in 8 min; Detector, 254 220 nm. The collected fraction was lyophilized to give 2-(benzo[d]thiazol-2-yl)-N-hydroxy-1,1-dimethylisoindoline-4-carboxamide (29 mg, 29%) as an off-white solid. $^1$H-NMR (DMSO, 400 MHz) δ (ppm): δ 11.22 (br, 1H), 9.23 (br, 1H), 7.81 (d, J=7.6 Hz, 1H), 7.60-7.53 (m, 3H), 7.48-7.44 (m, 1H), 7.31-7.27 (m, 1H), 7.09-7.05 (m, 1H), 4.98 (s, 2H), 1.82 (s, 6H). MS: (ESI, m/z): 340[M+H]$^+$.

The following compounds were prepared according to the procedures described above for 2-(benzo[d]thiazol-2-yl)-N-hydroxy-1,1-dimethylisoindoline-4-carboxamide.

| Ex. | Structure | Name | $^1$HNMR | (ESI, m/z) [M + H]$^+$ |
|---|---|---|---|---|
| 22-2 | 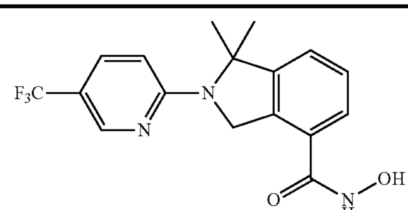 | N-hydroxy-1,1-dimethyl-2-(5-(trifluoromethyl)pyridin-2-yl)isoindoline-4-carboxamide | (DMSO, 300 MHz, ppm): δ8.49 (s, 1H), 7.85 (d, J = 9.6 Hz, 1H), 7.58-7.54 (m, 2H), 7.47-7.42 (m, 1H), 6.71 (d, J = 8.4 Hz, 1H), 4.93 (s, 2H), 1.80 (s, 6H). | 352 |

-continued

| Ex. | Structure | Name | ¹HNMR | (ESI, m/z) [M + H]⁺ |
|---|---|---|---|---|
| 22-3 | 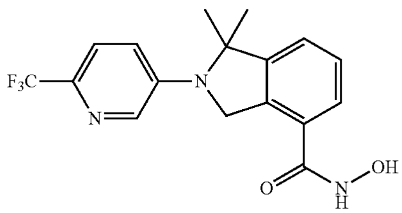 [SMILES: CC1(C)c2cccc(C(=O)NO)c2CN1c1ccc(C(F)(F)F)nc1] | N-hydroxy-1,1-dimethyl-2-(6-(trifluoromethyl)pyridin-3-yl)isoindoline-4-carboxamide | (DMSO, 400 MHz, ppm): 8.28 (s, 1H), 7.60 (d, J = 9.2 Hz, 1H), 7.55-7.51 (m, 2H), 7.41-7.38 (m, 1H), 7.31-7.29 (m, 1H), 4.83 (s, 2H), 1.67 (s, 6H) | 352 |
| 22-4 | 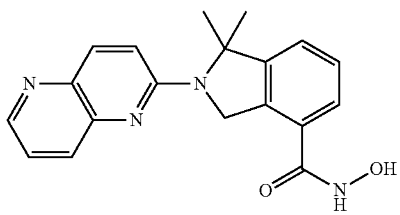 [SMILES: CC1(C)c2cccc(C(=O)NO)c2CN1c1ccc2ncccc2n1] | N-hydroxy-1,1-dimethyl-2-(1,5-naphthyridin-2-yl)isoindoline-4-carboxamide | (DMSO, 300 MHz, ppm): 11.19 (br, 1H), 9.17 (br, 1H), 8.59-8.57 (m, 1H), 8.14 (d, J = 9.3 Hz, 1H), 8.00 (d, J = 9 Hz, 1H), 7.60-7.53 (m, 3H), 7.48-7.43 (m, 1H), 7.28-7.25 (m, 1H), 5.08 (s, 2H), 1.79 (s, 6H). | 335 |
| 22-5 | 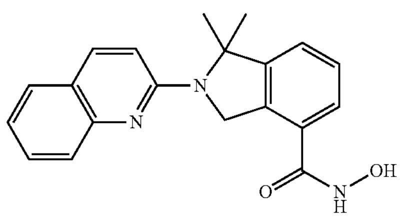 [SMILES: CC1(C)c2cccc(C(=O)NO)c2CN1c1ccc2ccccc2n1] | N-hydroxy-1,1-dimethyl-2-(quinolin-2-yl)isoindoline-4-carboxamide | (DMSO, 300 MHz, ppm): 11.31 (br, 1H), 8.44-7.91 (m, 3H), 7.79 (br, 2H), 7.69-7.61 (m, 2H), 7.54-7.50 (m, 2H), 5.37 (s, 2H), 7.91 (s, 6H). | 334 |
| 22-6 | 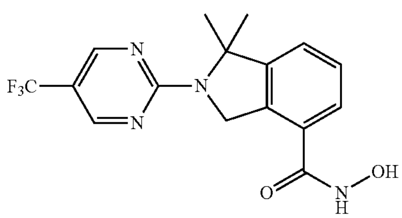 [SMILES: CC1(C)c2cccc(C(=O)NO)c2CN1c1ncc(C(F)(F)F)cn1] | N-hydroxy-1,1-dimethyl-2-(5-(trifluoromethyl)pyrimidin-2-yl)isoindoline-4-carboxamide | (DMSO, 400 MHz, ppm): 11.17 (br, 1H), 9.11 (br, 1H), 8.80 (s, 2H), 7.59-7.56 (m, 2H), 7.47-7.43 (m, 1H), 5.10 (s, 2H), 1.80 (s, 6H). | 353 |
| 22-7 | 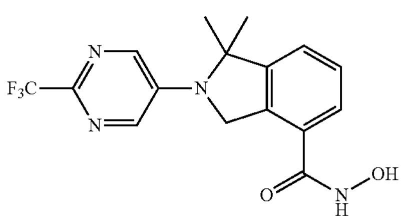 [SMILES: CC1(C)c2cccc(C(=O)NO)c2CN1c1cnc(C(F)(F)F)nc1] | N-hydroxy-1,1-dimethyl-2-(2-(trifluoromethyl)pyrimidin-5-yl)isoindoline-4-carboxamide | (DMSO, 400 MHz, ppm): 8.55 (s, 2H), 7.62-7.60 (m, 2H), 7.49-7.47 (m, 1H), 4.96 (s, 2H), 1.74 (s, 6H). | 353 |
| 22-9 | 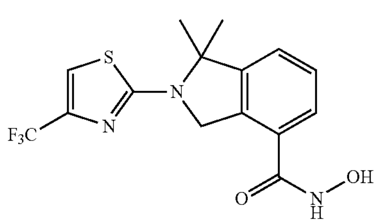 [SMILES: CC1(C)c2cccc(C(=O)NO)c2CN1c1nc(C(F)(F)F)cs1] | N-hydroxy-1,1-dimethyl-2-(4-(trifluoromethyl)thiazol-2-yl)isoindoline-4-carboxamide | (DMSO, 400 MHz, ppm): 11.20 (br, 1H), 9.51 (br, 1H), 7.62-7.56 (m, 3H), 7.49-7.43 (m, 1H), 4.87 (s, 2H), 1.77 (s, 6H). | 358 |

Example 22-8. N-Hydroxy-1,1-dimethyl-2-(5-(trifluoromethyl)pyrazin-2-yl)isoindoline-4-carboxamide

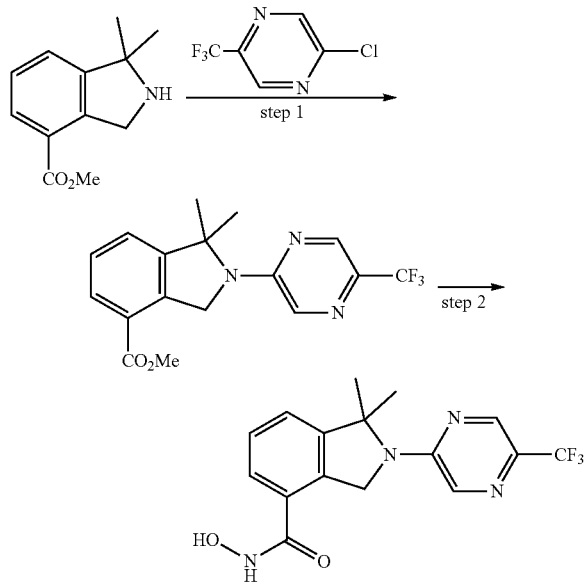

Step 1. Methyl 1,1-dimethyl-2-(5-(trifluoromethyl)pyrazin-2-yl)isoindoline-4-carboxylate A mixture of methyl 1,1-dimethyl-2,3-dihydro-1H-isoindole-4-carboxylate (100 mg, 0.49 mmol), 2-chloro-5-(trifluoromethyl)pyrazine (180 mg, 0.99 mmol), $2^{nd}$ Generation RuPhos precatalyst (38 mg, 0.05 mmol), RuPhos (23 mg, 0.05 mmol) and cesium carbonate (477 mg, 1.46 mmol) in toluene (3 mL) was stirred for 12 h at 110° C. The reaction mixture was cooled to room temperature, poured into water (50 mL), and extracted with ethyl acetate (3×50 mL). The combined organic layers were dried over anhydrous sodium sulfate, filtered, and concentrated under vacuum. The crude product was purified by silica gel chromatography (eluting with 1:5 ethyl acetate/petroleum ether) to afford methyl 1,1-dimethyl-2-(5-(trifluoromethyl)pyrazin-2-yl)isoindoline-4-carboxylate (150 mg, 88%) as a yellow solid. LCMS: (ES, m/z): 352 [M+H]⁺

Step 2. N-Hydroxy-1,1-dimethyl-2-(5-(trifluoromethyl)pyrazin-2-yl)isoindoline-4-carboxamide Hydroxyl amine (50% in water, 1.69 mL, 25.6 mmol) and 1 M aqueous sodium hydroxide solution (0.86 mL, 0.86 mmol) were added to a solution of methyl 1,1-dimethyl-2-[5-(trifluoromethyl)pyrazin-2-yl]isoindole-4-carboxylate (150 mg, 0.43 mmol) in THF:MeOH (4:1, 3.0 mL). The resulting solution stirred for 3 h at room temperature, and the solids were filtered out. The mixture was purified by Prep-HPLC with the following conditions: Column, XBridge Prep C18 OBD Column, 19×150 mm, 5 μm; mobile phase, water (0.1% formic acid) and acetonitrile (40.0% acetonitrile up to 50.0% in 8 min); Detector, UV 254/220 nm. The collected fraction was lyophilized to afford N-hydroxy-1,1-dimethyl-2-(5-(trifluoromethyl)pyrazin-2-yl)isoindoline-4-carboxamide (17.4 mg, 12%) as a white solid. ¹H-NMR (DMSO, 400 MHz) δ (ppm): δ 11.21 (br s, 1H), 9.16 (br s, 1H), 8.59 (s, 1H), 8.16 (br s, 1H), 7.59 (d, J=7.6 Hz, 2H), 7.49-7.45 (m, 1H), 5.09 (s, 2H), 1.80 (s, 6H). LCMS: (ES, m/z): 353 [M+H]⁺.

Example 23-1. N-hydroxy-1,1-dimethyl-2-(6-(trifluoromethyl)quinolin-2-yl)isoindoline-4-carboxamide

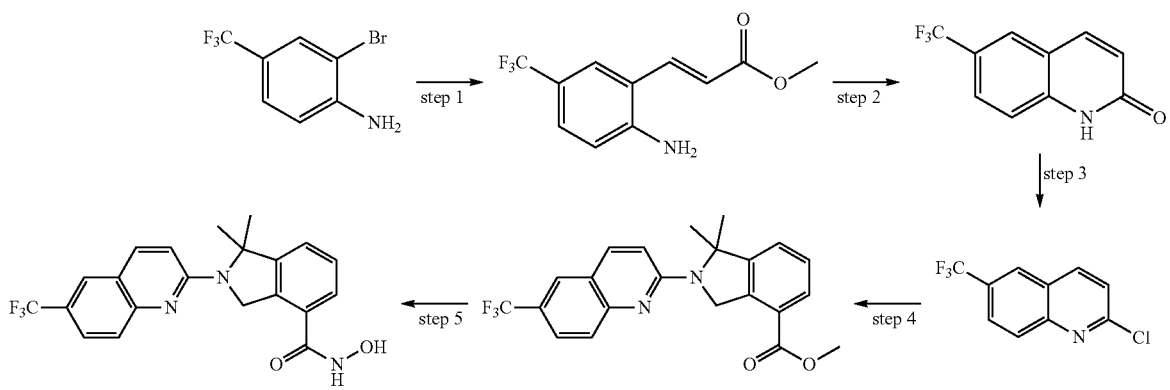

Step 1. (E)-methyl 3-(2-amino-5-(trifluoromethyl)phenyl)acrylate

A solution of 2-bromo-4-(trifluoromethyl)aniline (5.00 g, 20.8 mmol), tri(o-tolyl)phosphine (1.27 g, 4.18 mmol), palladium (II) acetate (460 mg, 2.78 mmol), methyl prop-2-enoate (9.00 g, 104 mmol), and triethylamine (6.57 mL, 47.1 mmol) in acetonitrile (100 mL) was heated to 90° C. overnight. The reaction mixture was filtered, and the filtrate was concentrated under vacuum. The residue was purified via column chromatography on silica gel (eluting with 25% ethyl acetate-petroleum ether) to give (E)-methyl 3-(2-amino-5-(trifluoromethyl)phenyl)acrylate (3.4 g, 67%) as a yellow solid. MS: (ES, m/z): 246[M+H]⁺.

Step 2. 6-(trifluoromethyl)quinolin-2(1H)-one

A solution of (E)-methyl 3-(2-amino-5-(trifluoromethyl)phenyl)acrylate (3.4 g, 13.87 mmol) and conc. HCl (25 mL) in tetrahydrofuran (40 mL) and water (25 mL) was heated to reflux overnight. The resulting solution was diluted with 80 mL of water, and the pH value of the solution was adjusted to 7 with 2 M aqueous NaOH solution. The resulting solution was extracted with 3×150 mL of ethyl acetate, and the combined organic phases were washed with 3×200 mL of brine, dried over anhydrous sodium sulfate, filtered, and concentrated under vacuum. The residue was purified via column chromatography on silica gel (eluting with dichloromethane/methanol (20:1) to give 6-(trifluoromethyl)quinolin-2(1H)-one (2.16 g, 73%) as a white solid. MS: (ES, m/z) 214[M+H]$^+$ Step 3. 2-chloro-6-(trifluoromethyl)quinolone A mixture of 6-(trifluoromethyl)quinolin-2(1H)-one (1.2 g, 5.63 mmol, 1.00 equiv) and phosphoroyl trichloride (25 mL) was heated to reflux for 1.5 hr. The resulting mixture was concentrated under vacuum, and the residue was diluted with 50 mL of water. The pH value of the solution was adjusted to 7 with 2 M aqueous NaHCO$_3$ solution. The resulting solution was extracted with 3×100 mL of ethyl acetate, and the combined organic phases were washed with 3×150 mL of brine, dried over anhydrous sodium sulfate, filtered, and concentrated under vacuum. The residue was purified via column chromatography on silica gel (eluting with 5% ethyl acetate/petroleum ether) to afford 2-chloro-6-(trifluoromethyl)quinolone (1.2 g (92%) as a white solid. MS: (ES, m/z): 232[M+H]$^+$ Step 4. methyl 1,1-dimethyl-2-(6-(trifluoromethyl) quinolin-2-yl)isoindoline-4-carboxylate A solution of 2-chloro-6-(trifluoromethyl)quinoline (450 mg, 1.94 mmol), methyl 1,1-dimethyl-2,3-dihydro-1H-isoindole-4-carboxylate (200 mg, 0.97 mmol), RuPhos (91 mg, 0.19 mmol), RuPhos 2G (76 mg, 0.10 mmol), and cesium carbonate (954 mg, 2.93 mmol) in toluene (10 mL) stirred overnight at 100° C. The reaction mixture was cooled to room temperature and filtered. The filtrate was concentrated under vacuum. The residue was purified via column chromatography on silica gel (eluting with 5% ethyl acetate/petroleum ether) to give methyl 1,1-dimethyl-2-(6-(trifluoromethyl)quinolin-2-yl)isoindoline-4-carboxylate (65 mg, 17%) as a light yellow solid. MS: (ES, m/z): 401[M+H]$^+$.

Step 5. N-hydroxy-1,1-dimethyl-2-(6-(trifluoromethyl)quinolin-2-yl)isoindoline-4-carboxamide Hydroxyl amine (50% in water, 1.28 mL, 20.9 mmol) and 1 M aqueous sodium hydroxide solution (0.70 mL, 0.70 mmol) were added to a solution of methyl 1,1-dimethyl-2-(6-(trifluoromethyl)quinolin-2-yl)isoindoline-4-carboxylate (70 mg, 0.17 mmol) in THF:MeOH (4:1, 4.0 mL). The resulting solution stirred for 4 h at room temperature. The resulting mixture was partially concentrated under vacuum. The crude product was purified by Prep-HPLC with the following conditions: Column, XBridge Prep C18 OBD Column, 5 um, 19×150 mm; mobile phase, A:water with 0.1% FA, B: ACN; Flow rate, 20 mL/min; Gradient, 18% B to 58% B in 8 min; Detector, 254&220 nm. The collected fraction was lyophilized to give N-hydroxy-1,1-dimethyl-2-(6-(trifluoromethyl)quinolin-2-yl)isoindoline-4-carboxamide (28.6 mg, 41%) as a white solid. $^1$H-NMR (DMSO, 400 MHz) δ (ppm): 511.20 (br, 1H), 9.18 (br, 1H), 8.27-8.16 (m, 2H), 7.76 (s, 2H), 7.60-7.56 (m, 2H), 7.48-7.44 (m, 1H), 7.15 (br, 1H), 5.10 (s, 2H), 1.92 (s, 6H). MS: (ES, m/z): 402[M+H]$^+$.

The following compound was prepared according to the procedures described above for N-hydroxy-1,1-dimethyl-2-(6-(trifluoromethyl)quinolin-2-yl)isoindoline-4-carboxamide.

| Ex. | Structure | Name | $^1$HNMR | (ES, m/z) [M + H]$^+$ |
|---|---|---|---|---|
| 23-2 | 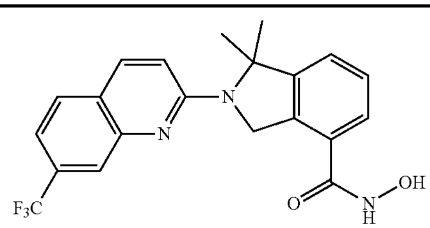 | N-hydroxy-1,1-dimethyl-2-(7-(trifluoromethyl)quinolin-2-yl)isoindoline-4-carboxamide | (DMSO, 400 MHz, ppm): 9.15 (s, 1H), 8.22 (d, J = 9.2 Hz, 1H), 7.97 (d, J = 8.0 Hz, 1H), 7.91 (s, 1H), 7.60-7.57 (m, 2H), 7.49-7.45 (m, 2H), 7.15 (s, 1H), 5.09 (s, 2H), 1.93 (s, 6H) | 402 |

Example 24-1. N-hydroxy-1,1-dimethyl-2-(6-(trifluoromethyl)-1,5-naphthyridin-2-yl)isoindoline-4-carboxamide

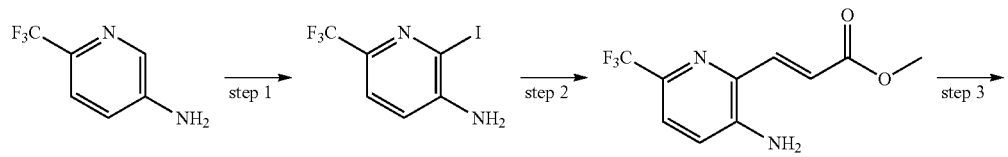

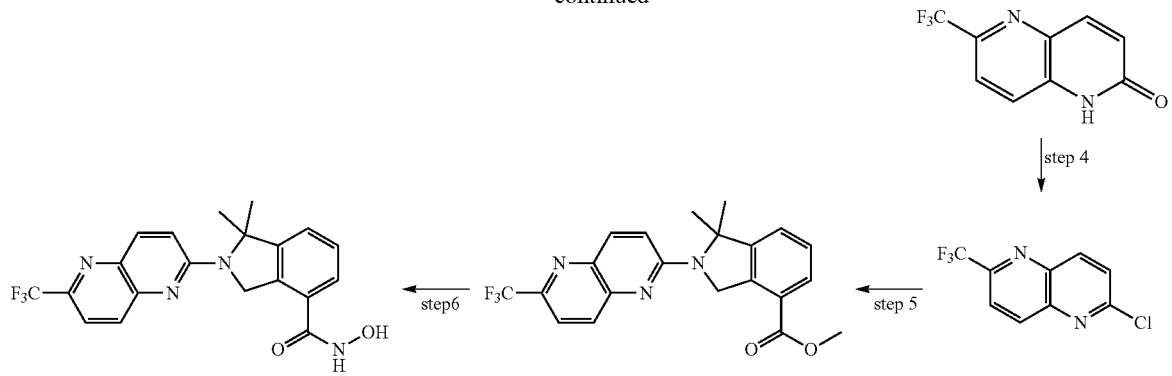

Step 1. 2-iodo-6-(trifluoromethyl)pyridin-3-amine

A solution of 6-(trifluoromethyl)pyridin-3-amine (1 g, 6.17 mmol), iodine (1.57 g, 6.17 mmol), and silver sulfate (1.92 g, 6.17 equiv) in ethanol (40 mL) stirred overnight at room temperature. The reaction mixture was filtered, and the filtrate was concentrated under vacuum. The residue was dissolved in 20 mL of water, and the pH value of the solution was adjusted to 8 with 1 M aqueous NaOH solution. The resulting solution was extracted with 3×30 mL of dichloromethane, and the combined organic phases were washed with 30 mL of brine, dried over anhydrous sodium sulfate, filtered, and concentrated under vacuum. The residue was purified via column chromatography on silica gel (eluting with 1:3 ethyl acetate/petroleum ether) to give 2-iodo-6-(trifluoromethyl)pyridin-3-amine (1.2 g, 68%) as a gray solid. MS: (ESI, m/z): 289[M+H]$^+$.

Step 2. methyl (2E)-3-[3-amino-6-(trifluoromethyl)pyridin-2-yl]prop-2-enoate A solution of 2-iodo-6-(trifluoromethyl)pyridin-3-amine (1.1 g, 3.82 mmol), triethylamine (1.60 mL, 11.5 mmol), palladium (II) acetate (231 mg, 1.03 mmol), tri(o-toly)lphosphine (86 g, 2.06 mmol), and methyl prop-2-enoate (1.6 g, 18.59 mmol, 5.00 equiv) in acetonitrile (100 mL) stirred overnight at 90° C. in an oil bath. The resulting mixture was concentrated under vacuum. The reaction was then quenched by the addition of 20 mL of water. The resulting solution was extracted with 3×30 mL of ethyl acetate, and the combined organic phases were washed with 50 mL of brine, dried over anhydrous sodium sulfate, filtered, and concentrated under vacuum. The residue was purified via column chromatography on silica gel (eluting with 1:3 ethyl acetate/petroleum ether) to give methyl (2E)-3-[3-amino-6-(trifluoromethyl)pyridin-2-yl]prop-2-enoate (900 mg, 96%) as a yellow solid. MS: (ESI, m/z): 247[M+H]$^+$.

Step 3. 6-(trifluoromethyl)-1,2-dihydro-1,5-naphthyridin-2-one

A solution of methyl (2E)-3-[3-amino-6-(trifluoromethyl)pyridin-2-yl]prop-2-enoate (900 mg, 3.66 mmol) and 6 M aqueous HCl (6 mL, 36 mmol) in tetrahydrofuran (7.0 mL) stirred for 50 h at 75° C. in an oil bath. The reaction was then quenched by the addition of 30 mL of water. The pH value of the solution was adjusted to 7 with 2 M aqueous NaHCO$_3$ solution. The resulting solution was extracted with 3×30 mL of ethyl acetate, and the combined organic phases were washed with 50 mL of brine, dried over anhydrous sodium sulfate, filtered, and concentrated under vacuum. The residue was purified via column chromatography on silica gel (eluting with 50% ethyl acetate-petroleum ether) to give 6-(trifluoromethyl)-1,2-dihydro-1,5-naphthyridin-2-one (550 mg, 70%) as a white solid. MS: (ESI, m/z): 215[M+H]$^+$.

Step 4. 2-chloro-6-(trifluoromethyl)-1,5-naphthyridine

A mixture of 6-(trifluoromethyl)-1,2-dihydro-1,5-naphthyridin-2-one (200 mg, 0.93 mmol) and phosphoroyl trichloride (5 mL) stirred for 3 h at 105° C. in an oil bath. The resulting mixture was concentrated under vacuum, and the reaction was then quenched by the addition of 10 mL of ice/water. The mixture was extracted with 3×20 mL of ethyl acetate, and the combined organic layers were washed with 20 mL of brine, dried over anhydrous sodium sulfate, filtered, and concentrated under vacuum to give 2-chloro-6-(trifluoromethyl)-1,5-naphthyridine (230 mg) as a white solid. MS: (ESI, m/z): 233[M+H]$^+$

Step 5. methyl 1,1-dimethyl-2-[6-(trifluoromethyl)-1,5-naphthyridin-2-yl]-2,3-dihydro-1H-isoindole-4-carboxylate A mixture of 2-chloro-6-(trifluoromethyl)-1,5-naphthyridine (250 mg, 1.07 mmol), methyl 1,1-dimethyl-2,3-dihydro-1H-isoindole-4-carboxylate (440 mg, 2.14 mmol), RuPhos 2G (83 mg, 0.10 mmol), RuPhos (51 mg, 0.10 mmol), and cesium carbonate (874 mg, 2.68 mmol) in toluene (5 mL) stirred overnight at 105° C. in an oil bath. The resulting mixture was concentrated under vacuum, and the reaction was then quenched by the addition of 20 mL of water. The resulting solution was extracted with 3×20 mL of ethyl acetate, and the combined organic phases were washed with 20 mL of brine, dried over anhydrous sodium sulfate, filtered, and concentrated under vacuum. The residue was purified via column chromatography on silica gel (eluting with 1:2 ethyl acetate/petroleum ether) to give methyl 1,1-dimethyl-2-[6-(trifluoromethyl)-1,5-naphthyridin-2-yl]-2,3-dihydro-1H-isoindole-4-carboxylate (80 mg, 19%) as a yellow oil. MS: (ESI, m/z): 402[M+H]$^+$.

Step 6. N-hydroxy-1,1-dimethyl-2-[6-(trifluoromethyl)-1,5-naphthyridin-2-yl]-2,3-dihydro-1H-isoindole-4-carboxamide Hydroxyl amine (50% in water, 0.73 mL, 12 mmol) and 1 M aqueous sodium hydroxide solution (0.40 mL, 0.40 mmol) were added to a solution of methyl 1,1-dimethyl-2-[6-(trifluoromethyl)-1,5-naphthyridin-2-yl]-2,3-dihydro-1H-isoindole-4-carboxylate (80 mg, 0.20 mmol) in THF:MeOH (4:1, 2.0 mL). The resulting solution stirred for 2 h at room temperature. The solids were filtered out. The crude product was purified by Prep-HPLC with the following conditions: Column: XBridge Prep C18 OBD Column, 5 um, 19×150 mm; Mobile Phase A: water with 0.1% FA, Mobile Phase B: ACN; Flow rate: 20 mL/min; Gradient: 38% B to 65% B in 6.5 min; 254&220 nm. The collected fraction was lyophilized to give N-hydroxy-1,1-dimethyl-2-[6-(trifluoromethyl)-1,5-naphthyridin-2-yl]-2,3-dihydro-1H-isoindole-4-carboxamide (15.6 mg, 19%) as an off-white solid. $^1$H-NMR (DMSO, 300 MHz) δ (ppm): 11.17 (br, 1H), 9.16 (br, 1H), 8.27-8.21 (m, 2H), 7.97 (d, J=8.7 Hz, 1H), 7.63-7.59 (m, 2H), 7.51-7.46 (m, 2H), 5.16 (s, 2H), 1.94 (s, 6H). MS: (ESI, m/z): 403[M+H]$^+$ Example 25-1. 2-(benzo[d]oxazol-2-yl)-N-hydroxy-1,1-dimethylisoindoline-4-carboxamide

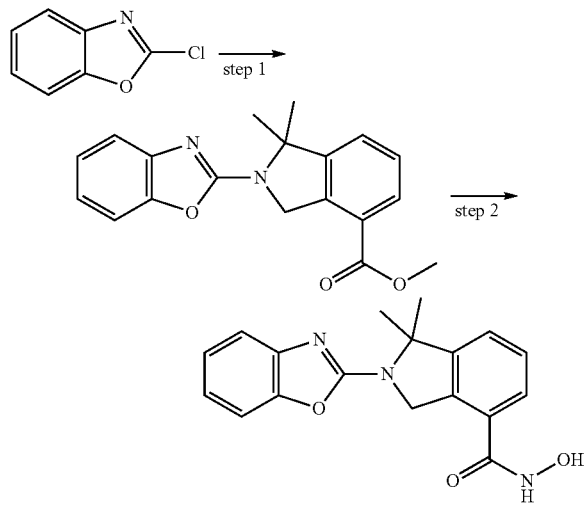

Step 1. methyl 2-(benzo[d]oxazol-2-yl)-1,1-dimethylisoindoline-4-carboxylate

A solution of 2-chloro-1,3-benzoxazole (337 mg, 2.19 mmol), methyl 1,1-dimethyl-2,3-dihydro-1H-isoindole-4-carboxylate (150 mg, 0.73 mmol), and triethylamine (0.30 mL, 2.18 mmol) in acetonitrile (6 mL) stirred overnight at 85° C. The reaction mixture was cooled to room temperature, and the resulting solution was diluted with 30 mL of water. The resulting solution was extracted with 3×20 mL of ethyl acetate, and the combined organic layers were washed with brine, dried over anhydrous sodium sulfate, filtered, and concentrated under vacuum. The residue was purified via column chromatography on silica gel (eluting with 10% ethyl acetate/petroleum ether) to give methyl 2-(benzo[d]oxazol-2-yl)-1,1-dimethylisoindoline-4-carboxylate (125 mg, 53%) as a white solid. MS: (ESI, m/z): 323[M+H]$^+$ Step 2. 2-(benzo[d]oxazol-2-yl)-N-hydroxy-1,1-dimethylisoindoline-4-carboxamide Hydroxyl amine (50% in water, 2.74 mL, 44.7 mmol) and 1 M aqueous sodium hydroxide solution (1.49 mL, 1.49 mmol) were added to a solution of methyl 2-(1,3-benzoxazol-2-yl)-1,1-dimethyl-2,3-dihydro-1H-isoindole-4-carboxylate (120 mg, 0.37 mmol) in THF:MeOH (4:1, 5.0 mL). The resulting solution stirred for 4 h at room temperature. The resulting mixture was concentrated under vacuum. The crude product was purified by Prep-HPLC with the following conditions: Column, XBridge BEH C18 OBD Prep Column, 5 um, 19×250 mm; mobile phase, A: Water with 10 mmol NH$_4$HCO$_3$, Mobile Phase B: ACN; Flow rate: 30 mL/min; Gradient: 20% B to 60% B in 8 min; Detector, 254&220 nm. The collected fraction was lyophilized to give 2-(benzo[d]oxazol-2-yl)-N-hydroxy-1,1-dimethylisoindoline-4-carboxamide (42 mg, 35%) as a white solid. $^1$H-NMR (DMSO, 400 MHz) δ (ppm): 9.92 (br, 2H), 7.63-7.58 (m, 2H), 7.50-7.46 (m, 2H), 7.37 (d, J=7.6 Hz, 1H), 7.20-7.16 (m, 1H), 7.06-7.02 (m, 1H), 5.15 (s, 2H), 1.79 (s, 6H). MS: (ESI, m/z): 324[M+H]$^+$.

Example 26-1. N-hydroxy-1,1-dimethyl-2-(5-(trifluoromethyl)oxazolo[4,5-b]pyridin-2-yl)isoindoline-4-carboxamide

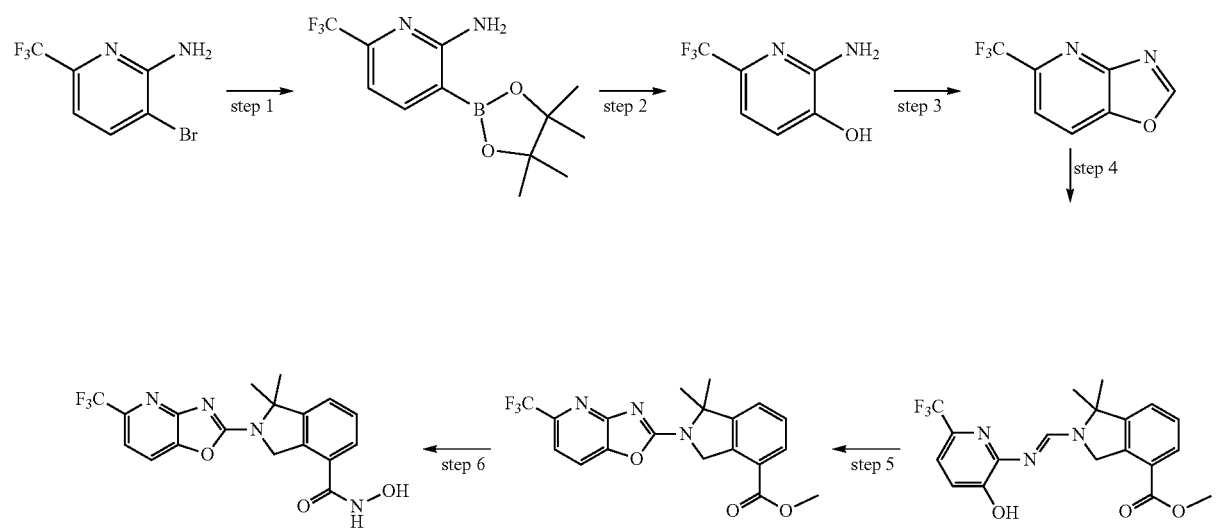

Step 1. 3-(4,4,5,5-tetramethyl-1,3,2-dioxaborolan-2-yl)-6-(trifluoromethyl)pyridin-2-amine A mixture of 3-bromo-6-(trifluoromethyl)pyridin-2-amine (1.2 g, 4.98 mmol), bis(pinacolato)diboron (1.9 g, 7.48 mmol), Pd$_2$(dba)$_3$-chloroform adduct (258 mg, 0.25 mmol), tricyclohexylphosphine tetrafluoroborate (183 mg, 0.50 mmol), and potassium acetate (733 mg, 7.47 mmol) in 1,4-dioxane (25 mL) stirred overnight at 80° C. The reaction mixture was cooled to room temperature and filtered. The filtrate was concentrated under vacuum. The residue was purified via column chromatography on silica gel (eluting with 1:10 ethyl acetate/petroleum ether) to give 3-(4,4,5,5-tetramethyl-1,3,2-dioxaborolan-2-yl)-6-(trifluoromethyl)pyridin-2-amine (1.16 g, 81%) as a yellow solid. MS: (ESI, m/z): 289[M+H]$^+$.

Step 2. 2-amino-6-(trifluoromethyl)pyridin-3-ol

A solution of 3-(tetramethyl-1,3,2-dioxaborolan-2-yl)-6-(trifluoromethyl)pyridin-2-amine (1.16 g, 4.03 mmol) and 30% aqueous hydrogen peroxide (9.00 mL, 8.0 mmol) in tetrahydrofuran (30 mL) stirred for 2 h at room temperature. The resulting solution was extracted with 3×20 mL of ethyl acetate, and the combined organic phases were washed with brine, dried over anhydrous sodium sulfate, filtered, and concentrated under vacuum. The residue was purified via column chromatography on silica gel (eluting with 25% ethyl acetate-petroleum ether) to give (394 mg, 55%) as yellow oil. MS: (ESI, m/z): 179[M+H]$^+$.

Step 3. 5-(trifluoromethyl)oxazolo[4,5-b]pyridine

A mixture of 2-amino-6-(trifluoromethyl)pyridin-3-ol (394 mg, 2.21 mmol) and trimethyl orthoformate (8 mL) was irradiated with microwave radiation for 40 min at 150° C. The reaction mixture was cooled to room temperature and concentrated under vacuum. The residue was purified via column chromatography on silica gel (eluting with 25% ethyl acetate-petroleum ether) to give 5-(trifluoromethyl)oxazolo[4,5-b]pyridine (112 mg, 27%) as a light yellow solid. MS: (ESI, m/z): 189[M+H]$^+$.

Step 4. methyl (E)-2-(((3-hydroxy-6-(trifluoromethyl)pyridin-2-yl)imino)methyl)-1,1-dimethylisoindoline-4-carboxylate A solution of 5-(trifluoromethyl)oxazolo[4,5-b]pyridine (112 mg, 0.60 mmol), methyl 1,1-dimethyl-2,3-dihydro-1H-isoindole-4-carboxylate (122 mg, 0.59 mmol) and trifluoromethanesulfonic acid (10.2 mg, 0.06 mmol) in acetonitrile (5 mL) stirred overnight at 60° C. The reaction mixture was cooled to room temperature and concentrated under vacuum. The residue purified via column chromatography on silica gel (eluting with 20% ethyl acetate-petroleum ether) to give methyl (E)-2-(((3-hydroxy-6-(trifluoromethyl)pyridin-2-yl)imino)methyl)-1,1-dimethylisoindoline-4-carboxylate (138 mg, 59%) as an off-white solid. MS: (ESI, m/z): 394[M+H]$^+$.

Step 5. methyl 1,1-dimethyl-2-(5-(trifluoromethyl)oxazolo[4,5-b]pyridin-2-yl)isoindoline-4-carboxylate A mixture of methyl (E)-2-(((3-hydroxy-6-(trifluoromethyl)pyridin-2-yl)imino)methyl)-1,1-dimethylisoindoline-4-carboxylate (136 mg, 0.35 mmol) and (diacetoxyiodo)benzene (123 mg, 0.38 mmol) in dichloromethane (5 mL) stirred for 4 h at room temperature. The resulting mixture was concentrated under vacuum. The residue was purified via column chromatography on silica gel (eluting with 20% ethyl acetate-petroleum ether) to give methyl 1,1-dimethyl-2-(5-(trifluoromethyl)oxazolo[4,5-b]pyridin-2-yl)isoindoline-4-carboxylate (120 mg, 89%) as a light yellow solid. MS: (ESI, m/z): 392[M+H]$^+$.

Step 6. N-hydroxy-1,1-dimethyl-2-(5-(trifluoromethyl)oxazolo[4,5-b]pyridin-2-yl)isoindoline-4-carboxamide Hydroxyl amine (50% in water, 2.07 mL, 33.8 mmol) and 1 M aqueous sodium hydroxide solution (1.12 mL, 1.12 mmol) were added to a solution of methyl 1,1-dimethyl-2-(5-(trifluoromethyl)oxazolo[4,5-b]pyridin-2-yl)isoindoline-4-carboxylate (110 mg, 0.28 mmol) in THF:MeOH (4:1, 5.0 mL). The resulting solution stirred for 3 h at room temperature. The solids were filtered out. The crude product was purified by Prep-HPLC with the following conditions: Column: XBridge Prep C18 OBD Column, 5 um, 19×150 mm; mobile phase, A: water with 0.1% FA, Mobile Phase B: ACN; Flow rate, 20 mL/min; Gradient, 27% B to 60% B in 8 min; Detector, 254&220 nm. The collected fraction was lyophilized to give N-hydroxy-1,1-dimethyl-2-(5-(trifluoromethyl)oxazolo[4,5-b]pyridin-2-yl)isoindoline-4-carboxamide (38.5 mg, 35%) as a white solid. R-NMR (DMSO, 400 MHz) δ (ppm): 11.14 (br, 1H), 9.16 (br, 1H), 8.01 (d, J=8.0 Hz, 1H), 7.64-7.60 (m, 2H), 7.53-7.46 (m, 2H), 5.24 (s, 2H), 1.81 (s, 6H). MS: (ESI, m/z): 393[M+H]$^+$ The following compound was prepared according to the procedures described above for N-hydroxy-1,1-dimethyl-2-(5-(trifluoromethyl)oxazolo[4,5-b]pyridin-2-yl)isoindoline-4-carboxamide:

| Ex. | Structure | Name | $^1$HNMR | (ESI, m/z) [M + H]$^+$ |
|---|---|---|---|---|
| 26-2 | 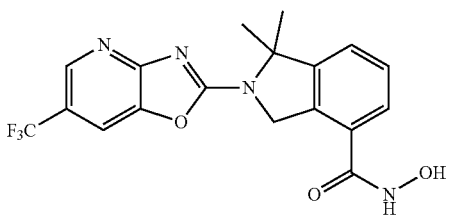 [SMILES: CC1(C)c2cccc(C(=O)NO)c2CN1c1nc2ncc(C(F)(F)F)cc2o1] | N-hydroxy-1,1-dimethyl-2-(6-(trifluoromethyl)oxazolo[4,5-b]pyridin-2-yl)isoindoline-4-carboxamide | (DMSO, 400 MHz, ppm): 11.23 (br, 1H), 9.19 (br, 1H), 8.54 (s, 1H), 8.28 (s, 1H), 7.64-7.60 (m, 2H), 7.50-7.47 (m, 1H), 5.24 (s, 2H), 1.82 (s, 6H). | 393 |

Example 27-1. 2-(6-cyano-5-(trifluoromethyl)pyridin-2-yl)-N-hydroxy-1,1-dimethylisoindoline-4-carboxamide

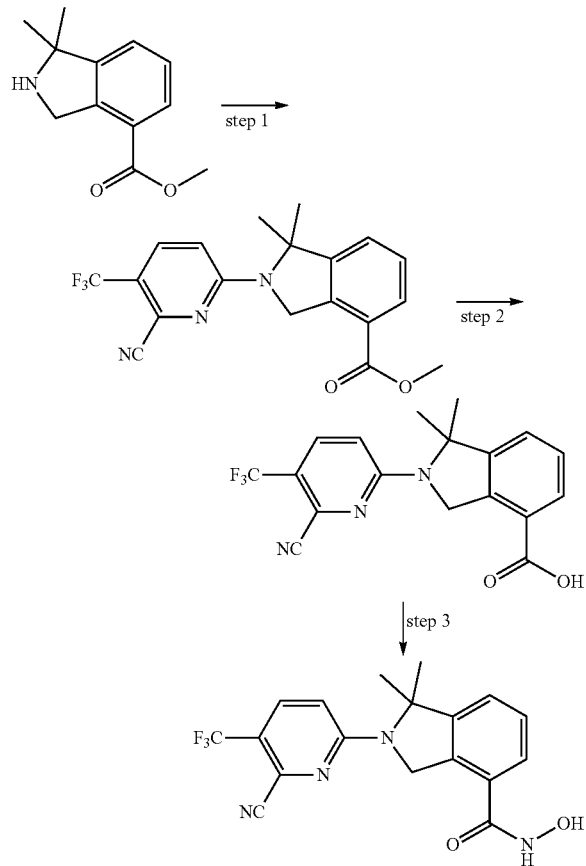

Step 1. methyl 2-(6-cyano-5-(trifluoromethyl)pyridin-2-yl)-1,1-dimethylisoindoline-4-carboxylate A solution of methyl 1,1-dimethylisoindoline-4-carboxylate (200 mg, 0.97 mmol), 6-chloro-3-(trifluoromethyl)picolinonitrile (200 mg, 0.97 mmol), RuPhos 2G (70 mg, 0.10 mmol), RuPhos (90 mg, 0.19 mmol), and cesium carbonate (960 mg, 2.95 mmol) in toluene (10 mL) stirred for 3 h at 110° C. The reaction mixture was cooled to room temperature and then concentrated under vacuum. The residue was purified via column chromatography on silica gel (eluting with 1:10 ethyl acetate/petroleum ether) to give methyl 2-(6-cyano-5-(trifluoromethyl)pyridin-2-yl)-1,1-dimethylisoindoline-4-carboxylate (80 mg, 22%) as a white solid. MS: (ESI, m/z): 376 [M+H]$^+$.

Step 2. 2-(6-cyano-5-(trifluoromethyl)pyridin-2-yl)-1,1-dimethylisoindoline-4-carboxylic acid A solution of methyl 2-(6-cyano-5-(trifluoromethyl)pyridin-2-yl)-1,1-dimethylisoindoline-4-carboxylate (80 mg, 0.21 mmol) and 1 M aqueous lithium hydroxide solution (1.1 mL, 1.05 mmol) in tetrahydrofuran (5 mL) stirred overnight at room temperature. The pH value of the solution was adjusted to 3 with 2 M aqueous of HCl solution. The resulting solution was extracted with 3×20 mL of ethyl acetate, and the combined organic phases were washed with brine, dried over anhydrous sodium sulfate, filtered, and concentrated under vacuum to give 2-(6-cyano-5-(trifluoromethyl)pyridin-2-yl)-1,1-dimethylisoindoline-4-carboxylic acid (50 mg, 65%) as a green solid. MS: (ESI, m/z): 362[M+H]$^+$.

Step 3. 2-(6-cyano-5-(trifluoromethyl)pyridin-2-yl)-N-hydroxy-1,1-dimethylisoindoline-4-carboxamide A solution of 2-(6-cyano-5-(trifluoromethyl)pyridin-2-yl)-1,1-dimethylisoindoline-4-carboxylic acid (50 mg, 0.14 mmol), NMM (14 mg, 0.14 mmol), isopropyl chloroformate (1.0 M in toluene, 0.14 mL, 0.14 mmol) in DMA (3 mL) was stirred for 10 minutes at room temperature. Hydroxylamine hydrochloride (10 mg, 0.14 mmol) was added, and the resulting solution stirred overnight at room temperature. The crude product was purified by prep-HPLC with the following conditions: Column: XBridge Prep C18 OBD Column, 5 um, 19×150 mm; Mobile Phase A: Water (0.1% FA), Mobile Phase B: ACN; Flow rate: 20 mL/min; Gradient: 24% B to 80% B in 8 mins; 254&220 nm. The collected fraction was lyophilized to give 2-(6-cyano-5-(trifluoromethyl)pyridin-2-yl)-N-hydroxy-1,1-dimethylisoindoline-4-carboxamide (14.4 mg, 28%) as an off-white solid. $^1$H-NMR (DMSO, 400 MHz) δ (ppm): 11.16 (br, 1H), 9.12 (br, 1H), 8.08-8.02 (m, 1H), 7.59-7.54 (m, 2H), 7.48-7.44 (m, 1H), 6.92 (s, 1H), 4.99 (m, 2H), 1.78 (s, 6H). MS: (ESI, m/z): 377[M+H]$^+$ The following compound was prepared according to the procedures described above for 2-(6-cyano-5-(trifluoromethyl)pyridin-2-yl)-N-hydroxy-1,1-dimethylisoindoline-4-carboxamide.

| Ex. | Structure | Name | $^1$HNMR | (ESI/, m/z) [M + H]$^+$ |
|---|---|---|---|---|
| 27-2 | (structure shown) | 2-(4-cyano-5-(trifluoromethyl)pyridin-2-yl)-N-hydroxy-1,1-dimethylisoindoline-4-carboxamide | (DMSO, 400 MHz, ppm): 10.92 (br, 1H), 9.17 (br, 1H), 8.67 (s, 1H), 7.58-7.55 (m, 2H), 7.47-7.43 (m, 1H), 7.20 (s, 1H), 5.02 (s, 1H), 1.79 (s, 6H). | 377 |

Example 28-1. N-hydroxy-1,1-dimethyl-2-(4-(trifluoromethyl)benzoyl)isoindoline-4-carboxamide

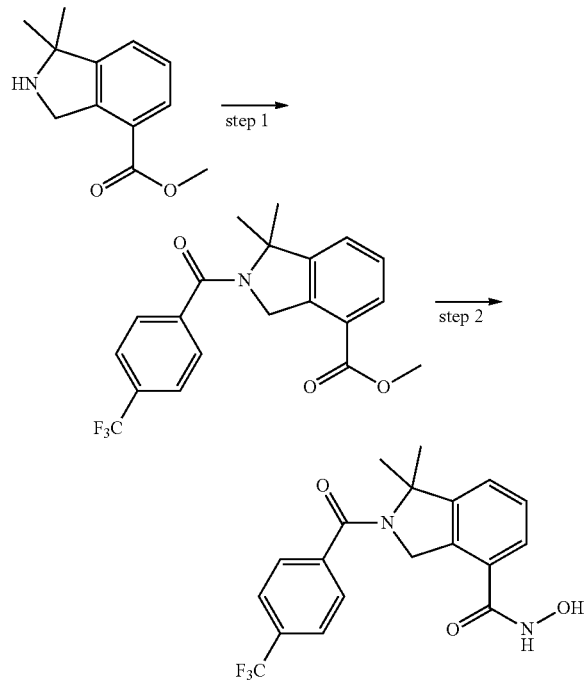

Step 1. methyl 1,1-dimethyl-2-(4-(trifluoromethyl)benzoyl)isoindoline-4-carboxylate A solution of 4-(trifluoromethyl)benzoic acid (278 mg, 1.46 mmol), DMTMM (404 mg, 1.46 mmol), and methyl 1,1-dimethylisoindoline-4-carboxylate (100 mg, 0.49 mmol) in N,N-dimethylformamide (5 mL) stirred for 12 h at room temperature. The mixture was diluted with 30 mL of ethyl acetate and washed with 2×30 mL of water. The organic phase was washed with 30 mL of brine, dried over anhydrous sodium sulfate, filtered, and concentrated under vacuum. The residue was purified via column chromatography on silica gel (eluting with 50% ethyl acetate-petroleum ether) to give methyl 1,1-dimethyl-2-(4-(trifluoromethyl)benzoyl)isoindoline-4-carboxylate (80 mg, 44%) as a yellow solid. MS: (ESI, m/z): 378[M+H]$^+$

Step 2. N-hydroxy-1,1-dimethyl-2-(4-(trifluoromethyl)benzoyl)isoindoline-4-carboxamide Hydroxyl amine (50% in water, 1.36 mL, 22.3 mmol) and 1 M aqueous sodium hydroxide solution (0.37 mL, 0.37 mmol) were added to a solution of methyl 1,1-dimethyl-2-(4-(trifluoromethyl)benzoyl)isoindoline-4-carboxylate (70 mg, 0.19 mmol) in THF:MeOH (4:1, 2.0 mL). The resulting solution stirred for 8 h at room temperature. The crude product was purified by Prep-HPLC with the following conditions: Column: XBridge Prep C18 OBD Column, 5 um, 19×150 mm; Mobile Phase A: water (0.1% FA), Mobile Phase B: ACN; Flow rate: 20 mL/min; Gradient: 30% B to 82% B in 8 min; 254&220 nm. The collected fraction was lyophilized to give N-hydroxy-1, 1-dimethyl-2-(4-(trifluoromethyl)benzoyl)isoindoline-4-carboxamide (25.1 mg, 33%) as a white solid. $^1$H-NMR (DMSO, 400 MHz) δ (ppm): 11.16 (br, 1H), 9.04 (br, 1H), 7.86 (d, J=8 Hz, 2H), 7.72 (d, 7=8 Hz, 2H), 7.54-7.49 (m, 2H), 7.44-7.41 (m, 1H), 4.78 (s, 2H), 1.81 (s, 6H). MS: (ESI, m/z): 379[M+H]$^+$.

The following compound was prepared according to the procedures described above for N-hydroxy-1, 1-dimethyl-2-(4-(trifluoromethyl)benzoyl)isoindoline-4-carboxamide.

| Ex. | Structure | Name | $^1$HNMR | (ESI/, m/z) [M + H]$^+$ |
|---|---|---|---|---|
| 28-2 | 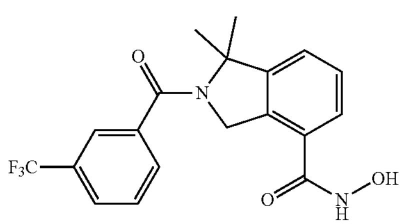 [SMILES: CC1(C)c2cccc(C(=O)NO)c2CN1C(=O)c1cccc(C(F)(F)F)c1] | N-hydroxy-1,1-dimethyl-2-(3-(trifluoromethyl)benzoyl)isoindoline-4-carboxamide | (DMSO, 400 MHz, ppm): 11.05 (br, 1H), 9.00 (br, 1 H), 7.84 (d, J = 8 Hz, 2H), 7.70 (d, J = 8 Hz, 2H), 7.53-7.39 (m, 3H), 4.76 (s, 2H), 1.80 (s, 6H). | 379 |
| 28-3 | 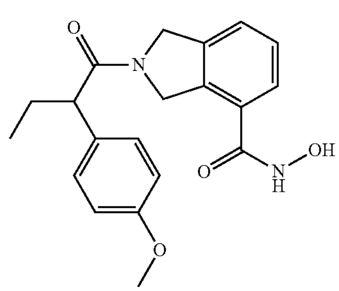 [SMILES: CCC(C(=O)N1Cc2cccc(C(=O)NO)c2C1)c1ccc(OC)cc1] | N-hydroxy-2-(2-(4-methoxyphenyl)butanoyl)isoindoline-4-carboxamide | $^1$H NMR (300 MHz, DMSO-d$_6$) δ ppm 11.16 (br s, 1H) 9.12 (br s, 1 H) 7.30-7.54 (m, 3 H) 7.24 (dd, J = 11.58, 8.65 Hz, 2 H) 6.88 (dd, J = 8.79, 2.35 Hz, 2 H) 4.99-5.24 (m, 1 H) 4.45-4.84 (m, 3 H) 3.70 (d, J = 0.88 Hz, 4 H) 1.86-2.05 (m, 1 H) 1.60 (tt, J = 13.85, 6.96 Hz, 1 H) 0.72-0.88 (m, 3 H) | 355 |

Example 29-1. N4-hydroxy-1,1-dimethyl-N2-(4-(trifluoromethyl)phenyl)isoindoline-2,4-dicarboxamide

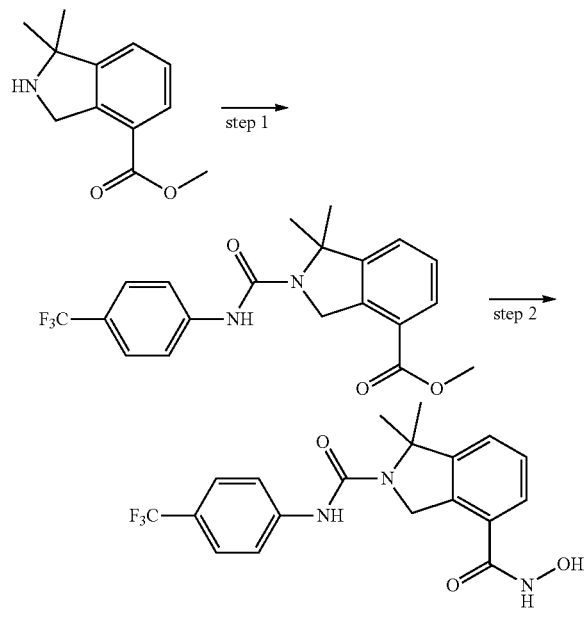

Step 1. methyl 1,1-dimethyl-2-(4-(trifluoromethyl)phenylcarbamoyl)isoindoline-4-carboxylate A solution of methyl 1,1-dimethylisoindoline-4-carboxylate (150 mg, 0.73 mmol), triethylamine (0.30 mL, 2.19 mmol), and 4-(trifluoromethyl)phenyl isothiocyanate (164 mg, 0.88 mmol) in dichloromethane (2 mL) stirred for 4 h at room temperature. The reaction mixture was then poured into 20 mL of water and extracted with 3×15 mL of dichloromethane. The combined organic phases were washed with 15 mL of brine, dried over anhydrous sodium sulfate, filtered, and concentrated under vacuum. The residue was purified via column chromatography on silica gel (eluting with 25% ethyl acetate-petroleum ether) to give methyl 1,1-dimethyl-2-(4-(trifluoromethyl)phenylcarbamoyl)isoindoline-4-carboxylate (100 mg, 35%) as a white solid. MS: (ESI, m/z): 393[M+H]$^+$.

Step 2. N4-hydroxy-1,1-dimethyl-N2-(4-(trifluoromethyl)phenyl)isoindoline-2,4-dicarboxamide Hydroxyl amine (50% in water, 1.86 mL, 30.6 mmol) and 1 M aqueous sodium hydroxide solution (0.51 mL, 0.51 mmol) were added to a solution of methyl 1,1-dimethyl-2-(4-(trifluoromethyl)phenylcarbamoyl)isoindoline-4-carboxylate (100 mg, 0.25 mmol) in THF:MeOH (4:1, 2.0 mL). The resulting solution stirred for 2 h at room temperature. The crude product was purified by Prep-HPLC with the following conditions: Column: XBridge Prep C18 OBD Column, 5 um, 19×150 mm; Mobile Phase A: water (0.1% FA), Mobile Phase B: ACN; Flow rate: 20 mL/min; Gradient: 40% B to 50% B in 8 min; 254 220 nm. The collected fraction was lyophilized to give N4-hydroxy-1,1-dimethyl-N2-(4-(trifluoromethyl)phenyl)isoindoline-2,4-dicarboxamide (18.5 mg, 18%) as a white solid. $^1$H-NMR (DMSO, 400 MHz) δ (ppm): 11.15 (br, 1H), 8.67 (br, 1H), 7.79 (d, J=8.4 Hz, 2H), 7.60 (d, J=8.4 Hz, 2H), 7.53-7.49 (m, 2H), 7.44-7.40 (m, 1H), 5.08 (s, 2H), 1.71 (s, 6H). MS: (ESI, m/z): 394[M+H]$^+$.

Example 30-1. N4-hydroxy-1,1-dimethyl-N2-(6-(trifluoromethyl)pyridin-3-yl)isoindoline-2,4-dicarboxamide

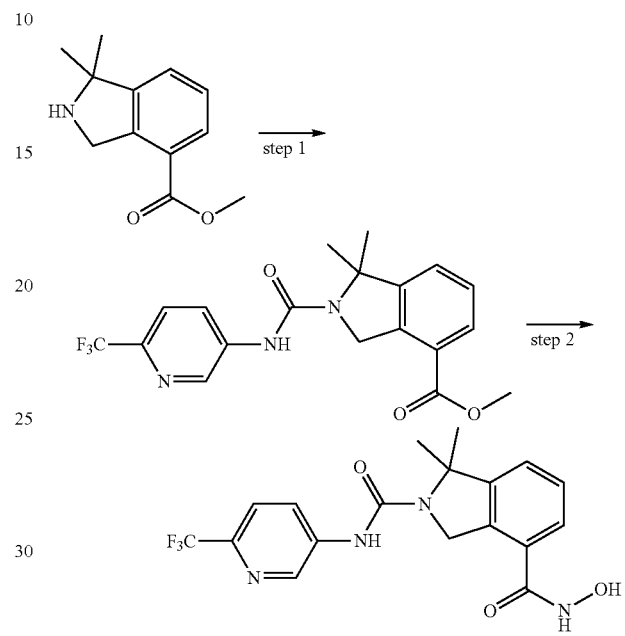

Step 1. methyl 1,1-dimethyl-2-(6-(trifluoromethyl)pyridin-3-ylcarbamoyl)isoindoline-4-carboxylate A mixture of 6-(trifluoromethyl)pyridin-3-amine (95 mg, 0.59 mmol), triphosgene (26 mg, 0.09 mmol), and N,N-diisopropylethylamine (0.51 mL, 2.92 mmol) in tetrahydrofuran (5 mL) stirred for 30 min at room temperature. Methyl 1,1-dimethylisoindoline-4-carboxylate (60 mg, 0.29 mmol) was added, and the resulting solution stirred for 2 h at room temperature. The reaction mixture was poured into 15 mL of water and extracted with 3×30 mL of dichloromethane. The combined organic phases were washed with brine, dried over anhydrous sodium sulfate, filtered, and concentrated under vacuum. The residue was purified via column chromatography on silica gel (eluting with 1:5 ethyl acetate/petroleum ether) to give methyl 1,1-dimethyl-2-(6-(trifluoromethyl)pyridin-3-ylcarbamoyl)isoindoline-4-carboxylate (51 mg, 44%) as a yellow solid. MS: (ESI, m/z): 394[M+H]$^+$.

Step 2. N4-hydroxy-1,1-dimethyl-N2-(6-(trifluoromethyl)pyridin-3-yl)isoindoline-2,4-dicarboxamide Hydroxyl amine (50% in water, 0.96 mL, 15.6 mmol) and 1 M aqueous sodium hydroxide solution (0.26 mL, 0.26 mmol) were added to a solution of methyl 1,1-dimethyl-2-(6-(trifluoromethyl)pyridin-3-ylcarbamoyl)isoindoline-4-carboxylate (51 mg, 0.13 mmol) in THF:MeOH (4:1, 3.0 mL). The resulting solution stirred for 2 h at room temperature. The crude product was purified by Prep-HPLC with the following conditions: Colum:, XBridge Shield RP18 OBD Column, 5 um, 19×150 mm; mobile phase, water (0.1% FA) and ACN (30.0% ACN up to 50.0% in 7 min); Detector, UV 254 nm. The collected fraction was lyophilized to give N4-hydroxy-1,1-dimethyl-N2-(6-(trifluoromethyl)pyridin-3-yl)isoindoline-2,4-dicarboxamide (31.3 mg, 61%) as an off-white solid. $^1$H-NMR (DMSO, 300 MHz), δ (ppm): 11.18 (br, 1H), 8.92 (d, J=6.9 Hz, 2H), 8.27 (d, J=9 Hz, 1H), 7.79 (d, J=8.7 Hz, 1H), 7.52 (t, J=6.5 Hz, 1H), 7.53-7.40 (m, 3H), 5.10 (s, 2H), 1.71 (s, 6H). MS: (ES, m/z):395[M+H]$^+$.

The following compounds were prepared according to the procedures described above for N4-hydroxy-1,1-dimethyl-N2-(6-(trifluoromethyl)pyridin-3-yl)isoindoline-2,4-dicarboxamide.

| Ex. | Structure | Name | $^1$HNMR | (ESI/, m/z) [M + H]$^+$ |
|---|---|---|---|---|
| 30-2 | 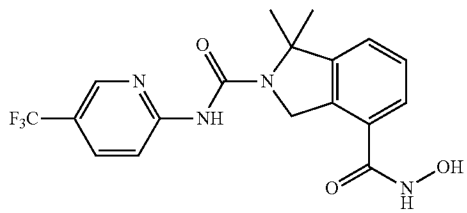 [SMILES: CC1(C)c2cccc(C(=O)NO)c2CN1C(=O)Nc1ccc(C(F)(F)F)cn1] | N4-hydroxy-1,1-dimethyl-N2-(5-(trifluoromethyl)pyridin-2-yl)isoindoline-2,4-dicarboxamide | (DMSO, 300 MHz, ppm): 9.16 (br, 1H), 8.63 (s, 1H), 8.07 (d, J = 1.5 Hz, 2H), 7.56-7.39 (m, 3H), 5.20 (s, 2H), 1.73 (s, 6H). | 395 |
| 30-3 | 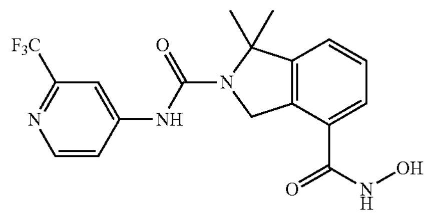 [SMILES: CC1(C)c2cccc(C(=O)NO)c2CN1C(=O)Nc1ccnc(C(F)(F)F)c1] | N4-hydroxy-1,1-dimethyl-N2-(2-(trifluoromethyl)pyridin-4-yl)isoindoline-2,4-dicarboxamide | (DMSO, 300 MHz, ppm): 11.13 (br, 1H), 9.14 (s, 1H), 8.50 (d, J = 5.7 Hz, 1H), 8.16 (s, 1H), 7.89-7.87 (m, 1H), 7.53-7.50 (m, 2H), 7.45-7.40 (m, 1H). 5.09 (s, 2H), 1.71 (s, 6H). | 395 |
| 30-4 | 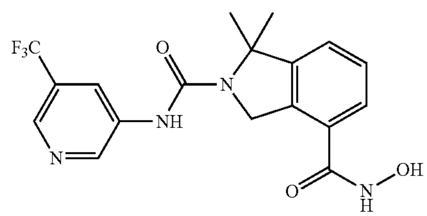 [SMILES: CC1(C)c2cccc(C(=O)NO)c2CN1C(=O)Nc1cncc(C(F)(F)F)c1] | N4-hydroxy-1,1-dimethyl-N2-(5-(trifluoromethyl)pyridin-3-yl)isoindoline-2,4-dicarboxamide | (DMSO, 300 MHz, ppm): 11.10 (br, 1H), 9.15 (br, 1H), 8.63 (s, 1H), 8.07 (d, J = 1.5Hz, 2H), 7.56-7.38 (m, 3H), 5.19 (s, 2H), 1.71 (s, 6H). | 395 |
| 30-5 | 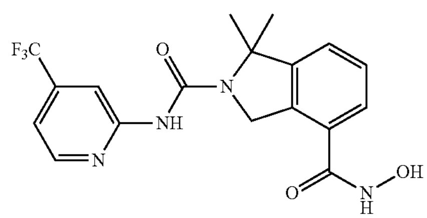 [SMILES: CC1(C)c2cccc(C(=O)NO)c2CN1C(=O)Nc1cc(C(F)(F)F)ccn1] | N4-hydroxy-1,1-dimethyl-N2-(4-(trifluoromethyl)pyridin-2-yl)isoindoline-2,4-dicarboxamide | (DMSO, 300 MHz, ppm): 9.11 (br, 1H), 8.53 (d, J = 5.1 Hz, 1H), 8.24 (s, 1H), 7.55 (d, J = 7.5 Hz, 1H), 7.49 (d, J = 7.2 Hz, 1H), 7.44-7.39 (m, 1H), 7.33 (d, J = 5.1 Hz, 1H), 5.20 (s, 2H), 1.71 (s, 6H). | 395 |
| 30-6 | 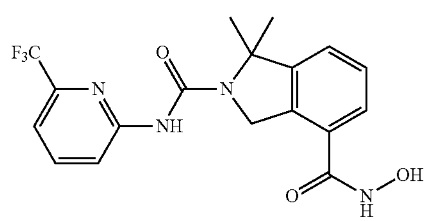 [SMILES: CC1(C)c2cccc(C(=O)NO)c2CN1C(=O)Nc1cccc(C(F)(F)F)n1] | N4-hydroxy-1,1-dimethyl-N2-(6-(trifluoromethyl)pyridin-2-yl)isoindoline-2,4-dicarboxamide | (DMSO, 300 MHz, ppm): 11.12 (br, 1H), 9.08 (be, 2H), 8.15 (d, J = 8.4 Hz, 1H), 7.99-7.94 (m, 1H), 7.55-7.39 (m, 4H), 5.21 (s, 2H), 1.70 (s, 6H). | 395 |
| 30-7 | 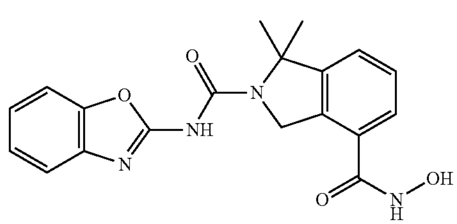 [SMILES: CC1(C)c2cccc(C(=O)NO)c2CN1C(=O)Nc1nc2ccccc2o1] | N2-(benzo[d]oxazol-2-yl)-N4-hydroxy-1,1-dimethylisoindoline-2,4-dicarboxamide | (DMSO, 300 MHz, ppm): 11.50 (br, 1H), 9.16 (br, 1H), 7.53-7.32 (m, 5H), 7.24-7.14 (m, 2H), 5.01 (s, 2H), 1.73 (s, 6H). | 367 |

Example 31-1. N4-hydroxy-1,1-dimethyl-N2-(5,6,7,8-tetrahydroisoquinolin-3-yl)isoindoline-2,4-dicarboxamide

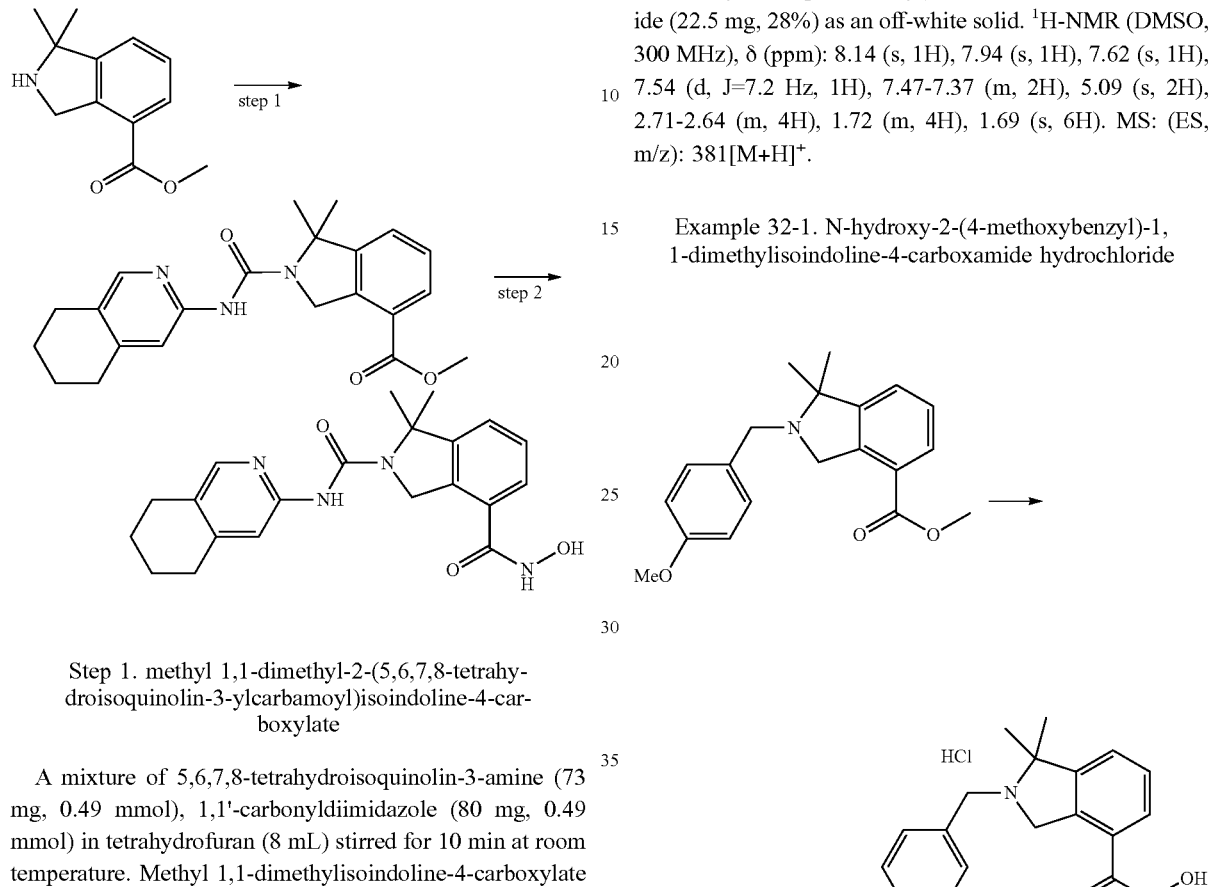

Step 1. methyl 1,1-dimethyl-2-(5,6,7,8-tetrahydroisoquinolin-3-ylcarbamoyl)isoindoline-4-carboxylate A mixture of 5,6,7,8-tetrahydroisoquinolin-3-amine (73 mg, 0.49 mmol), 1,1'-carbonyldiimidazole (80 mg, 0.49 mmol) in tetrahydrofuran (8 mL) stirred for 10 min at room temperature. Methyl 1,1-dimethylisoindoline-4-carboxylate (100 mg, 0.49 mmol) was added, and the resulting stirred for 5 h at room temperature. The reaction mixture was then poured into 15 mL of water and extracted with 3×30 mL of dichloromethane. The combined organic phases were washed with brine, dried over anhydrous sodium sulfate, filtered, and concentrated under vacuum. The residue was purified via column chromatography on silica gel (eluting with 1:2 ethyl acetate/petroleum ether) to give methyl 1,1-dimethyl-2-(5,6,7,8-tetrahydroisoquinolin-3-ylcarbamoyl)isoindoline-4-carboxylate (80 mg, 43%) as an off-white solid. MS: (ESI, m/z): 380 [M+H]$^+$.

Step 2. N4-hydroxy-1,1-dimethyl-N2-(5,6,7,8-tetrahydroisoquinolin-3-yl)isoindoline-2,4-dicarboxamide Hydroxyl amine (50% in water, 1.55 mL, 25.3 mmol) and 1 M aqueous sodium hydroxide solution (0.53 mL, 0.53 mmol) were added to a solution of methyl 1,1-dimethyl-2-(5,6,7,8-tetrahydroisoquinolin-3-ylcarbamoyl)isoindoline-4-carboxylate (80 mg, 0.21 mmol) in THF:MeOH (4:1, 5.0 mL). The resulting solution stirred for 2 h at room temperature. The crude product was purified by Prep-HPLC with the following conditions: Column, XBridge Prep C18 OBD Column, 5 um, 19×150 mm; mobile phase, water (10 mmol/L NH$_4$HCO$_3$) and ACN (25.0% ACN up to 50.0% in 8 min); Detector, UV 254 220 nm. The collected fraction was lyophilized to give N4-hydroxy-1,1-dimethyl-N2-(5,6,7,8-tetrahydroisoquinolin-3-yl)isoindoline-2,4-dicarboxamide (22.5 mg, 28%) as an off-white solid. $^1$H-NMR (DMSO, 300 MHz), δ (ppm): 8.14 (s, 1H), 7.94 (s, 1H), 7.62 (s, 1H), 7.54 (d, J=7.2 Hz, 1H), 7.47-7.37 (m, 2H), 5.09 (s, 2H), 2.71-2.64 (m, 4H), 1.72 (m, 4H), 1.69 (s, 6H). MS: (ES, m/z): 381[M+H]$^+$.

Example 32-1. N-hydroxy-2-(4-methoxybenzyl)-1,1-dimethylisoindoline-4-carboxamide hydrochloride

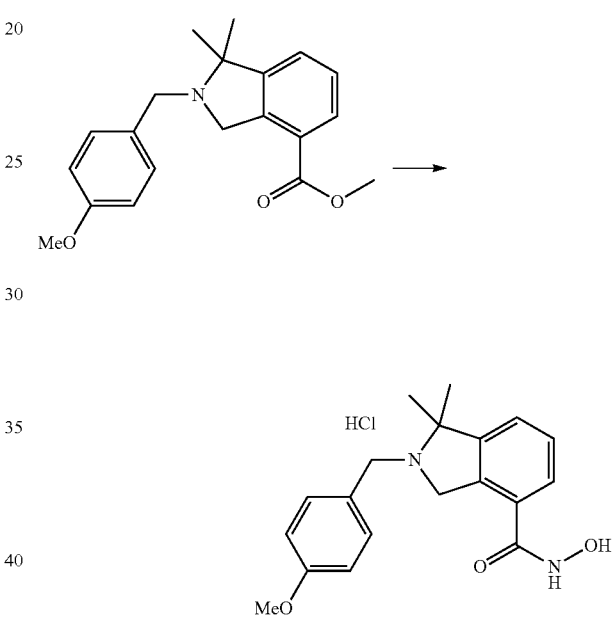

Hydroxyl amine (50% in water, 0.51 mL, 8.4 mmol) and 1 M aqueous sodium hydroxide solution (0.28 mL, 0.28 mmol) were added to a solution of methyl 2-(4-methoxybenzyl)-1,1-dimethylisoindoline-4-carboxylate (45 mg, 0.14 mmol) in THF:MeOH (4:1, 3.0 mL). The resulting solution stirred for 1 day at room temperature. The crude product was purified by Prep-HPLC with the following conditions: Column: SUNFIRE, 19×250 mm, 5 um; Mobile Phase A: water/0.05% FA, Mobile Phase B: ACN; Flow rate: 25 mL/min; Gradient: 5-30% B in 8 min; 254 nm. The collected fraction was lyophilized with 1 M aqueous HCl (1 mL) to give N-hydroxy-2-(4-methoxybenzyl)-1,1-dimethylisoindoline-4-carboxamide hydrochloride (13.8 mg, 28%) as a yellow oil. $^1$H-NMR-PH-FMA-PJ94-1093-0: (400 MHz, DMSO-dd, ppm): δ 11.42 (br, 1H), 10.83 (br, 1H), 7.65-7.46 (m, 5H), 7.06-7.04 (m, 2H), 4.94-4.64 (m, 1H), 4.64-4.61 (m, 1H), 4.48-4.43 (m, 1H), 4.34-4.28 (m, 1H), 3.81 (s, 3H), 1.89 (s, 3H), 1.56 (s, 3H). MS: (ESI, m/z): 327 [M−HCl+H]$^+$.

Example 33-1. N-hydroxy-1,1-dimethyl-2-(5-(trifluoromethyl)pyridin-2-yl)-2,3-dihydro-1H-pyrrolo[3,4-c]pyridine-4-carboxamide

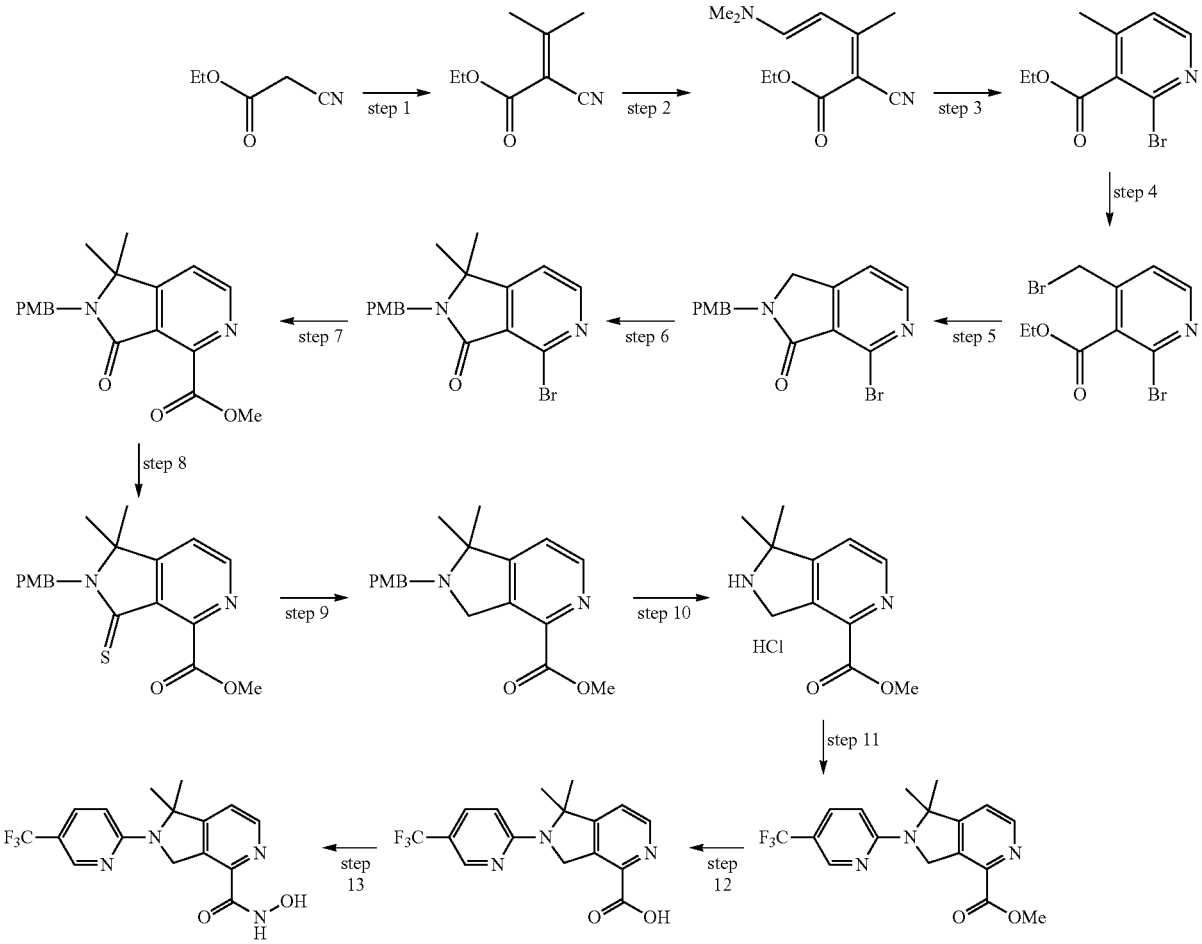

Step 1. ethyl 2-cyano-3-methylbut-2-enoate

A solution of ethyl 2-cyanoacetate (45.2 g, 399 mmol) and acetone (59 mL, 798.91 mmol) in piperidine (2 mL) and acetic acid (50 mL) stirred for 24 h at 90° C. in an oil bath. The reaction mixture was cooled to room temperature and then concentrated under vacuum. The residue was diluted with 200 mL of water and extracted with 3×200 mL of ethyl acetate. The combined organic phases were washed with 50 mL of brine, dried over anhydrous sodium sulfate, filtered, and concentrated under vacuum. The residue was purified via column chromatography on silica gel (eluting with 1:50 ethyl acetate/petroleum ether) to afford ethyl 2-cyano-3-methylbut-2-enoate (33.4 g, 55%) as a yellow liquid. MS: (ESI, m/z): 154[M+H]+.

Step 2. (2Z,4E)-ethyl 2-cyano-5-(dimethylamino)-3-methylpenta-2,4-dienoate

N,N-Dimethylformamide dimethyl acetal (30.0 mL, 225 mmol) was added dropwise to a solution of ethyl 2-cyano-3-methylbut-2-enoate (31.4 g, 205 mmol) in ethanol (216 mL). The resulting solution stirred for 15 h at 80° C. in an oil bath. The reaction mixture was cooled to room temperature and concentrated under vacuum. The residue was purified via column chromatography on silica gel (eluting with 25% ethyl acetate-petroleum ether) to give (2Z,4E)-ethyl 2-cyano-5-(dimethylamino)-3-methylpenta-2,4-dienoate (33.5 g, 78%) as a yellow solid. MS: (ESI, m/z): 209[M+H]+.

Step 3. ethyl 2-bromo-4-methylnicotinate

Hydrogen bromide (40% in acetic acid, 130 mL) was added dropwise to a 40° C. solution of (2Z,4E)-ethyl 2-cyano-5-(dimethylamino)-3-methylpenta-2,4-dienoate (33.5 g, 160.86 mmol) in acetic acid (130 mL), and the resulting solution was stirred for 15 h at 55° C. in an oil bath. The reaction mixture was cooled to room temperature and then poured into 300 mL of water/ice. The pH value of the solution was adjusted to 9 with 2 M aqueous sodium carbonate solution. The resulting mixture was extracted with 300 mL of ethyl acetate, and the combined organic phases were washed with brine, dried over anhydrous sodium sulfate, filtered, and concentrated under vacuum. The residue was purified via column chromatography on silica gel (eluting with 25% ethyl acetate-petroleum ether) to afford ethyl 2-bromo-4-methylnicotinate (31.96 g, 81%) as a yellow oil. MS: (ESI, m/z): 244[M+H]+.

Step 4. ethyl 2-bromo-4-(bromomethyl)nicotinate

A solution of ethyl 2-bromo-4-methylnicotinate (15.0 g, 61.5 mmol), N-bromosuccinimide (21.98 g, 123.5 mmol), AIBN (1.01 g, 6.17 mmol), and acetic acid (3.71 g, 61.7 mmol) in carbon tetrachloride (80 mL) stirred for 7 h at 60° C. under a 300 W tungsten lamp. After cooling to room temperature, reaction mixture was filtered, and the filtrate was concentrated under vacuum. The residue was diluted with 200 mL of saturated aqueous sodium bicarbonate solution and extracted with 3×200 mL of ethyl acetate. The combined organic phases were washed with 200 mL of brine, dried over anhydrous sodium sulfate, filtered, and concentrated under vacuum to give ethyl 2-bromo-4-(bromomethyl)nicotinate (23.98 g) as a red oil. MS: (ESI, m/z): 322[M+H]+.

Step 5. 4-bromo-2-(4-methoxybenzyl)-1,2-dihydropyrrolo[3,4-c]pyridin-3-one

A solution of ethyl 2-bromo-4-(bromomethyl)nicotinate (23.98 g, 74.25 mmol), 4-methoxybenzylamine (9.75 mL, 74.7 mmol) and triethylamine (15.6 mL g, 112 mmol) in methanol (60 mL) stirred for 7 h at 80° C. in an oil bath. The reaction was cooled to room temperature and concentrated under vacuum. The residue was diluted with 200 mL of water and extracted with 3×200 mL of ethyl acetate. The combined organic phases were washed with 200 mL of brine, dried over anhydrous sodium sulfate, filtered, and concentrated under vacuum. The residue was purified via column chromatography on silica gel (eluting with 50% ethyl acetate-hexane) to afford (4-bromo-2-(4-methoxybenzyl)-1,2-dihydropyrrolo[3,4-c]pyridin-3-one (5.0 g, 20%) as a yellow solid. MS: (ESI, m/z): 333[M+H]+.

Step 6. 4-bromo-2-(4-methoxybenzyl)-1,1-dimethyl-1,2-dihydropyrrolo[3,4-c]pyridin-3-one A solution of 4-bromo-2-(4-methoxybenzyl)-1,2-dihydropyrrolo[3,4-c]pyridin-3-one (4.5 g, 13.5 mmol) in THF (60 mL) was added dropwise to a 0° C. solution of sodium hydride (60% dispersion in mineral oil, 1.63 g, 40.8 mmol) in THF (240 mL), and the resulting solution stirred for 30 min at 0° C. Iodomethane (2.53 mL, 40.7 mmol) was added at 0° C., and the reaction mixture stirred for 1 h at 0° C. The reaction mixture was then poured into 300 mL of water/ice and extracted with 3×250 mL of ethyl acetate. The combined organic phases were washed with brine, dried over anhydrous sodium sulfate, filtered, and concentrated under vacuum. The residue was purified via column chromatography on silica gel (eluting with 50% ethyl acetate-hexane) to give 4-bromo-2-(4-methoxybenzyl)-1,1-dimethyl-1,2-dihydropyrrolo[3,4-c]pyri din-3-one (2.2 g, 45%) as a yellow solid. MS: (ESI, m/z): 361[M+H]+.

Step 7. methyl 2-(4-methoxybenzyl)-1,1-dimethyl-3-oxo-2,3-dihydro-1H-pyrrolo[3,4-c]pyridine-4-carboxylate A 100-mL pressure tank reactor was charged with 4-bromo-2-(4-methoxybenzyl)-1,1-dimethyl-1,2-dihydropyrrolo[3,4-c]pyri din-3-one (2.0 g, 5.54 mmol), [1,1'-bis(diphenylphosphino)ferrocene]dichloropalladium (II) (410 mg, 0.56 mmol), triethylamine (2.31 mL, 16.6 mmol) and methanol (50 mL). Carbon monoxide (g, 60 atm) was introduced into the system, and the reaction mixture stirred overnight at 130° C. The system mixture was cooled to room temperature, and the reaction mixture was concentrated under vacuum. The residue was purified via column chromatography on silica gel (eluting with 50% ethyl acetate-hexane) to give methyl 2-(4-methoxybenzyl)-1,1-dimethyl-3-oxo-2,3-dihydro-1H-pyrrolo[3,4-c]pyridine-4-carboxylate (1.1 g, 58%) as a red solid. MS: (ESI, m/z): 341[M+H]+.

Step 8. methyl 2-(4-methoxybenzyl)-1,1-dimethyl-3-thioxo-2,3-dihydro-1H-pyrrolo[3,4-c]pyridine-4-carboxylate A solution of methyl 2-(4-methoxybenzyl)-1,1-dimethyl-3-oxo-2,3-dihydro-1H-pyrrolo[3,4-c]pyridine-4-carboxylate (1.10 g, 3.23 mmol) and phosphorus pentasulfide (718 mg, 3.23 mmol) in 1,4-dioxane (150 mL) stirred overnight at 130° C. in an oil bath. The reaction mixture was cooled to room temperature and concentrated under vacuum. The residue was purified via column chromatography on silica gel (eluting with 50% ethyl acetate-hexane) to give methyl 2-(4-methoxybenzyl)-1,1-dimethyl-3-thioxo-2,3-dihydro-1H-pyrrolo[3,4-c]pyridine-4-carboxylate (500 mg, 43%) as a yellow solid. MS: (ESI, m/z): 357[M+H]+.

Step 9. methyl 2-(4-methoxybenzyl) 1,1-dimethyl-2,3-dihydro-1H-pyrrolo[3,4-c]pyridine-4-carboxylate A solution of methyl 2-(4-methoxybenzyl)-1,1-dimethyl-3-thioxo-2,3-dihydro-1H-pyrrolo[3,4-c]pyridine-4-carboxylate (500 mg, 1.40 mmol) and nickel(II) chloride hexahydrate (3.98 g, 16.74 mmol) in THF:MeOH (4:1, 60 mL) stirred for 2 h at room temperature. Sodium borohydride (319 mg, 8.43 mmol) was added portionwise, and the mixture stirred for 2 h at room temperature. The reaction mixture was filtered, and the filtrate was concentrated under vacuum. The crude product was purified by reversed phase Prep-HPLC with the following conditions: column: C18, 20-45 um, 100 A; mobile phase: water (0.1% FA) and ACN (5% ACN up to 20% in 15 min); Detector, UV 220 & 254 nm. The collected fraction was concentrated under vacuum to give methyl 2-(4-methoxybenzyl)-1,1-dimethyl-2,3-dihydro-1H-pyrrolo[3,4-c]pyridine-4-carboxylate (150 mg, 33%) as an off-white oil. MS: (ESI, m/z): 327[M+H]+.

Step 10. methyl 1,1-dimethyl-2,3-dihydro-1H-pyrrolo[3N-c]pyridine-4-carboxylate hydrochloride A solution of methyl 2-(4-methoxybenzyl)-1,1-dimethyl-2,3-dihydro-1H-pyrrolo[3,4-c]pyridine-4-carboxylate (150 mg, 0.46 mmol) in trifluoroacetic acid (15 mL) stirred for 8 h at 90° C. in an oil bath. The resulting mixture was cooled to room temperature and then concentrated under vacuum. The crude product was purified by Prep-HPLC with the following condition: Column: XBridge Shield RP18 OBD Column, 5 um, 19×150 mm; mobile phase, water (0.1% FA) and ACN (8% up to 15.0% in 4 min); Detector, UV 254 nm & 220 nm. The collected fraction was lyophilized with 1 drop of 2 M aqueous HCl solution to give methyl 1,1-dimethyl-2,3-dihydro-1H-pyrrolo[3,4-c]pyridine-4-carboxylate hydrochloride (40 mg, 36%) as an off-white solid. MS: (ESI, m/z): 207[M–HCl+H]+.

Step 11. methyl 1,1-dimethyl-2-(5-(trifluoromethyl)pyrindin-2-yl)-2,3-dihydro-1H-pyrrolo [3,4-c]pyridine-4-carboxylate A solution of methyl 1,1-dimethyl-2,3-dihydro-1H-pyrrolo[3,4-c]pyridine-4-carboxylate hydrochloride (140 mg, 0.58 mmol), 2-chloro-5-(trifluoromethyl)pyridine (209 mg, 1.15 mmol), RuPhos 2G (45 mg, 0.06 mmol), RuPhos (27 mg, 0.06 mmol), and cesium carbonate (567 mg, 1.74 mmol) in toluene (5 mL) stirred overnight at 110° C. in an oil bath. The reaction mixture was cooled to room temperature and then poured into 20 mL of water. The resulting solution was extracted with 3×20 mL of ethyl acetate, and the combined organic phases were washed with brine, dried over anhydrous sodium sulfate, filtered, and concentrated under vacuum. The residue was purified by preparative thin layer chromatography on silica gel plates (eluting with 25% ethyl acetate-petroleum ether) to give methyl 1,1-dimethyl-2-(5-(trifluoromethyl)pyridin-2-yl)-2,3-dihydro-1H-pyrrolo[3,4-c]pyridine-4-carboxylate (65 mg, 32%) as a yellow solid. MS: (ES, m/z): 352[M+H]+.

Step 12. 1,1-dimethyl-2-(5-(trifluoromethyl)pyridin-2-yl)-2,3-dihydro-1H-pyrrolo[3,4-c]pyridine-4-carboxylic acid 1 M aqueous sodium hydroxide solution (0.38 mL, 0.38 mmol) was added to a solution of methyl 1,1-dimethyl-2-(5-(trifluoromethyl)pyridin-2-yl)-2,3-dihydro-1H-pyrrolo[3,4-c]pyridine-4-carboxylate (65 mg, 0.19 mmol) in tetrahydrofuran (4 mL) and methanol (1 mL), and the resulting solution was stirred for 1 h at room temperature. The reaction mixture was cooled to 0° C., and the pH value was adjusted to 7 with 2 M aqueous HCl solution. The resulting solution was extracted with 3×20 mL of ethyl acetate, and the combined organic phases were washed with brine, dried over anhydrous sodium sulfate, and concentrated under vacuum. The crude product was purified by reversed phase Prep-HPLC with the following conditions: column: C18, 20-45 um, 100 A; mobile phase, water (0.05% NH$_4$HCO$_3$) and ACN (5% ACN up to 50% in 30 min); Detector, UV 220 & 254 nm. The collected fraction was lyophilized to give 1,1-dimethyl-2-(5-(trifluoromethyl)pyri din-2-yl)-2,3-dihydro-1H-pyrrolo[3,4-c]pyridine-4-carboxylic acid (40 mg, 64%) as a white solid. MS: (ESI, m/z): 338[M+H]+.

Step 13. N-hydroxy-1,1-dimethyl-2-(5-(trifluoromethyl)pyridin-2-yl)-2,3-dihydro-1H-pyrrolo[3,4-c]pyridine-4-carboxamide A solution of 1,1-dimethyl-2-(5-(trifluoromethyl)pyridin-2-yl)-2,3-dihydro-1H-pyrrolo[3,4-c]pyridine-4-carboxylic acid (40 mg, 0.12 mmol) in DMA (2 mL) was cooled to 0° C., and isopropyl chloroformate (1.0 M in toluene, 0.59 mL, 0.59 mmol) and NMM (60 mg, 0.59 mmol) was added. The resulting solution was stirred for 30 min at room temperature and then cooled to 0° C. Hydroxylamine hydrochloride (41 mg, 0.59 mmol) was added, and the resulting solution stirred overnight at room temperature. The reaction mixture was quenched by the addition of methanol (2 drops). The crude product was purified by Prep-HPLC with the following conditions: Column: Xbridge Phenyl OBD Column, 5 um, 19×150 mm; mobile phase, water (0.1% FA) and ACN (40.0% ACN up to 70.0% in 7 min); Detector, UV 254/220 nm. The collected fraction was lyophilized to give N-hydroxy-1,1-dimethyl-2-(5-(trifluoromethyl)pyridin-2-yl)-2,3-dihydro-1H-pyrrolo[3,4-c]pyridine-4-carboxamide (10.5 mg, 25%) as an off-white solid. 1H-NMR: (DMSO, 400 MHz, ppm): δ 11.47 (br, 1H), 9.15 (br, 1H), 8.60 (d, J=4.8 Hz, 1H), 8.50 (s, 1H), 7.89-7.86 (m, 1H), 7.69 (d, J=4.8 Hz, 1H), 6.76, (d, J=8.8 Hz, 1H), 5.06 (s, 2H), 1.83 (s, 6H) MS: (ESI, m/z): 353[M+H]+.

Example 34-1 N-hydroxy-2-(5-phenyl-6-(trifluoromethyl)-1H-benzo[d]imidazol-2-yl)isoindoline-4-carboxamide

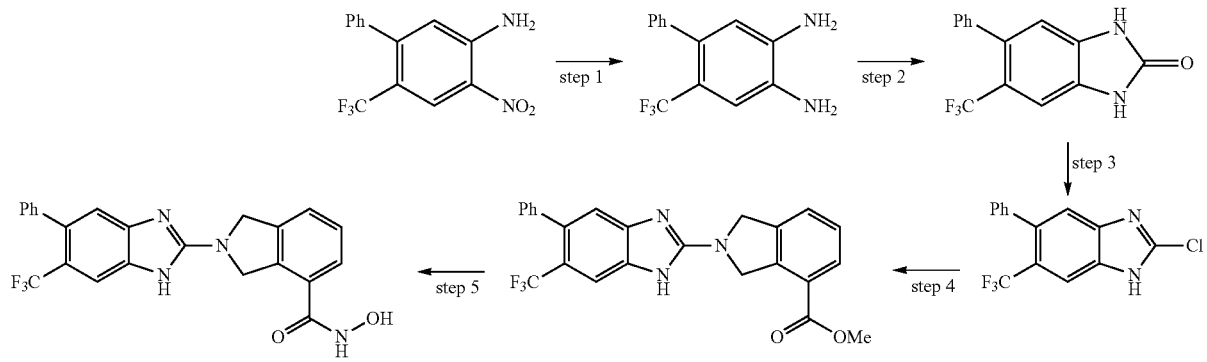

Step 1: 6-(trifluoromethyl)-[1,1'-biphenyl]-3,4-diamine

Hydrogen gas was introduced into a solution of 2-nitro-5-phenyl-4-(trifluoromethyl) aniline (500 mg, 1.77 mmol) and 10% palladium on carbon (37.7 mg) in methanol (30 mL). The resulting mixture stirred for 19 h at room temperature. The reaction mixture was filtered, and the filtrate was concentrated under vacuum to afford 6-(trifluoromethyl)-[1,1'-biphenyl]-3,4-diamine (450 mg, 100%) as brown oil. MS: (ESI, m/z): 253[M+H]+.

Step 2: 5-phenyl-6-(trifluoromethyl)-1,3-dihydro-2H-benzo[d]imidazol-2-one 1,1'-Carbonyldiimidazole (376 mg, 2.32 mmol) was added in portions to a 0° C. solution of 6-(trifluoromethyl)-[1,1'-biphenyl]-3,4-diamine (450 mg, 1.78 mmol) in tetrahydrofuran (20 mL), and the resulting solution stirred for 20 h at room temperature. The reaction mixture was concentrated under vacuum. The residue was purified via column chromatography on silica gel (eluting with ethyl acetate/petroleum ether (1:2)) to afford 5-phenyl-6-(trifluoromethyl)-1,3-dihydro-2H-benzo[d]imidazol-2-one (341 mg, 69%) as an orange solid. MS: (ESI, m/z): 279[M+H]+.

Step 3: 2-chloro-5-phenyl-6-(trifluoromethyl)-1H-benzo[d]imidazole

A mixture of 5-phenyl-6-(trifluoromethyl)-1,3-dihydro-2H-benzo[d]imidazol-2-one (341 mg, 1.23 mmol) in phosphorus oxychloride (5 mL) stirred for 4 h at 105° C. in an oil bath. The resulting mixture was cooled to room temperature and then concentrated under vacuum. The residue was diluted with 20 mL of water, and the pH value of the solution was adjusted to 8 with saturated aqueous sodium bicarbonate solution. The resulting solution was extracted with 3×25 mL of ethyl acetate, and the combined organic phases were washed with 20 mL of water and 20 mL of brine, dried over anhydrous sodium sulfate, filtered, and concentrated under vacuum to afford 2-chloro-5-phenyl-6-(trifluoromethyl)-1H-benzo[d]imidazole (310 mg, 85%) as brown oil. MS: (ESI, m/z): 297[M+H]⁺.

Step 4: methyl 2-(5-phenyl-6-(trifluoromethyl)-1H-benzo[d]imidazol-2-yl)isoindoline-4-carboxylate A mixture of 2-chloro-5-phenyl-6-(trifluoromethyl)-1H-benzo[d]imidazole (150 mg, 0.51 mmol,), methyl 2,3-dihydro-1H-isoindole-4-carboxylate hydrochloride (108 mg, 0.51 mmol), potassium carbonate (209 mg, 1.51 mmol), and copper(I) bromide (36 mg, 0.25 mmol) in isopropanol (5 mL) stirred for 17 h at 110° C. and was then cooled to room temperature. The mixture was filtered, and the filtrate was concentrated under vacuum. The residue was purified via column chromatography on silica gel (eluting with ethyl acetate/petroleum ether (1:2)) to afford methyl 2-(5-phenyl-6-(trifluoromethyl)-1H-benzo[d]imidazol-2-yl)isoindoline-4-carboxylate (36 mg, 16%) as a light brown solid. MS: (ESI, m/z): 438[M+H]⁺.

Step 5: N-hydroxy-2-(5-phenyl-6-(trifluoromethyl)-1H-benzo[d]imidazol-2-yl)isoindoline-4-carboxamide Hydroxyl amine (50% in water, 0.16 mL, 2.47 mmol) and 1 M aqueous sodium hydroxide solution (0.16 mL, 0.16 mmol) were added to a solution of methyl 2-(5-phenyl-6-(trifluoromethyl)-1H-benzo[d]imidazol-2-yl)isoindoline-4-carboxylate (36 mg, 0.08 mmol) in THF:MeOH (4:1, 1.5 mL). The resulting solution stirred for 3 h at room temperature. The crude product was purified by Prep-HPLC with the following conditions: Column: Sunfire C18 19×150, 5 um, 19×100 mm; Mobile phase: water with 0.05% TFA and ACN (6% ACN up to 40% in 7 min); Flow rate: 25 ml/min; Detector: 254, 220 nm. The collected fraction was lyophilized to afford N-hydroxy-2-(5-phenyl-6-(trifluoromethyl)-1H-benzo[d]imidazol-2-yl)isoindoline-4-carboxamide (15.6 mg, 43%) as a white solid. ¹H-NMR (DMSO, 400 MHz) δ (ppm): 11.34 (s, 1H), 9.14 (br, 1H), 7.71-7.62 (m, 3H), 7.52-7.41 (m, 5H), 7.35-7.33 (m, 2H), 7.28 (s, 1H), 5.22 (s, 2H), 5.06 (s, 2H). MS: (ESI, m/z): 439[M+H]⁺.

Example 35-1. N-hydroxy-2-(7-phenyl-5-(trifluoromethyl)-1H-benzo[d]imidazol-2-yl)isoindoline-4-carboxamide

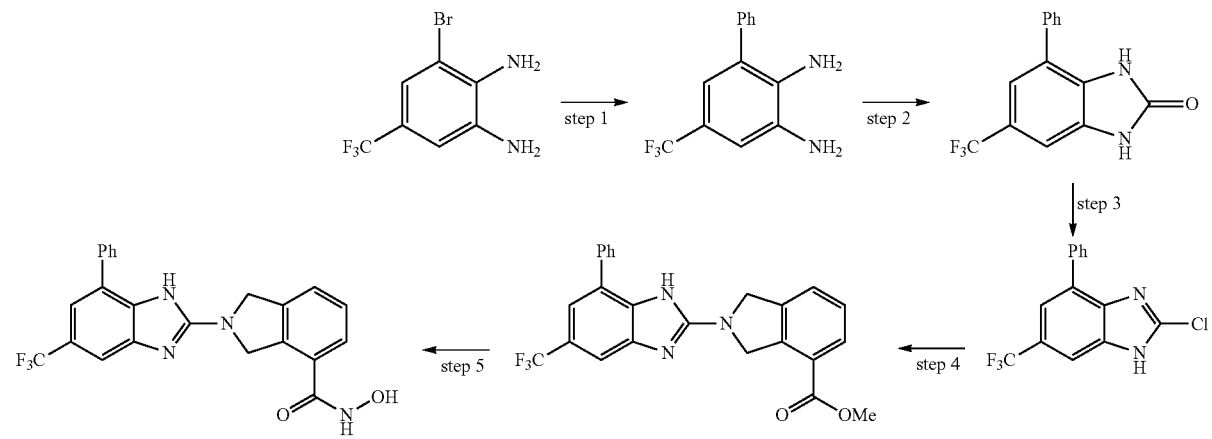

Step 1: 5-((trifluoromethyl)-1,1'-biphenyl)-2,3-diamine

A solution of 3-bromo-5-(trifluoromethyl)benzene-1,2-diamine (2 g, 7.84 mmol), phenylboronic acid (1.9 g, 15.68 mmol), potassium carbonate (2.2 g, 15.68 mmol), [1,1'-bis(diphenylphosphino)ferrocene]dichloropalladium(II), complex with dichloromethane (320 mg, 0.39 mmol) in dioxane (30 mL) and water (10 mL) stirred overnight at 110° C. in an oil bath. The resulting mixture was cooled to room temperature and then concentrated under vacuum. The residue was diluted with 50 mL water and extracted with 3×40 mL of ethyl acetate. The combined organic phases were washed with 100 mL of brine, dried over anhydrous sodium sulfate, filtered, and concentrated under vacuum. The residue was purified via column chromatography on silica gel (eluting with ethyl acetate/petroleum ether (1:10)) to afford 5-(trifluoromethyl)-[1,1'-biphenyl]-2,3-diamine (1.34 g, 68%) as yellow oil. MS: (ESI, m/z): 253[M+H]⁺.

Step 2: 4-phenyl-6-(trifluoromethyl)-1,3-dihydro-2H-benzo[d]imidazol-2-one

A solution of 5-(trifluoromethyl)-[1,1'-biphenyl]-2,3-diamine (1.34 g, 5.31 mmol,) and 1,1'-carbonyldiimidazole (1.1 g, 6.79 mmol) in tetrahydrofuran (15 mL) stirred overnight at room temperature. The resulting mixture was concentrated under vacuum. The residue was dissolved in 30 mL of ethyl acetate and washed with water (20 mL) and brine (20 mL), dried over anhydrous sodium sulfate, filtered, and concentrated under vacuum. The residue was purified via column chromatography on silica gel (eluting with ethyl acetate/petroleum ether (1:8)) to afford 4-phenyl-6-(trifluoromethyl)-1,3-dihydro-2H-benzo[d]imidazol-2-one (0.67 g, 45%) as a yellow solid. MS: (ESI, m/z): 279[M+H]⁺.

Step 3: 2-chloro-4-phenyl-6-(trifluoromethyl)-1H-benzo[d]imidazole

A mixture of 4-phenyl-6-(trifluoromethyl)-1,3-dihydro-2H-benzo[d]imidazol-2-one (670 mg, 2.41 mmol) in phosphorus oxychloride (6 mL) stirred overnight at 105° C. in an oil bath. The resulting mixture was cooled to room temperature and then concentrated under vacuum. The residue was diluted with 30 mL of water, and the pH value of the solution was adjusted to 8 with saturated aqueous sodium bicarbonate solution. The resulting solution was extracted with 3×30 mL of ethyl acetate, and the combined organic phases were washed with 50 mL of water and 50 mL of brine, dried over anhydrous sodium sulfate, filtered, and concentrated under vacuum to afford 2-chloro-4-phenyl-6-(trifluoromethyl)-1H-benzo[d]imidazole (0.61 g, 85%) as a white solid. MS: (ESI, m/z): 297[M+H]$^+$.

Step 4: methyl 2-(7-phenyl-5-(trifluoromethyl)-1H-benzo[d]imidazol-2-yl)isoindoline-4-carboxylate A mixture of 2-chloro-4-phenyl-6-(trifluoromethyl)-1H-benzo[d] (300 mg, 1.01 mmol), methyl 2,3-dihydro-1H-isoindole-4-carboxylate hydrochloride (220 mg, 1.03 mmol), potassium carbonate (420 mg, 3.04 mmol), and copper(I) bromide (150 mg, 1.05 mmol) in isopropanol (5 mL) stirred overnight at 110° C. in an oil bath and was then cooled to room temperature. The resulting mixture was diluted with 20 mL of water and extracted with 3×10 mL of ethyl acetate. The combined organic phases were washed with 20 mL brine, dried over anhydrous sodium sulfate, filtered, and concentrated under vacuum. The residue was purified via column chromatography on silica gel (eluting with ethyl acetate/petroleum ether (1:10)) to afford methyl 2-(7-phenyl-5-(trifluoromethyl)-1H-benzo[d]imidazol-2-yl) isoindoline-4-carboxylate (65 mg, 15%) as a white solid. MS: (ESI, m/z): 438[M+H]$^+$.

Step 5: N-hydroxy-2-(7-phenyl-5-(trifluoromethyl)-1H-benzo[d]imidazol-2-yl)isoindoline-4-carboxamide Hydroxyl amine (50% in water, 0.30 mL, 4.46 mmol) and 1 M aqueous sodium hydroxide solution (0.30 mL, 0.30 mmol) were added to a solution of methyl 2-(7-phenyl-5-(trifluoromethyl)-1H-benzo[d]imidazol-2-yl)isoindoline-4-carboxylate (65 mg, 0.15 mmol) in THF:MeOH (4:1, 1.0 mL). The resulting solution was stirred for 1 h at room temperature. The crude product was purified by Prep-HPLC with the following conditions: Column: Sunfire C18 19×150, 5 um, 19×100 mm; Mobile phase: water with 0.05% TFA and ACN (8% ACN up to 60% in 8 min); Flow rate: 25 ml/min; Detector: 254, 220 nm. The collected fraction was lyophilized to afford N-hydroxy-2-(7-phenyl-5-(trifluoromethyl)-1H-benzo[d]imidazol-2-yl)isoindoline-4-carboxamide (19.2 mg, 29%) as a off-white solid. $^1$H-NMR (DMSO, 400 MHz) δ (ppm): 11.28 (br, 1H), 9.13 (br, 1H), 8.00-7.89 (m, 2H), 7.63-7.40 (m, 8H), 5.18 (s, 2H), 4.98 (s, 2H). MS: (ESI, m/z): 439[M+H]$^+$.

The following compound was prepared according to the procedures described above for N-hydroxy-2-(7-phenyl-5-(trifluoromethyl)-1H-benzo[d]imidazol-2-yl)isoindoline-4-carboxamide.

| Ex. | Structure | Name | $^1$HNMR | (ESI, m/z) [M + H]$^+$ |
|---|---|---|---|---|
| 35-2 | Ph (structure shown) | N-hydroxy-2-(7-phenyl-1H-benzo[d]imidazol-2-yl)isoindoline-4-carboxamide | (DMSO, 400 MHz, ppm): 11.32 (br, 1H), 9.14 (br, 1H), 7.83-7.65 (m, 2H), 7.63-7.42 (m, 8H), 7.36-7.33 (m, 1H), 7.27 (d, J = 6.8 Hz, 1H), 5.24 (s, 2H), 5.02 (s, 2H) | 371 |

Example 36-1. 2-(benzo[d]oxazol-2-yl)-N-hydroxy-1-oxoisoindoline-4-carboxamide

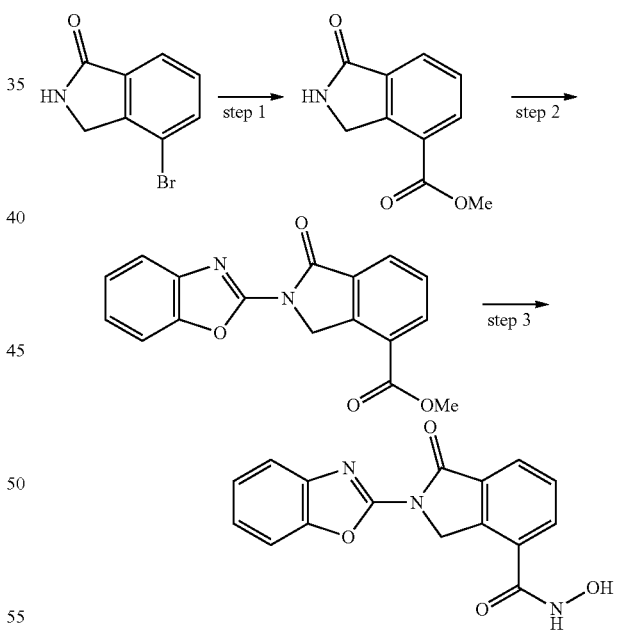

Step 1: methyl 1-oxoisoindoline-4-carboxylate

Carbon monoxide (g, 10 atm) was introduced into a 250-mL pressure tank reactor charged with a solution of 4-bromoisoindolin-1-one (3.0 g, 14.2 mmol), sodium acetate (2.32 g, 28.3 mmol), and Pd(dppf)C$_{1-2}$ (517 mg, 0.71 mmol) in methanol (150 mL). The resulting solution stirred for 24 h at 100° C. and was then cooled to room temperature. The resulting solution was concentrated under vacuum and the residue was diluted with 50 mL of water and extracted with 3×50 mL of ethyl acetate. The combined organic phases were washed with 100 mL of brine, dried over anhydrous sodium sulfate, filtered, and concentrated under vacuum. The residue was purified via column chromatography on silica gel (eluting with ethyl acetate/petroleum ether (1:1)) to afford methyl 1-oxoisoindoline-4-carboxylate (2.08 g, 77%) as a light brown solid. $^1$H-NMR (DMSO, 300 MHz) δ (ppm): 8.75 (s, 1H), 8.15 (d, J=7.5 Hz, 1H), 7.94 (d, J=7.5 Hz, 1H,), 7.65 (m, 1H), 4.60 (s, 2H), 3.89 (s, 3H). MS: (ESI, m/z): 192[M+H]$^+$.

Step 2: methyl 2-(benzo[d]oxazol-2-yl)-1-oxoisoindoline-4-carboxylate

A solution of methyl 1-oxoisoindoline-4-carboxylate (192 mg, 1.00 mmol), 2-chloro-1,3-benzoxazole (307 mg, 2.00 mmol), XantPhos (24 mg, 0.04 mmol), Pd(dba)$_3$-chloroform adduct (10 mg, 0.01 mmol), and cesium carbonate (890 mg, 2.73 mmol) in toluene (10 mL) was irradiated for 1 h at 120° C. in the microwave. The resulting solution was cooled to room temperature and then diluted with 20 mL of water. The resulting solution was extracted with 50 mL of ethyl acetate, and the combined organic phases were washed with 50 mL of brine, dried over anhydrous sodium sulfate, filtered, and concentrated under vacuum. The residue was purified via column chromatography on silica gel (eluting with 50% ethyl acetate-petroleum ether) to afford methyl 2-(benzo[d]oxazol-2-yl)-1-oxoisoindoline-4-carboxylate (105 mg, 34%) as a yellow solid. MS: (ESI, m/z): 309[M+H]$^+$.

Step 3. 2-(benzo[d]oxazol-2-yl)-N-hydroxy-1-oxoisoindoline-4-carboxamide

A solution of methyl 2-(benzo[d]oxazol-2-yl)-1-oxoisoindoline-4-carboxylate (103 mg, 0.33 mmol) and hydroxylamine (50% in water, 0.5 mL, 8.2 mmol) in THF:MeOH (4:1, 2.5 mL) stirred for 5 min at room temperature and then 1 M aqueous sodium hydroxide solution (0.5 mL, 0.5 mmol) was added. The resulting solution stirred for 2 h at room temperature and then the pH value of the solution was adjusted to 6 with 1 M aqueous HCl solution. The resulting mixture was concentrated under vacuum. The residue was purified by reversed phase Prep-HPLC with the following conditions: Column: X Bridge C18 19×150 mm; 5 um, mobile phase, water (0.05% TFA) and ACN (30% increasing to 35% within 8 min); Flow rate: 15 mL/min Detector, UV 254 nm. The collected fraction was lyophilized to give 2-(benzo[d]oxazol-2-yl)-N-hydroxy-1-oxoisoindoline-4-carboxamide (15.6 mg, 15%) as a pink solid. $^1$H-NMR (DMSO, 300 MHz) δ (ppm): 11.51 (br, 1H), 9.27 (br, 1H), 8.02-8.05 (m, 2H), 7.66-7.75 (m, 3H), 7.32-7.37 (m, 2H), 5.39 (s, 2H). MS: (ESI, m/z): 310[M+H]$^+$.

The following compound was prepared according to the procedures described above for 2-(benzo[d]oxazol-2-yl)-N-hydroxy-1-oxoisoindoline-4-carboxamide

| Ex. | Structure | Name | $^1$HNMR | (ESI, m/z) [M + H]$^+$ |
|---|---|---|---|---|
| 36-2 | 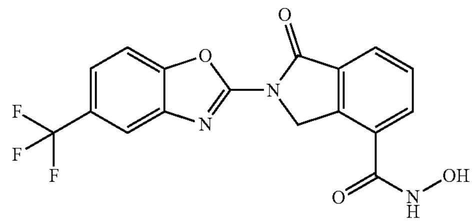 [SMILES: O=C(NO)c1cccc2c1CN(c1nc3cc(C(F)(F)F)ccc3o1)C2=O] | N-hydroxy-1-oxo-2-(5-(trifluoromethyl)benzo[d]oxazol-2-yl)isoindoline-4-carboxamide | | 378 |

Example 37-1. N-hydroxy-2-(4-(trifluoromethyl)phenyl)-1H-indole-7-carboxamide

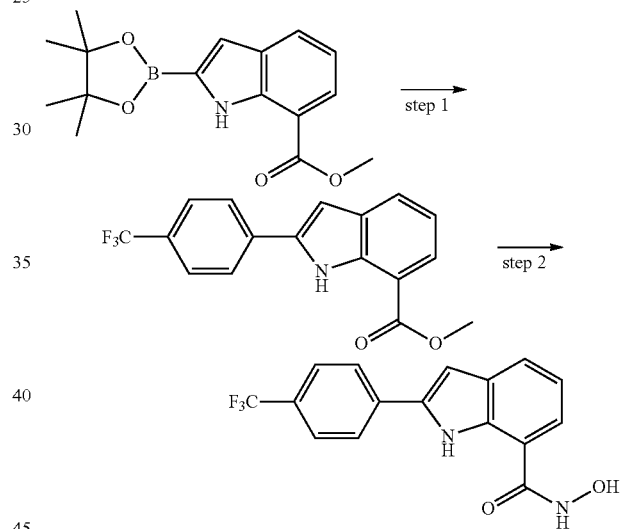

Step 1. methyl 2-(4-(trifluoromethyl)phenyl)-1H-indole-7-carboxylate

A solution of methyl 2-(4,4,5,5-tetramethyl-1,3,2-dioxaborolan-2-yl)-1H-indole-7-carboxylate (400 mg, 1.33 mmol), 1-bromo-4-(trifluoromethyl)benzene (595 mg, 2.64 mmol), XPhos 2G (105 mg, 0.13 mmol), XPhos (63 mg, 0.13 mmol), and cesium carbonate (1.08 g, 3.31 mmol) in 1,4-dioxane (8 mL) and water (2 mL) stirred for 3 h at 90° C. in an oil bath. The reaction mixture was cooled to room temperature and then poured into 20 mL of water. The resulting solution was extracted with 3×20 mL of ethyl acetate, and the combined organic phases were washed with brine and dried over anhydrous sodium sulfate, filtered, and concentrated under vacuum. The residue was purified via column chromatography on silica gel (eluting with ethyl acetate/petroleum ether (1:20)) to afford methyl 2-(4-(trifluoromethyl)phenyl)-1H-indole-7-carboxylate (300 mg, 71%) as a white solid. MS: (ESI, m/z): 320[M+H]$^+$.

Step 2. N-hydroxy-2-(4-(trifluoromethyl)phenyl)-1H-indole-7-carboxamide

Hydroxyl amine (50% in water, 0.92 mL, 15.0 mmol) and 1 M aqueous sodium hydroxide solution (0.50 mL, 0.50 mmol) were added to a solution of methyl 2-(4-(trifluoromethyl)phenyl)-1H-indole-7-carboxylate (80 mg, 0.25 mmol) in THF:MeOH (4:1, 1.0 mL). The resulting solution was stirred for 2 h at room temperature. The crude product was purified by Prep-HPLC with the following conditions: Column: XBridge Prep OBD C18 Column, 19×250 mm, 5 um; mobile phase, water (0.1% FA) and ACN (25.0% ACN up to 55.0% in 7 min); Detector, UV 254&220 nm. The collected fraction was lyophilized to give N-hydroxy-2-(4-(trifluoromethyl)phenyl)-1H-indole-7-carboxamide (44.4 mg, 55%) as a white solid. $^1$H-NMR: (DMSO, 300 MHz, ppm): δ 11.30 (s, 1H), 11.17 (s, 1H), 9.09 (s, 1H), 8.13 (d, J=8.1 Hz, 2H), 7.81 (d, 7=8.1 Hz, 2H), 7.75 (d, 7=7.2 Hz, 1H), 7.52 (d, 7=7.2 Hz, 1H), 7.15 (s, 1H), 7.12-7.07 (m, 1H). MS: (ESI, m/z): 321[M+H]$^+$.

The following compounds were prepared according to the procedures described above for N-hydroxy-2-(4-(trifluoromethyl)phenyl)-1H-indole-7-carboxamide.

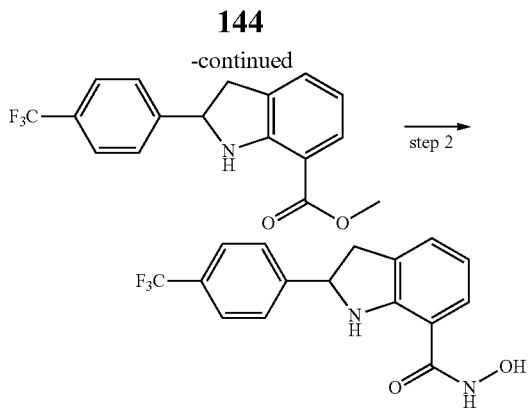

Step 1. methyl 2-(4-(trifluoromethyl)phenyl)indoline-7-carboxylate

Tri ethyl silane (727 mg, 6.30 mmol) was added dropwise to a 50° C. solution of methyl 2-(4-(trifluoromethyl)phenyl)-1H-indole-7-carboxylate (200 mg, 0.63 mmol) in trifluoroacetic acid (10 mL), and the resulting mixture stirred for 2 h at 50° C. in an oil bath. The reaction mixture was cooled to room temperature and then quenched by the addition of 2 mL of methanol. The resulting mixture was concentrated under vacuum. The residue was diluted with 20 mL of ethyl acetate, washed with 2×50 mL of saturated sodium bicarbonate solution, dried over anhydrous sodium sulfate, filtered, and concentrated under vacuum. The residue was purified via column chromatography on silica gel (eluting with 1:10 ethyl acetate/petroleum ether) to afford methyl 2-(4-(trifluoromethyl)phenyl)indoline-7-carboxylate (100 mg, 50%) as a light yellow solid. MS: (ESI, m/z): 322[M+H]$^+$.

| Ex. | Structure | Name | $^1$HNMR | (ESI, m/z) [M + H]$^+$ |
|---|---|---|---|---|
| 37-2 | F$_3$C-phenyl-indole-C(O)NHOH | N-hydroxy-2-(4-(trifluoromethyl)phenyl)-1H-indole-4-carboxamide | (DMSO, 400 MHz, ppm): 11.97 (s, 1H), 11.00 (s, 1H), 8.99 (s, 1H), 8.09 (d, J = 8.4 Hz, 2H), 7.84 (d, J = 8.0 Hz, 2H), 7.58-7.56 (m, 1H), 7.37-7.33 (m, 2H), 7.20-7.16 (m, 1H) | 321 |
| 37-3 | F$_3$C-pyrazine-indole-C(O)NHOH | N-hydroxy-2-(5-(trifluoromethyl)pyrazin-2-yl)-1H-indole-7-carboxamide | (DMSO, 400 MHz, ppm): 11.50 (s, 1H), 11.16 (s, 1H), 9.56 (s, 1H), 9.24 (s, 1H), 9.21 (s, 1H), 7.89 (d, J = 7.2 Hz, 1H), 7.72 (d, J = 7.2 Hz, 1H), 7.69 (s, 1H), 7.20-7.16 (m, 1H) | 323 |
| 37-4 | F$_3$C-pyrazine-indole-C(O)NHOH | N-hydroxy-2-(5-(trifluoromethyl)pyrazin-2-yl)-1H-indole-4-carboxamide | (DMSO, 400 MHz, ppm): 12.23 (s, 1H), 11.06 (s, 1H), 9.49 (s, 1H), 9.13 (s, 1H), 9.02 (s, 1H), 7.81 (s, 1H), 7.62 (d, J = 8.4, 1H), 7.35 (d, J = 6.8 Hz, 1H), 7.27-7.23 (m, 1H) | 323 |

Example 38-1. N-hydroxy-2-(4-(trifluoromethyl)phenyl)indoline-7-carboxamide

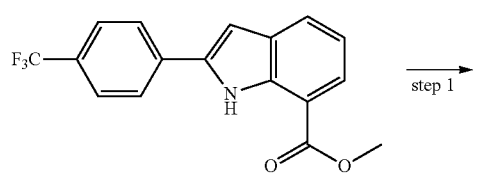

Step 2. N-hydroxy-2-(4-(trifluoromethyl)phenyl)indoline-7-carboxamide

Hydroxyl amine (50% in water, 1.14 mL, 18.6 mmol) and 1 M aqueous sodium hydroxide solution (0.62 mL, 0.62 mmol) were added to a solution of methyl 2-(4-(trifluoromethyl)phenyl)indoline-7-carboxylate (100 mg, 0.31 mmol) in THF:MeOH (4:1, 3.0 mL). The resulting solution stirred overnight at room temperature. The crude product was purified by Prep-HPLC with the following conditions: Column: XBridge Prep C18 OBD Column, 19×150 mm 5 um; mobile phase, water (10 mmol/L NH$_4$HCO$_3$) and ACN (25.0% ACN up to 55.0% in 7 min); Detector, UV 254 & 220 nm. The collected fraction was lyophilized to give N-hydroxy-2-(4-(trifluoromethyl)phenyl)indoline-7-carboxamide (32.7 mg, 33%) as an off-white solid. $^1$H-NMR (DMSO 400 MHz, ppm): δ 8.86 (s, 1H), 7.71 (d, J=8.4 Hz, 2H), 7.57 (d, J=8.4 Hz, 2H), 7.30 (d, J=8.0 Hz, 1H), 7.10 (d, J=7.2 Hz, 1H), 6.56-6.52 (m, 1H), 5.14-5.10 (m, 1H), 3.54-3.47 (m, 1H), 2.80-2.74 (m, 1H), MS: (ESI, m/z): 323[M+H]$^+$.

The following compound was prepared according to the procedures described above for N-hydroxy-2-(4-(trifluoromethyl)phenyl)indoline-7-carboxamide.

| Ex. | Structure | Name | $^1$HNMR | (ESI, m/z) [M + H]$^+$ |
|---|---|---|---|---|
| 38-2 | 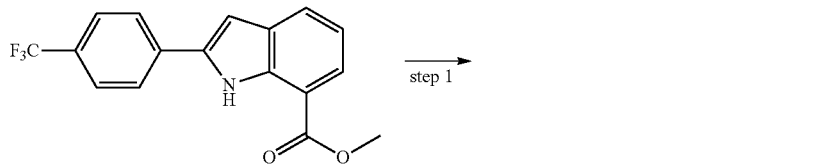 | N-hydroxy-2-(4-(trifluoromethyl)phenyl)indoline-4-carboxamide | (DMSO, 400 MHz, ppm): 8.91 (s, 1H), 7.71 (d, J = 8.0 Hz, 2H), 7.61 (d, J = 8.0 Hz, 2H), 7.03-6.99 (m, 1H), 6.77 (d, J = 7.6 Hz, 1H), 6.67 (d, J = 7.6 Hz, 1H), 5.01-4.97 (m, 1H), 3.71-3.64 (m, 1H), 2.96-2.90 (m, 1H) | 323 |

Example 39-1. (R)—N-hydroxy-2-(4-(trifluoromethyl)phenyl)indoline-7-carboxamide and

Example 39-2. (S)—N-hydroxy-2-(4-(trifluoromethyl)phenyl)indoline-7-carboxamide

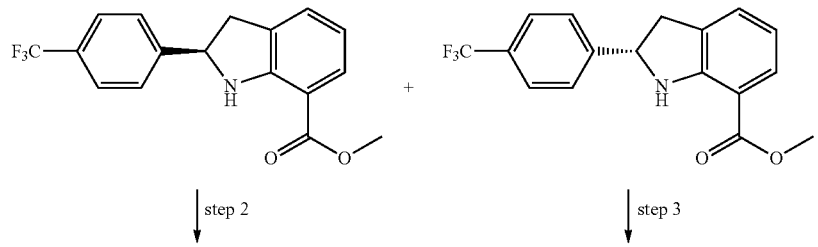

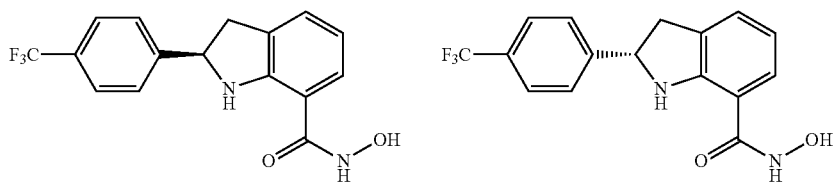

Step 1. (R)-methyl 2-(4-(trifluoromethyl)phenyl) indoline-7-carboxylate and (S)-methyl 2-(4-(trifluoromethyl)phenyl) indoline-7-carboxylate Racemic methyl 2-(4-(trifluoromethyl)phenyl)indoline-7-carboxylate (150 mg) was separated by Chiral-Prep-HPLC with the following conditions: Column, Chiralpak IB, 2×25 cm, 5 um; Mobile Phase A:Hex, Mobile Phase B: EtOH; Flow rate: 20 mL/min; Gradient: 30% B to 30% B in 10 min; 254/220 nm; RT1:4.25; RT2:5.55. The first eluting isomer (Rt=4.25 min) was collected and concentrated under vacuum to give (R)-methyl 2-(4-(trifluoromethyl)phenyl) indoline-7-carboxylate (67 mg, 33%) as an off-white solid (assigned as R-isomer) MS: (ESI, m/z): 322[M+H]$^+$. The second eluting isomer (Rt=5.55 min) was collected and concentrated under vacuum to give (S)-methyl 2-(4-(trifluoromethyl)phenyl)indoline-7-carboxylate (70 mg, 35%) as an off-white solid (assigned as S-isomer). MS: (ESI, m/z): 322[M+H]$^+$.

Step 2. (R)—N-hydroxy-2-(4-(trifluoromethyl)phenyl)indoline-7-carboxamide

Hydroxyl amine (50% in water, 1.37 mL, 22.4 mmol) and 1 M aqueous sodium hydroxide solution (0.75 mL, 0.75 mmol) were added to a solution of (R)-methyl 2-(4-(trifluoromethyl)phenyl)indoline-7-carboxylate (60 mg, 0.19 mmol) in THF:MeOH (4:1, 3.0 mL). The resulting solution stirred at room temperature for 2 h. The crude product was purified by Prep-HPLC with the following conditions: Column, XBridge Shield RP18 OBD Column, 5 um, 19×150 mm; mobile phase, water (10 mmol/L NH$_4$HCO$_3$) and ACN (20.0% ACN up to 50.0% in 7 min, up to 70.0% in 3 min); Detector, UV 254/220 nm. The collected fraction was lyophilized to give (R)—N-hydroxy-2-(4-(trifluoromethyl)phenyl)indoline-7-carboxamide (14.4 mg, 24%) of the as an off-white solid (assigned as R-isomer). $^1$H-NMR (DMSO, 300 MHz), δ (ppm): 7.70 (d, J=8.1 Hz, 2H), 7.55 (d, J=8.1 Hz, 2H), 7.29 (d, J=8.1 Hz, 1H), 7.08 (d, J=7.5 Hz, 1H), 6.95 (s, 1H), 6.55-6.50 (m, 1H), 5.13-5.07 (m, 1H), 3.53-3.40 (m, 1H), 2.80-2.72 (m, 1H). MS: (ES, m/z):323[M+H]$^+$.

Step 3. (S)—N-hydroxy-2-(4-(trifluoromethyl)phenyl)indoline-7-carboxamide

Hydroxyl amine (50% in water, 1.14 mL, 18.6 mmol) and 1 M aqueous sodium hydroxide solution (0.64 mL, 0.64 mmol) were added to a solution of (S)-methyl 2-(4-(trifluoromethyl)phenyl)indoline-7-carboxylate (51 mg, 0.16 mmol) in THF:MeOH (4:1, 3.0 mL). The resulting solution stirred at room temperature for 2 h. The crude product was purified by Prep-HPLC with the following conditions: Column, XB ridge Shield RP18 OBD Column, 5 um, 19×150 mm; mobile phase, water (10 mmol/L NH$_4$HCO$_3$) and ACN (20.0% ACN up to 50.0% in 7 min, up to 70.0% in 3 min); Detector, UV 254/220 nm. The collected fraction was concentrated under vacuum to give (S)—N-hydroxy-2-(4-(trifluoromethyl)phenyl)indoline-7-carboxamide (13.1 mg, 26%) as an off-white solid (assigned as S-isomer). $^1$H-NMR (DMSO, 300 MHz), δ (ppm): 7.69 (d, J=8.1 Hz, 2H), 7.55 (d, J=8.1 Hz, 2H), 7.29 (d, J=8.1 Hz, 1H), 7.07 (d, J=6.9 Hz, 1H), 6.95 (s, 1H), 6.55-6.50 (m, 1H), 5.13-5.07 (m, 1H), 3.53-3.45 (m, 1H), 2.79-2.72 (m, 1H). MS: (ES, m/z): 323[M+H]$^+$.

Example 40-1. (R)—N-hydroxy-3,3-dimethyl-2-(5-(trifluoromethyl)pyridin-2-yl)indoline-7-carboxamide and Example 40-2. (S)—N-hydroxy-3,3-dimethyl-2-(5-(trifluoromethyl)pyridin-2-yl)indoline-7-carboxamide

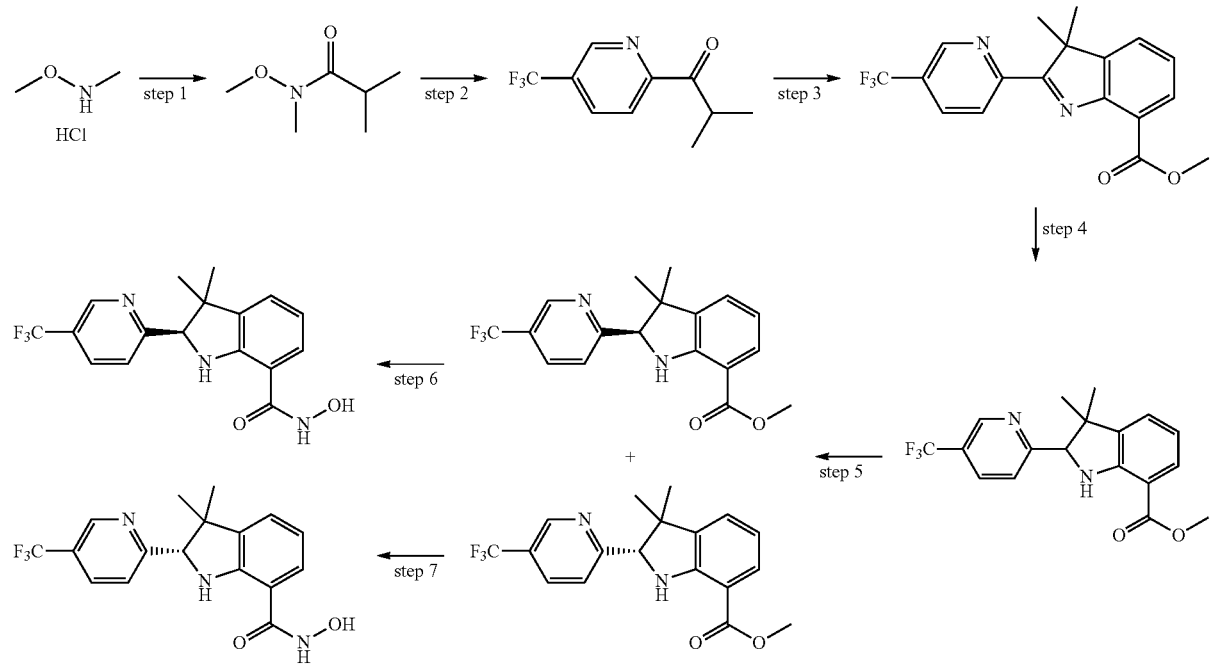

Step 1. N-methoxy-N-methylisobutyramide

2-Methylpropanoyl chloride (26.0 g, 246 mmol) was added to a 0° C. solution of methoxy(methyl)amine hydrochloride (20.0 g, 205 mmol) and triethylamine (85 mL, 615 mmol) in dichloromethane (200 mL), and the resulting solution stirred for 3.5 h at room temperature. The reaction was then quenched by the addition of 300 mL of ice water.

The resulting solution was extracted with 3×300 mL of dichloromethane, and the combined organic phases were washed with brine, dried over anhydrous sodium sulfate, filtered, and concentrated under vacuum to give N-methoxy-N-methylisobutyramide (20.7 g, 67%) as a yellow oil. MS (ESI, m/z): 132 [M+H]+

Step 2. 2-methyl-1-(5-(trifluoromethyl)pyridin-2-yl)propan-1-one n-Butyllithium (2.5 M in n-hexane, 22.0 mL, 44.4 mmol) was added dropwise to a −80° C. solution of 2-bromo-5-(trifluoromethyl)pyridine (5.0 g, 22.1 mmol) in THF (35 mL), and the resulting solution stirred for 10 minutes. N-methoxy-N-methylisobutyramide (3.49 g, 26.61 mmol) was added at −80° C., and the reaction mixture stirred for 1 h at −80° C. The reaction was then quenched by the addition of 40 mL of saturated aqueous ammonium chloride solution, and the mixture was allowed to warm to room temperature. The resulting solution was extracted with 3×40 mL of ethyl acetate, and the combined organic phases were washed with brine, dried over anhydrous sodium sulfate, filtered, and concentrated under vacuum. The residue was purified via column chromatography on silica gel (eluting with 1:7 ethyl acetate/petroleum ether) to give 2-methyl-1-(5-(trifluoromethyl)pyridin-2-yl)propan-1-one (550 mg, 8% yield) as a yellow solid. MS (ESI, m/z): 218 [M+H]+.

Step 3. methyl 3,3-dimethyl-2-(5-(trifluoromethyl)pyridin-2-yl)-3H-indole-7-carboxylate A solution of 2-methyl-1-(5-(trifluoromethyl)pyridin-2-yl)propan-1-one (570 mg, 1.84 mmol), methyl 2-hydrazinylbenzoate (557 mg, 2.76 mmol) and acetic acid (31 μL, 0.55 mmol) in toluene (5 mL) stirred for 4 h at 110° C. The resulting mixture was cooled to room temperature and concentrated under vacuum. The residue was dissolved in 5 mL of acetic acid and stirred for 4 h at 118° C. The resulting mixture was cooled to room temperature and concentrated under vacuum. The residue was then diluted by the addition of 5 mL of diethyl ether. The pH value of the solution was adjusted to 7 with solid potassium carbonate. The mixture was filtered, and the filtrate was concentrated under vacuum. The crude product was purified by Prep-HPLC with the following conditions: Column, C18 silica gel; mobile phase A: 0.1% FA in water, B: ACN, increasing B from 0% to 100% within 30 min; Detector, UV 254 nm. The collected fraction was concentrated under vacuum to give methyl 3,3-dimethyl-2-(5-(trifluoromethyl)pyridin-2-yl)-3H-indole-7-carboxylate (240 mg, 38%) as a yellow solid. MS (ESI, m/z): 349 [M+H]+.

Step 4. methyl 3,3-dimethyl-2-(5-(trifluoromethyl)pyridin-2-yl)indoline-7-carboxylate Sodium borohydride (30 mg, 0.79 mmol) was added to a 0-10° C. solution of methyl 3,3-dimethyl-2-(5-(trifluoromethyl)pyridin-2-yl)-3H-indole-7-carboxylate (240 mg, 0.69 mmol) in, THF:MeOH (6:1, 5 mL), and the resulting solution stirred for 40 min at room temperature. The reaction mixture was diluted with 10 mL of ethyl acetate, and the pH value of the solution was adjusted to 6 with 1 M aqueous HCl solution. Potassium carbonate (powder) was added to adjust the pH to 8, and the mixture was filtered. The filtrate was concentrated under vacuum and the residue was purified by Prep-HPLC with the following conditions: Column, C18 silica gel; mobile phase A: 0.1% FA in water, B: CAN; Gradient: increasing B from 0 to 100% within 30 min; Detector, UV 254 nm. The collected fraction was concentrated under vacuum to give methyl 3,3-dimethyl-2-(5-(trifluoromethyl)pyridin-2-yl)indoline-7-carboxylate (186 mg, 77%) as yellow oil. MS (ESI, m/z): 351 [M+H]+.

Step 5. (R)-methyl 3,3-dimethyl-2-(5-(trifluoromethyl)pyridin-2-yl)indoline-7-carboxylate and (S)-methyl 3,3-dimethyl-2-(5-(trifluoromethyl)pyridin-2-yl)indoline-7-carboxylate Methyl 3,3-dimethyl-2-(5-(trifluoromethyl)pyridin-2-yl)indoline-7-carboxylate (200 mg) was separated by Chiral-Prep-HPLC with the following conditions: Column: Chiralpak IB, 2×25 cm, 5 um; Mobile Phase A:Hexane, Mobile Phase B: EtOH; Flow rate: 20 mL/min; Gradient: 5% B to 5% B in 9.5 min; 220/254 nm. The first eluting isomer (Rt=6.01 min) was collected and concentrated under vacuum to give (R)-methyl 3,3-dimethyl-2-(5-(trifluoromethyl)pyridin-2-yl)indoline-7-carboxylate (50 mg, 25%) as a yellow oil (assigned as R-isomer). The second eluting isomer (Rt=7.71 min) was collected and concentrated under vacuum to give (S)-methyl 3,3-dimethyl-2-(5-(trifluoromethyl)pyridin-2-yl)indoline-7-carboxylate (50 mg, 25%) as a yellow oil. MS (ESI, m/z): 351[M+H]+

Step 6. (R)—N-hydroxy-3,3-dimethyl-2-(5-(trifluoromethyl)pyridin-2-yl)indoline-7-carboxamide Hydroxyl amine (50% in water, 1.05 mL, 17.1 mmol) and 1 M aqueous sodium hydroxide solution (0.43 mL, 0.43 mmol) were added to a 0-10° C. solution of (R)-methyl 3,3-dimethyl-2-(5-(trifluoromethyl)pyridin-2-yl)indoline-7-carboxylate (50 mg, 0.14 mmol) in THF:MeOH (4:1, 1.0 mL). The resulting solution stirred at room temperature for 2 days. The mixture was purified by Prep-HPLC with the following conditions: Column: XBridge C18 OBD Prep Column, 100 A, 5 um, 19 mm×250 mm; Mobile Phase A: water (0.1% FA), Mobile Phase B: ACN; Flow rate: 20 mL/min; Gradient: 40% B to 60% B in 8 min; 254 nm. The collected fraction was lyophilized to give (R)—N-hydroxy-3,3-dimethyl-2-(5-(trifluoromethyl)pyridin-2-yl)indoline-7-carboxamide (27.5 mg, 57%) as a white solid (assigned as R-isomer). 1H-NMR (400 MHz, DMSO-d6) δ (ppm): 10.99 (s, 1H), 8.96 (s, 1H), 8.87 (s, 1H), 8.22-8.20 (m, 1H), 7.70 (d, J=8.4 Hz, 1H), 7.32 (d, J=8.0 Hz, 1H), 7.13 (d, J=6.8 Hz, 1H), 6.97 (s, 1H), 6.64-6.60 (m, 1H), 4.81 (s, 1H), 1.50 (s, 3H), 0.61 (s, 3H). MS (ESI, m/z): 352[M+H]+.

Step 7. (S)—N-hydroxy-3,3-dimethyl-2-(5-(trifluoromethyl)pyridin-2-yl)indoline-7-carboxamide Hydroxyl amine (50% in water, 1.05 mL, 17.1 mmol) and 1 M aqueous sodium hydroxide solution (0.43 mL, 0.43 mmol) were added to a 0-10° C. solution of (S)-methyl 3,3-dimethyl-2-(5-(trifluoromethyl)pyridin-2-yl)indoline-7-carboxylate (50 mg, 0.14 mmol) in THF:MeOH (4:1, 1.0 mL). The resulting solution stirred at room temperature for 5 days. The mixture was purified by Prep-HPLC with the following conditions: Column: XBridge Prep C18 OBD Column, 19×150 mm 5 um; mobile phase, water (0.1% FA) and ACN (25.0% ACN up to 55.0% in 7 min); Detector, UV 254/220 nm. The collected fraction was lyophilized to give (S)—N-hydroxy-3,3-dimethyl-2-(5-(trifluoromethyl)pyridin-2-yl)indoline-7-carboxamide (13.7 mg, 28%) as a white solid (assigned as S-isomer). 1H-NMR (400 MHz, DMSO-d6) δ (ppm): 10.98 (s, 1H), 8.96 (s, 1H), 8.89 (s, 1H), 8.22-8.20 (m, 1H), 7.70 (d, J=8.4 Hz, 1H), 7.32 (d, J=8.0 Hz, 1H), 7.13 (d, J=6.8 Hz, 1H), 6.96 (s, 1H), 6.64-6.60 (m, 1H), 4.81 (s, 1H), 1.50 (s, 3H), 0.61 (s, 3H). MS (ESI, m/z): 352[M+H]⁺.

The following compounds were prepared according to the procedures described above for (R)- and (S)—N-hydroxy-3,3-dimethyl-2-(5-(trifluoromethyl)pyridin-2-yl)indoline-7-carboxamide.

| Ex. | Structure | Name | ¹HNMR | (ES, m/z) [M + H]⁺ |
|---|---|---|---|---|
| 40-3 | 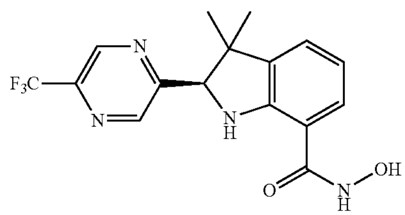 | (R)-N-hydroxy-3,3-dimethyl-2-(5-(trifluoromethyl)pyrazin-2-yl)indoline-7-carboxamide | (DMSO, 400 MHz, ppm): 10.98(s, 1H), 9.17(s, 1H), 8.94(s, 1H), 7.33(d, J = 7.2 Hz, 1H), 7.16(d, J = 7.2 Hz, 1H), 6.67-6.63(m, 1H), 4.85(s, 1H), 1.50(s, 3H), 0.67(s, 3H) | 353 |
| 40-4 | 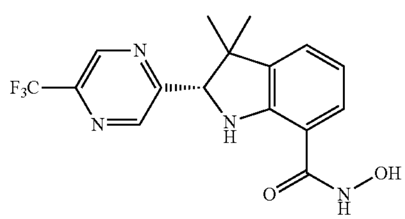 [SMILES: CC1(C)c2cccc(C(=O)NO)c2N[C@@H]1c1cnc(C(F)(F)F)cn1] | (S)-N-hydroxy-3,3-dimethyl-2-(5-(trifluoromethyl)pyrazin-2-yl)indoline-7-carboxamide | (DMSO, 400 MHz, ppm): 10.98(s, 1H), 9.17(s, 1H), 8.94(s, 1H), 7.33(d, J = 7.2 Hz, 1H), 7.16(d, J = 7.2 Hz, 1H), 6.67-6.63(m, 1H), 4.85(s, 1H), 1.50(s, 3H), 0.67(s, 3H) | 353 |
| 40-5 | 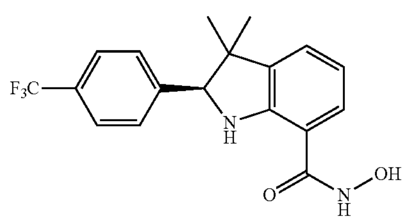 [SMILES: CC1(C)c2cccc(C(=O)NO)c2N[C@H]1c1ccc(C(F)(F)F)cc1] | (S)-N-hydroxy-3,3-dimethyl-2-(4-(trifluoromethyl)phenyl)indoline-7-carboxamide | (DMSO, 300 MHz, ppm): 11.01-10.98 (br, 1H), 8.86 (s, 1H), 7.73 (d, J = 8.1 Hz, 2H), 7.58 (d, J = 8.1 Hz, 2H), 7.34-7.31 (m, 2H), 7.13(d, J = 6.9 Hz, 1H), 6.79 (s, 1H), 6.65-6.60 (m, 1H), 4.75 (s, 1H), 1.41 (s, 3H), 0.65 (s, 3H). | 351 |
| 40-6 | 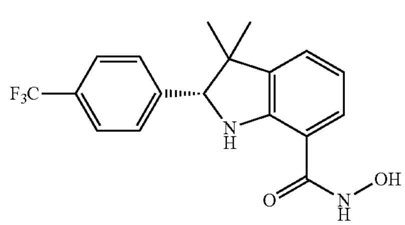 [SMILES: CC1(C)c2cccc(C(=O)NO)c2N[C@@H]1c1ccc(C(F)(F)F)cc1] | (R)-N-hydroxy-3,3-dimethyl-2-(4-(trifluoromethyl)phenyl)indoline-7-carboxamide | (DMSO, 300 MHz, ppm): 10.99 (s, 1H), 8.85 (s, 1H), 7.72 (d, J = 8.1 Hz, 2H), 7.57 (d, J = 8.1 Hz, 2H), 7.34-7.31 (m, 2H), 7.13 (d, J = 6.9 Hz, 1H), 6.79 (s, 1H), 6.65-6.60 (m, 1H), 4.75 (s, 1H), 1.41 (s, 3H), 0.61 (s, 3H). | 351 |

Example 41-1.
2-benzoyl-N-hydroxyisoindoline-4-carboxamide

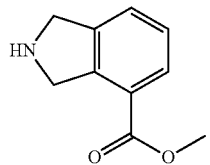

step 1

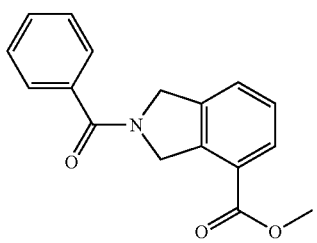

step 2

Step 2.
2-benzoyl-N-hydroxyisoindoline-4-carboxamide

A solution of methyl 2-benzoylisoindoline-4-carboxylate (50 mg, 0.16 mmol) and hydroxylamine (50% in water, 0.5 mL, 8.2 mmol) in THF:MeOH (4:1, 2.5 mL) stirred for 5 min at room temperature and then 1 M aqueous sodium hydroxide solution (0.5 mL, 0.5 mmol) was added. The resulting solution stirred for 2 h at room temperature and then concentrated to dryness. The residue was purified by reversed phase Prep-HPLC with the following conditions: Column: X Bridge C18 19×150 mm; 5 um, mobile phase, water (0.05% HCO$_2$H) and ACN (0% increasing to 35% within 8 min); Flow rate: 15 mL/min Detector, UV 254 nm. The collected fraction was lyophilized to give 2-benzoyl-N-hydroxyisoindoline-4-carboxamide (15.7 mg, 35%) as a white solid. $^1$H NMR (300 MHz, DMSO-d$_6$) δ ppm 11.07-11.31 (m, 1H) 8.99-9.22 (m, 1H) 7.43-7.70 (m, 6H) 7.22-7.43 (m, 2H) 4.69-5.18 (m, 4H). MS: (ESI, m/z): 283[M+H]$^+$.

The following compound was prepared according to the procedures described above for 2-benzoyl-N-hydroxyisoin-doline-4-carboxamide.

| Ex. | Structure | Name | $^1$HNMR | (ESI, m/z) [M + H]$^+$ |
|---|---|---|---|---|
| 41-2 | 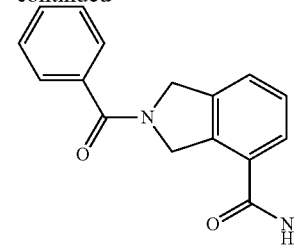 | N-hydroxy-2-(4-methoxybenzyl) isoindoline-4-carboxamide | $^1$H NMR (300 MHz, DMSO-d$_6$) δ ppm 10.91 (br dd, J = 3.08, 1.91 Hz, 1 H) 8.79-9.02 (m, 1 H) 7.10-7.51 (m, 5 H) 6.84 (br d, J = 8.50 Hz, 2 H) 3.59-4.00 (m, 9 H) | 299 |

-continued

Step 1: methyl 2-benzoylisoindoline-4-carboxylate

A solution of methyl isoindoline-4-carboxylate (50 mg, 0.282 mmol), benzoyl chloride (0.033 ml, 0.282 mmol), and potassium carbonate (117 mg, 0.847 mmol) in acetonitrile (3 ml) was heated with stirring at 50° C. overnight. The solution was cooled to room temperature and then diluted with 10 mL of water. The solution was extracted with 2×10 mL of ethyl acetate, and the combined organic phases were concentrated to dryness to afford methyl 2-benzoylisoindo-line-4-carboxylate (50 mg, 60%) as crude material. MS: (ESI, m/z): 282[M+H]$^+$.

Example 42-1.
N-hydroxy-2-phenylisoindoline-4-carboxamide

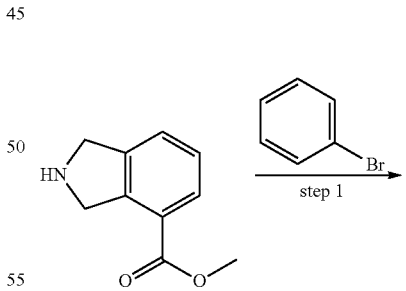

step 1

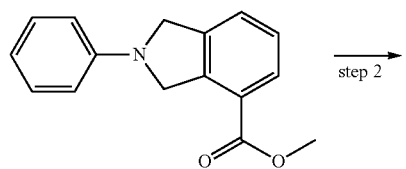

step 2

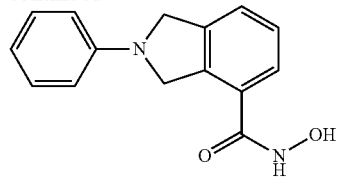

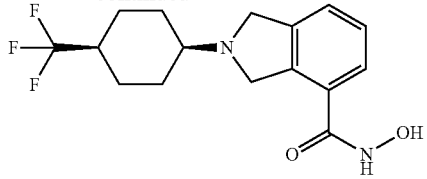

Step 1. methyl 2-phenylisoindoline-4-carboxylate

A solution of methyl isoindoline-4-carboxylate (100 mg, 0.56 mmol), bromobenzene (89 mg, 0.56 mmol), Xphos 3G (10 mg, 0.012 mmol), and sodium tert-butoxide (70 mg, 0.73 mmol) in dioxane (5 mL) stirred overnight at 80° C. The reaction mixture was cooled to room temperature and filtered. The filtrate was concentrated under vacuum, and the residue was purified by column chromatography on silica gel (eluting with 10-40% ethyl acetate/hexanes) to give methyl 2-phenylisoindoline-4-carboxylate (20 mg, 14% yield) as a white solid. MS (ESI, m/z): 254 [M+H]$^+$.

Step 2. N-hydroxy-2-phenylisoindoline-4-carboxamide

Hydroxyl amine (50% in water, 0.26 mL, 3.9 mmol) and 1 M aqueous sodium hydroxide solution (0.23 mL, 0.23 mmol) were added to a solution of methyl 2-phenylisoindoline-4-carboxylate (20 mg, 0.079 mmol) in THF:MeOH (4:1, 2.5 mL). The resulting solution stirred for 4 h at room temperature. The resulting mixture was concentrated and the crude product was purified by Prep-HPLC with the following conditions: Column: XBridge Prep C18 OBD Column, 5 um, 19×150 mm; mobile phase, A: water with 0.1% FA, B: ACN; Flow rate, 23 mL/min; Gradient, 35% B to 85% B in 8 min; Detector, 254 220 nm. The collected fraction was lyophilized to give N-hydroxy-2-phenylisoindoline-4-carboxamide (6.1 mg, 30%) as an off-white solid. $^1$H NMR (300 MHz, DMSO-d$_6$) δ ppm 10.94-11.28 (m, 1H) 8.90-9.21 (m, 1H) 7.43-7.55 (m, 2H) 7.28-7.38 (m, 1H) 7.19 (dd, J=8.50, 7.33 Hz, 2H) 6.53-6.68 (m, 3H) 4.44-4.79 (m, 4H). MS: (ESI, m/z): 255[M+H]$^+$.

Example 43-1. N-hydroxy-2-((1s, 4s)-4-(trifluoromethyl)cyclohexyl)isoindoline-4-carboxamide

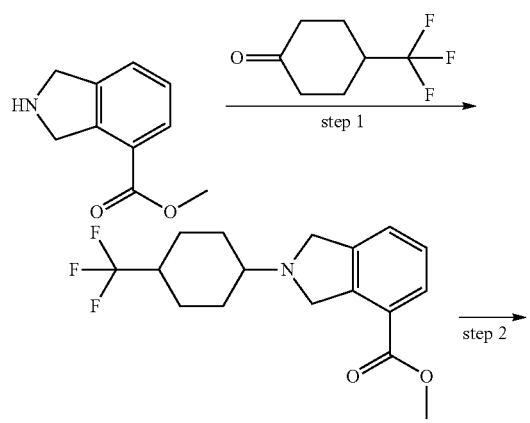

Step 1. methyl 2-(4-(trifluoromethyl)cyclohexyl)isoindoline-4-carboxylate

Methyl isoindoline-4-carboxylate (25 mg, 0.141 mmol) is taken up in DCE (3 ml), then 4-(trifluoromethyl)cyclohexanone (0.019 ml, 0.141 mmol) is added followed by acetic acid (8.08 μl, 0.141 mmol) (2 drops). The reaction is stirred at ambient temperature for 30 mins then sodium triacetoxyborohydride (44.9 mg, 0.212 mmol) is added and continued to stir for 12 hours. The reaction was diluted with DCM, washed with brine. Organic layer is separated and concentrated to dryness. Methyl 2-(4-(trifluoromethyl)cyclohexyl)isoindoline-4-carboxylate (40 mg) is carried on to the next step as the crude product MS (ESI, m/z): 228 [M+H]$^+$.

Step 2. N-hydroxy-2-((1s, 4s)-4-(trifluoromethyl)cyclohexyl)isoindoline-4-carboxamide Hydroxyl amine (50% in water, 0.7 mL, 10.6 mmol) and 1 M aqueous sodium hydroxide solution (0.7 mL, 0.7 mmol) were added to a solution of Methyl 2-(4-(trifluoromethyl)cyclohexyl)isoindoline-4-carboxylate (40 mg, 0.122 mmol) in THF:MeOH (1:1, 2.0 mL). The resulting solution stirred for 4 h at room temperature. The resulting mixture was concentrated and the crude product was purified by Prep-HPLC with the following conditions: Column: Waters SunFire C18, 5 um, 19×150 mm; mobile phase, A: water with 0.1% FA, B: ACN with 0.1% FA; Flow rate, 23 mL/min; Gradient, 0% B to 5% B in 5 min; Detector, 254 220 nm. The collected fraction was lyophilized to give 2 peaks with same molecular weight. Peak 2 was collected, and the compound was assigned as N-hydroxy-2-((1s, 4s)-4-(trifluoromethyl)cyclohexyl)isoindoline-4-carboxamide (2 mg, 5%) as an off-white solid. MS: (ESI, m/z): 329[M+H]$^+$.

Example 44-1. N-hydroxy-2-(4-hydroxy-5-phenyl-4-(trifluoromethyl)-4H-imidazol-2-yl)isoindoline-4-carboxamide

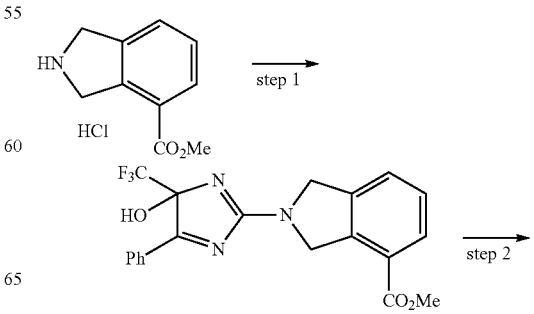

-continued

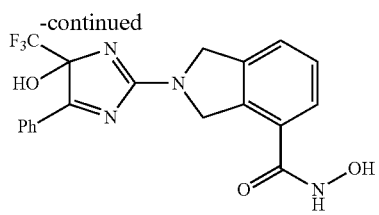

Step 1. methyl 2-(4-hydroxy-5-phenyl-4-(trifluoromethyl)-4H-imidazol-2-yl)isoindoline-4-carboxylate Sodium hydroxide (100 mg, 2.5 mmol) was added to a mixture of methyl isoindoline-4-carboxylate hydrochloride (132 mg, 0.62 mmol) and methyl carbamimidothioate (67 mg, 0.75 mmol) in ethanol (3 mL) and water (3 mL) was added. The solution was heated in a sealed tube at 100° C. for 4 h. The solvent was removed and brine (10 mL) and ethyl acetate (10 mL) were added. The aqueous layer was separated and extracted with ethyl acetate (2×10 mL), and the combined organic extracts were dried over anhydrous sodium sulfate, filtered, and concentrated. The residue was dissolved in acetonitrile (8 mL) and 3,3,3-trifluoro-1-phenylpropane-1,2-dione (138 mg, 0.68 mmol) and potassium carbonate (256 mg, 1.9 mmol) were added. The mixture was heated at 100° C. overnight and then cooled to room temperature. The mixture was filtered, and the filtrate was concentrated. The residue was purified via column chromatography on silica gel (eluting with 2:1 hexanes/ethyl acetate) to give the methyl 2-(4-hydroxy-5-phenyl-4-(trifluoromethyl)-4H-imidazol-2-yl)isoindoline-4-carboxylate (44 mg, 18%) as a light yellow solid. MS: (ESI, m/z): 404[M+H].

Step 2. N-hydroxy-2-(4-hydroxy-5-phenyl-4-(trifluoromethyl)-4H-imidazol-2-yl)isoindoline-4-carboxamide A mixture of methyl 2-(4-hydroxy-5-phenyl-4-(trifluoromethyl)-4H-imidazol-2-yl)isoindoline-4-carboxylate (0.2 M in 4:1 THF:MeOH, 150 µL, 30 µmol), hydroxyl amine (50% in water, 120 µL) and 1M aqueous sodium hydroxide solution (1 M in water, 100 µL). The vial was shaken at room temperature overnight, and the solvent was removed under reduced pressure. The residue was dissolved in DMSO (500 µL) and acetic acid (40 µL) and purified by prep-HPLC with the following conditions: Column: Waters SunFire C18, 5 um, 19×150 mm; mobile phase, A: water with 0.1% formic acid, B: acetonitrile with 0.1% formic acid; Flow rate, 23 mL/min; Gradient, 0% B to 5% B in 5 min; Detector, 254, 220 nm. The collected fraction was concentrated to give N-hydroxy-2-(4-hydroxy-5-phenyl-4-(trifluoromethyl)-4H-imidazol-2-yl)isoindoline-4-carboxamide (2.6 mg, 21%) as an off-white solid MS: (ESI, m/z): 405[M+H].

Example 45-1. N-hydroxy-2-(5-(trifluoromethyl)pyridin-2-yl)isoindoline-4-carboxamide

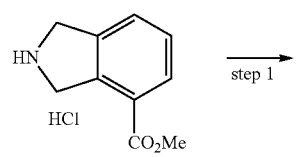

-continued

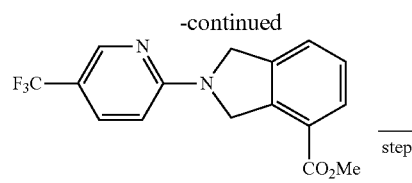

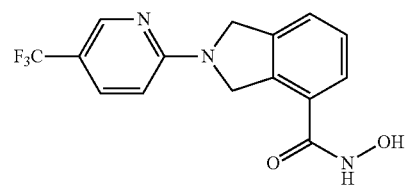

Step 1. methyl 2-(5-(trifluoromethyl)pyridin-2-yl)isoindoline-4-carboxylate

A mixture of 2-bromo-5-(trifluoromethyl)pyridine (0.2 M in DMF, 165 µL, 33 µmol), methyl isoindoline-4-carboxylate hydrochloride (0.2 M in DMF, 150 µL, 30 µmol) and triethylamine (40 µL) was shaken at 100° C. overnight. Water (500 µL) and ethyl acetate (600 µL) were added, and the aqueous layer was extracted with ethyl acetate (600 µL). The combined organic extracts were concentrated to give methyl 2-(5-(trifluoromethyl)pyridin-2-yl)isoindoline-4-carboxylate as a brown oil which was used in the next step without further purification. MS: (ESI, m/z): 323 [M+H].

Step 2. N-hydroxy-2-(5-(trifluoromethyl)pyridin-2-yl)isoindoline-4-carboxamide Methyl 2-(5-(trifluoromethyl)pyridin-2-yl)isoindoline-4-carboxylate (from step 1) was dissolved in THF:MeOH (4:1, 200 µL) and hydroxyl amine (50% in water, 120 µL) and aqueous sodium hydroxide (1 M, 100 µL) were added. The mixture was shaken at room temperature overnight, and the solvent was removed under reduced pressure. The residue was dissolved in DMSO (500 µL) and acetic acid (40 µL) and purified by prep-HPLC with the following conditions: Column: Waters SunFire C18, 5 um, 19×150 mm; mobile phase, A: water with 0.1% formic acid, B: acetonitrile with 0.1% formic acid; Flow rate, 23 mL/min; Gradient, 0% B to 5% B in 5 min; Detector, 254, 220 nm. The collected fraction was concentrated to give N-hydroxy-2-(5-(trifluoromethyl)pyridin-2-yl)isoindoline-4-carboxamide (3.7 mg, 38%) as an off-white solid. MS: (ESI, m/z): 324[M+H].

The following compound was synthesized according to the procedures describe above for N-hydroxy-2-(5-(trifluoromethyl)pyridin-2-yl)isoindoline-4-carboxamide.

| Example | Structure | Name | LC-MS [M + 1]+ | HPLC RT (min) |
|---|---|---|---|---|
| 45-2 | 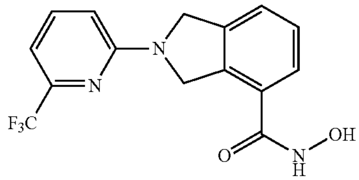 [SMILES: O=C(NO)c1cccc2c1CN(c1cccc(C(F)(F)F)n1)C2] | N-hydroxy-2-(6-(trifluoromethyl)pyridin-2-yl)isoindoline-4-carboxamide | 324.03 | 1.34 |

Example 50-1. 1,1-Dimethyl-2-(5-(trifluoromethyl)pyrazin-2-yl)isoindoline-4-carboxamide

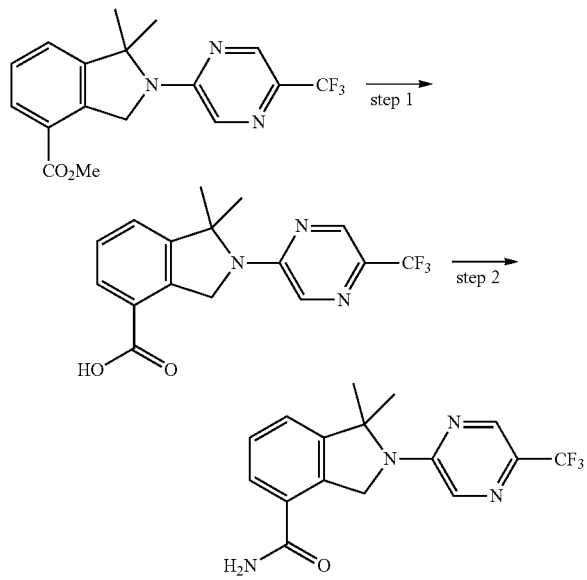

Step 1. 1,1-Dimethyl-2-(5-(trifluoromethyl)pyrazin-2-yl)isoindoline-4-carboxylic acid A solution of lithium hydroxide (68 mg, 2.86 mmol) in water (1 mL) was added to a mixture of methyl 1,1-dimethyl-2-(5-(trifluoromethyl)pyrazin-2-yl)isoindoline-4-carboxylate (100 mg, 0.29 mmol) in tetrahydrofuran (5 mL). The resulting solution stirred for 12 h at 25° C. The mixture was concentrated under vacuum, and the residue was purified by reversed phase column with the following conditions: Column, C18 silica gel, 40 g, 20-45 µm, 100 A; mobile phase, water with 0.05% trifluoroacetic acid and acetonitrile (0% up to 60% acetonitrile in 30 min); Detector, UV 254/220 nm. The collected fraction was concentrated to afford 1,1-dimethyl-2-(5-(trifluoromethyl)pyrazin-2-yl)isoindoline-4-carboxylic acid (75 mg, 78%) as an off-white solid. LCMS: (ES, m/z): 338 [M+H]+.

Step 2. 1,1-Dimethyl-2-(5-(trifluoromethyl)pyrazin-2-yl)isoindoline-4-carboxamide A mixture of 1,1-dimethyl-2-(5-(trifluoromethyl)pyrazin-2-yl)isoindoline-4-carboxylic acid (75 mg, 0.22 mmol), HATU (103 mg, 0.27 mmol), N,N-diisopropylethylamine amine (0.12 mL, 0.66 mmol), and ammonium chloride (14 mg, 0.27 mmol) in N,N-dimethylformamide (3 mL) was stirred for 2 h at 25° C. The mixture was poured into water (30 mL) and extracted with ethyl acetate (3×30 mL). The combined organic layers were dried over anhydrous sodium sulfate, filtered, and concentrated under vacuum. The crude product was purified by Prep-HPLC with the following conditions: Column, XBridge Prep C18 OBD Column, 19×150 mm, 5 µm; mobile phase, water (0.1% formic acid) and acetonitrile (25.0% acetonitrile up to 55.0% in 7 min); Detector, uv 254 220 nm. The collected fraction was lyophilized to afford 1,1-dimethyl-2-(5-(trifluoromethyl)pyrazin-2-yl)isoindoline-4-carboxamide (25.5 mg, 34%) as an off-white solid. $^1$H-NMR (DMSO, 400 MHz) δ (ppm): δ 8.59 (s, 1H), 8.19 (br s, 1H), 8.02 (s, 1H), 7.78 (d, J=7.6 Hz, 1H), 7.59 (d, J=7.6 Hz, 1H), 7.50-7.47 (m, 2H), 5.13 (s, 2H), 1.80 (s, 6H). LCMS: (ES, m/z): 337 [M+H]+.

Example 46. In Vitro Histone Deacetylase Assay I

The probe binding HDAC11 assay was performed using a time resolved fluorescence (TRF) assay format. Recombinant N-terminal GST tag full-length human HD AC 11 was expressed and purified from baculovirus in Sf9 insect cells (SignalChem, #H93-30G-1000). Each assay was performed in 1536 black well microplates (Corning, #3936) in a final volume of 8 µL in assay buffer containing 50 mM HEPES (pH 7.5), 50 mM KCl, 50 mM NaCl, 0.5 mM GSH (L-Glutathione reduced, Sigma #G4251), 0.03% BGG (0.22 µM filtered, Sigma, #G7516-25G), and 0.01% Triton X-100 (Sigma, #T9284-10L). 100 nL of 10-point, 3-fold serial dilution in DMSO was pre-dispensed into respective wells of 1536 assay plates for a final test concentration range of 25 µM to 1.3 nM respectively. The final concentration in the assay of HD AC 11 and probe (a fluorescein labeled HD AC 11 inhibitor) was 2.5 nM and 20 nM respectively. 4 µL of 2× probe and 2× anti-GST Terbium (Cisbio, #61GSTXLB) was added to assay plates followed by 4 µL of 2×HDAC11. Plates were incubated for 16 hours at room temperature before time resolved fluorescence was read on the Envision (Excitation at 340 nm, and Emission at 485 nm and 535 nm, Perkin Elmer).

Data from HD AC 11 Assays were reported as percent inhibition (inh) compared with control wells based on the following equation: % inh=1−((FLU−AveLow)/(AveHigh−AveLow)) where FLU=measured time resolved fluorescence. AveLow=average time resolved fluorescence of no enzyme control (n=32). AveHigh=average time resolved fluorescence of DMSO control (n=32). IC$_{50}$ values were determined by curve fitting of the standard 4 parameter logistic fitting algorithm included in the Activity Base software package: IDBS XE Designer Model205. Data is fitted using the Levenburg Marquardt algorithm.

As set forth in Table-2 below, "+++" indicates an IC$_{50}$ below 0.5 µM; "++" indicates an IC$_{50}$ between 0.5 µM and 1 µM; and "+" indicates an IC$_{50}$ above 1 µM.

TABLE 2

IC$_{50}$ Ranges for Compounds of the Disclosure

| Compound No. | HDAC11 IC$_{50}$ Range |
|---|---|
| 1-1 | +++ |
| 1-2 | + |
| 1-3 | + |
| 1-4 | + |
| 1-5 | ++ |
| 2-1 | +++ |
| 2-2 | +++ |
| 3-1 | + |
| 4-1 | + |
| 5-1 | +++ |
| 5-2 | + |
| 6-1 | ++ |
| 6-2 | + |
| 7-1 | + |
| 7-2 | +++ |
| 7-3 | + |
| 7-4 | +++ |
| 7-5 | + |
| 8-1 | + |
| 9-1 | ++ |
| 9-2 | + |
| 10-1 | + |
| 11-1 | +++ |
| 12-1 | +++ |
| 13-1 | + |
| 14-1 | + |
| 15-1 | +++ |
| 16-1 | +++ |
| 17-1 | +++ |
| 18-1 | +++ |
| 18-2 | +++ |
| 18-3 | +++ |
| 19-1 | +++ |
| 19-2 | +++ |
| 20-1 | + |
| 20-2 | +++ |
| 21-1 | +++ |
| 22-1 | +++ |
| 22-2 | +++ |
| 22-3 | +++ |
| 22-5 | +++ |
| 22-6 | +++ |
| 22-7 | +++ |
| 22-8 | +++ |
| 22-9 | + |
| 23-1 | +++ |
| 23-2 | ++ |
| 24-1 | +++ |
| 25-1 | +++ |
| 26-1 | +++ |
| 26-2 | +++ |
| 27-1 | +++ |
| 27-2 | +++ |
| 28-1 | + |
| 28-2 | + |
| 29-1 | +++ |
| 30-1 | ++ |
| 30-2 | + |
| 30-3 | +++ |
| 30-4 | + |
| 30-5 | +++ |
| 36-2 | +++ |
| 30-6 | + |
| 30-7 | + |
| 31-1 | ++ |
| 32-1 | + |
| 33-1 | ++ |
| 34-1 | +++ |
| 35-1 | ++ |
| 35-2 | + |
| 36-1 | + |
| 37-1 | ++ |
| 37-2 | ++ |
| 37-3 | +++ |
| 37-4 | +++ |
| 38-1 | ++ |
| 38-2 | + |
| 39-1 | +++ |
| 39-2 | + |
| 40-1 | + |
| 40-2 | +++ |
| 40-3 | +++ |
| 40-4 | + |
| 40-5 | ++ |
| 40-6 | + |
| 1-6 | + |
| 1-7 | + |
| 28-3 | + |
| 41-1 | + |
| 41-2 | + |
| 42-1 | + |
| 44-1 | + |
| 45-1 | +++ |
| 45-2 | + |

Example 47. In Vitro Histone Deacetylase Assay II

The measurement of HDAC11 deacetylase activity was performed using an electrophoretic mobility shift assay by Nanosyn (Santa Clara, Calif.). Full length human recombinant HDAC11 protein was expressed in baculoviral system and purified by affinity chromatography. The enzymatic reactions were assembled in 384 well plates in a total volume of 25 µL in a reaction buffer composing: 100 mM HEPES, pH 7.5, 25 mM KCl, 0.1% bovine serum albumin, 0.01% Triton X-100, 1% DMSO (from compounds), 2 µM of the fluorescently labeled peptide substrate and enzyme. The enzyme was added at a final concentration of 10 nM. The peptide substrate FAM-RHKK(tri-fluor-Ac)—NH$_2$ was used. The compounds were tested at 12 concentrations spaced by 3× dilution intervals. Negative control samples (0%-inhibition in the absence of inhibitor) and positive control samples (100%-inhibition) were assembled in replicates of four in each assay plate. The reactions were incubated at 25° C. and quenched by the addition of 45 µL of termination buffer (100 mM HEPES, pH 7.5, 0.01% Triton X-100, 0.05% SDS).

The terminated assay plates were analyzed on LabChip® 3000 microfluidic electrophoresis instrument (Perkin Elmer/Caliper Life Sciences). The fluorescence intensity of the electrophoretically separated de-acetylated product and substrate peptide was measured. Activity in each sample was determined as the product to sum ratio (PSR): P/(S+P), where P is the peak height of the product peptide and S is the peak height of the substrate peptide. Percent inhibition ($P_{inh}$) is determined using the following equation:

$$P_{inh} = (PSR0\% - PSR_{inh})/(PSR0\% - PSR100\%)*100,$$

where $PSR_{inh}$ is the product sum ratio in the presence of inhibitor, PSR0% is the average product sum ration in the absence of inhibitor and PSR100% is the average product sum ratio in 100%-inhibition control samples. The IC$_{50}$ values of inhibitors were determined by fitting the percent inhibition curves with 4 parameter dose-response model using XLfit 4 software.

The assay described herein as Example 47 was used in Examples 48-52.

Example 48. Structure Activity Relationship of Hydroxamic Acid Regiochemistry

Initial studies explored the impact of the hydroxamic acid position on both the HDAC6 and HDAC11 activities. As shown in Table 3, the regiochemistry of the hydroxamic acid substituent affected the potency of both HDAC11 and HDAC6. Substitution at the 6-position (compound 50-5) afforded similar HDAC6 activity but resulted in loss of HDAC 11 potency relative to the initial lead (50-4). Installing the hydroxamic acid group at the 8-position (50-6), resulted in a 20-fold loss in potency vs. HDAC6 but only a 2-fold loss in activity vs. HDAC11, meaning it could potentially be tolerated. The largest impact was observed when the hydroxamic acid was substituted at the 5-position. While compound 50-2 exhibited only modest HDAC11 activity, no significant HDAC6 potency was observed.

As set forth in Table 3 below, for $IC_{50}$: "+++" indicates an $IC_{50}$ below 0.5 μM; "++" indicates an $IC_{50}$ between 0.51 μM and 2.0 μM; and "+" indicates an $IC_{50}$ above 2 μM.

TABLE 3

SAR of the Hydroxamic Acid Regiochemistry

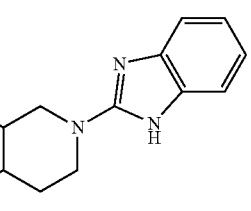

| Cmpd. No. | Position of Hydroxamic Acid | HDAC 11 $IC_{50}$ (μM)[a] | HDAC 6 $IC_{50}$ (μM)[a] |
|---|---|---|---|
| 50-4 | 7 | + | +++ |
| 50-2 | 5 | ++ | + |
| 50-5 | 6 | + | +++ |
| 50-6 | 8 | + | +++ |

[a] Activity was measured using electrophoretic mobility shift assays with full length human recombinant HDAC proteins and fluorescently labeled peptide substrates. Reported as the mean of at least two separate assay runs.

Example 49. Optimization of Hydroxamic Acid Core

Table 4 highlights efforts to study the hydroxamic acid core. Working from the tetrahydroisoquinoline, changes to the ring size of the saturated ring were examined. Thus, isoindoline and 2,3,4,5-tetrahydrobenzodiazepine cores were explored. Both isoindolines (1-6) and benzodiazepine (50-3) cores were tolerated and exhibited >10-fold increases in potency against HDAC 11 while maintaining selectivity over HDAC6. While tetrahydrobenzodiazepine 50-2 showed better potency vs. HDAC11, optimization efforts were focused on the isoindoline 1-6 due to its combination of reasonable potency and significant microsomal stability relative to 50-3.

As set forth in Table 4 below, for $IC_{50}$: "+++" indicates an $IC_{50}$ below 0.5 μM; "++" indicates an $IC_{50}$ between 0.51 μM and 1.0 μM; and "+" indicates an $IC_{50}$ above 1 μM. For m-$CL_{int}$: "+++" indicates a m-$CL_{int}$ below 50 μL/min/mg; "++" indicates a m-$CL_{int}$ between 51 μL/min/mg and 100 μL/min/mg; and "+" indicates a m-$CL_{int}$ above 100 μL/min/mg. For solubility: "+++" indicates solubility >55 μM; "++" indicates 30 μM<solubility ≤55 μM; "+" indicates solubility ≤30 μM. For LipE: "+++" indicates a LipE>6.5; "++" indicates 5.5<LipE≤6.5; "+" indicates LipE≤5.5.

TABLE 4

Optimization of Hydroxamic Acid Core

| No. | Structure | HDAC11[a] $IC_{50}$ (μM) | HDAC6[a] $IC_{50}$ (μM) | m-$CL_{int}$[b] (μL/min/mg) | LipE[c] |
|---|---|---|---|---|---|
| 50-2 | 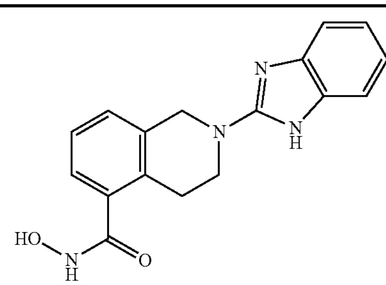 | + | + | +++ | + |
| 1-6 | 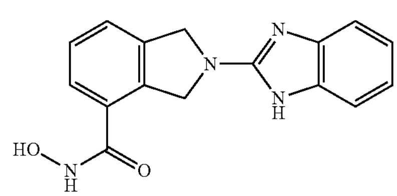 [SMILES: O=C(NO)c1cccc2c1CN(c1nc3ccccc3[nH]1)C2] | +++ | + | +++ | ++ |

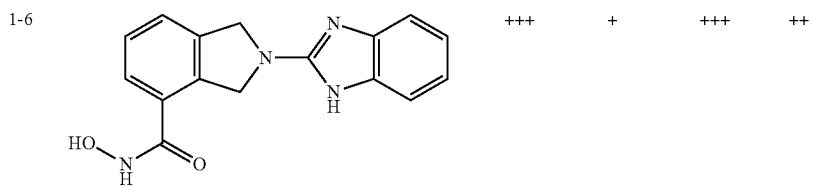

TABLE 4-continued

Optimization of Hydroxamic Acid Core

| No. | Structure | HDAC11[a] IC$_{50}$ (µM) | HDAC6[a] IC$_{50}$ (µM) | m-CL-$_{int}$[b] (µL/min/mg) | LipE[c] |
|---|---|---|---|---|---|
| 50-3 | 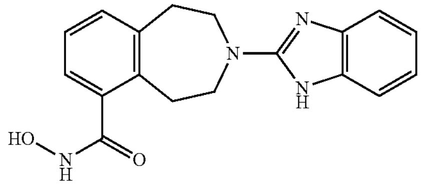 [SMILES: O=C(NO)c1cccc2c1CCN(c1nc3ccccc3[nH]1)CC2] | +++ | + | + | + |

[a]Activity was measured using electrophoretic mobility shift assays with full length human recombinant HDAC proteins and fluorescently labeled peptide substrates. Reported as the mean of at least two separate assay runs.
[b]In vitro intrinsic clearance after incubation with mouse liver microsomes.
[c]Lipophilic efficiency = pIC$_{50}$ HDAC11-clogD$_{7.4}$.

Example 50. Optimization of N-Aryl Substituent

Further optimization of the heterocyclic ring at the 2-position of the isoindoline ring is summarized in Table 5. A variety of replacements for the benzimidazole ring (1-6) were explored, with benzoxazole (15-1), benzothiazole (7-4), pyridine (45-1), and quinoline (7-2) analogs all showing improved potency vs. HD AC 11, albeit with a significant loss of microsomal stability, as measured by m-CL$_{int}$ (intrinsic clearance after incubation with mouse liver microsomes). Saturating one of the aromatic rings (1-4) or eliminating one of the rings (to afford imidazole 1-2) resulted in loss of potency and microsomal stability. Of note, introduction of the lipophilic trifluoromethyl group (12-1) resulted in a significant increase in both potency and LipE but again with loss of microsomal stability relative to 1-6. In the absence of a co-crystal structure of HD AC 11, a homology model based on internal co-crystal structures of HDAC8 was generated. Modeling of compound 12-1 into the homology model supported a lipophilic binding hypothesis with the trifluoromethyl group predicted to efficiently fill a small pocket adjacent to the zinc binding site formed by hydrophobic residues and backbone carbonyls.

As set forth in Table 5 below, for IC$_{50}$: "+++" indicates an IC$_{50}$ below 0.5 µM; "++" indicates an IC$_{50}$ between 0.51 µM and 1.0 µM; and "+" indicates an IC$_{50}$ above 1 µM. For m-CL$_{int}$: "+++" indicates a m-CL$_{int}$ below 50 µL/min/mg; "++" indicates a m-CL$_{int}$ between 51 µL/min/mg and 100 µL/min/mg; and "+" indicates a m-CL$_{int}$ above 100 µL/min/mg. For LipE: "+++" indicates a LipE>6.5; "++" indicates 5.5<LipE≤6.5; "+" indicates LipE≤5.5.

TABLE 5

Optimization of N-Aryl Substituent

| Compound No. | HDAC11[a] IC$_{50}$ (µM) | m-CL$_{int}$[b] (µL/min/mg) | LipE[c] |
|---|---|---|---|
| 1-6 | + | +++ | ++ |
| 15-1 | +++ | + | +++ |
| 7-4 | +++ | + | + |
| 12-1 | +++ | + | ++ |
| 45-1 | +++ | ++ | ++ |
| 7-2 | +++ | ++ | + |
| 1-2 | + | ++ | ++ |
| 1-4 | + | + | ++ |

[a]Activity was measured using electrophoretic mobility shift assays with full length human recombinant HDAC proteins and fluorescently labeled peptide substrates. Reported as the mean of at least two separate assay runs.
[b]In vitro intrinsic clearance after incubation with mouse liver microsomes.
[c]Lipophilic efficiency = pIC$_{50}$ HDAC11 − clogD$_{7.4}$.

Example 51. Optimization of N-Arylisoindolines

As mentioned above, while altering the core and A-aryl substituent led to improvements in both potency and LipE, these changes also resulted in compounds with poor microsomal stability. Without wishing to be bound by any particular theory, it was hypothesized that the two benzylic methylene groups present in the isoindoline core were the most likely sites of metabolism and hypothesized that blocking these sites would afford compounds with improved microsomal stability.

Initial efforts focused on substitution of the benzyl group at the 1-position (Table 6). The less-hindered benzylic group was expected to be more prone to oxidation relative to the 3-position (which is presumably shielded by the neighboring hydroxamic acid). Thus, introduction of the gem-dimethyl group afforded compound 17-1 which retained the potency and LipE of the parent compound (12-1) with a significant increase in stability. This trend was consistent across all analogs, including benzoxazole 18-1 and pyridines 22-2 and 22-3. The solubility and permeability of the isoindolines was also examined. Pyridines, such as 22-2 and 22-3, and related pyrimidine (22-6 and 22-7) and pyrazine (22-8) analogs were identified as suitable candidates.

Cellular activity was next measured via a bioluminescence resonance energy transfer (BRET) target engagement assay using HD AC 11 fused to Nanoluc luciferase and a proprietary compound labeled with a fluorescent tracer. In general, compounds exhibited a five- to twenty-fold shift between the biochemical and cellular assays, with many having cellular IC$_{50}$ values of less than 100 nM. Specifically, (trifluoromethyl)pyridine (22-3) and (trifluoromethyl)pyrazine (22-8) analogs, displayed IC$_{50}$ values of less than 20 nM.

Compound 22-8 was envisioned as a potentially useful tool compound based on its overall potency and in vitro ADME profile. To enable a more thorough exploration of HD AC 11 biology, a structurally matched companion inactive control analog was sought to use in tandem with 22-8. Thus, compound 50-1 was synthesized and profiled for this purpose (Example 50-1), and, as expected, replacing the hydroxamic acid necessary for zinc binding in the active site with a primary amide resulted in loss of all HDAC11 activity (Table 6). Furthermore, 22-8 was determined to be a highly-selective HD AC 11 inhibitor showing greater than 1000-fold selectivity against the other 10 members of the HD AC family (Table 5), while 50-1 was found to be inactive against all HDACs.

As set forth in Table 6 below, for $IC_{50}$: "+++" indicates an $IC_{50}$ below 0.5 μM; "++" indicates an $IC_{50}$ between 0.51 μM and 1.0 μM; and "+" indicates an $IC_{50}$ above 1 μM. For m-$CL_{int}$: "+++" indicates a m-$CL_{int}$ below 50 μL/min/mg; "++" indicates a m-$CL_{int}$ between 51 μL/min/mg and 100 μL/min/mg; and "+" indicates a m-$CL_{int}$ above 100 μL/min/mg. For solubility: "+++" indicates solubility >55 μM; "++" indicates 30 μM<solubility ≤55 μM; "+" indicates solubility ≤30 μM. For PAMPA: "+++" indicates PAMPA>10 cm/s; "++" indicates 1 cm/s<PAMPA≤10 cm/s; "+" indicates ≤1 cm/s. For $clogD_{7.4}$: "+++" indicates $clogD_{7.4}$>2.5; "++" indicates 2.0<$clogD_{7.4}$≤2.5; and "+" indicates $clogD_{7.4}$≤2.0. For LipE: "+++" indicates a LipE>6.5; "++" indicates 5.5<LipE≤6.5; "+" indicates LipE≤5.5.

TABLE 6

Optimization of N-Arylisoindolines

| | $HDAC11^a$ $IC_{50}$ (μM) | HDAC11 $BRET^b$ $IC_{50}$ (μM) | m-$CL_{int}{}^c$ (μL/min/mg) | Solubility$^d$ (μM) | $PAMPA^e$ ($10^{-6}$ cm/s) | $clogD_{7.4}{}^f$ | $LipE^g$ |
|---|---|---|---|---|---|---|---|
| 17-1 | +++ | NT | +++ | ++ | + | +++ | ++ |
| 18-1 | +++ | NT | +++ | + | ++ | +++ | ++ |
| 18-2 | +++ | +++ | +++ | +++ | + | + | +++ |
| 22-2 | +++ | +++ | +++ | + | +++ | +++ | ++ |
| 22-3 | +++ | +++ | +++ | ++ | ++ | ++ | ++ |
| 22-6 | +++ | +++ | +++ | ++ | +++ | ++ | ++ |
| 22-7 | +++ | +++ | +++ | +++ | NT | + | ++ |
| 22-8 | +++ | +++ | +++ | ++ | +++ | ++ | ++ |
| 50-1 | + | + | +++ | + | +++ | +++ | + |

$^a$Activity was measured using electrophoretic mobility shift assays with full length human recombinant HDAC proteins and fluorescently labeled peptide substrates. Reported as the mean of at least two separate assay runs. NT = not tested.
$^b$BRET Cell assay.
$^c$In vitro intrinsic clearance after incubation with mouse liver microsomes.
$^d$Kinetic solubility at pH 7.4.
$^e$Permeability measured via parallel artificial membrane permeability assay.
$^f$Calculated logD value at pH 7.4.
$^g$Lipophilic efficiency = $pIC_{50}$ HDAC11 − $clogD_{7.4}$.

As set forth in Table 7 below, for $IC_{50}$: "+++" indicates an $IC_{50}$ below 0.5 μM; "++" indicates an $IC_{50}$ between 0.51 μM and 1.0 μM; and "+" indicates an $IC_{50}$ above 1 μM.

TABLE 7

HDAC Activity Profiles of 22-8 and 50-1$^a$
HDAC $IC_{50}$ (μM)

| | 1 | 2 | 3 | 4 | 5 | 6 | 7 | 8 | 9 | 10 | 11 |
|---|---|---|---|---|---|---|---|---|---|---|---|
| 22-8 | + | + | + | + | + | + | + | + | + | + | +++ |
| 50-1 | + | + | + | + | + | + | + | + | + | + | + |

$^a$Activity was measured using electrophoretic mobility shift assays with full length human recombinant HDAC proteins and fluorescently labeled peptide substrates. Reported as the mean of at least two separate assay runs.

Example 52. Pharmacokinetic Profile of 22-8

Based on its overall in vitro profile, 22-8 was advanced to mouse PK studies to measure its suitability as an in vivo tool compound. The pharmacokinetic properties of 22-8 were assessed in male Balb/c nude mice following both intravenous (i.v.) and intraperitoneal (i.p.) dosing (Table 8). The compound displayed a moderate clearance (42 mL/min/kg) and high volume of distribution, resulting in a half-life of 9.4 h after i.v. dosing. When dosed i.p., 22-8 had a similar 0/2 (10.2 h) and improved exposure, resulting in a bioavailability of 81%. 22-8 also maintained free drug levels over the cellular $IC_{50}$ for up to 4 h after a single 5 mg/kg i.p. dose, thus providing a potentially useful tool for further understanding the biology of HDAC11 in vitro and in vivo.

TABLE 8

Pharmacokinetic Profile of 22-8$^a$

| IV Dose (mg/kg) | $t_{1/2}$ (h) | $C_0$ (μM) | $AUC_{last}$ (μM*h) | $V_{ss}$ (L/kg) | CL (mL/min/kg) |
|---|---|---|---|---|---|
| 1 | 9.4 | 3.5 | 1.0 | 18 | 42 |

TABLE 8-continued

Pharmacokinetic Profile of 22-8$^a$

| IP Dose (mg/kg) | $t_{1/2}$ (h) | $C_{max}$ (μM) | $AUC_{last}$ (μM*h) | Bioavailability (% F) |
|---|---|---|---|---|
| 5 | 10.2 | 4.2 | 3.8 | 81 |

$^a$Dosed in male Balb/c nude mice (n = 3). Dosing formulation: 5% DMA/1% Tween 80/94% sterile water

EQUIVALENTS

While the present invention has been described in conjunction with the specific embodiments set forth above, many alternatives, modifications and other variations thereof will be apparent to those of ordinary skill in the art. All such alternatives, modifications and variations are intended to fall within the spirit and scope of the present invention.

The invention claimed is:
1. A compound of Formula I:

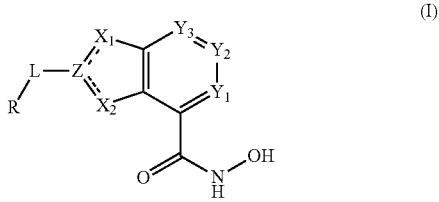

and pharmaceutically acceptable salts thereof, wherein:
i) Z is N, and $X_1$ and $X_2$ are each, independently, at each occurrence, —$CR^1R^2$—, =$CR^1$—, or —C(O)—, as valency permits, provided that only one of $X_1$ and $X_2$ is —C(O)—; or
ii) Z is C or CH, $X_1$ is $NR^3$, and $X_2$ is —$CR^1R^2$—, =$CR^1$—, or —C(O)—, as valency permits; or
iii) Z is C or CH, $X_1$ is —$CR^1R^2$—, =$CR^1$—, or —C(O)—, as valency permits, and $X_2$ is $NR^3$;
the dotted line between $Z\text{---}X_1$ and $Z\text{---}X_2$ is absent or represents a bond, provided that, at most, only one of the dotted lines represents a bond;
$Y_1$, $Y_2$, and $Y_3$ are each $CR^1$;
L is a bond, —$(CR^1R^2)_p$—, —$C(O)NR^3$—, —$NR^3C(O)$—, —$O(CR^1R^2)_pC(O)$—, —$C(O)(CR^1R^2)_pO$—, —$(CR^1R^2)_pC(O)$—, or —$C(O)(CR^1R^2)_p$—;
R is —$C_4$-$C_8$cycloalkenyl, —$C_3$-$C_8$cycloalkyl, heterocyclyl, aryl, or heteroaryl containing 1-5 heteroatoms selected from the group consisting of N, S, P, and O, wherein each cycloalkenyl, cycloalkyl, heterocyclyl, aryl, or heteroaryl is optionally substituted with one or more substituents selected from the group consisting of —OH, halogen, oxo, —$NO_2$, —CN, —$R^1$, —$R^2$, —$SR^3$, —$OR^3$, —$NHR^3$, —$NR^3R^4$, —$S(O)_2NR^3R^4$, —$S(O)_2R^1$, —$C(O)R^1$, —$C(O)OR^1$, —$NR^3S(O)_2R^1$, —$S(O)R^1$, —$S(O)NR^3R^4$, and —$NR^3S(O)R^1$;
$R^1$ and $R^2$ are independently, at each occurrence, —H, —$R^3$, —$R^4$, —$C_1$-$C_6$alkyl, —$C_2$-$C_6$alkenyl, —$C_4$-$C_8$cycloalkenyl, —$C_2$-$C_6$alkynyl, —$C_3$-$C_8$cycloalkyl, heterocyclyl, aryl, heteroaryl containing 1-5 heteroatoms selected from the group consisting of N, S, P and O, —OH, halogen, —$NO_2$, —CN, —$NHC_1$-$C_6$alkyl, —$N(C_1$-$C_6$alkyl$)_2$, —$S(O)_2N(C_1$-$C_6$alkyl$)_2$, —$N(C_1$-$C_6$alkyl)S(O)$_2R^5$, —$S(O)_2(C_1$-$C_6$alkyl), —$(C_1$-$C_6$alkyl)S(O)$_2R^5$, —$C(O)C_1$-$C_6$alkyl, —$C(O)OC_1$-$C_6$alkyl, —$N(C_1$-$C_6$alkyl)S(O)$_2C_1$-$C_6$alkyl, or —$(CHR^5)_pNR^3R^4$, wherein each alkyl, alkenyl, cycloalkenyl, alkynyl, cycloalkyl, heterocyclyl, aryl, or heteroaryl is optionally substituted with one or more substituents selected from the group consisting of —OH, halogen, —$NO_2$, oxo, —CN, —$R^5$, —$OR^3$, —$NHR^3$, —$NR^3R^4$, —$S(O)_2N(R^3)_2$—, —$S(O)_2R^5$, —$C(O)R^5$, —$C(O)OR^5$, —$NR^3S(O)_2R^5$, —$S(O)R^5$, —$S(O)NR^3R^4$, —$NR^3S(O)R^5$, heterocyclyl, aryl, and heteroaryl;
or $R^1$ and $R^2$ can combine with the carbon atom to which they are both attached to form a spirocycle, spiroheterocycle, or spirocycloalkenyl, each optionally substituted with one or more independent occurrences of $R^3$ and $R^4$;
or $R^1$ and $R^2$, when on adjacent atoms, can combine to form a cycloalkyl, a heterocycle, a heteroaryl containing 1-5 heteroatoms selected from the group consisting of N, S, P and O, or a cycloalkenyl, each optionally substituted with one or more independent occurrences of $R^3$ and $R^4$;
or $R^1$ and $R^2$, when on non-adjacent atoms, can combine to form an optionally bridging cycloalkyl, an optionally bridging heterocycle, or an optionally bridging cycloalkenyl, each optionally substituted with one or more independent occurrences of $R^3$ and $R^4$;
$R^3$ and $R^4$ are independently, at each occurrence, —H, —$C_1$-$C_6$alkyl, —$C_2$-$C_6$alkenyl, —$C_4$-$C_8$cycloalkenyl, —$C_2$-$C_6$alkynyl, —$C_3$-$C_8$cycloalkyl, heterocyclyl, aryl, heteroaryl containing 1-5 heteroatoms selected from N, S, P, and O, —$S(O)_2N(C_1$-$C_6$alkyl$)_2$, —$S(O)_2(C_1$-$C_6$alkyl), —$(C_1$-$C_6$alkyl)S(O)$_2R^5$, —$C(O)C_1$-$C_6$alkyl, —$C(O)OC_1$-$C_6$alkyl, or —$(CHR^5)_pN(C_1$-$C_6$alkyl$)_2$, wherein each alkyl, alkenyl, cycloalkenyl, alkynyl, cycloalkyl, heterocyclyl, aryl, or heteroaryl is optionally substituted with one or more substituents selected from the group consisting of —OH, halogen, —$NO_2$, oxo, —CN, —$R^5$, —$O(C_1$-$C_6)$alkyl, —NH($C_1$-$C_6$)alkyl, —$N(C_1$-$C_6$alkyl)2, —$S(O)_2N(C_1$-$C_6$alkyl$)_2$, —$S(O)_2NHC_1$-$C_6$alkyl, —$C(O)C_1$-$C_6$alkyl, —$C(O)OC_1$-$C_6$alkyl, —$N(C_1$-$C_6$alkyl)S(O)$_2C_1$-$C_6$alkyl, —$S(O)R^5$, —$S(O)N(C_1$-$C_6$alkyl$)_2$, —$N(C_1$-$C_6$alkyl)S(O)$R^5$, heterocyclyl, aryl, and heteroaryl;

$R^5$ is independently, at each occurrence, —H, —$C_1$-$C_6$alkyl, —$C_2$-$C_6$alkenyl, —$C_4$-$C_8$cycloalkenyl, —$C_2$-$C_6$alkynyl, —$C_3$-$C_8$cycloalkyl, heterocyclyl, aryl, heteroaryl containing 1-5 heteroatoms selected from N, S, P and O, —OH, halogen, —$NO_2$, —CN, —$NHC_1$-$C_6$alkyl, —$N(C_1$-$C_6$alkyl$)_2$, —$S(O)_2NH(C_1$-$C_6$alkyl), —$S(O)_2N(C_1$-$C_6$alkyl$)_2$, —$S(O)_2C_1$-$C_6$alkyl, —$C(O)C_1$-$C_6$alkyl, —$C(O)OC_1$-$C_6$alkyl, —$N(C_1$-$C_6$alkyl)SO$_2$ $C_1$-$C_6$alkyl, —$S(O)(C_1$-$C_6$alkyl), —$S(O)N(C_1$-$C_6$alkyl$)_2$, —$N(C_1$-$C_6$alkyl)S(O)($C_1$-$C_6$alkyl) or —$(CH_2)_pN(C_1$-$C_6$alkyl$)_2$; and p is 0, 1, 2, 3, 4, 5, or 6;

provided that when $X_2$ is —C(O)—, $X_1$ is $CH_2$, $Y_1$, $Y_2$ and $Y_3$ are each CH, and L is a bond, then R is a group other than substituted or unsubstituted phenyl; and provided that the compound is not:

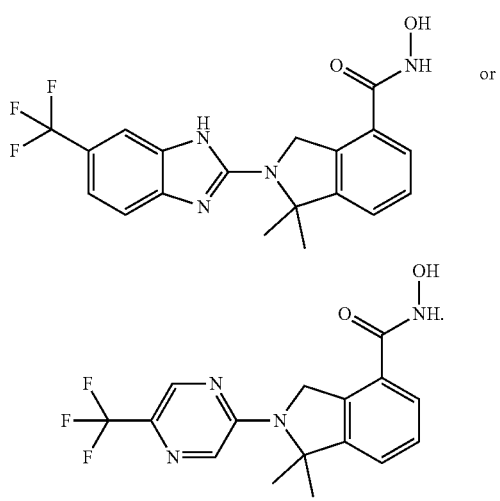

2. The compound of claim 1, wherein the compound is selected from one of:

I-A

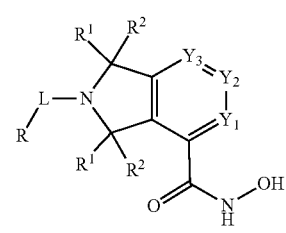

-continued

I-B
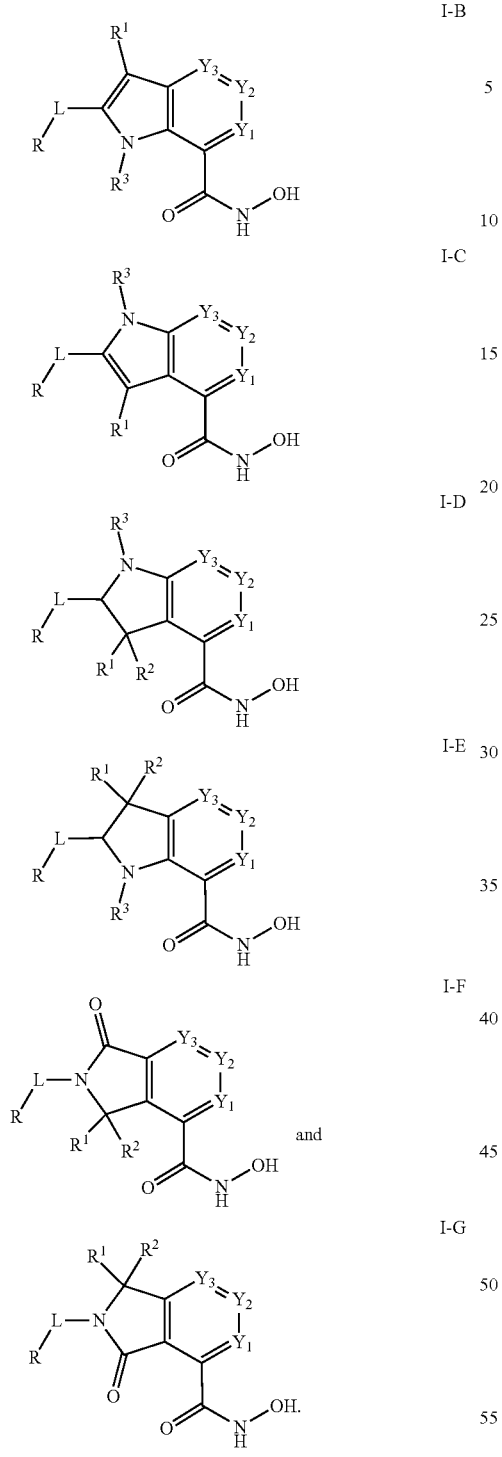

I-C

I-D

I-E

I-F
and

I-G

3. The compound of claim 1, wherein L is a bond.
4. The compound of claim 1, wherein L is —C(O)—.
5. The compound of claim 1, wherein L is —(CR$^1$R$^2$)$_p$—, —C(O)NR$^3$—, —NR$^3$C(O)—, —C(O)(CR$^1$R$^2$)$_p$O—, or —(CR$^1$R$^2$)$_p$C(O)—, wherein p is 1 or 2.
6. The compound of claim 1, wherein the compound has Formula II-A-i, II-A-ii, II-B-i, II-B-ii, II-C-i, II-C-ii, II-D-i, II-D-ii, II-E-i, II-E-ii, II-F-i, or II-F-ii:

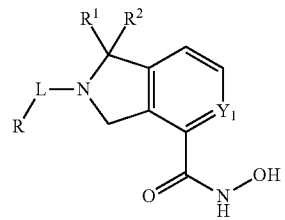
(II-A-i)

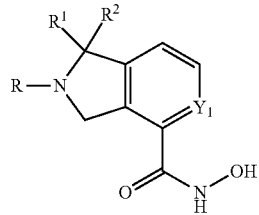
(II-A-ii)

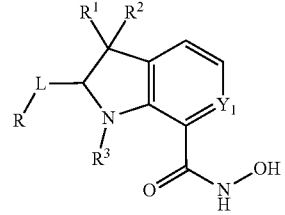
(II-B-i)

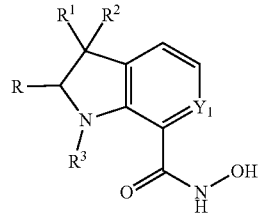
(II-B-ii)

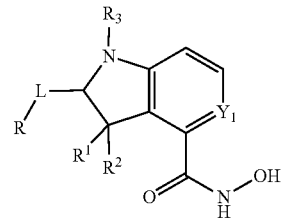
(II-C-i)

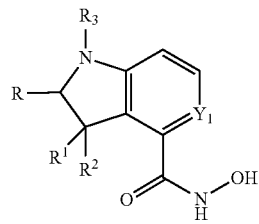
(II-C-ii)

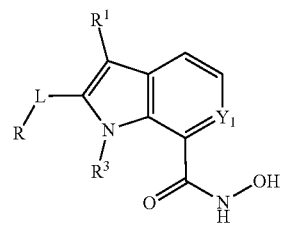
(II-D-i)

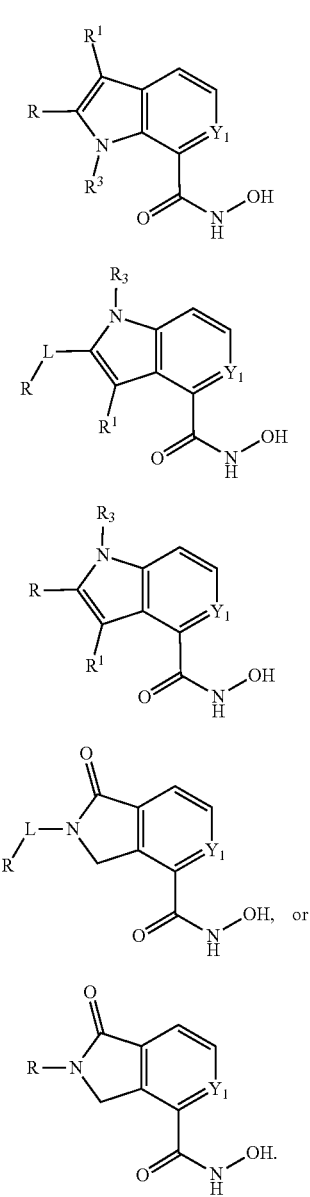

P, or O, wherein the aryl is optionally substituted with one or more —OH, halogen, oxo, —NO₂, —CN, —R¹, —R², —SR³, —OR³, —NHR³, —NR³R⁴, —S(O)₂NR³R⁴, —S(O)₂R¹, —C(O)R¹, —C(O)OR¹, —NR³S(O)₂R¹, —S(O)R¹, —S(O)NR³R⁴, —NR³S(O)R¹, heterocyclyl, aryl, or heteroaryl.

10. The compound of claim 1, wherein R is phenyl containing 1-5 heteroatoms selected from the group consisting of N, S, P, or O, wherein the phenyl is optionally substituted with one or more —OH, halogen, oxo, —NO₂, —CN, —R¹, —R², —SR³, —OR³, —NHR³, —NR³R⁴, —S(O)₂NR³R⁴, —S(O)₂R¹, —C(O)R¹, —C(O)OR¹, —NR³S(O)₂R¹, —S(O)R¹, —S(O)NR³R⁴, —NR³S(O)R¹, heterocyclyl, aryl, or heteroaryl.

11. The compound of claim 1, wherein R is a group selected from:

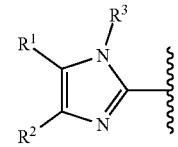

i

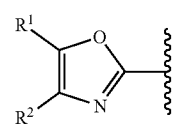

ii

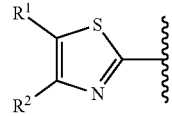

iii

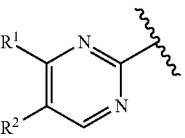

iv

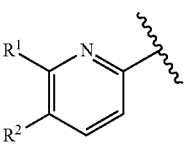

v

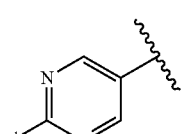

vi

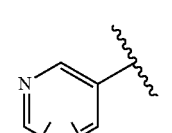

vii

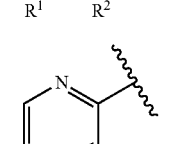

viii and

7. The compound of claim 1, wherein R is heterocyclyl, aryl, or heteroaryl containing 1-5 heteroatoms selected from the group consisting of N, S, P, or O, wherein each heterocyclyl, aryl, or heteroaryl is optionally substituted with one or more —OH, halogen, oxo, —NO₂, —CN, —R¹, —R², —SR³, —OR³, —NHR³, —NR³R⁴, —S(O)₂NR³R⁴, —S(O)₂R¹, —C(O)R¹, —C(O)OR¹, —NR³S(O)₂R¹, —S(O)R¹, —S(O)NR³R⁴, —NR³S(O)R¹, heterocyclyl, aryl, or heteroaryl.

8. The compound of claim 1, wherein R is heteroaryl containing 1-5 heteroatoms selected from the group consisting of N, S, P, or O, wherein the heteroaryl is optionally substituted with one or more —OH, halogen, oxo, —NO₂, —CN, —R¹, —R², —SR³, —OR³, —NHR³, —NR³R⁴, —S(O)₂NR³R⁴, —S(O)₂R¹, —C(O)R¹, —C(O)OR¹, —NR³S(O)₂R¹, —S(O)R¹, —S(O)NR³R⁴, —NR³S(O)R¹, heterocyclyl, aryl, or heteroaryl.

9. The compound of claim 1, wherein R is aryl containing 1-5 heteroatoms selected from the group consisting of N, S, -continued

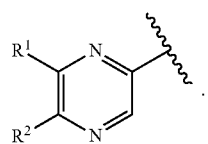

ix

12. The compound of claim 1, wherein:
i) Z is N, and $X_1$ and $X_2$ are each, independently, at each occurrence, —$CR^1R^2$—, =$CR^1$—, or —C(O)—, as valency permits, provided that only one of $X_1$ and $X_2$ is —C(O)—; or
ii) Z is C or CH, $X_1$ is $NR^3$, and $X_2$ is —$CR^1R^2$—, =$CR^1$—, or —C(O)—, as valency permits; or
iii) Z is C or CH, $X_1$ is —$CR^1R^2$—, =$CR^1$—, or —C(O)—, as valency permits, and $X_2$ is $NR^3$;
the dotted line between Z---$X_1$ and Z---$X_2$ is absent or represents a bond, provided that, at most, only one of the dotted lines represents a bond;
$Y_1$, $Y_2$, and $Y_3$ are each $CR^1$;
L is a bond, —$(CR^1R^2)_p$—, —C(O)$NR^3$—, —$NR^3$C(O)—, —$(CR^1R^2)_pC(O)$—, or —C(O)$(CR^1R^2)_p$—;
R is —$C_3$-$C_8$cycloalkyl, heterocyclyl, aryl, or heteroaryl containing 1-5 heteroatoms selected from the group consisting of N, S, P, and O, wherein each cycloalkyl, heterocyclyl, aryl, or heteroaryl is optionally substituted with one or more substituents selected from the group consisting of —OH, —$R^1$, —$R^2$, and —$OR^3$ $R^1$ and $R^2$ are independently, at each occurrence, —H, —$C_1$-$C_6$alkyl, or aryl, wherein each alkyl or aryl is optionally substituted with one or more substituents selected from the group consisting of halogen and —$OR^3$;
or $R^1$ and $R^2$, when on adjacent atoms, can combine to form a cycloalkyl or a heterocycle, each optionally substituted with one or more independent occurrences of $R^3$ and $R^4$;
$R^3$ and $R^4$ are independently, at each occurrence, —H, —$C_1$-$C_6$alkyl, or —C(O)$C_1$-$C_6$alkyl, wherein each alkyl is optionally substituted with one or more halogen; and
p is 0 or 1.

13. The compound of claim 1, wherein:
Z is N;
$X_1$ and $X_2$ are each —$CR^1R^2$—;
the dotted line between Z---$X_1$ and Z---$X_2$ is absent;
$Y_1$, $Y_2$, and $Y_3$ are each $CR^1$;
L is a bond;
R is a 5- to 10-membered heteroaryl containing 1-5 heteroatoms selected from the group consisting of N, S, P, and O, wherein heteroaryl is optionally substituted with one or more —$R^1$ and —$R^2$;
$R^1$ and $R^2$ are independently, at each occurrence, —H or —$C_1$-$C_6$alkyl, wherein each alkyl is optionally substituted with one or more halogen;
or $R^1$ and $R^2$, when on adjacent atoms, can combine to form a cycloalkyl.

14. The compound of claim 1 having the structure:

| Example | Structure | Name |
|---------|-----------|------|
| 1-1 | 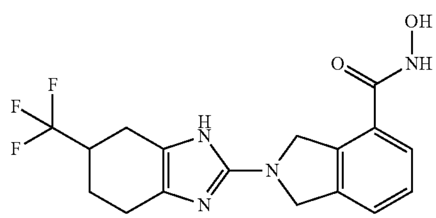 [SMILES: O=C(NO)c1cccc2c1CN(c1nc3c([nH]1)CC(C(F)(F)F)CC3)C2] | N-hydroxy-2-(6-(trifluoromethyl)-4,5,6,7-tetrahydro-1H-benzo[d]imidazol-2-yl)isoindoline-4-carboxamide |
| 1-2 | 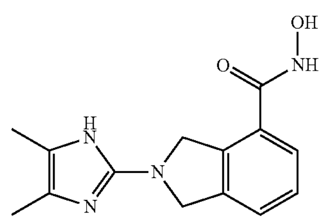 [SMILES: Cc1nc(N2Cc3cccc(C(=O)NO)c3C2)[nH]c1C] | 2-(4,5-dimethyl-1H-imidazol-2-yl)-N-hydroxyisoindoline-4-carboxamide |
| 1-3 | 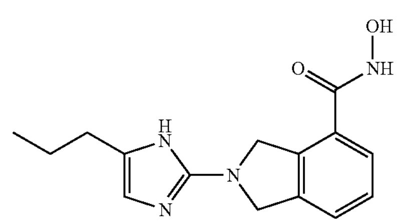 [SMILES: CCCc1cnc(N2Cc3cccc(C(=O)NO)c3C2)[nH]1] | N-hydroxy-2-(5-propyl-1H-imidazol-2-yl)isoindoline-4-carboxamide |

| Example | Structure | Name |
|---------|-----------|------|
| 1-4 | 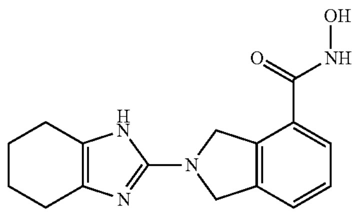 [SMILES: O=C(NO)c1cccc2c1CN(c1nc3c([nH]1)CCCC3)C2] | N-hydroxy-2-(4,5,6,7-tetrahydro-1H-benzo[d]imidazol-2-yl)isoindoline-4-carboxamide |
| 1-5 | 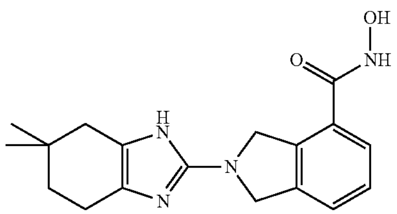 [SMILES: CC1(C)CCc2nc(N3Cc4cccc(C(=O)NO)c4C3)[nH]c2C1] | 2-(6,6-dimethyl-4,5,6,7-tetrahydro-1H-benzo[d]imidazol-2-yl)-N-hydroxyisoindoline-4-carboxamide |
| 1-6 | 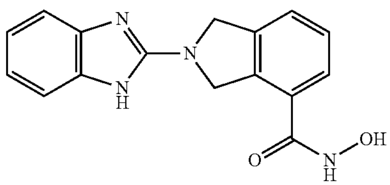 [SMILES: O=C(NO)c1cccc2c1CN(c1nc3ccccc3[nH]1)C2] | 2-(1H-benzo[d]imidazol-2-yl)-N-hydroxyisoindoline-4-carboxamide |
| 2-1 | 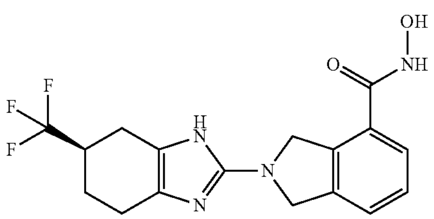 [SMILES: O=C(NO)c1cccc2c1CN(c1nc3c([nH]1)C[C@H](C(F)(F)F)CC3)C2] | (R)-N-hydroxy-2-(6-(trifluoromethyl)-4,5,6,7-tetrahydro-1H-benzo[d]imidazol-2-yl)isoindoline-4-carboxamide |
| 2-2 | 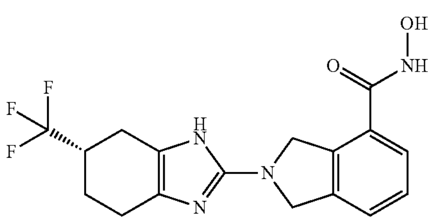 [SMILES: O=C(NO)c1cccc2c1CN(c1nc3c([nH]1)C[C@@H](C(F)(F)F)CC3)C2] | (S)-N-hydroxy-2-(6-(trifluoromethyl)-4,5,6,7-tetrahydro-1H-benzo[d]imidazol-2-yl)isoindoline-4-carboxamide |
| 3-1 | 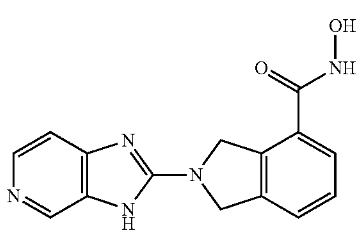 [SMILES: O=C(NO)c1cccc2c1CN(c1nc3ccncc3[nH]1)C2] | N-hydroxy-2-(3H-imidazo[4,5-c]pyridin-2-yl)isoindoline-4-carboxamide |
| 4-1 | 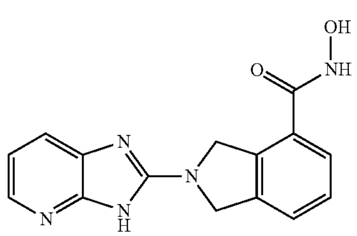 [SMILES: O=C(NO)c1cccc2c1CN(c1nc3cccnc3[nH]1)C2] | N-hydroxy-2-(3H-imidazo[4,5-b]pyridin-2-yl)isoindoline-4-carboxamide |

-continued
| Example | Structure | Name |
|---|---|---|
| 5-1 | 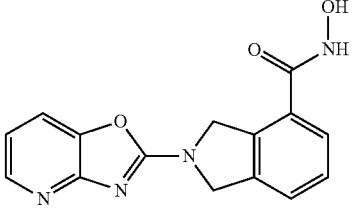 [SMILES: O=C(NO)c1cccc2c1CN(c1nc3ncccc3o1)C2] | N-hydroxy-2-(oxazolo[4,5-b]pyridin-2-yl)isoindoline-4-carboxamide |
| 5-2 | 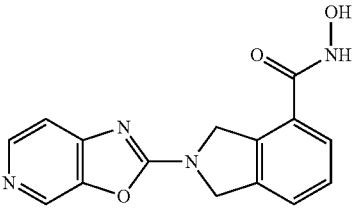 [SMILES: O=C(NO)c1cccc2c1CN(c1nc3ccncc3o1)C2] | N-hydroxy-2-(oxazolo[5,4-c]pyridin-2-yl)isoindoline-4-carboxamide |
| 6-1 | 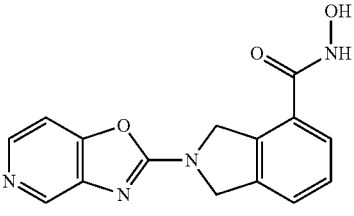 [SMILES: O=C(NO)c1cccc2c1CN(c1nc3cnccc3o1)C2] | N-hydroxy-2-(oxazolo[4,5-c]pyridin-2-yl)isoindoline-4-carboxamide |
| 6-2 | 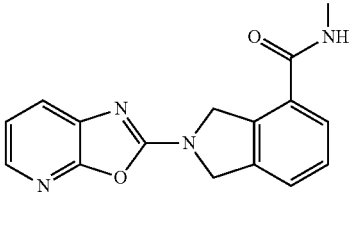 | N-hydroxy-2-(oxazolo[5,4-b]pyridin-2-yl)isoindoline-4-carboxamide |
| 7-1 | 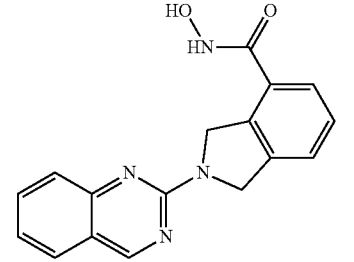 [SMILES: O=C(NO)c1cccc2c1CN(c1ncc3ccccc3n1)C2] | N-hydroxy-2-(quinazolin-2-yl)isoindoline-4-carboxamide |
| 7-2 | 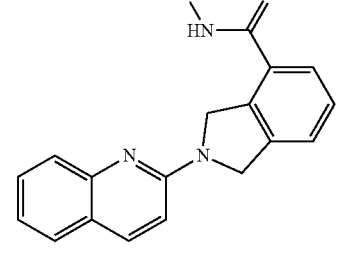 | N-hydroxy-2-(quinolin-2-yl)isoindoline-4-carboxamide |

-continued

| Example | Structure | Name |
|---|---|---|
| 7-3 | 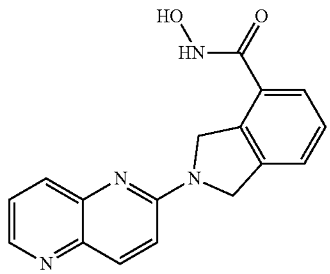 [SMILES: O=C(NO)c1cccc2c1CN(c1ccc3ncccc3n1)C2] | N-hydroxy-2-(1,5-naphthyridin-2-yl)isoindoline-4-carboxamide |
| 7-4 | 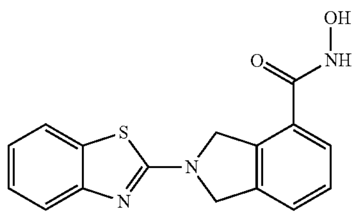 | 2-(benzo[d]thiazol-2-yl)-N-hydroxyisoindoline-4-carboxamide |
| 7-5 | 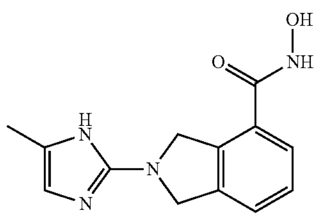 [SMILES: Cc1cnc(N2Cc3cccc(C(=O)NO)c3C2)[nH]1] | N-hydroxy-2-(5-methyl-1H-imidazol-2-yl)isoindoline-4-carboxamide |
| 8-1 | 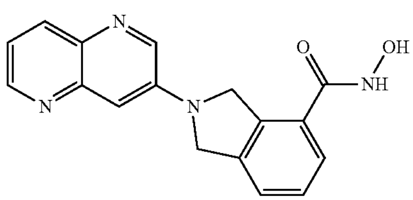 [SMILES: O=C(NO)c1cccc2c1CN(c1cnc3cccnc3c1)C2] | N-hydroxy-2-(1,5-naphthyridin-3-yl)isoindoline-4-carboxamide |
| 9-1 | 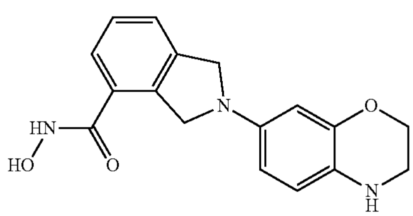 [SMILES: O=C(NO)c1cccc2c1CN(c1ccc3c(c1)OCCN3)C2] | 2-(3,4-dihydro-2H-benzo[b][1,4]oxazin-7-yl)-N-hydroxyisoindoline-4-carboxamide |
| 9-2 | 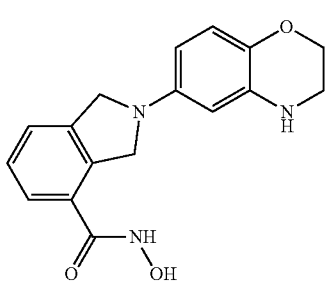 [SMILES: O=C(NO)c1cccc2c1CN(c1ccc3c(c1)NCCO3)C2] | 2-(3,4-dihydro-2H-benzo[b][1,4]oxazin-6-yl)-N-hydroxyisoindoline-4-carboxamide |

-continued

| Example | Structure | Name |
|---------|-----------|------|
| 10-1 | 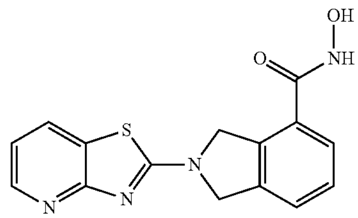 | N-hydroxy-2-(thiazolo[4,5-b]pyridin-2-yl)isoindoline-4-carboxamide |
| 11-1 | 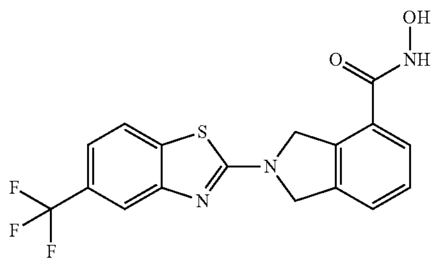 [SMILES: O=C(NO)c1cccc2c1CN(c1nc3cc(C(F)(F)F)ccc3s1)C2] | N-hydroxy-2-(5-(trifluoromethyl)benzo[d]thiazol-2-yl)isoindoline-4-carboxamide |
| 12-1 | 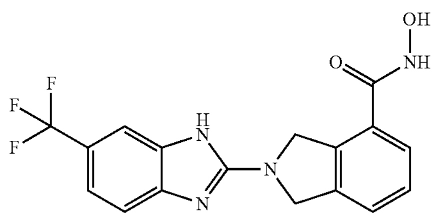 [SMILES: O=C(NO)c1cccc2c1CN(c1nc3ccc(C(F)(F)F)cc3[nH]1)C2] | N-hydroxy-2-(6-(trifluoromethyl)-1H-benzo[d]imidazol-2-yl)isoindoline-4-carboxamide |
| 13-1 | 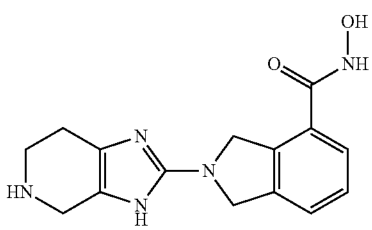 [SMILES: O=C(NO)c1cccc2c1CN(c1nc3c([nH]1)CNCC3)C2] | N-hydroxy-2-(4,5,6,7-tetrahydro-3H-imidazo[4,5-c]pyridin-2-yl)isoindoline-4-carboxamide |
| 14-1 | 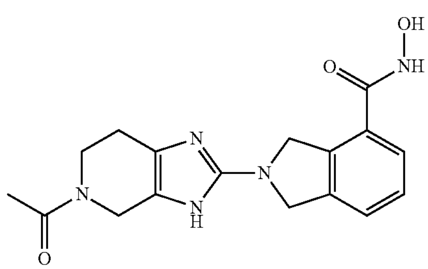 [SMILES: CC(=O)N1CCc2nc(N3Cc4cccc(C(=O)NO)c4C3)[nH]c2C1] | 2-(5-acetyl-4,5,6,7-tetrahydro-3H-imidazo[4,5-c]pyridin-2-yl)-N-hydroxyisoindoline-4-carboxamide |
| 15-1 | 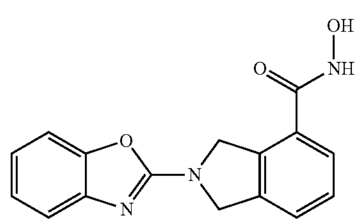 | 2-(benzo[d]oxazol-2-yl)-N-hydroxyisoindoline-4-carboxamide |

-continued

| Example | Structure | Name |
|---|---|---|
| 16-1 | 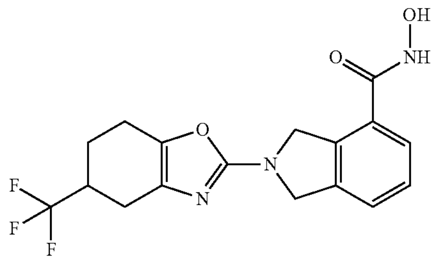 [SMILES: O=C(NO)c1cccc2c1CN(c1nc3c(o1)CCC(C(F)(F)F)C3)C2] | N-hydroxy-2-(5-(trifluoromethyl)-4,5,6,7-tetrahydrobenzo[d]oxazol-2-yl)isoindoline-4-carboxamide |
| 18-1 | 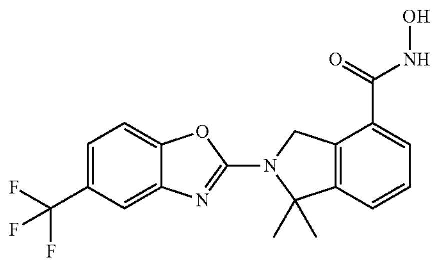 [SMILES: CC1(C)c2cccc(C(=O)NO)c2CN1c1nc2cc(C(F)(F)F)ccc2o1] | N-hydroxy-1,1-dimethyl-2-(5-(trifluoromethyl)benzo[d]oxazol-2-yl)isoindoline-4-carboxamide |
| 18-2 | 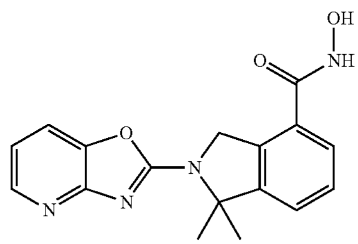 [SMILES: CC1(C)c2cccc(C(=O)NO)c2CN1c1nc2ncccc2o1] | N-hydroxy-1,1-dimethyl-2-(oxazolo[4,5-b]pyridin-2-yl)isoindoline-4-carboxamide |
| 18-3 | 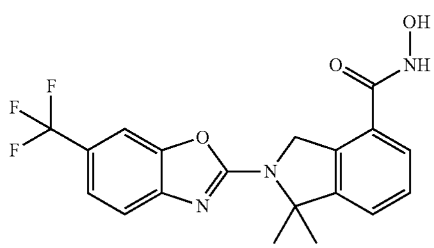 | N-hydroxy-1,1-dimethyl-2-(6-(trifluoromethyl)benzo[d]oxazol-2-yl)isoindoline-4-carboxamide |
| 19-1 | 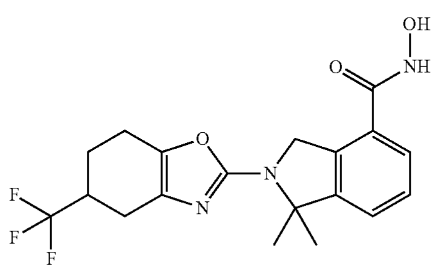 [SMILES: CC1(C)c2cccc(C(=O)NO)c2CN1c1nc2c(o1)CCC(C(F)(F)F)C2] | N-hydroxy-1,1-dimethyl-2-(5-(trifluoromethyl)-4,5,6,7-tetrahydrobenzo[d]oxazol-2-yl)isoindoline-4-carboxamide |
| 19-2 | 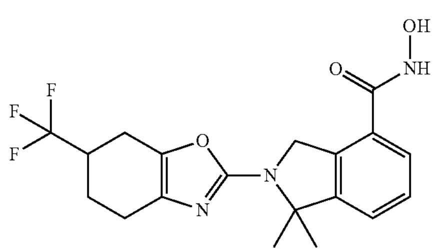 [SMILES: CC1(C)c2cccc(C(=O)NO)c2CN1c1nc2c(o1)CC(C(F)(F)F)CC2] | N-hydroxy-1,1-dimethyl-2-(6-(trifluoromethyl)-4,5,6,7-tetrahydrobenzo[d]oxazol-2-yl)isoindoline-4-carboxamide |

-continued

| Example | Structure | Name |
|---|---|---|
| 20-1 | 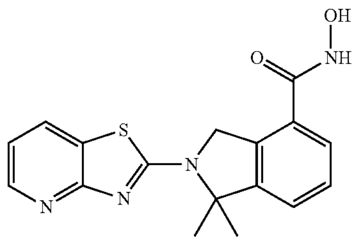 | N-hydroxy-1,1-dimethyl-2-(thiazolo[4,5-b]pyridin-2-yl)isoindoline-4-carboxamide |
| 20-2 | 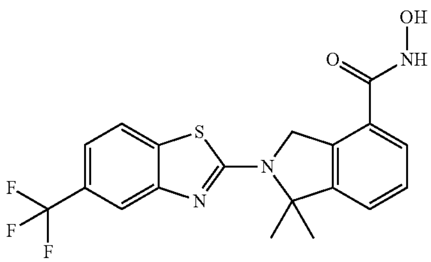 | N-hydroxy-1,1-dimethyl-2-(5-(trifluoromethyl)benzo[d]thiazol-2-yl)isoindoline-4-carboxamide |
| 21-1 | 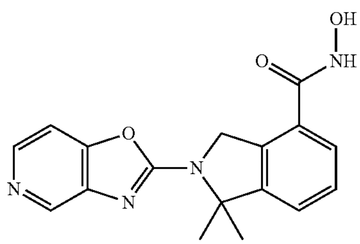 [SMILES: CC1(C)c2cccc(C(=O)NO)c2CN1c1nc2cnccc2o1] | N-hydroxy-1,1-dimethyl-2-(oxazolo[4,5-c]pyridin-2-yl)isoindoline-4-carboxamide |
| 22-1 | 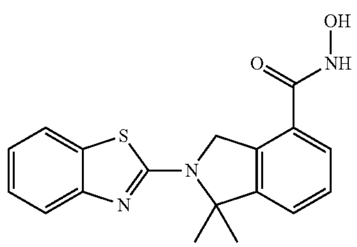 | 2-(benzo[d]thiazol-2-yl)-N-hydroxy-1,1-dimethylisoindoline-4-carboxamide |
| 22-2 | 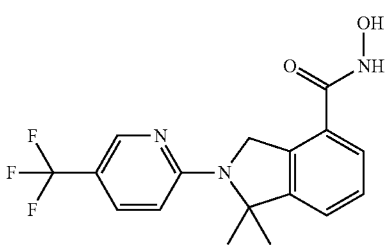 [SMILES: CC1(C)c2cccc(C(=O)NO)c2CN1c1ccc(C(F)(F)F)cn1] | N-hydroxy-1,1-dimethyl-2-(5-(trifluoromethyl)pyridin-2-yl)isoindoline-4-carboxamide |
| 22-3 | 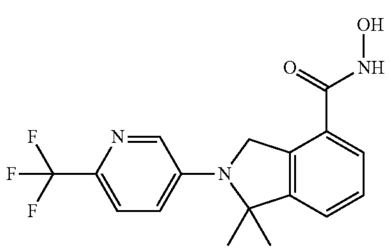 [SMILES: CC1(C)c2cccc(C(=O)NO)c2CN1c1ccc(C(F)(F)F)nc1] | N-hydroxy-1,1-dimethyl-2-(6-(trifluoromethyl)pyridin-3-yl)isoindoline-4-carboxamide |

-continued

| Example | Structure | Name |
|---|---|---|
| 22-4 | 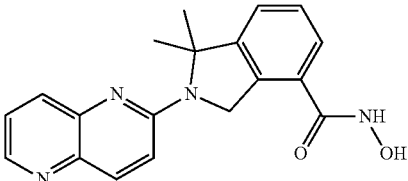 | N-hydroxy-1,1-dimethyl-2-(1,5-naphthyridin-2-yl)isoindoline-4-carboxamide |
| 22-5 | 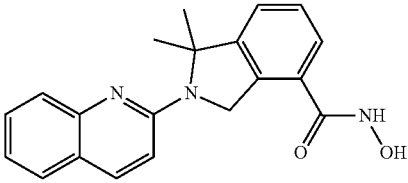 [SMILES: CC1(C)c2cccc(C(=O)NO)c2CN1c1ccc2ccccc2n1] | N-hydroxy-1,1-dimethyl-2-(quinolin-2-yl)isoindoline-4-carboxamide |
| 22-6 | 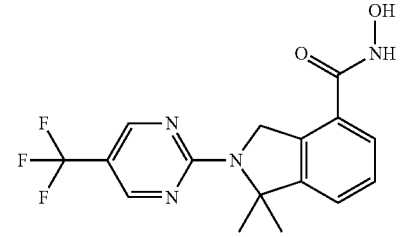 | N-hydroxy-1,1-dimethyl-2-(5-(trifluoromethyl)pyrimidin-2-yl)isoindoline-4-carboxamide |
| 22-7 | 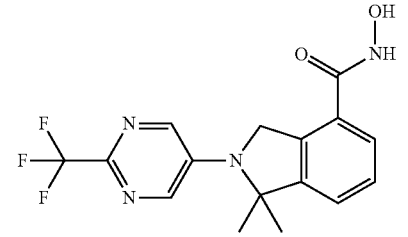 | N-hydroxy-1,1-dimethyl-2-(2-(trifluoromethyl)pyrimidin-5-yl)isoindoline-4-carboxamide |
| 22-9 | 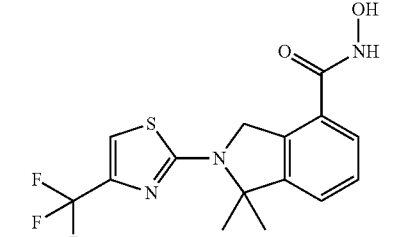 | N-hydroxy-1,1-dimethyl-2-(4-(trifluoromethyl)thiazol-2-yl)isoindoline-4-carboxamide |
| 23-1 | 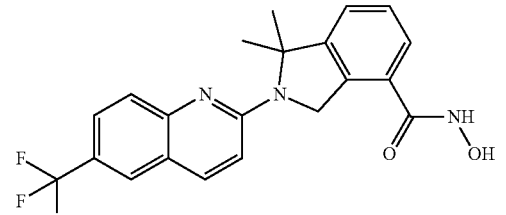 | N-hydroxy-1,1-dimethyl-2-(6-(trifluoromethyl)quinolin-2-yl)isoindoline-4-carboxamide |
| 23-2 | 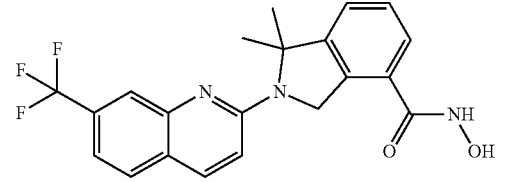 [SMILES: CC1(C)c2cccc(C(=O)NO)c2CN1c1ccc2ccc(C(F)(F)F)cc2n1] | N-hydroxy-1,1-dimethyl-2-(7-(trifluoromethyl)quinolin-2-yl)isoindoline-4-carboxamide |

-continued

| Example | Structure | Name |
|---|---|---|
| 24-1 | 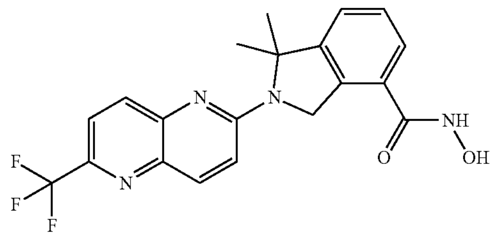 [SMILES: CC1(C)c2cccc(C(=O)NO)c2CN1c1ccc2nc(C(F)(F)F)ccc2n1] | N-hydroxy-1,1-dimethyl-2-(6-(trifluoromethyl)-1,5-naphthyridin-2-yl)isoindoline-4-carboxamide |
| 25-1 | 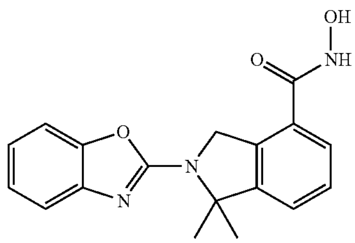 [SMILES: CC1(C)c2cccc(C(=O)NO)c2CN1c1nc2ccccc2o1] | 2-(benzo[d]oxazol-2-yl)-N-hydroxy-1,1-dimethylisoindoline-4-carboxamide |
| 26-1 | 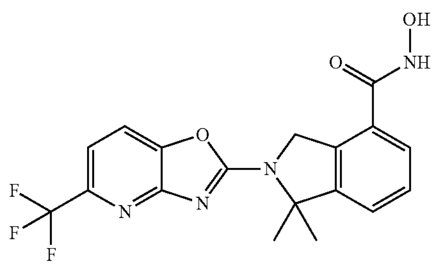 [SMILES: CC1(C)c2cccc(C(=O)NO)c2CN1c1nc2nc(C(F)(F)F)ccc2o1] | N-hydroxy-1,1-dimethyl-2-(5-(trifluoromethyl)oxazolo[4,5-b]pyridin-2-yl)isoindoline-4-carboxamide |
| 26-2 | 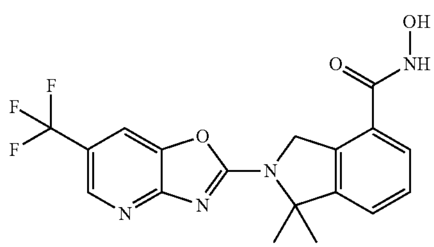 [SMILES: CC1(C)c2cccc(C(=O)NO)c2CN1c1nc2ncc(C(F)(F)F)cc2o1] | N-hydroxy-1,1-dimethyl-2-(6-(trifluoromethyl)oxazolo[4,5-b]pyridin-2-yl)isoindoline-4-carboxamide |
| 27-1 | 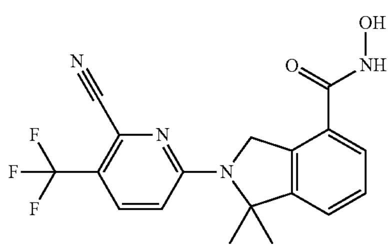 [SMILES: CC1(C)c2cccc(C(=O)NO)c2CN1c1ccc(C(F)(F)F)c(C#N)n1] | 2-(6-cyano-5-(trifluoromethyl)pyridin-2-yl)-N-hydroxy-1,1-dimethylisoindoline-4-carboxamide |
| 27-2 | 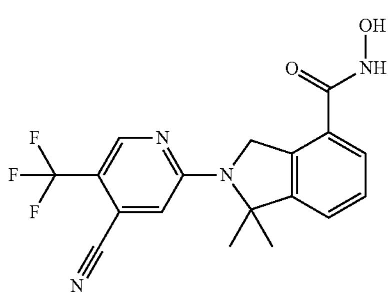 [SMILES: CC1(C)c2cccc(C(=O)NO)c2CN1c1cc(C#N)c(C(F)(F)F)cn1] | 2-(4-cyano-5-(trifluoromethyl)pyridin-2-yl)-N-hydroxy-1,1-dimethylisoindoline-4-carboxamide |

-continued

| Example | Structure | Name |
|---|---|---|
| 28-1 | 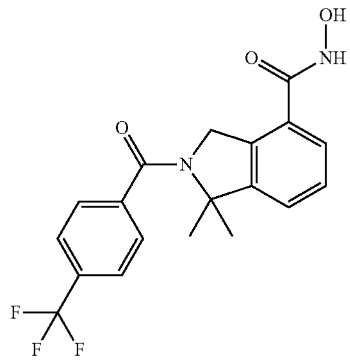 [SMILES: CC1(C)c2cccc(C(=O)NO)c2CN1C(=O)c1ccc(C(F)(F)F)cc1] | N-hydroxy-1,1-dimethyl-2-(4-(trifluoromethyl)benzoyl)isoindoline-4-carboxamide |
| 28-2 | 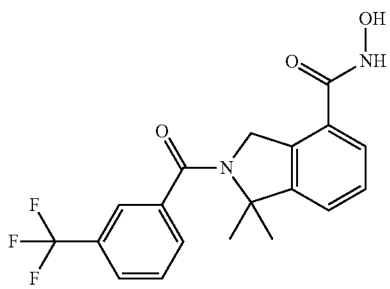 [SMILES: CC1(C)c2cccc(C(=O)NO)c2CN1C(=O)c1cccc(C(F)(F)F)c1] | N-hydroxy-1,1-dimethyl-2-(3-(trifluoromethyl)benzoyl)isoindoline-4-carboxamide |
| 29-1 | 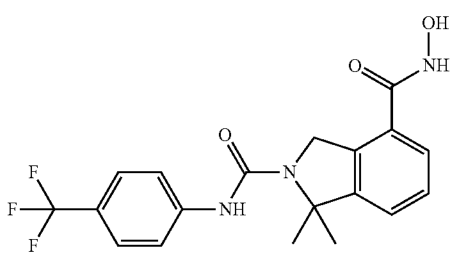 [SMILES: CC1(C)c2cccc(C(=O)NO)c2CN1C(=O)Nc1ccc(C(F)(F)F)cc1] | N4-hydroxy-1,1-dimethyl-N2-(4-(trifluoromethyl)phenyl)isoindoline-2,4-dicarboxamide |
| 30-1 | 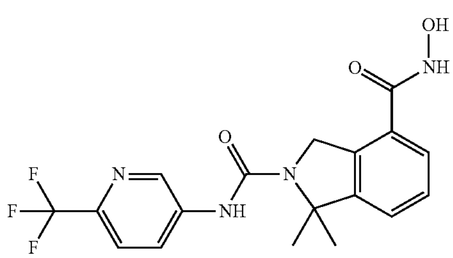 [SMILES: CC1(C)c2cccc(C(=O)NO)c2CN1C(=O)Nc1ccc(C(F)(F)F)nc1] | N4-hydroxy-1,1-dimethyl-N2-(6-(trifluoromethyl)pyridin-3-yl)isoindoline-2,4-dicarboxamide |
| 30-2 | 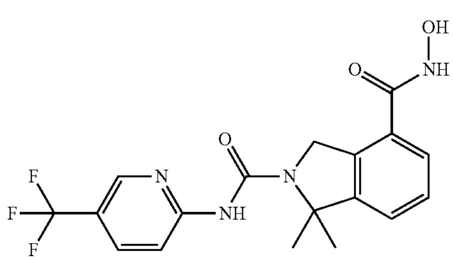 [SMILES: CC1(C)c2cccc(C(=O)NO)c2CN1C(=O)Nc1ccc(C(F)(F)F)cn1] | N4-hydroxy-1,1-dimethyl-N2-(5-(trifluoromethyl)pyridin-2-yl)isoindoline-2,4-dicarboxamide |

-continued

| Example | Structure | Name |
|---|---|---|
| 30-3 | 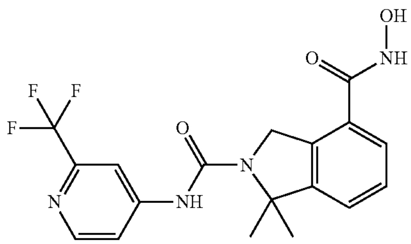 [SMILES: CC1(C)c2cccc(C(=O)NO)c2CN1C(=O)Nc1ccnc(C(F)(F)F)c1] | N4-hydroxy-1,1-dimethyl-N2-(2-(trifluoromethyl)pyridin-4-yl)isoindoline-2,4-dicarboxamide |
| 30-4 | 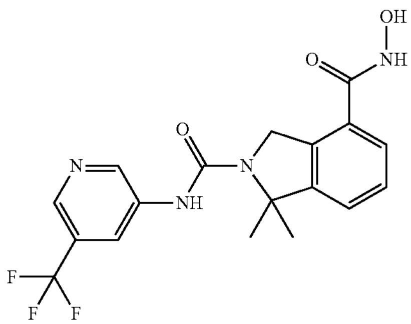 [SMILES: CC1(C)c2cccc(C(=O)NO)c2CN1C(=O)Nc1cncc(C(F)(F)F)c1] | N4-hydroxy-1,1-dimethyl-N2-(5-(trifluoromethyl)pyridin-3-yl)isoindoline-2,4-dicarboxamide |
| 30-5 | 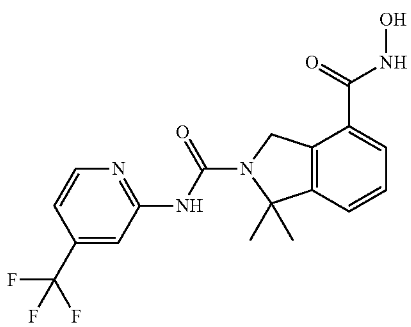 [SMILES: CC1(C)c2cccc(C(=O)NO)c2CN1C(=O)Nc1cc(C(F)(F)F)ccn1] | N4-hydroxy-1,1-dimethyl-N2-(4-(trifluoromethyl)pyridin-2-yl)isoindoline-2,4-dicarboxamide |
| 30-6 | 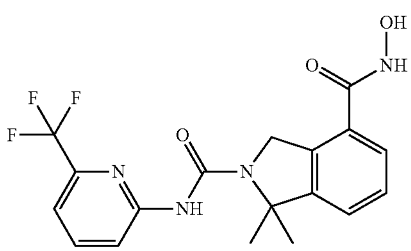 [SMILES: CC1(C)c2cccc(C(=O)NO)c2CN1C(=O)Nc1cccc(C(F)(F)F)n1] | N4-hydroxy-1,1-dimethyl-N2-(6-(trifluoromethyl)pyridin-2-yl)isoindoline-2,4-dicarboxamide |
| 30-7 | 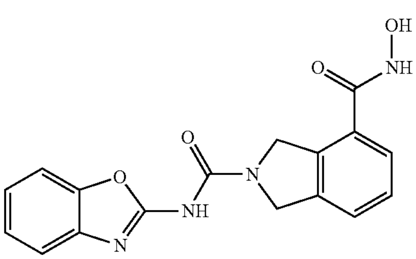 [SMILES: O=C(NO)c1cccc2c1CN(C(=O)Nc1nc3ccccc3o1)C2] | N2-(benzo[d]oxazol-2-yl)-N4-hydroxy-1,1-dimethylisoindoline-2,4-dicarboxamide |
| 31-1 | 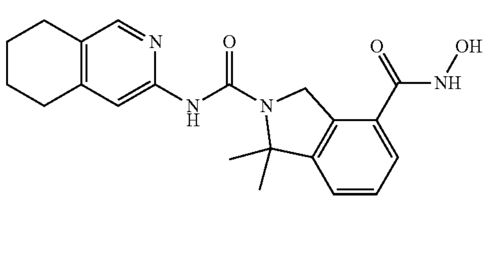 [SMILES: CC1(C)c2cccc(C(=O)NO)c2CN1C(=O)Nc1cc2c(cn1)CCCC2] | N4-hydroxy-1,1-dimethyl-N2-(5,6,7,8-tetrahydroisoquinolin-3-yl)isoindoline-2,4-dicarboxamide |

-continued

| Example | Structure | Name |
|---|---|---|
| 32-1 | 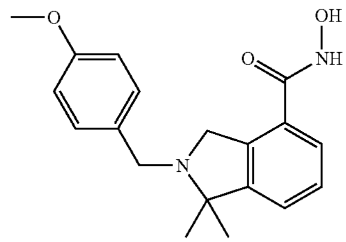 [SMILES: COc1ccc(CN2Cc3c(C(=O)NO)cccc3C2(C)C)cc1] | N-hydroxy-2-(4-methoxybenzyl)-1,1-dimethylisoindoline-4-carboxamide |
| 34-1 | 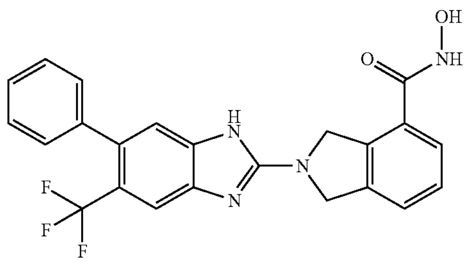 [SMILES: O=C(NO)c1cccc2c1CN(c1nc3cc(C(F)(F)F)c(-c4ccccc4)cc3[nH]1)C2] | N-hydroxy-2-(6-phenyl-5-(trifluoromethyl)-1H-benzo[d]imidazol-2-yl)isoindoline-4-carboxamide |
| 35-1 | 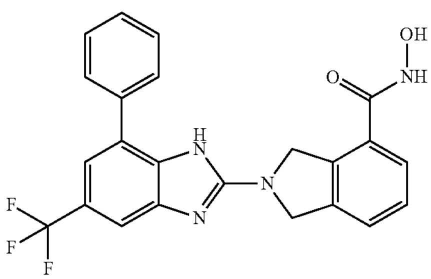 [SMILES: O=C(NO)c1cccc2c1CN(c1nc3cc(C(F)(F)F)cc(-c4ccccc4)c3[nH]1)C2] | N-hydroxy-2-(7-phenyl-5-(trifluoromethyl)-1H-benzo[d]imidazol-2-yl)isoindoline-4-carboxamide |
| 35-2 | 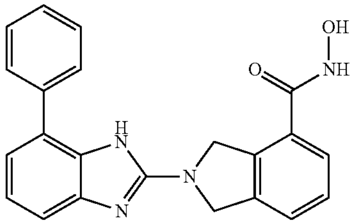 [SMILES: O=C(NO)c1cccc2c1CN(c1nc3cccc(-c4ccccc4)c3[nH]1)C2] | N-hydroxy-2-(7-phenyl-1H-benzo[d]imidazol-2-yl)isoindoline-4-carboxamide |
| 36-1 | 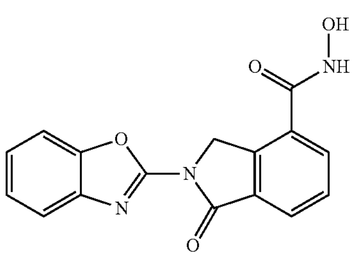 [SMILES: O=C(NO)c1cccc2c1CN(c1nc3ccccc3o1)C2=O] | 2-(benzo[d]oxazol-2-yl)-N-hydroxy-1-oxoisoindoline-4-carboxamide |
| 37-1 | 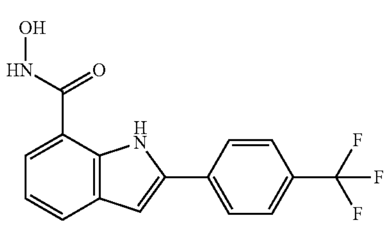 [SMILES: O=C(NO)c1cccc2cc(-c3ccc(C(F)(F)F)cc3)[nH]c12] | N-hydroxy-2-(4-(trifluoromethyl)phenyl)-1H-indole-7-carboxamide |

-continued

| Example | Structure | Name |
|---------|-----------|------|
| 37-2 | 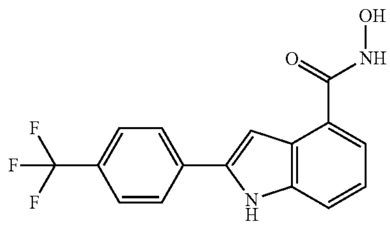 [SMILES: O=C(NO)c1cccc2[nH]c(-c3ccc(C(F)(F)F)cc3)cc12] | N-hydroxy-2-(4-(trifluoromethyl)phenyl)-1H-indole-4-carboxamide |
| 37-3 | 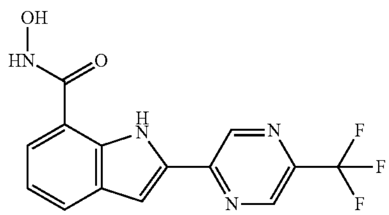 | N-hydroxy-2-(5-(trifluoromethyl)pyrazin-2-yl)-1H-indole-7-carboxamide |
| 37-4 | 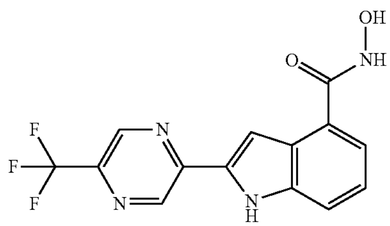 [SMILES: O=C(NO)c1cccc2[nH]c(-c3cnc(C(F)(F)F)cn3)cc12] | N-hydroxy-2-(5-(trifluoromethyl)pyrazin-2-yl)-1H-indole-4-carboxamide |
| 38-1 | 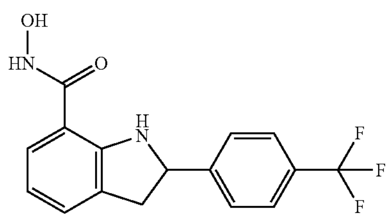 | N-hydroxy-2-(4-(trifluoromethyl)phenyl)indoline-7-carboxamide |
| 38-2 | 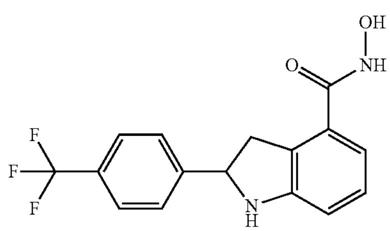 | N-hydroxy-2-(4-(trifluoromethyl)phenyl)indoline-4-carboxamide |
| 39-1 | 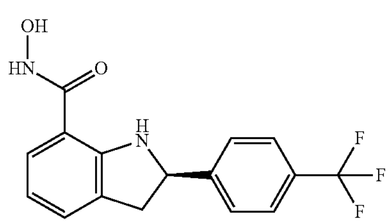 [SMILES: O=C(NO)c1cccc2c1N[C@@H](c1ccc(C(F)(F)F)cc1)C2] | (R)-N-hydroxy-2-(4-(trifluoromethyl)phenyl)indoline-7-carboxamide |
| 39-2 | 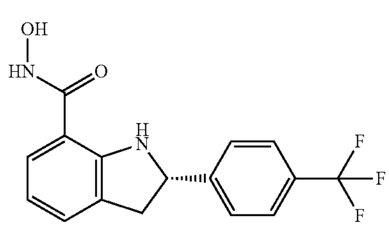 [SMILES: O=C(NO)c1cccc2c1N[C@H](c1ccc(C(F)(F)F)cc1)C2] | (S)-N-hydroxy-2-(4-(trifluoromethyl)phenyl)indoline-7-carboxamide |

| Example | Structure | Name |
|---|---|---|
| 40-1 | 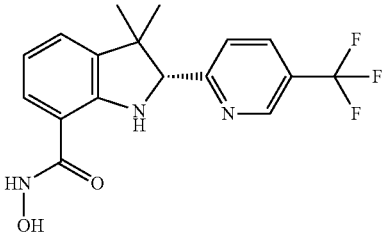 [SMILES: CC1(C)c2cccc(C(=O)NO)c2N[C@H]1c1ccc(C(F)(F)F)cn1] | (R)-N-hydroxy-3,3-dimethyl-2-(5-(trifluoromethyl)pyridin-2-yl)indoline-7-carboxamide |
| 40-2 | 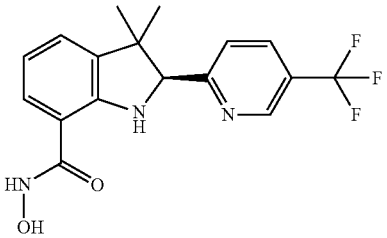 [SMILES: CC1(C)c2cccc(C(=O)NO)c2N[C@@H]1c1ccc(C(F)(F)F)cn1] | (S)-N-hydroxy-3,3-dimethyl-2-(5-(trifluoromethyl)pyridin-2-yl)indoline-7-carboxamide |
| 40-3 | 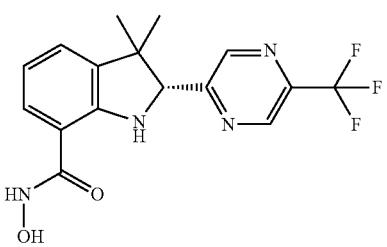 [SMILES: CC1(C)c2cccc(C(=O)NO)c2N[C@H]1c1cnc(C(F)(F)F)cn1] | (R)-N-hydroxy-3,3-dimethyl-2-(5-(trifluoromethyl)pyrazin-2-yl)indoline-7-carboxamide |
| 40-4 | 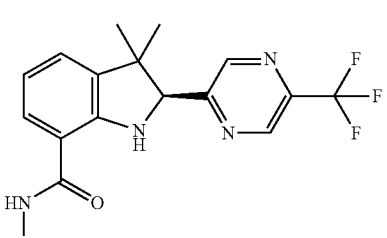 | (S)-N-hydroxy-3,3-dimethyl-2-(5-(trifluoromethyl)pyrazin-2-yl)indoline-7-carboxamide |
| 40-5 | 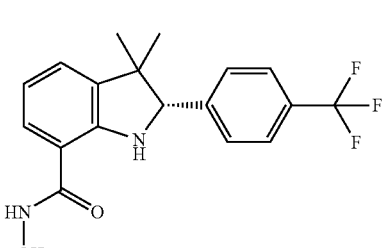 | (S)-N-hydroxy-3,3-dimethyl-2-(4-(trifluoromethyl)phenyl)indoline-7-carboxamide |
| 40-6 | 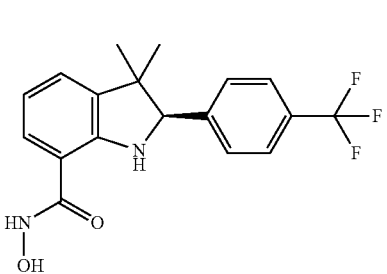 [SMILES: CC1(C)c2cccc(C(=O)NO)c2N[C@@H]1c1ccc(C(F)(F)F)cc1] | (R)-N-hydroxy-3,3-dimethyl-2-(4-(trifluoromethyl)phenyl)indoline-7-carboxamide |

-continued

| Example | Structure | Name |
|---|---|---|
| 1-6 | 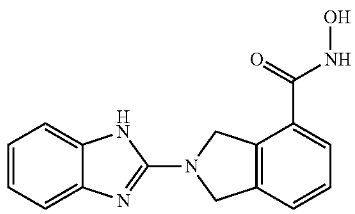 [SMILES: O=C(NO)c1cccc2c1CN(c1nc3ccccc3[nH]1)C2] | 2-(1H-benzo[d]imidazol-2-yl)-N-hydroxyisoindoline-4-carboxamide |
| 1-7 | 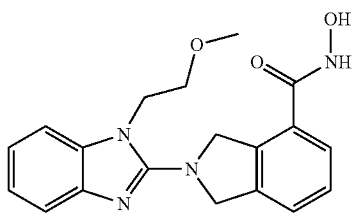 [SMILES: COCCn1c(N2Cc3cccc(C(=O)NO)c3C2)nc2ccccc21] | N-hydroxy-2-(1-(2-methoxyethyl)-1H-benzo[d]imidazol-2-yl)isoindoline-4-carboxamide |
| 28-3 | 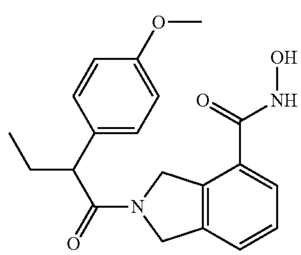 [SMILES: CCC(C(=O)N1Cc2cccc(C(=O)NO)c2C1)c1ccc(OC)cc1] | N-hydroxy-2-(2-(4-methoxyphenyl)butanoyl)isoindoline-4-carboxamide |
| 41-1 | 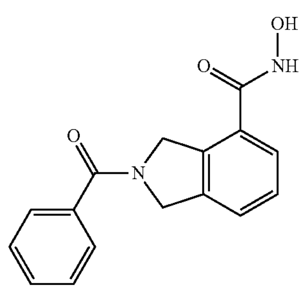 [SMILES: O=C(NO)c1cccc2c1CN(C(=O)c1ccccc1)C2] | 2-benzoyl-N-hydroxyisoindoline-4-carboxamide |
| 41-2 | 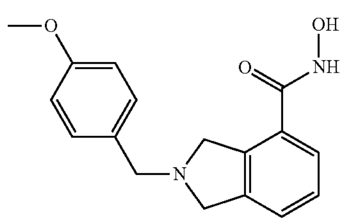 [SMILES: COc1ccc(CN2Cc3cccc(C(=O)NO)c3C2)cc1] | N-hydroxy-2-(4-methoxybenzyl)isoindoline-4-carboxamide |
| 42-1 | 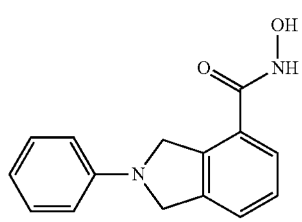 [SMILES: O=C(NO)c1cccc2c1CN(c1ccccc1)C2] | N-hydroxy-2-phenylisoindoline-4-carboxamide |

| Example | Structure | Name |
|---|---|---|
| 44-1 | 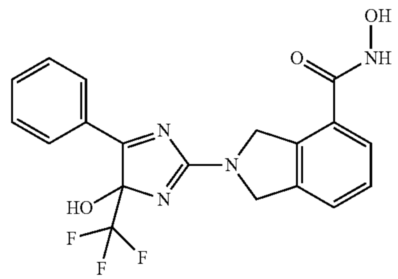 [SMILES: O=C(NO)c1cccc2c1CN(C1=NC(O)(C(F)(F)F)C(c3ccccc3)=N1)C2] | N-hydroxy-2-(4-hydroxy-5-phenyl-4-(trifluoromethyl)-4H-imidazol-2-yl)isoindoline-4-carboxamide |
| 45-1 | 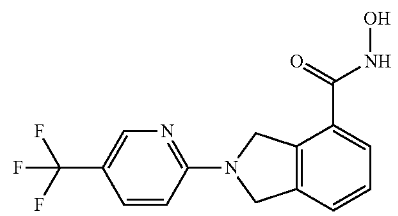 [SMILES: O=C(NO)c1cccc2c1CN(c1ccc(C(F)(F)F)cn1)C2] | N-hydroxy-2-(5-(trifluoromethyl)pyridin-2-yl)isoindoline-4-carboxamide |
| 45-2 | 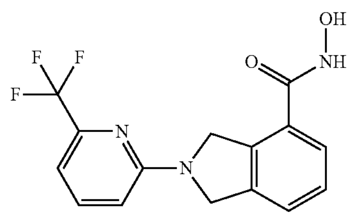 [SMILES: O=C(NO)c1cccc2c1CN(c1cccc(C(F)(F)F)n1)C2] | N-hydroxy-2-(6-(trifluoromethyl)pyridin-2-yl)isoindoline-4-carboxamide |
| 36-2 | 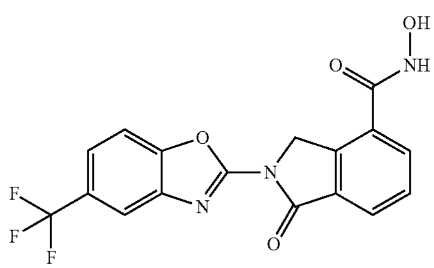 [SMILES: O=C(NO)c1cccc2c1CN(c1nc3cc(C(F)(F)F)ccc3o1)C2=O] | N-hydroxy-1-oxo-2-(5-(trifluoromethyl)benzo[d]oxazol-2-yl)isoindoline-4-carboxamide; or |
| 43-1 | 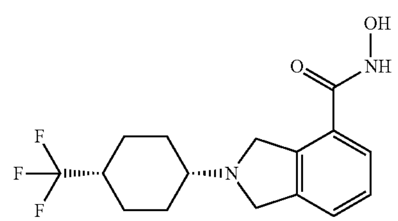 [SMILES: O=C(NO)c1cccc2c1CN([C@H]1CC[C@@H](C(F)(F)F)CC1)C2] | N-hydroxy-2-((1s,4s)-4-(trifluoromethyl)cyclohexyl)isoindoline-4-carboxamide. |

15. A pharmaceutical composition comprising a compound of claim 1 and a pharmaceutically acceptable carrier.

16. A pharmaceutical composition comprising a compound of claim 14 and a pharmaceutically acceptable carrier.

* * * * *

UNITED STATES PATENT AND TRADEMARK OFFICE
CERTIFICATE OF CORRECTION

| | | |
|---|---|---|
| PATENT NO. | : 11,535,607 B2 | Page 1 of 1 |
| APPLICATION NO. | : 17/049094 | |
| DATED | : December 27, 2022 | |
| INVENTOR(S) | : Xiaozhang Zheng et al. | |

It is certified that error appears in the above-identified patent and that said Letters Patent is hereby corrected as shown below:

On the Title Page

Related U.S. Application Data (60): Please replace the text:
"62/669,285, filed on May 9, 2019"
With:
--62/669,285, filed on May 9, 2018--

Signed and Sealed this
Sixteenth Day of July, 2024

Katherine Kelly Vidal
*Director of the United States Patent and Trademark Office*